US011654158B2

(12) United States Patent
Boyerinas

(10) Patent No.: US 11,654,158 B2
(45) Date of Patent: May 23, 2023

(54) TGFBETA SIGNAL CONVERTOR

(71) Applicant: 2seventy bio, Inc., Cambridge, MA (US)

(72) Inventor: Benjamin Boyerinas, Brookline, MA (US)

(73) Assignee: 2seventy bio, Inc., Cambridge, MA (US)

( * ) Notice: Subject to any disclaimer, the term of this patent is extended or adjusted under 35 U.S.C. 154(b) by 0 days.

(21) Appl. No.: 16/348,450

(22) PCT Filed: Nov. 17, 2017

(86) PCT No.: PCT/US2017/062358
§ 371 (c)(1),
(2) Date: May 8, 2019

(87) PCT Pub. No.: WO2018/094244
PCT Pub. Date: May 24, 2018

(65) Prior Publication Data
US 2019/0350974 A1 Nov. 21, 2019

Related U.S. Application Data

(60) Provisional application No. 62/467,496, filed on Mar. 6, 2017, provisional application No. 62/467,496, filed on Mar. 6, 2017.

(51) Int. Cl.
| | |
|---|---|
| *C07K 14/725* | (2006.01) |
| *A61K 39/00* | (2006.01) |
| *C07K 14/705* | (2006.01) |
| *A61P 35/00* | (2006.01) |
| *A61K 35/17* | (2015.01) |
| *C07K 14/495* | (2006.01) |
| *C07K 14/54* | (2006.01) |
| *A61K 38/00* | (2006.01) |
| *A61K 38/17* | (2006.01) |

(52) U.S. Cl.
CPC .......... *A61K 35/17* (2013.01); *A61K 39/0011* (2013.01); *A61P 35/00* (2018.01); *C07K 14/495* (2013.01); *C07K 14/5434* (2013.01); *C07K 14/7051* (2013.01); *A61K 38/00* (2013.01); *A61K 38/1793* (2013.01); *C07K 14/70575* (2013.01); *C07K 2319/02* (2013.01); *C07K 2319/03* (2013.01); *C07K 2319/50* (2013.01)

(58) Field of Classification Search
None
See application file for complete search history.

(56) References Cited

U.S. PATENT DOCUMENTS

| | | | |
|---|---|---|---|
| 4,751,180 A | 6/1988 | Cousens et al. | |
| 4,935,233 A | 6/1990 | Bell et al. | |
| 5,994,136 A | 11/1999 | Naldini et al. | |
| 6,013,516 A | 1/2000 | Verma et al. | |
| 6,682,907 B1 | 1/2004 | Chameau et al. | |
| 6,692,736 B2 | 2/2004 | Yu et al. | |
| 2009/0222936 A1 | 9/2009 | Richmond et al. | |
| 2015/0266973 A1 | 9/2015 | Jarjour et al. | |
| 2016/0075755 A1 | 3/2016 | Valdes et al. | |
| 2017/0360913 A1* | 12/2017 | Zhao | A61K 39/001104 |
| 2018/0244797 A1* | 8/2018 | Pulé | C07K 14/46 |

FOREIGN PATENT DOCUMENTS

| | | |
|---|---|---|
| JP | 2009514541 A | 4/2009 |
| JP | 2016520302 A | 7/2016 |
| WO | WO-2007054250 A1 | 5/2007 |
| WO | WO 2012/006635 | 1/2012 |
| WO | WO2012138858 | 10/2012 |
| WO | WO-2014172584 A1 | 10/2014 |
| WO | WO 2015/017214 | 2/2015 |
| WO | WO 2016/122738 | 8/2016 |
| WO | WO2016122738 | 8/2016 |
| WO | WO 2016/164089 | 10/2016 |
| WO | WO2017029512 | 2/2017 |
| WO | WO 2018/094244 | 5/2018 |

OTHER PUBLICATIONS

Bird, Robert E., et al. "Single-chain antigen-binding proteins." Science (1988); 242.4877: 423-427.
Challita, P. et al., "Multiple modifications in cis elements of the long terminal repeat of retroviral vectors lead to increased expression and decreased DNA methylation in embryonic carcinoma cells." J Virol. (1995); 69(2): 748-755.
Chaudhary, Vuay K., et al. "A rapid method of cloning functional variable-region antibody genes in *Escherichia coli* as single-chain immunotoxins." Proceedings of the National Academy of Sciences (1990); 87.3: 1066-1070 (and correction).
Clever, J. et al., "RNA Secondary Structure and Binding Sites for gag Gene Products in the 5' Packaging Signal of Human Immunodeficiency Virus Type 1." J. of Virology (1995); 69(4): 2101-2109.
Cooper, Laurence JN, et al. "T-cell clones can be rendered specific for CD19: Toward the selective augmentation of the graft-versus-B-lineage leukemia effect." Blood (2003); 101.4: 1637-1644.
Cullen, B.R., "Human Immunodeficiency Virus as a Prototypic Complex Retrovirus", Journal of Virology (1991); 65(3): 1053-1056.
Cullen et al., "Regulatory Pathways Governing HIV-1 Replication", Cell (1989); 58: 423-426.
De Felipe et al., "Targeting of proteins derived from self-processing polyproteins containing multiple signal sequences." Traffic (2004); 5.8: 616-626.

(Continued)

*Primary Examiner* — Daniel C Gamett
(74) *Attorney, Agent, or Firm* — Cooley LLP

(57) ABSTRACT

The present disclosure provides improved compositions for adoptive T cell therapies for treating, preventing, or ameliorating at least one symptom of a cancer, infectious disease, autoimmune disease, inflammatory disease, and immunodeficiency, or condition associated therewith.

20 Claims, 24 Drawing Sheets
Specification includes a Sequence Listing.

(56) References Cited

OTHER PUBLICATIONS

Desjarlais et al., "Use of a zinc-finger consensus sequence framework and specificity rules to design specific DNA binding proteins." Proceedings of the National Academy of Sciences (1993); 90.6: 2256-2260.
Desjarlais et al., "Length-encoded multiplex binding site determination: application to zinc finger proteins," Proceedings of the National Academy of Sciences (1994); 91.23: 11099-11103.
Donnelly, M. et al., "The 'cleavage' activities of foot-and-mouth disease virus 2A site-directed mutants and naturally occurring '2A-like' sequences." J Gen Virol. (2001); 82 (Pt 5): 1027-1041.
Duke et al., Sequence and structural elements that contribute to efficient encephalomyocarditis virus RNA translation, J Virol. Mar. 1992;66(3):1602-9.
Dull et al., "A third-generation lentivirus vector with a conditional packaging system", Journal of Virology (1998); 72(11): 8463-8671.
International Search Report and Written Opinion dated Apr. 3, 2018, for International Application No. PCT/US2017/062358, 15 pages.
Huang et al., "Role of the hepatitis B virus posttranscriptional regulatory element in export of intronless transcripts," Molecular and Cellular Biology (1995); 15(7): 3864-3869.
Huez et al., "Two independent internal ribosome entry sites are involved in translation initiation of vascular endothelial growth factor mRNA," Mol Cell Biol. Nov. 1998;18(11):6178-90.
Irion, S. et al., "Identification and targeting of the ROSA26 locus in human embryonic stem cells", Nat Biotechnol. (2007); 25(12):1477-1482.
Jackson, et al., "The novel mechanism of initiation of picornavirus RNA translation", Trends Biochem Sci. (1990); 15(12): 477-483.
Jackson, et al., "Internal initiation of translation in eukaryotes: the picornavirus paradigm and beyond", RNA. (1995); 1(10): 985-1000.
Kim, Yang-Gyun, et al. "Hybrid restriction enzymes: zinc finger fusions to Fok I cleavage domain." Proceedings of the National Academy of Sciences (1996); 93.3: 1156-1160.
Kutner, et al., "Simplified production and concentration of HIV-1-based lentiviral vectors using HYPERFlask vessels and anion exchange membrane chromatography", BMC Biotechnol. (2009); 9:10. p. 1-7.
Kutner et al., "Production, concentration and titration of pseudotyped HIV-1-based lentiviral vectors", Nature Protocols (2009); 4: 495-505.
Liu et al., "Design of polydactyl zinc-finger proteins for unique addressing within complex genomes," Proceedings of the National Academy of Sciences (1997); 94.11: 5525-5530.
Liu et al., "HnRNP L binds a cis-acting RNA sequence element that enables intron-dependent gene expression," Genes & Dev. (1995); 9: 1766-1780.
Maratea et al., "Deletion and fusion analysis of the phage phi X174 lysis gene E," Gene. 1985;40(1):39-46.
Murphy et al., "Genetic construction, expression, and melanoma-selective cytotoxicity of a diphtheria toxin-related alpha-melanocyte-stimulating hormone fusion protein," Proc Natl Acad Sci U S A. Nov. 1986;83(21):8258-62.
Naldini L. et al., "Efficient transfer, integration, and sustained long-term expression of the transgene in adult rat brains injected with a lentiviral vector", Proc Natl Acad Sci USA (1996); 93(21): 11382-11388.
Naldini, L. et al., "In vivo gene delivery and stable transduction of nondividing cells by a lentiviral vector", Science (1996); 272(5259): 263-267.

Naldini, L., "Lentiviruses as gene transfer agents for delivery to non-dividing cells", Curr Opin Biotechnol. (1998); 5: 457-463.
Patel, S. et al., "Impact of chimeric immune receptor extracellular protein domains on T cell function." Gene Ther (1999); 6(3): 412-419.
Pomerantz, et al., "Structure-based design of transcription factors." Science (1995); 267.5194: 93-96.
Pomerantz, et al., "Analysis of homeodomain function by structure-based design of a transcription factor," Proc Natl Acad Sci U S A. Oct. 10, 1995;92(21):9752-6.
Ryan, M. et al., "Virus-encoded proteinases of the picornavirus super-group." J Gen Virol. (1997); 78 (Pt 4): 699-723.
Szymczak, Andrea L., et al. "Correction of multi-gene deficiency in vivo using a single'self-cleaving'2A peptide-based retroviral vector." Nature Biotechnology (2004); 22.5: 589-594.
Zennou et al., "HIV-1 genome nuclear import is mediated by a central DNA flap," Cell. Apr. 14, 2000;101(2):173-85.
Zufferey et al., "Multiply attenuated lentiviral vector achieves efficient gene delivery in vivo", Nat Biotechnol. (1997), 15(9): 871-875.
Zufferey, R. et al., "Woodchuck hepatitis virus posttranscriptional regulatory element enhances expression of transgenes delivered by retroviral vectors." J Virol. (1999); 73(4): 2886-2892.
Extended European Search Report dated Mar. 30, 2020, for European Application No. 17872043.9, 12 pages.
Jena et al., "Driving CAR-Based T-Cell Therapy to Success," Curr Hematol Malig Rep. Mar. 2014; 9(1): 50-56.
Shi et al., "Chimeric antigen receptor for adoptive immunotherapy of cancer: latest research and future prospects," Molecular Cancer 2014, 13:219, 8 pages.
Yang, S. et al., "Development of optimal bicistronic lentiviral vectors facilitates high-level TCR gene expression and robust tumor cell recognition", Gene Therapy, Nov. 2008, vol. 15, No. 21, pp. 1411-1423.
Asao et al., "Cutting Edge: The Common γ-Chain is an Indispensable Subunit of the IL-21 Receptor Complex," The Journal of Immunology, 2001, 167, 1-5.
Cheung et al., "Accessory Protein-Like is Essential for IL-18-Mediated Signaling," The Journal of Immunology, 2005, 174, 5351-5357.
Fukuo, "Interleukin 2, IL-2," The Journal of Japan Atherosclerosis Society, 1996, 24, 4-5, 155-161.
Liu, X. et al. (2016). "A chimeric switch-receptor targeting PD1 augments the efficacy of second-generation CAR T cells in advanced solid tumors," Cancer Res. 76:1578-1590.
Office Action for Japanese Application No. JP20190526305 dated Jul. 4, 2022, 10 pages.
Office Action issued by the Japanese Patent Office for Application No. 2019-526305, dated Oct. 4, 2021, 9 pages.
Ozaki et al., "Cytokine and Cytokine Receptor Pleiotropy and Redundancy," The Journal of Biological Chemistry, Aug. 16, 2002, 277,33, 29355-29358.
Takara Bio Inc., Idenshidonyujikken handobukku (handbook of gene transfer experimentation), Nov. 2015, p. 1-10.
Wang, Z., et al., "Detection of RNA Interference (RNAi) Mediated mRNA Cleavage in Fresh Injected Tumor Tissue from Patients in a Phase I Trial of pbi-shRNA™ Lipoplex Targeting Stathmin-1," Molecular Therapy, May 2014, vol. 22, Supplement 1, pp. S298-S299.
Zhang, C. et al. (2017). "Engineering CAR-T cells," Biomaker Res. 5:22, 6 total pages.

* cited by examiner

FIGURE 3
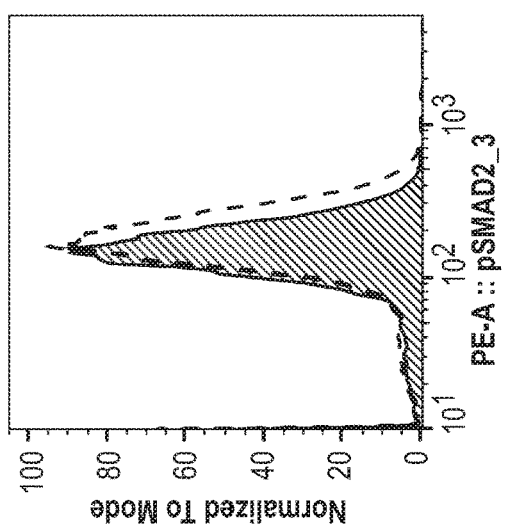
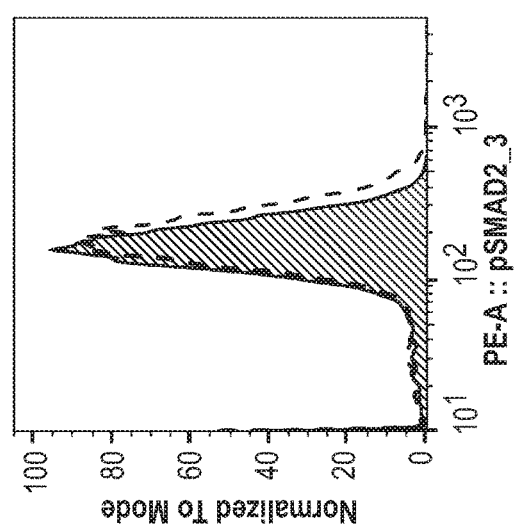
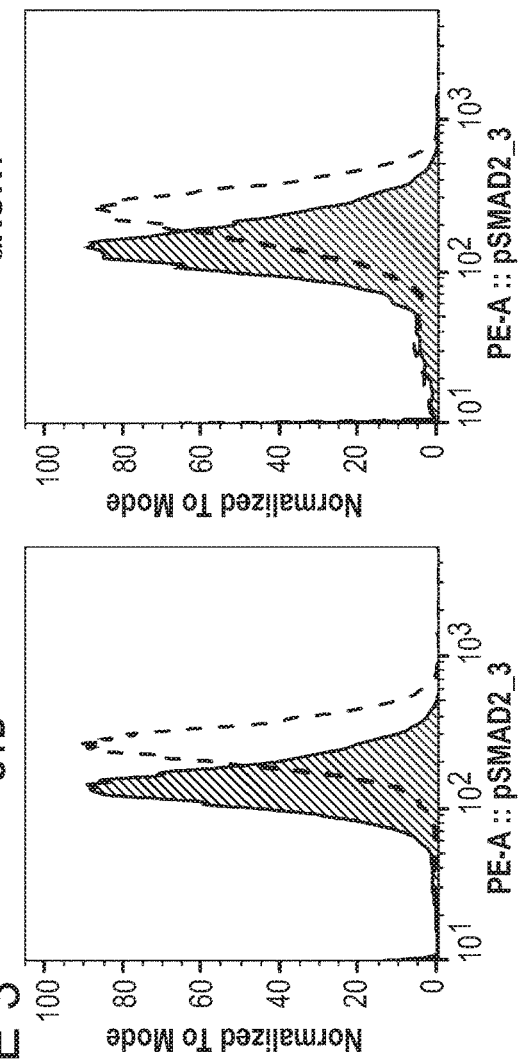
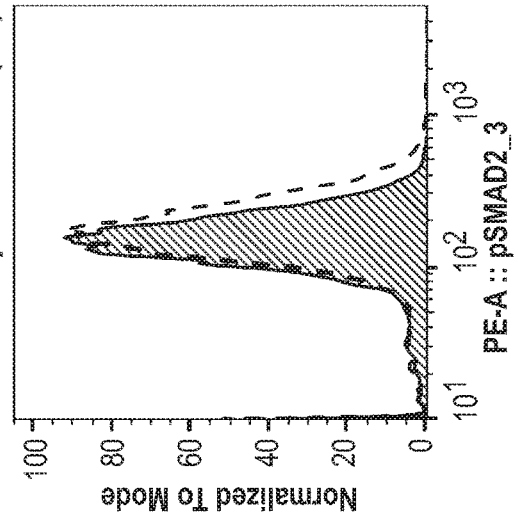

FIGURE 20
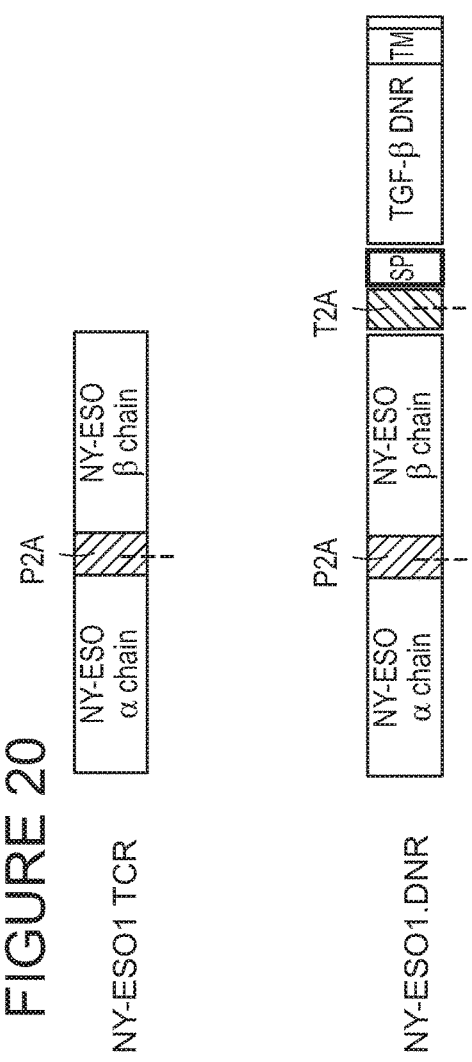
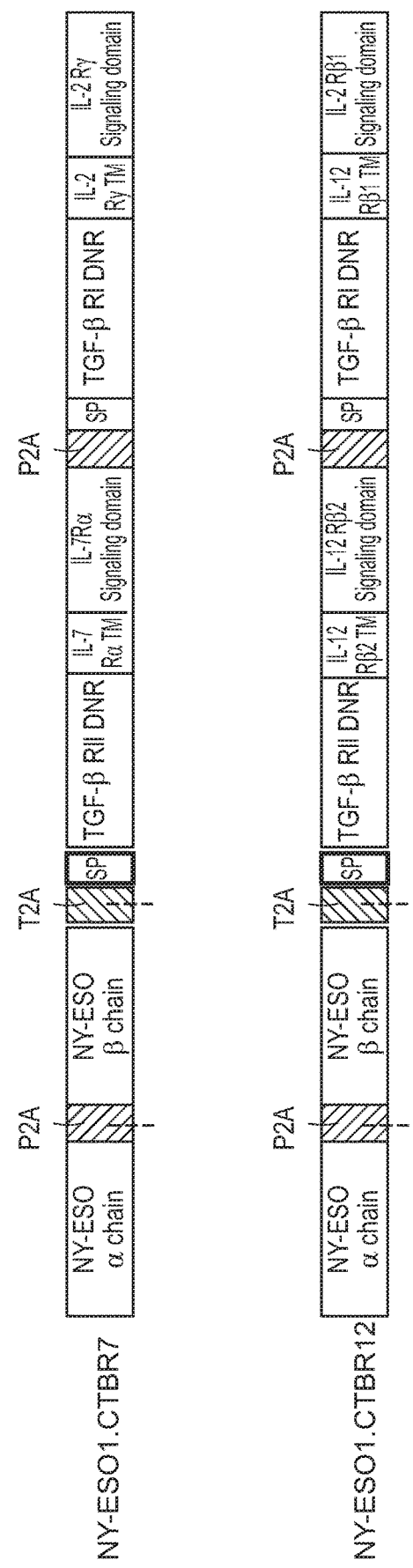

FIGURE 23
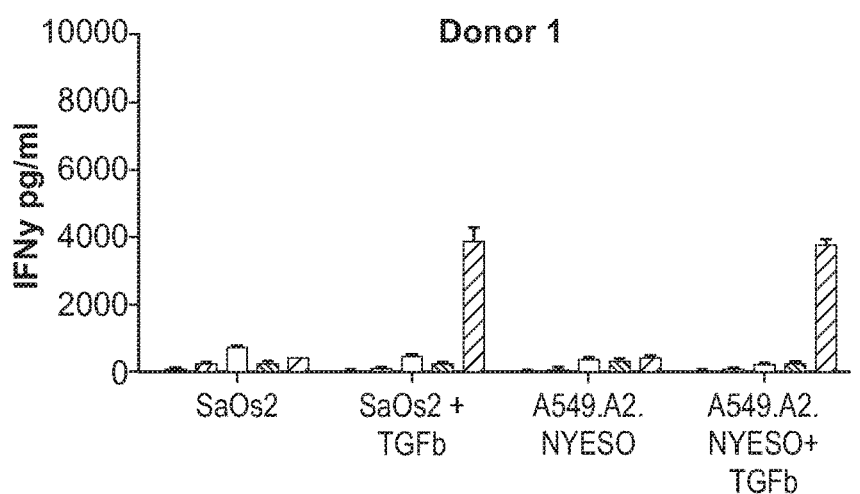
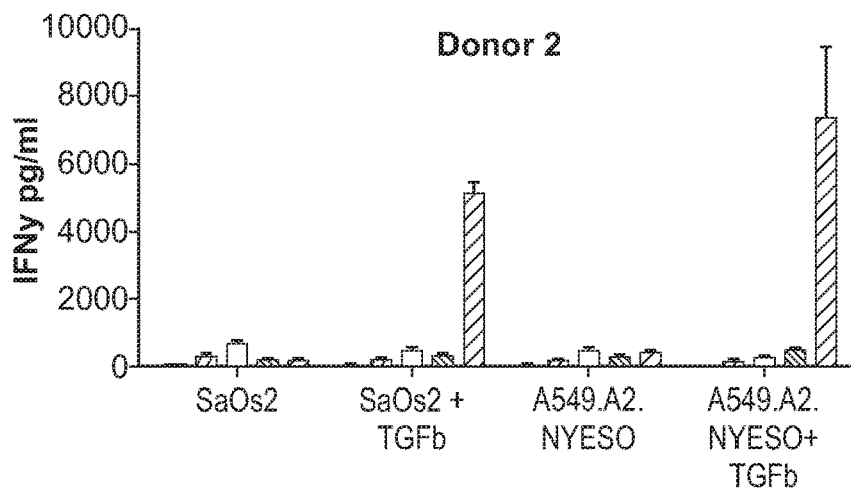
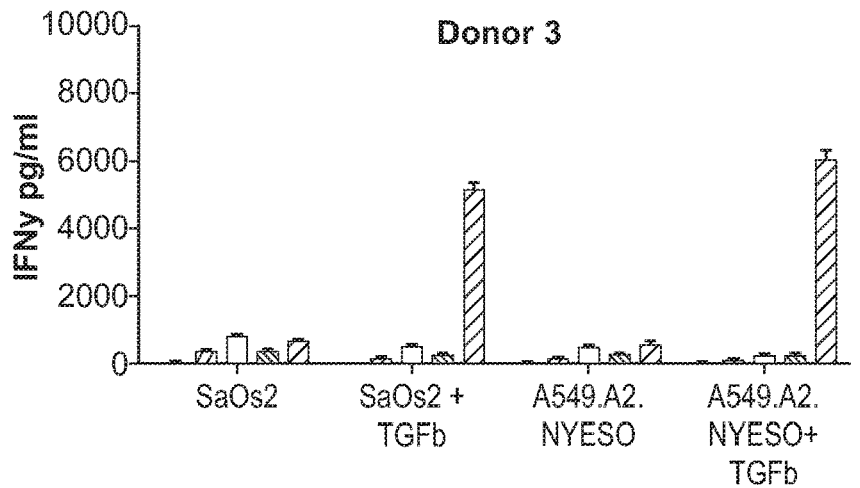

SEQUENCE LISTING

```
<160> NUMBER OF SEQ ID NOS: 76

<210> SEQ ID NO 1
<211> LENGTH: 507
<212> TYPE: PRT
<213> ORGANISM: Homo sapiens

<400> SEQUENCE: 1

Met Glu Ala Ala Val Ala Ala Pro Arg Pro Arg Leu Leu Leu Leu Val
1               5                   10                  15

Leu Ala Ala Ala Ala Ala Ala Ala Ala Leu Leu Pro Gly Ala Thr
            20                  25                  30

Ala Leu Gln Cys Phe Cys His Leu Cys Thr Lys Asp Asn Phe Thr Cys
        35                  40                  45

Val Thr Asp Gly Leu Cys Phe Val Ser Val Thr Glu Thr Thr Asp Lys
    50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Gly Pro Phe Ser Val Lys Ser Ser Pro Gly Leu Gly Pro Val
        115                 120                 125

Glu Leu Ala Ala Val Ile Ala Gly Pro Val Cys Phe Val Cys Ile Ser
    130                 135                 140

Leu Met Leu Met Val Tyr Ile Cys His Asn Arg Thr Val Ile His His
145                 150                 155                 160

Arg Val Pro Asn Glu Glu Asp Pro Ser Leu Asp Arg Pro Phe Ile Ser
                165                 170                 175
```

Glu Gly Thr Thr Leu Lys Asp Leu Ile Tyr Asp Met Thr Thr Ser Gly
            180                 185                 190

Ser Gly Ser Gly Leu Pro Leu Leu Val Gln Arg Thr Ile Ala Arg Thr
            195                 200                 205

Ile Val Leu Gln Glu Ser Ile Gly Lys Gly Arg Phe Gly Glu Val Trp
            210                 215                 220

Arg Gly Lys Trp Arg Gly Glu Glu Val Ala Val Lys Ile Phe Ser Ser
225                 230                 235                 240

Arg Glu Glu Arg Ser Trp Phe Arg Glu Ala Glu Ile Tyr Gln Thr Val
                245                 250                 255

Met Leu Arg His Glu Asn Ile Leu Gly Phe Ile Ala Ala Asp Asn Lys
            260                 265                 270

Asp Asn Gly Thr Trp Thr Gln Leu Trp Leu Val Ser Asp Tyr His Glu
            275                 280                 285

His Gly Ser Leu Phe Asp Tyr Leu Asn Arg Tyr Thr Val Thr Val Glu
            290                 295                 300

Gly Met Ile Lys Leu Ala Leu Ser Thr Ala Ser Gly Leu Ala His Leu
305                 310                 315                 320

His Met Glu Ile Val Gly Thr Gln Gly Lys Pro Ala Ile Ala His Arg
                325                 330                 335

Asp Leu Lys Ser Lys Asn Ile Leu Val Lys Lys Asn Gly Thr Cys Cys
            340                 345                 350

Ile Ala Asp Leu Gly Leu Ala Val Arg His Asp Ser Ala Thr Asp Thr
            355                 360                 365

Ile Asp Ile Ala Pro Asn His Arg Val Gly Thr Lys Arg Tyr Met Ala
            370                 375                 380

Pro Glu Val Leu Asp Asp Ser Ile Asn Met Lys His Phe Glu Ser Phe
385                 390                 395                 400

Lys Arg Ala Asp Ile Tyr Ala Met Gly Leu Val Phe Trp Glu Ile Ala
                405                 410                 415

Arg Arg Cys Ser Ile Gly Gly Ile His Glu Asp Tyr Gln Leu Pro Tyr
            420                 425                 430

Tyr Asp Leu Val Pro Ser Asp Pro Ser Val Glu Met Arg Lys Val
            435                 440                 445

Val Cys Glu Gln Lys Leu Arg Pro Asn Ile Pro Asn Arg Trp Gln Ser
450                 455                 460

Cys Glu Ala Leu Arg Val Met Ala Lys Ile Met Arg Glu Cys Trp Tyr
465                 470                 475                 480

Ala Asn Gly Ala Ala Arg Leu Thr Ala Leu Arg Ile Lys Lys Thr Leu
            485                 490                 495

Ser Gln Leu Ser Gln Gln Glu Gly Ile Lys Met
            500                 505

<210> SEQ ID NO 2
<211> LENGTH: 567
<212> TYPE: PRT
<213> ORGANISM: Homo sapiens

<400> SEQUENCE: 2

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

```
Asn Asn Asp Met Ile Val Thr Asp Asn Asn Gly Ala Val Lys Phe Pro
         35                  40                  45

Gln Leu Cys Lys Phe Cys Asp Val Arg Phe Ser Thr Cys Asp Asn Gln
 50                  55                  60

Lys Ser Cys Met Ser Asn Cys Ser Ile Thr Ser Ile Cys Glu Lys Pro
 65                  70                  75                  80

Gln Glu Val Cys Val Ala Val Trp Arg Lys Asn Asp Glu Asn Ile Thr
                 85                  90                  95

Leu Glu Thr Val Cys His Asp Pro Lys Leu Pro Tyr His Asp Phe Ile
                100                 105                 110

Leu Glu Asp Ala Ala Ser Pro Lys Cys Ile Met Lys Glu Lys Lys Lys
            115                 120                 125

Pro Gly Glu Thr Phe Phe Met Cys Ser Cys Ser Ser Asp Glu Cys Asn
        130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Phe Tyr Cys Tyr Arg Val Asn
            180                 185                 190

Arg Gln Gln Lys Leu Ser Ser Thr Trp Glu Thr Gly Lys Thr Arg Lys
            195                 200                 205

Leu Met Glu Phe Ser Glu His Cys Ala Ile Ile Leu Glu Asp Asp Arg
        210                 215                 220

Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                245                 250                 255

Glu Val Tyr Lys Ala Lys Leu Lys Gln Asn Thr Ser Glu Gln Phe Glu
            260                 265                 270

Thr Val Ala Val Lys Ile Phe Pro Tyr Glu Glu Tyr Ala Ser Trp Lys
        275                 280                 285

Thr Glu Lys Asp Ile Phe Ser Asp Ile Asn Leu Lys His Glu Asn Ile
        290                 295                 300

Leu Gln Phe Leu Thr Ala Glu Glu Arg Lys Thr Glu Leu Gly Lys Gln
305                 310                 315                 320

Tyr Trp Leu Ile Thr Ala Phe His Ala Lys Gly Asn Leu Gln Glu Tyr
                325                 330                 335

Leu Thr Arg His Val Ile Ser Trp Glu Asp Leu Arg Lys Leu Gly Ser
            340                 345                 350

Ser Leu Ala Arg Gly Ile Ala His Leu His Ser Asp His Thr Pro Cys
        355                 360                 365

Gly Arg Pro Lys Met Pro Ile Val His Arg Asp Leu Lys Ser Ser Asn
    370                 375                 380

Ile Leu Val Lys Asn Asp Leu Thr Cys Cys Leu Cys Asp Phe Gly Leu
385                 390                 395                 400

Ser Leu Arg Leu Asp Pro Thr Leu Ser Val Asp Asp Leu Ala Asn Ser
                405                 410                 415

Gly Gln Val Gly Thr Ala Arg Tyr Met Ala Pro Glu Val Leu Glu Ser
            420                 425                 430

Arg Met Asn Leu Glu Asn Val Glu Ser Phe Lys Gln Thr Asp Val Tyr
        435                 440                 445
```

```
Ser Met Ala Leu Val Leu Trp Glu Met Thr Ser Arg Cys Asn Ala Val
450                 455                 460

Gly Glu Val Lys Asp Tyr Glu Pro Pro Phe Gly Ser Lys Val Arg Glu
465                 470                 475                 480

His Pro Cys Val Glu Ser Met Lys Asp Asn Val Leu Arg Asp Arg Gly
            485                 490                 495

Arg Pro Glu Ile Pro Ser Phe Trp Leu Asn His Gln Gly Ile Gln Met
                500                 505                 510

Val Cys Glu Thr Leu Thr Glu Cys Trp Asp His Asp Pro Glu Ala Arg
            515                 520                 525

Leu Thr Ala Gln Cys Val Ala Glu Arg Phe Ser Glu Leu Glu His Leu
530                 535                 540

Asp Arg Leu Ser Gly Arg Ser Cys Ser Glu Glu Lys Ile Pro Glu Asp
545                 550                 555                 560

Gly Ser Leu Asn Thr Thr Lys
                565

<210> SEQ ID NO 3
<211> LENGTH: 662
<212> TYPE: PRT
<213> ORGANISM: Homo sapines

<400> SEQUENCE: 3

Met Glu Pro Leu Val Thr Trp Val Val Pro Leu Leu Phe Leu Phe Leu
1               5                   10                  15

Leu Ser Arg Gln Gly Ala Ala Cys Arg Thr Ser Glu Cys Cys Phe Gln
                20                  25                  30

Asp Pro Pro Tyr Pro Asp Ala Asp Ser Gly Ser Ala Ser Gly Pro Arg
            35                  40                  45

Asp Leu Arg Cys Tyr Arg Ile Ser Ser Asp Arg Tyr Glu Cys Ser Trp
50                  55                  60

Gln Tyr Glu Gly Pro Thr Ala Gly Val Ser His Phe Leu Arg Cys Cys
65                  70                  75                  80

Leu Ser Ser Gly Arg Cys Cys Tyr Phe Ala Ala Gly Ser Ala Thr Arg
                85                  90                  95

Leu Gln Phe Ser Asp Gln Ala Gly Val Ser Val Leu Tyr Thr Val Thr
                100                 105                 110

Leu Trp Val Glu Ser Trp Ala Arg Asn Gln Thr Glu Lys Ser Pro Glu
            115                 120                 125

Val Thr Leu Gln Leu Tyr Asn Ser Val Lys Tyr Glu Pro Pro Leu Gly
130                 135                 140

Asp Ile Lys Val Ser Lys Leu Ala Gly Gln Leu Arg Met Glu Trp Glu
145                 150                 155                 160

Thr Pro Asp Asn Gln Val Gly Ala Glu Val Gln Phe Arg His Arg Thr
                165                 170                 175

Pro Ser Ser Pro Trp Lys Leu Gly Asp Cys Gly Pro Gln Asp Asp Asp
            180                 185                 190

Thr Glu Ser Cys Leu Cys Pro Leu Glu Met Asn Val Ala Gln Glu Phe
            195                 200                 205

Gln Leu Arg Arg Arg Gln Leu Gly Ser Gln Gly Ser Ser Trp Ser Lys
            210                 215                 220

Trp Ser Ser Pro Val Cys Val Pro Pro Glu Asn Pro Pro Gln Pro Gln
225                 230                 235                 240

Val Arg Phe Ser Val Glu Gln Leu Gly Gln Asp Gly Arg Arg Arg Leu
                245                 250                 255
```

-continued

```
Thr Leu Lys Glu Gln Pro Thr Gln Leu Glu Leu Pro Glu Gly Cys Gln
            260                 265                 270

Gly Leu Ala Pro Gly Thr Glu Val Thr Tyr Arg Leu Gln Leu His Met
            275                 280                 285

Leu Ser Cys Pro Cys Lys Ala Lys Ala Thr Arg Thr Leu His Leu Gly
290                 295                 300

Lys Met Pro Tyr Leu Ser Gly Ala Ala Tyr Asn Val Ala Val Ile Ser
305                 310                 315                 320

Ser Asn Gln Phe Gly Pro Gly Leu Asn Gln Thr Trp His Ile Pro Ala
            325                 330                 335

Asp Thr His Thr Glu Pro Val Ala Leu Asn Ile Ser Val Gly Thr Asn
            340                 345                 350

Gly Thr Thr Met Tyr Trp Pro Ala Arg Ala Gln Ser Met Thr Tyr Cys
            355                 360                 365

Ile Glu Trp Gln Pro Val Gly Gln Asp Gly Gly Leu Ala Thr Cys Ser
            370                 375                 380

Leu Thr Ala Pro Gln Asp Pro Asp Pro Ala Gly Met Ala Thr Tyr Ser
385                 390                 395                 400

Trp Ser Arg Glu Ser Gly Ala Met Gly Gln Glu Lys Cys Tyr Tyr Ile
            405                 410                 415

Thr Ile Phe Ala Ser Ala His Pro Glu Lys Leu Thr Leu Trp Ser Thr
            420                 425                 430

Val Leu Ser Thr Tyr His Phe Gly Gly Asn Ala Ser Ala Ala Gly Thr
            435                 440                 445

Pro His His Val Ser Val Lys Asn His Ser Leu Asp Ser Val Ser Val
            450                 455                 460

Asp Trp Ala Pro Ser Leu Leu Ser Thr Cys Pro Gly Val Leu Lys Glu
465                 470                 475                 480

Tyr Val Val Arg Cys Arg Asp Glu Asp Ser Lys Gln Val Ser Glu His
            485                 490                 495

Pro Val Gln Pro Thr Glu Thr Gln Val Thr Leu Ser Gly Leu Arg Ala
            500                 505                 510

Gly Val Ala Tyr Thr Val Gln Val Arg Ala Asp Thr Ala Trp Leu Arg
            515                 520                 525

Gly Val Trp Ser Gln Pro Gln Arg Phe Ser Ile Glu Val Gln Val Ser
            530                 535                 540

Asp Trp Leu Ile Phe Phe Ala Ser Leu Gly Ser Phe Leu Ser Ile Leu
545                 550                 555                 560

Leu Val Gly Val Leu Gly Tyr Leu Gly Leu Asn Arg Ala Ala Arg His
            565                 570                 575

Leu Cys Pro Pro Leu Pro Thr Pro Cys Ala Ser Ser Ala Ile Glu Phe
            580                 585                 590

Pro Gly Gly Lys Glu Thr Trp Gln Trp Ile Asn Pro Val Asp Phe Gln
            595                 600                 605

Glu Glu Ala Ser Leu Gln Glu Ala Leu Val Val Glu Met Ser Trp Asp
            610                 615                 620

Lys Gly Glu Arg Thr Glu Pro Leu Glu Lys Thr Glu Leu Pro Glu Gly
625                 630                 635                 640

Ala Pro Glu Leu Ala Leu Asp Thr Glu Leu Ser Leu Glu Asp Gly Asp
            645                 650                 655

Arg Cys Lys Ala Lys Met
            660
```

<210> SEQ ID NO 4
<211> LENGTH: 776
<212> TYPE: PRT
<213> ORGANISM: Homo sapiens

<400> SEQUENCE: 4

```
Met Ala His Thr Phe Arg Gly Cys Ser Leu Ala Phe Met Phe Ile Ile
1               5                   10                  15

Thr Trp Leu Leu Ile Lys Ala Lys Ile Asp Ala Cys Lys Arg Gly Asp
            20                  25                  30

Val Thr Val Lys Pro Ser His Val Ile Leu Leu Gly Ser Thr Val Asn
        35                  40                  45

Ile Thr Cys Ser Leu Lys Pro Arg Gln Gly Cys Phe His Tyr Ser Arg
    50                  55                  60

Arg Asn Lys Leu Ile Leu Tyr Lys Phe Asp Arg Arg Ile Asn Phe His
65                  70                  75                  80

His Gly His Ser Leu Asn Ser Gln Val Thr Gly Leu Pro Leu Gly Thr
                85                  90                  95

Thr Leu Phe Val Cys Lys Leu Ala Cys Ile Asn Ser Asp Glu Ile Gln
            100                 105                 110

Ile Cys Gly Ala Glu Ile Phe Val Gly Val Ala Pro Glu Gln Pro Gln
        115                 120                 125

Asn Leu Ser Cys Ile Gln Lys Gly Glu Gln Gly Thr Val Ala Cys Thr
    130                 135                 140

Trp Glu Arg Gly Arg Asp Thr His Leu Tyr Thr Glu Tyr Thr Leu Gln
145                 150                 155                 160

Leu Ser Gly Pro Lys Asn Leu Thr Trp Gln Lys Gln Cys Lys Asp Ile
                165                 170                 175

Tyr Cys Asp Tyr Leu Asp Phe Gly Ile Asn Leu Thr Pro Glu Ser Pro
            180                 185                 190

Glu Ser Asn Phe Thr Ala Lys Val Thr Ala Val Asn Ser Leu Gly Ser
        195                 200                 205

Ser Ser Ser Leu Pro Ser Thr Phe Thr Phe Leu Asp Ile Val Arg Pro
    210                 215                 220

Leu Pro Pro Trp Asp Ile Arg Ile Lys Phe Gln Lys Ala Ser Val Ser
225                 230                 235                 240

Arg Cys Thr Leu Tyr Trp Arg Asp Glu Gly Leu Val Leu Leu Asn Arg
                245                 250                 255

Leu Arg Tyr Arg Pro Ser Asn Ser Arg Leu Trp Asn Met Val Asn Val
            260                 265                 270

Thr Lys Ala Lys Gly Arg His Asp Leu Leu Asp Leu Lys Pro Phe Thr
        275                 280                 285

Glu Tyr Glu Phe Gln Ile Ser Ser Lys Leu His Leu Tyr Lys Gly Ser
    290                 295                 300

Trp Ser Asp Trp Ser Glu Ser Leu Arg Ala Gln Thr Pro Glu Glu Glu
305                 310                 315                 320

Pro Thr Gly Met Leu Asp Val Trp Tyr Met Lys Arg His Ile Asp Tyr
                325                 330                 335

Ser Arg Gln Gln Ile Ser Leu Phe Trp Lys Asn Leu Ser Val Ser Glu
            340                 345                 350

Ala Arg Gly Lys Ile Leu His Tyr Gln Val Thr Leu Gln Glu Leu Thr
        355                 360                 365

Gly Gly Lys Ala Met Thr Gln Asn Ile Thr Gly His Thr Ser Trp Thr
    370                 375                 380
```

Thr Val Ile Pro Arg Thr Gly Asn Trp Ala Val Ala Val Ser Ala Ala
385                 390                 395                 400

Asn Ser Lys Gly Ser Ser Leu Pro Thr Arg Ile Asn Ile Met Asn Leu
            405                 410                 415

Cys Glu Ala Gly Leu Leu Ala Pro Arg Gln Val Ser Ala Asn Ser Glu
            420                 425                 430

Gly Met Asp Asn Ile Leu Val Thr Trp Gln Pro Pro Arg Lys Asp Pro
            435                 440                 445

Ser Ala Val Gln Glu Tyr Val Val Glu Trp Arg Glu Leu His Pro Gly
450                 455                 460

Gly Asp Thr Gln Val Pro Leu Asn Trp Leu Arg Ser Arg Pro Tyr Asn
465                 470                 475                 480

Val Ser Ala Leu Ile Ser Glu Ile Pro Tyr Arg Val Ser Gln Asn Ser
                485                 490                 495

His Pro Ile Asn Ser Leu Gln Pro Arg Val Thr Tyr Val Leu Trp Met
            500                 505                 510

Thr Ala Leu Thr Ala Ala Gly Glu Ser Ser His Gly Asn Glu Arg Glu
            515                 520                 525

Phe Cys Leu Gln Gly Lys Ala Asn Trp Met Ala Phe Val Ala Pro Ser
530                 535                 540

Ile Cys Ile Ala Ile Ile Met Val Gly Ile Phe Ser Thr His Tyr Phe
545                 550                 555                 560

Gln Gln Lys Val Phe Val Leu Leu Ala Ala Leu Arg Pro Gln Trp Cys
                565                 570                 575

Ser Arg Glu Ile Pro Asp Pro Ala Asn Ser Thr Cys Ala Lys Lys Tyr
            580                 585                 590

Pro Ile Ala Glu Glu Lys Thr Gln Leu Pro Leu Asp Arg Leu Leu Ile
            595                 600                 605

Asp Trp Pro Thr Pro Glu Asp Pro Glu Pro Leu Val Ile Ser Glu Val
            610                 615                 620

Leu His Gln Val Thr Pro Val Phe Arg His Pro Pro Cys Ser Asn Trp
625                 630                 635                 640

Pro Gln Arg Glu Lys Gly Ile Gln Gly His Gln Ala Ser Glu Lys Asp
                645                 650                 655

Met Met His Ser Ala Ser Ser Pro Pro Pro Arg Ala Leu Gln Ala
            660                 665                 670

Glu Ser Arg Gln Leu Val Asp Leu Tyr Lys Val Leu Glu Ser Arg Gly
            675                 680                 685

Ser Asp Pro Lys Pro Glu Asn Pro Ala Cys Pro Trp Thr Val Leu Pro
690                 695                 700

Ala Gly Asp Leu Pro Thr His Asp Gly Tyr Leu Pro Ser Asn Ile Asp
705                 710                 715                 720

Asp Leu Pro Ser His Glu Ala Pro Leu Ala Asp Ser Leu Glu Glu Leu
                725                 730                 735

Glu Pro Gln His Ile Ser Leu Ser Val Phe Pro Ser Ser Ser Leu His
            740                 745                 750

Pro Leu Thr Phe Ser Cys Gly Asp Lys Leu Thr Leu Asp Gln Leu Lys
            755                 760                 765

Met Arg Cys Asp Ser Leu Met Leu
770                 775

<210> SEQ ID NO 5
<211> LENGTH: 459

<212> TYPE: PRT
<213> ORGANISM: Homo sapiens

<400> SEQUENCE: 5

Met Thr Ile Leu Gly Thr Thr Phe Gly Met Val Phe Ser Leu Leu Gln
1               5                   10                  15

Val Val Ser Gly Glu Ser Gly Tyr Ala Gln Asn Gly Asp Leu Glu Asp
            20                  25                  30

Ala Glu Leu Asp Asp Tyr Ser Phe Ser Cys Tyr Ser Gln Leu Glu Val
        35                  40                  45

Asn Gly Ser Gln His Ser Leu Thr Cys Ala Phe Glu Asp Pro Asp Val
    50                  55                  60

Asn Thr Thr Asn Leu Glu Phe Glu Ile Cys Gly Ala Leu Val Glu Val
65                  70                  75                  80

Lys Cys Leu Asn Phe Arg Lys Leu Gln Glu Ile Tyr Phe Ile Glu Thr
                85                  90                  95

Lys Lys Phe Leu Leu Ile Gly Lys Ser Asn Ile Cys Val Lys Val Gly
            100                 105                 110

Glu Lys Ser Leu Thr Cys Lys Lys Ile Asp Leu Thr Thr Ile Val Lys
        115                 120                 125

Pro Glu Ala Pro Phe Asp Leu Ser Val Ile Tyr Arg Glu Gly Ala Asn
    130                 135                 140

Asp Phe Val Val Thr Phe Asn Thr Ser His Leu Gln Lys Lys Tyr Val
145                 150                 155                 160

Lys Val Leu Met His Asp Val Ala Tyr Arg Gln Glu Lys Asp Glu Asn
                165                 170                 175

Lys Trp Thr His Val Asn Leu Ser Ser Thr Lys Leu Thr Leu Leu Gln
            180                 185                 190

Arg Lys Leu Gln Pro Ala Ala Met Tyr Glu Ile Lys Val Arg Ser Ile
        195                 200                 205

Pro Asp His Tyr Phe Lys Gly Phe Trp Ser Glu Trp Ser Pro Ser Tyr
    210                 215                 220

Tyr Phe Arg Thr Pro Glu Ile Asn Asn Ser Ser Gly Glu Met Asp Pro
225                 230                 235                 240

Ile Leu Leu Thr Ile Ser Ile Leu Ser Phe Phe Ser Val Ala Leu Leu
                245                 250                 255

Val Ile Leu Ala Cys Val Leu Trp Lys Lys Arg Ile Lys Pro Ile Val
            260                 265                 270

Trp Pro Ser Leu Pro Asp His Lys Lys Thr Leu Glu His Leu Cys Lys
        275                 280                 285

Lys Pro Arg Lys Asn Leu Asn Val Ser Phe Asn Pro Glu Ser Phe Leu
    290                 295                 300

Asp Cys Gln Ile His Arg Val Asp Asp Ile Gln Ala Arg Asp Glu Val
305                 310                 315                 320

Glu Gly Phe Leu Gln Asp Thr Phe Pro Gln Gln Leu Glu Glu Ser Glu
                325                 330                 335

Lys Gln Arg Leu Gly Gly Asp Val Gln Ser Pro Asn Cys Pro Ser Glu
            340                 345                 350

Asp Val Val Ile Thr Pro Glu Ser Phe Gly Arg Asp Ser Ser Leu Thr
        355                 360                 365

Cys Leu Ala Gly Asn Val Ser Ala Cys Asp Ala Pro Ile Leu Ser Ser
    370                 375                 380

Ser Arg Ser Leu Asp Cys Arg Glu Ser Gly Lys Asn Gly Pro His Val
385                 390                 395                 400

```
Tyr Gln Asp Leu Leu Leu Ser Leu Gly Thr Thr Asn Ser Thr Leu Pro
                405                 410                 415

Pro Pro Phe Ser Leu Gln Ser Gly Ile Leu Thr Leu Asn Pro Val Ala
            420                 425                 430

Gln Gly Gln Pro Ile Leu Thr Ser Leu Gly Ser Asn Gln Glu Glu Ala
        435                 440                 445

Tyr Val Thr Met Ser Ser Phe Tyr Gln Asn Gln
    450                 455

<210> SEQ ID NO 6
<211> LENGTH: 369
<212> TYPE: PRT
<213> ORGANISM: Homo sapiens

<400> SEQUENCE: 6

Met Leu Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125

Val Val Gln Leu Gln Asp Pro Arg Glu Pro Arg Arg Gln Ala Thr Gln
130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
        195                 200                 205

Ser Leu Pro Ser Val Asp Gly Gln Lys Arg Tyr Thr Phe Arg Val Arg
210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Pro Phe
                245                 250                 255

Leu Phe Ala Leu Glu Ala Val Val Ile Ser Val Gly Ser Met Gly Leu
            260                 265                 270

Ile Ile Ser Leu Leu Cys Val Tyr Phe Trp Leu Glu Arg Thr Met Pro
        275                 280                 285

Arg Ile Pro Thr Leu Lys Asn Leu Glu Asp Leu Val Thr Glu Tyr His
290                 295                 300
```

```
Gly Asn Phe Ser Ala Trp Ser Gly Val Ser Lys Gly Leu Ala Glu Ser
305                 310                 315                 320

Leu Gln Pro Asp Tyr Ser Glu Arg Leu Cys Leu Val Ser Glu Ile Pro
            325                 330                 335

Pro Lys Gly Gly Ala Leu Gly Glu Gly Pro Gly Ala Ser Pro Cys Asn
            340                 345                 350

Gln His Ser Pro Tyr Trp Ala Pro Pro Cys Tyr Thr Leu Lys Pro Glu
        355                 360                 365

Thr

<210> SEQ ID NO 7
<211> LENGTH: 551
<212> TYPE: PRT
<213> ORGANISM: Homo sapiens

<400> SEQUENCE: 7

Met Ala Ala Pro Ala Leu Ser Trp Arg Leu Pro Leu Leu Ile Leu Leu
1               5                   10                  15

Leu Pro Leu Ala Thr Ser Trp Ala Ser Ala Val Asn Gly Thr Ser
            20                  25                  30

Gln Phe Thr Cys Phe Tyr Asn Ser Arg Ala Asn Ile Ser Cys Val Trp
            35                  40                  45

Ser Gln Asp Gly Ala Leu Gln Asp Thr Ser Cys Gln Val His Ala Trp
50                  55                  60

Pro Asp Arg Arg Arg Trp Asn Gln Thr Cys Glu Leu Leu Pro Val Ser
65                  70                  75                  80

Gln Ala Ser Trp Ala Cys Asn Leu Ile Leu Gly Ala Pro Asp Ser Gln
                85                  90                  95

Lys Leu Thr Thr Val Asp Ile Val Thr Leu Arg Val Leu Cys Arg Glu
            100                 105                 110

Gly Val Arg Trp Arg Val Met Ala Ile Gln Asp Phe Lys Pro Phe Glu
        115                 120                 125

Asn Leu Arg Leu Met Ala Pro Ile Ser Leu Gln Val Val His Val Glu
130                 135                 140

Thr His Arg Cys Asn Ile Ser Trp Glu Ile Ser Gln Ala Ser His Tyr
145                 150                 155                 160

Phe Glu Arg His Leu Glu Phe Glu Ala Arg Thr Leu Ser Pro Gly His
                165                 170                 175

Thr Trp Glu Glu Ala Pro Leu Leu Thr Leu Lys Gln Lys Gln Glu Trp
            180                 185                 190

Ile Cys Leu Glu Thr Leu Thr Pro Asp Thr Gln Tyr Glu Phe Gln Val
        195                 200                 205

Arg Val Lys Pro Leu Gln Gly Glu Phe Thr Thr Trp Ser Pro Trp Ser
210                 215                 220

Gln Pro Leu Ala Phe Arg Thr Lys Pro Ala Ala Leu Gly Lys Asp Thr
225                 230                 235                 240

Ile Pro Trp Leu Gly His Leu Leu Val Gly Leu Ser Gly Ala Phe Gly
                245                 250                 255

Phe Ile Ile Leu Val Tyr Leu Leu Ile Asn Cys Arg Asn Thr Gly Pro
            260                 265                 270

Trp Leu Lys Lys Val Leu Lys Cys Asn Thr Pro Asp Pro Ser Lys Phe
        275                 280                 285

Phe Ser Gln Leu Ser Ser Glu His Gly Gly Asp Val Gln Lys Trp Leu
290                 295                 300
```

```
Ser Ser Pro Phe Pro Ser Ser Phe Ser Pro Gly Gly Leu Ala Pro
305                 310                 315                 320

Glu Ile Ser Pro Leu Glu Val Leu Glu Arg Asp Lys Val Thr Gln Leu
                325                 330                 335

Leu Leu Gln Gln Asp Lys Val Pro Glu Pro Ala Ser Leu Ser Ser Asn
            340                 345                 350

His Ser Leu Thr Ser Cys Phe Thr Asn Gln Gly Tyr Phe Phe His
            355                 360                 365

Leu Pro Asp Ala Leu Glu Ile Glu Ala Cys Gln Val Tyr Phe Thr Tyr
        370                 375                 380

Asp Pro Tyr Ser Glu Glu Asp Pro Asp Glu Gly Val Ala Gly Ala Pro
385                 390                 395                 400

Thr Gly Ser Ser Pro Gln Pro Leu Gln Pro Leu Ser Gly Glu Asp Asp
                405                 410                 415

Ala Tyr Cys Thr Phe Pro Ser Arg Asp Asp Leu Leu Leu Phe Ser Pro
            420                 425                 430

Ser Leu Leu Gly Gly Pro Ser Pro Ser Thr Ala Pro Gly Gly Ser
        435                 440                 445

Gly Ala Gly Glu Glu Arg Met Pro Pro Ser Leu Gln Glu Arg Val Pro
450                 455                 460

Arg Asp Trp Asp Pro Gln Pro Leu Gly Pro Pro Thr Pro Gly Val Pro
465                 470                 475                 480

Asp Leu Val Asp Phe Gln Pro Pro Pro Glu Leu Val Leu Arg Glu Ala
                485                 490                 495

Gly Glu Glu Val Pro Asp Ala Gly Pro Arg Glu Gly Val Ser Phe Pro
                500                 505                 510

Trp Ser Arg Pro Pro Gly Gln Gly Glu Phe Arg Ala Leu Asn Ala Arg
        515                 520                 525

Leu Pro Leu Asn Thr Asp Ala Tyr Leu Ser Leu Gln Glu Leu Gln Gly
            530                 535                 540

Gln Asp Pro Thr His Leu Val
545                 550

<210> SEQ ID NO 8
<211> LENGTH: 538
<212> TYPE: PRT
<213> ORGANISM: Homo sapiens

<400> SEQUENCE: 8

Met Pro Arg Gly Trp Ala Ala Pro Leu Leu Leu Leu Leu Leu Gln Gly
1               5                   10                  15

Gly Trp Gly Cys Pro Asp Leu Val Cys Tyr Thr Asp Tyr Leu Gln Thr
                20                  25                  30

Val Ile Cys Ile Leu Glu Met Trp Asn Leu His Pro Ser Thr Leu Thr
            35                  40                  45

Leu Thr Trp Gln Asp Gln Tyr Glu Glu Leu Lys Asp Glu Ala Thr Ser
        50                  55                  60

Cys Ser Leu His Arg Ser Ala His Asn Ala Thr His Ala Thr Tyr Thr
65                  70                  75                  80

Cys His Met Asp Val Phe His Phe Met Ala Asp Asp Ile Phe Ser Val
                85                  90                  95

Asn Ile Thr Asp Gln Ser Gly Asn Tyr Ser Gln Glu Cys Gly Ser Phe
            100                 105                 110
```

```
Leu Leu Ala Glu Ser Ile Lys Pro Ala Pro Phe Asn Val Thr Val
            115                 120                 125

Thr Phe Ser Gly Gln Tyr Asn Ile Ser Trp Arg Ser Asp Tyr Glu Asp
130                 135                 140

Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Arg Lys Leu Ile
                165                 170                 175

Ser Val Asp Ser Arg Ser Val Ser Leu Leu Pro Leu Glu Phe Arg Lys
            180                 185                 190

Asp Ser Ser Tyr Glu Leu Gln Val Arg Ala Gly Pro Met Pro Gly Ser
            195                 200                 205

Ser Tyr Gln Gly Thr Trp Ser Glu Trp Ser Asp Pro Val Ile Phe Gln
            210                 215                 220

Thr Gln Ser Glu Glu Leu Lys Glu Gly Trp Asn Pro His Leu Leu Leu
225                 230                 235                 240

Leu Leu Leu Leu Val Ile Val Phe Ile Pro Ala Phe Trp Ser Leu Lys
                245                 250                 255

Thr His Pro Leu Trp Arg Leu Trp Lys Lys Ile Trp Ala Val Pro Ser
            260                 265                 270

Pro Glu Arg Phe Phe Met Pro Leu Tyr Lys Gly Cys Ser Gly Asp Phe
            275                 280                 285

Lys Lys Trp Val Gly Ala Pro Phe Thr Gly Ser Ser Leu Glu Leu Gly
            290                 295                 300

Pro Trp Ser Pro Glu Val Pro Ser Thr Leu Glu Val Tyr Ser Cys His
305                 310                 315                 320

Pro Pro Arg Ser Pro Ala Lys Arg Leu Gln Leu Thr Glu Leu Gln Glu
            325                 330                 335

Pro Ala Glu Leu Val Glu Ser Asp Gly Val Pro Lys Pro Ser Phe Trp
            340                 345                 350

Pro Thr Ala Gln Asn Ser Gly Gly Ser Ala Tyr Ser Glu Glu Arg Asp
            355                 360                 365

Arg Pro Tyr Gly Leu Val Ser Ile Asp Thr Val Thr Val Leu Asp Ala
            370                 375                 380

Glu Gly Pro Cys Thr Trp Pro Cys Ser Cys Glu Asp Asp Gly Tyr Pro
385                 390                 395                 400

Ala Leu Asp Leu Asp Ala Gly Leu Glu Pro Ser Pro Gly Leu Glu Asp
                405                 410                 415

Pro Leu Leu Asp Ala Gly Thr Thr Val Leu Ser Cys Gly Cys Val Ser
            420                 425                 430

Ala Gly Ser Pro Gly Leu Gly Gly Pro Leu Gly Ser Leu Leu Asp Arg
            435                 440                 445

Leu Lys Pro Pro Leu Ala Asp Gly Glu Asp Trp Ala Gly Gly Leu Pro
450                 455                 460

Trp Gly Gly Arg Ser Pro Gly Gly Val Ser Glu Ser Glu Ala Gly Ser
465                 470                 475                 480

Pro Leu Ala Gly Leu Asp Met Asp Thr Phe Asp Ser Gly Phe Val Gly
                485                 490                 495

Ser Asp Cys Ser Ser Pro Val Glu Cys Asp Phe Thr Ser Pro Gly Asp
            500                 505                 510

Glu Gly Pro Pro Arg Ser Tyr Leu Arg Gln Trp Val Val Ile Pro Pro
            515                 520                 525
```

```
Pro Leu Ser Ser Pro Gly Pro Gln Ala Ser
    530                 535

<210> SEQ ID NO 9
<211> LENGTH: 541
<212> TYPE: PRT
<213> ORGANISM: Homo sapiens

<400> SEQUENCE: 9

Met Asn Cys Arg Glu Leu Pro Leu Thr Leu Trp Val Leu Ile Ser Val
1               5                   10                  15

Ser Thr Ala Glu Ser Cys Thr Ser Arg Pro His Ile Thr Val Val Glu
            20                  25                  30

Gly Glu Pro Phe Tyr Leu Lys His Cys Ser Cys Ser Leu Ala His Glu
        35                  40                  45

Ile Glu Thr Thr Thr Lys Ser Trp Tyr Lys Ser Gly Ser Gln Glu
    50                  55                  60

His Val Glu Leu Asn Pro Arg Ser Ser Ser Arg Ile Ala Leu His Asp
65                  70                  75                  80

Cys Val Leu Glu Phe Trp Pro Val Glu Leu Asn Asp Thr Gly Ser Tyr
                85                  90                  95

Phe Phe Gln Met Lys Asn Tyr Thr Gln Lys Trp Lys Leu Asn Val Ile
            100                 105                 110

Arg Arg Asn Lys His Ser Cys Phe Thr Glu Arg Gln Val Thr Ser Lys
        115                 120                 125

Ile Val Glu Val Lys Lys Phe Phe Gln Ile Thr Cys Glu Asn Ser Tyr
    130                 135                 140

Tyr Gln Thr Leu Val Asn Ser Thr Ser Leu Tyr Lys Asn Cys Lys Lys
145                 150                 155                 160

Leu Leu Leu Glu Asn Asn Lys Asn Pro Thr Ile Lys Lys Asn Ala Glu
                165                 170                 175

Phe Glu Asp Gln Gly Tyr Tyr Ser Cys Val His Phe Leu His His Asn
            180                 185                 190

Gly Lys Leu Phe Asn Ile Thr Lys Thr Phe Asn Ile Thr Ile Val Glu
        195                 200                 205

Asp Arg Ser Asn Ile Val Pro Val Leu Leu Gly Pro Lys Leu Asn His
    210                 215                 220

Val Ala Val Glu Leu Gly Lys Asn Val Arg Leu Asn Cys Ser Ala Leu
225                 230                 235                 240

Leu Asn Glu Glu Asp Val Ile Tyr Trp Met Phe Gly Glu Glu Asn Gly
                245                 250                 255

Ser Asp Pro Asn Ile His Glu Glu Lys Glu Met Arg Ile Met Thr Pro
            260                 265                 270

Glu Gly Lys Trp His Ala Ser Lys Val Leu Arg Ile Glu Asn Ile Gly
        275                 280                 285

Glu Ser Asn Leu Asn Val Leu Tyr Asn Cys Thr Val Ala Ser Thr Gly
    290                 295                 300

Gly Thr Asp Thr Lys Ser Phe Ile Leu Val Arg Lys Ala Asp Met Ala
305                 310                 315                 320

Asp Ile Pro Gly His Val Phe Thr Arg Gly Met Ile Ile Ala Val Leu
                325                 330                 335

Ile Leu Val Ala Val Cys Leu Val Thr Val Cys Val Ile Tyr Arg
            340                 345                 350

Val Asp Leu Val Leu Phe Tyr Arg His Leu Thr Arg Arg Asp Glu Thr
        355                 360                 365
```

```
Leu Thr Asp Gly Lys Thr Tyr Asp Ala Phe Val Ser Tyr Leu Lys Glu
    370                 375                 380

Cys Arg Pro Glu Asn Gly Glu Glu His Thr Phe Ala Val Glu Ile Leu
385                 390                 395                 400

Pro Arg Val Leu Glu Lys His Phe Gly Tyr Lys Leu Cys Ile Phe Glu
            405                 410                 415

Arg Asp Val Val Pro Gly Gly Ala Val Val Asp Glu Ile His Ser Leu
                420                 425                 430

Ile Glu Lys Ser Arg Arg Leu Ile Ile Val Leu Ser Lys Ser Tyr Met
            435                 440                 445

Ser Asn Glu Val Arg Tyr Glu Leu Glu Ser Gly Leu His Glu Ala Leu
    450                 455                 460

Val Glu Arg Lys Ile Lys Ile Ile Leu Ile Glu Phe Thr Pro Val Thr
465                 470                 475                 480

Asp Phe Thr Phe Leu Pro Gln Ser Leu Lys Leu Leu Lys Ser His Arg
            485                 490                 495

Val Leu Lys Trp Lys Ala Asp Lys Ser Leu Ser Tyr Asn Ser Arg Phe
                500                 505                 510

Trp Lys Asn Leu Leu Tyr Leu Met Pro Ala Lys Thr Val Lys Pro Gly
            515                 520                 525

Arg Asp Glu Pro Glu Val Leu Pro Val Leu Ser Glu Ser
    530                 535                 540

<210> SEQ ID NO 10
<211> LENGTH: 599
<212> TYPE: PRT
<213> ORGANISM: Homo sapiens

<400> SEQUENCE: 10

Met Leu Cys Leu Gly Trp Ile Phe Leu Trp Leu Val Ala Gly Glu Arg
1               5                   10                  15

Ile Lys Gly Phe Asn Ile Ser Gly Cys Ser Thr Lys Lys Leu Leu Trp
            20                  25                  30

Thr Tyr Ser Thr Arg Ser Glu Glu Glu Phe Val Leu Phe Cys Asp Leu
        35                  40                  45

Pro Glu Pro Gln Lys Ser His Phe Cys His Arg Asn Arg Leu Ser Pro
    50                  55                  60

Lys Gln Val Pro Glu His Leu Pro Phe Met Gly Ser Asn Asp Leu Ser
65                  70                  75                  80

Asp Val Gln Trp Tyr Gln Gln Pro Ser Asn Gly Asp Pro Leu Glu Asp
                85                  90                  95

Ile Arg Lys Ser Tyr Pro His Ile Ile Gln Asp Lys Cys Thr Leu His
            100                 105                 110

Phe Leu Thr Pro Gly Val Asn Asn Ser Gly Ser Tyr Ile Cys Arg Pro
        115                 120                 125

Lys Met Ile Lys Ser Pro Tyr Asp Val Ala Cys Cys Val Lys Met Ile
    130                 135                 140

Leu Glu Val Lys Pro Gln Thr Asn Ala Ser Cys Glu Tyr Ser Ala Ser
145                 150                 155                 160

His Lys Gln Asp Leu Leu Leu Gly Ser Thr Gly Ser Ile Ser Cys Pro
                165                 170                 175

Ser Leu Ser Cys Gln Ser Asp Ala Gln Ser Pro Ala Val Thr Trp Tyr
            180                 185                 190
```

```
Lys Asn Gly Lys Leu Leu Ser Val Glu Arg Ser Asn Arg Ile Val Val
            195                 200                 205

Asp Glu Val Tyr Asp Tyr His Gln Gly Thr Tyr Val Cys Asp Tyr Thr
        210                 215                 220

Gln Ser Asp Thr Val Ser Ser Trp Thr Val Arg Ala Val Val Gln Val
225                 230                 235                 240

Arg Thr Ile Val Gly Asp Thr Lys Leu Lys Pro Asp Ile Leu Asp Pro
                245                 250                 255

Val Glu Asp Thr Leu Glu Val Glu Leu Gly Lys Pro Leu Thr Ile Ser
            260                 265                 270

Cys Lys Ala Arg Phe Gly Phe Glu Arg Val Phe Asn Pro Val Ile Lys
        275                 280                 285

Trp Tyr Ile Lys Asp Ser Asp Leu Glu Trp Glu Val Ser Val Pro Glu
        290                 295                 300

Ala Lys Ser Ile Lys Ser Thr Leu Lys Asp Glu Ile Ile Glu Arg Asn
305                 310                 315                 320

Ile Ile Leu Glu Lys Val Thr Gln Arg Asp Leu Arg Arg Lys Phe Val
                325                 330                 335

Cys Phe Val Gln Asn Ser Ile Gly Asn Thr Thr Gln Ser Val Gln Leu
            340                 345                 350

Lys Glu Lys Arg Gly Val Val Leu Leu Tyr Ile Leu Leu Gly Thr Ile
        355                 360                 365

Gly Thr Leu Val Ala Val Leu Ala Ala Ser Ala Leu Leu Tyr Arg His
        370                 375                 380

Trp Ile Glu Ile Val Leu Leu Tyr Arg Thr Tyr Gln Ser Lys Asp Gln
385                 390                 395                 400

Thr Leu Gly Asp Lys Lys Asp Phe Asp Ala Phe Val Ser Tyr Ala Lys
                405                 410                 415

Trp Ser Ser Phe Pro Ser Glu Ala Thr Ser Ser Leu Ser Glu Glu His
            420                 425                 430

Leu Ala Leu Ser Leu Phe Pro Asp Val Leu Glu Asn Lys Tyr Gly Tyr
        435                 440                 445

Ser Leu Cys Leu Leu Glu Arg Asp Val Ala Pro Gly Gly Val Tyr Ala
        450                 455                 460

Glu Asp Ile Val Ser Ile Ile Lys Arg Ser Arg Arg Gly Ile Phe Ile
465                 470                 475                 480

Leu Ser Pro Asn Tyr Val Asn Gly Pro Ser Ile Phe Glu Leu Gln Ala
                485                 490                 495

Ala Val Asn Leu Ala Leu Asp Asp Gln Thr Leu Lys Leu Ile Leu Ile
            500                 505                 510

Lys Phe Cys Tyr Phe Gln Glu Pro Glu Ser Leu Pro His Leu Val Lys
        515                 520                 525

Lys Ala Leu Arg Val Leu Pro Thr Val Thr Trp Arg Gly Leu Lys Ser
        530                 535                 540

Val Pro Pro Asn Ser Arg Phe Trp Ala Lys Met Arg Tyr His Met Pro
545                 550                 555                 560

Val Lys Asn Ser Gln Gly Phe Thr Trp Asn Gln Leu Arg Ile Thr Ser
                565                 570                 575

Arg Ile Phe Gln Trp Lys Gly Leu Ser Arg Thr Glu Thr Thr Gly Arg
            580                 585                 590

Ser Ser Gln Pro Lys Glu Trp
        595
```

<210> SEQ ID NO 11
<211> LENGTH: 569
<212> TYPE: PRT
<213> ORGANISM: Homo sapiens

<400> SEQUENCE: 11

```
Met Lys Val Leu Leu Arg Leu Ile Cys Phe Ile Ala Leu Leu Ile Ser
1               5                   10                  15

Ser Leu Glu Ala Asp Lys Cys Lys Glu Arg Glu Lys Ile Ile Leu
            20                  25                  30

Val Ser Ser Ala Asn Glu Ile Asp Val Arg Pro Cys Pro Leu Asn Pro
        35                  40                  45

Asn Glu His Lys Gly Thr Ile Thr Trp Tyr Lys Asp Asp Ser Lys Thr
    50                  55                  60

Pro Val Ser Thr Glu Gln Ala Ser Arg Ile His Gln His Lys Glu Lys
65                  70                  75                  80

Leu Trp Phe Val Pro Ala Lys Val Glu Asp Ser Gly His Tyr Tyr Cys
                85                  90                  95

Val Val Arg Asn Ser Ser Tyr Cys Leu Arg Ile Lys Ile Ser Ala Lys
            100                 105                 110

Phe Val Glu Asn Glu Pro Asn Leu Cys Tyr Asn Ala Gln Ala Ile Phe
        115                 120                 125

Lys Gln Lys Leu Pro Val Ala Gly Asp Gly Gly Leu Val Cys Pro Tyr
    130                 135                 140

Met Glu Phe Phe Lys Asn Glu Asn Asn Glu Leu Pro Lys Leu Gln Trp
145                 150                 155                 160

Tyr Lys Asp Cys Lys Pro Leu Leu Leu Asp Asn Ile His Phe Ser Gly
                165                 170                 175

Val Lys Asp Arg Leu Ile Val Met Asn Val Ala Glu Lys His Arg Gly
            180                 185                 190

Asn Tyr Thr Cys His Ala Ser Tyr Thr Tyr Leu Gly Lys Gln Tyr Pro
        195                 200                 205

Ile Thr Arg Val Ile Glu Phe Ile Thr Leu Glu Glu Asn Lys Pro Thr
    210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
                245                 250                 255

Ile Ala Tyr Trp Lys Trp Asn Gly Ser Val Ile Asp Glu Asp Asp Pro
            260                 265                 270

Val Leu Gly Glu Asp Tyr Tyr Ser Val Glu Asn Pro Ala Asn Lys Arg
        275                 280                 285

Arg Ser Thr Leu Ile Thr Val Leu Asn Ile Ser Glu Ile Glu Ser Arg
    290                 295                 300

Phe Tyr Lys His Pro Phe Thr Cys Phe Ala Lys Asn Thr His Gly Ile
305                 310                 315                 320

Asp Ala Ala Tyr Ile Gln Leu Ile Tyr Pro Val Thr Asn Phe Gln Lys
                325                 330                 335

His Met Ile Gly Ile Cys Val Thr Leu Thr Val Ile Ile Val Cys Ser
            340                 345                 350

Val Phe Ile Tyr Lys Ile Phe Lys Ile Asp Ile Val Leu Trp Tyr Arg
        355                 360                 365

Asp Ser Cys Tyr Asp Phe Leu Pro Ile Lys Ala Ser Asp Gly Lys Thr
    370                 375                 380
```

```
Tyr Asp Ala Tyr Ile Leu Tyr Pro Lys Thr Val Gly Glu Gly Ser Thr
385                 390                 395                 400

Ser Asp Cys Asp Ile Phe Val Phe Lys Val Leu Pro Glu Val Leu Glu
            405                 410                 415

Lys Gln Cys Gly Tyr Lys Leu Phe Ile Tyr Gly Arg Asp Asp Tyr Val
        420                 425                 430

Gly Glu Asp Ile Val Glu Val Ile Asn Glu Asn Val Lys Lys Ser Arg
            435                 440                 445

Arg Leu Ile Ile Ile Leu Val Arg Glu Thr Ser Gly Phe Ser Trp Leu
        450                 455                 460

Gly Gly Ser Ser Glu Glu Gln Ile Ala Met Tyr Asn Ala Leu Val Gln
465                 470                 475                 480

Asp Gly Ile Lys Val Val Leu Leu Glu Leu Glu Lys Ile Gln Asp Tyr
            485                 490                 495

Glu Lys Met Pro Glu Ser Ile Lys Phe Ile Lys Gln Lys His Gly Ala
            500                 505                 510

Ile Arg Trp Ser Gly Asp Phe Thr Gln Gly Pro Gln Ser Ala Lys Thr
        515                 520                 525

Arg Phe Trp Lys Asn Val Arg Tyr His Met Pro Val Gln Arg Arg Ser
        530                 535                 540

Pro Ser Ser Lys His Gln Leu Leu Ser Pro Ala Thr Lys Glu Lys Leu
545                 550                 555                 560

Gln Arg Glu Ala His Val Pro Leu Gly
                565

<210> SEQ ID NO 12
<211> LENGTH: 570
<212> TYPE: PRT
<213> ORGANISM: Homo sapiens

<400> SEQUENCE: 12

Met Thr Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175
```

Trp Tyr Met Gly Cys Tyr Lys Ile Gln Asn Phe Asn Val Ile Pro
            180                 185                 190

Glu Gly Met Asn Leu Ser Phe Leu Ile Ala Leu Ile Ser Asn Asn Gly
            195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
            275                 280                 285

Pro Asp Asp Ile Thr Ile Asp Val Thr Ile Asn Glu Ser Ile Ser His
            290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Glu Leu Ala Cys Gly Phe Gly Ala Thr Val
            355                 360                 365

Leu Leu Val Val Ile Leu Ile Val Val Tyr His Val Tyr Trp Leu Glu
            370                 375                 380

Met Val Leu Phe Tyr Arg Ala His Phe Gly Thr Asp Glu Thr Ile Leu
385                 390                 395                 400

Asp Gly Lys Glu Tyr Asp Ile Tyr Val Ser Tyr Ala Arg Asn Ala Glu
                405                 410                 415

Glu Glu Glu Phe Val Leu Leu Thr Leu Arg Gly Val Leu Glu Asn Glu
            420                 425                 430

Phe Gly Tyr Lys Leu Cys Ile Phe Asp Arg Asp Ser Leu Pro Gly Gly
            435                 440                 445

Ile Val Thr Asp Glu Thr Leu Ser Phe Ile Gln Lys Ser Arg Arg Leu
            450                 455                 460

Leu Val Val Leu Ser Pro Asn Tyr Val Leu Gln Gly Thr Gln Ala Leu
465                 470                 475                 480

Leu Glu Leu Lys Ala Gly Leu Glu Asn Met Ala Ser Arg Gly Asn Ile
                485                 490                 495

Asn Val Ile Leu Val Gln Tyr Lys Ala Val Lys Glu Thr Lys Val Lys
            500                 505                 510

Glu Leu Lys Arg Ala Lys Thr Val Leu Thr Val Ile Lys Trp Lys Gly
            515                 520                 525

Glu Lys Ser Lys Tyr Pro Gln Gly Arg Phe Trp Lys Gln Leu Gln Val
            530                 535                 540

Ala Met Pro Val Lys Lys Ser Pro Arg Arg Ser Ser Ser Asp Glu Gln
545                 550                 555                 560

Gly Leu Ser Tyr Ser Ser Leu Lys Asn Val
                565                 570

<210> SEQ ID NO 13
<211> LENGTH: 557

```
<212> TYPE: PRT
<213> ORGANISM: Homo sapiens

<400> SEQUENCE: 13

Met Met Val Val Leu Leu Gly Ala Thr Thr Leu Val Leu Val Ala Val
1               5                   10                  15

Ala Pro Trp Val Leu Ser Ala Ala Gly Gly Lys Asn Leu Lys Ser
            20                  25                  30

Pro Gln Lys Val Glu Val Asp Ile Ile Asp Asp Asn Phe Ile Leu Arg
            35                  40                  45

Trp Asn Arg Ser Asp Glu Ser Val Gly Asn Val Thr Phe Ser Phe Asp
        50                  55                  60

Tyr Gln Lys Thr Gly Met Asp Asn Trp Ile Lys Leu Ser Gly Cys Gln
65                  70                  75                  80

Asn Ile Thr Ser Thr Lys Cys Asn Phe Ser Ser Leu Lys Leu Asn Val
                85                  90                  95

Tyr Glu Glu Ile Lys Leu Arg Ile Arg Ala Glu Lys Glu Asn Thr Ser
            100                 105                 110

Ser Trp Tyr Glu Val Asp Ser Phe Thr Pro Phe Arg Lys Ala Gln Ile
        115                 120                 125

Gly Pro Pro Glu Val His Leu Glu Ala Glu Asp Lys Ala Ile Val Ile
    130                 135                 140

His Ile Ser Pro Gly Thr Lys Asp Ser Val Met Trp Ala Leu Asp Gly
145                 150                 155                 160

Leu Ser Phe Thr Tyr Ser Leu Val Ile Trp Lys Asn Ser Ser Gly Val
                165                 170                 175

Glu Glu Arg Ile Glu Asn Ile Tyr Ser Arg His Lys Ile Tyr Lys Leu
            180                 185                 190

Ser Pro Glu Thr Thr Tyr Cys Leu Lys Val Lys Ala Ala Leu Leu Thr
        195                 200                 205

Ser Trp Lys Ile Gly Val Tyr Ser Pro Val His Cys Ile Lys Thr Thr
    210                 215                 220

Val Glu Asn Glu Leu Pro Pro Pro Glu Asn Ile Glu Val Ser Val Gln
225                 230                 235                 240

Asn Gln Asn Tyr Val Leu Lys Trp Asp Tyr Thr Tyr Ala Asn Met Thr
                245                 250                 255

Phe Gln Val Gln Trp Leu His Ala Phe Leu Lys Arg Asn Pro Gly Asn
            260                 265                 270

His Leu Tyr Lys Trp Lys Gln Ile Pro Asp Cys Glu Asn Val Lys Thr
        275                 280                 285

Thr Gln Cys Val Phe Pro Gln Asn Val Phe Gln Lys Gly Ile Tyr Leu
    290                 295                 300

Leu Arg Val Gln Ala Ser Asp Gly Asn Asn Thr Ser Phe Trp Ser Glu
305                 310                 315                 320

Glu Ile Lys Phe Asp Thr Glu Ile Gln Ala Phe Leu Leu Pro Pro Val
                325                 330                 335

Phe Asn Ile Arg Ser Leu Ser Asp Ser Phe His Ile Tyr Ile Gly Ala
            340                 345                 350

Pro Lys Gln Ser Gly Asn Thr Pro Val Ile Gln Asp Tyr Pro Leu Ile
        355                 360                 365

Tyr Glu Ile Ile Phe Trp Glu Asn Thr Ser Asn Ala Glu Arg Lys Ile
    370                 375                 380

Ile Glu Lys Lys Thr Asp Val Thr Val Pro Asn Leu Lys Pro Leu Thr
385                 390                 395                 400
```

```
Val Tyr Cys Val Lys Ala Arg Ala His Thr Met Asp Glu Lys Leu Asn
            405                 410                 415

Lys Ser Ser Val Phe Ser Asp Ala Val Cys Glu Lys Thr Lys Pro Gly
            420                 425                 430

Asn Thr Ser Lys Ile Trp Leu Ile Val Gly Ile Cys Ile Ala Leu Phe
            435                 440                 445

Ala Leu Pro Phe Val Ile Tyr Ala Ala Lys Val Phe Leu Arg Cys Ile
450                 455                 460

Asn Tyr Val Phe Phe Pro Ser Leu Lys Pro Ser Ser Ile Asp Glu
465                 470                 475                 480

Tyr Phe Ser Glu Gln Pro Leu Lys Asn Leu Leu Ser Thr Ser Glu
            485                 490                 495

Glu Gln Ile Glu Lys Cys Phe Ile Ile Glu Asn Ile Ser Thr Ile Ala
            500                 505                 510

Thr Val Glu Glu Thr Asn Gln Thr Asp Glu Asp His Lys Lys Tyr Ser
            515                 520                 525

Ser Gln Thr Ser Gln Asp Ser Gly Asn Tyr Ser Asn Glu Asp Glu Ser
            530                 535                 540

Glu Ser Lys Thr Ser Glu Glu Leu Gln Gln Asp Phe Val
545                 550                 555

<210> SEQ ID NO 14
<211> LENGTH: 515
<212> TYPE: PRT
<213> ORGANISM: Homo sapiens

<400> SEQUENCE: 14

Met Leu Leu Ser Gln Asn Ala Phe Ile Phe Arg Ser Leu Asn Leu Val
1               5                   10                  15

Leu Met Val Tyr Ile Ser Leu Val Phe Gly Ile Ser Tyr Asp Ser Pro
            20                  25                  30

Asp Tyr Thr Asp Glu Ser Cys Thr Phe Lys Ile Ser Leu Arg Asn Phe
            35                  40                  45

Arg Ser Ile Leu Ser Trp Glu Leu Lys Asn His Ser Ile Val Pro Thr
50                  55                  60

His Tyr Thr Leu Leu Tyr Thr Ile Met Ser Lys Pro Glu Asp Leu Lys
65                  70                  75                  80

Val Val Lys Asn Cys Ala Asn Thr Thr Arg Ser Phe Cys Asp Leu Thr
            85                  90                  95

Asp Glu Trp Arg Ser Thr His Glu Ala Tyr Val Thr Val Leu Glu Gly
            100                 105                 110

Phe Ser Gly Asn Thr Thr Leu Phe Ser Cys Ser His Asn Phe Trp Leu
            115                 120                 125

Ala Ile Asp Met Ser Phe Glu Pro Pro Glu Phe Glu Ile Val Gly Phe
130                 135                 140

Thr Asn His Ile Asn Val Met Val Lys Phe Pro Ser Ile Val Glu Glu
145                 150                 155                 160

Glu Leu Gln Phe Asp Leu Ser Leu Val Ile Glu Glu Gln Ser Glu Gly
            165                 170                 175

Ile Val Lys Lys His Lys Pro Glu Ile Lys Gly Asn Met Ser Gly Asn
            180                 185                 190

Phe Thr Tyr Ile Ile Asp Lys Leu Ile Pro Asn Thr Asn Tyr Cys Val
            195                 200                 205
```

Ser Val Tyr Leu Glu His Ser Asp Glu Gln Ala Val Ile Lys Ser Pro
    210                 215                 220
Leu Lys Cys Thr Leu Leu Pro Pro Gly Gln Glu Ser Glu Ser Ala Glu
225                 230                 235                 240
Ser Ala Lys Ile Gly Gly Ile Ile Thr Val Phe Leu Ile Ala Leu Val
                    245                 250                 255
Leu Thr Ser Thr Ile Val Thr Leu Lys Trp Ile Gly Tyr Ile Cys Leu
                260                 265                 270
Arg Asn Ser Leu Pro Lys Val Leu Asn Phe His Asn Phe Leu Ala Trp
                275                 280                 285
Pro Phe Pro Asn Leu Pro Pro Leu Glu Ala Met Asp Met Val Glu Val
290                 295                 300
Ile Tyr Ile Asn Arg Lys Lys Lys Val Trp Asp Tyr Asn Tyr Asp Asp
305                 310                 315                 320
Glu Ser Asp Ser Asp Thr Glu Ala Ala Pro Arg Thr Ser Gly Gly Gly
                    325                 330                 335
Tyr Thr Met His Gly Leu Thr Val Arg Pro Leu Gly Gln Ala Ser Ala
                340                 345                 350
Thr Ser Thr Glu Ser Gln Leu Ile Asp Pro Glu Ser Glu Glu Glu Pro
                355                 360                 365
Asp Leu Pro Glu Val Asp Val Glu Leu Pro Thr Met Pro Lys Asp Ser
370                 375                 380
Pro Gln Gln Leu Glu Leu Leu Ser Gly Pro Cys Glu Arg Arg Lys Ser
385                 390                 395                 400
Pro Leu Gln Asp Pro Phe Pro Glu Glu Asp Tyr Ser Ser Thr Glu Gly
                    405                 410                 415
Ser Gly Gly Arg Ile Thr Phe Asn Val Asp Leu Asn Ser Val Phe Leu
                420                 425                 430
Arg Val Leu Asp Asp Glu Asp Ser Asp Leu Glu Ala Pro Leu Met
                    435                 440                 445
Leu Ser Ser His Leu Glu Glu Met Val Asp Pro Glu Asp Pro Asp Asn
450                 455                 460
Val Gln Ser Asn His Leu Leu Ala Ser Gly Glu Gly Thr Gln Pro Thr
465                 470                 475                 480
Phe Pro Ser Pro Ser Ser Glu Gly Leu Trp Ser Glu Asp Ala Pro Ser
                    485                 490                 495
Asp Gln Ser Asp Thr Ser Glu Ser Asp Val Asp Leu Gly Asp Gly Tyr
                500                 505                 510
Ile Met Arg
        515

<210> SEQ ID NO 15
<211> LENGTH: 575
<212> TYPE: PRT
<213> ORGANISM: Homo sapiens

<400> SEQUENCE: 15

Met Trp Ser Leu Leu Leu Cys Gly Leu Ser Ile Ala Leu Pro Leu Ser
1               5                   10                  15
Val Thr Ala Asp Gly Cys Lys Asp Ile Phe Met Lys Asn Glu Ile Leu
                20                  25                  30
Ser Ala Ser Gln Pro Phe Ala Phe Asn Cys Thr Phe Pro Pro Ile Thr
                35                  40                  45

```
Ser Gly Glu Val Ser Val Thr Trp Tyr Lys Asn Ser Ser Lys Ile Pro
 50                  55                  60

Val Ser Lys Ile Ile Gln Ser Arg Ile His Gln Asp Glu Thr Trp Ile
 65                  70                  75                  80

Leu Phe Leu Pro Met Glu Trp Gly Asp Ser Gly Val Tyr Gln Cys Val
                 85                  90                  95

Ile Lys Gly Arg Asp Ser Cys His Arg Ile His Val Asn Leu Thr Val
                100                 105                 110

Phe Glu Lys His Trp Cys Asp Thr Ser Ile Gly Gly Leu Pro Asn Leu
            115                 120                 125

Ser Asp Glu Tyr Lys Gln Ile Leu His Leu Gly Lys Asp Ser Leu
            130                 135                 140

Thr Cys His Leu His Phe Pro Lys Ser Cys Val Leu Gly Pro Ile Lys
145                 150                 155                 160

Trp Tyr Lys Asp Cys Asn Glu Ile Lys Gly Glu Arg Phe Thr Val Leu
                165                 170                 175

Glu Thr Arg Leu Leu Val Ser Asn Val Ser Ala Glu Asp Arg Gly Asn
            180                 185                 190

Tyr Ala Cys Gln Ala Ile Leu Thr His Ser Gly Lys Gln Tyr Glu Val
            195                 200                 205

Leu Asn Gly Ile Thr Val Ser Ile Thr Glu Arg Ala Gly Tyr Gly Gly
210                 215                 220

Ser Val Pro Lys Ile Ile Tyr Pro Lys Asn His Ser Ile Glu Val Gln
225                 230                 235                 240

Leu Gly Thr Thr Leu Ile Val Asp Cys Asn Val Thr Asp Thr Lys Asp
                245                 250                 255

Asn Thr Asn Leu Arg Cys Trp Arg Val Asn Asn Thr Leu Val Asp Asp
            260                 265                 270

Tyr Tyr Asp Glu Ser Lys Arg Ile Arg Glu Gly Val Glu Thr His Val
            275                 280                 285

Ser Phe Arg Glu His Asn Leu Tyr Thr Val Asn Ile Thr Phe Leu Glu
290                 295                 300

Val Lys Met Glu Asp Tyr Gly Leu Pro Phe Met Cys His Ala Gly Val
305                 310                 315                 320

Ser Thr Ala Tyr Ile Ile Leu Gln Leu Pro Ala Pro Asp Phe Arg Ala
                325                 330                 335

Tyr Leu Ile Gly Gly Leu Ile Ala Leu Val Ala Val Ala Val Ser Val
            340                 345                 350

Val Tyr Ile Tyr Asn Ile Phe Lys Ile Asp Ile Val Leu Trp Tyr Arg
            355                 360                 365

Ser Ala Phe His Ser Thr Glu Thr Ile Val Asp Gly Lys Leu Tyr Asp
370                 375                 380

Ala Tyr Val Leu Tyr Pro Lys Pro His Lys Glu Ser Gln Arg His Ala
385                 390                 395                 400

Val Asp Ala Leu Val Leu Asn Ile Leu Pro Glu Val Leu Glu Arg Gln
                405                 410                 415

Cys Gly Tyr Lys Leu Phe Ile Phe Gly Arg Asp Glu Phe Pro Gly Gln
            420                 425                 430

Ala Val Ala Asn Val Ile Asp Glu Asn Val Lys Leu Cys Arg Arg Leu
            435                 440                 445

Ile Val Ile Val Val Pro Glu Ser Leu Gly Phe Gly Leu Leu Lys Asn
450                 455                 460
```

```
Leu Ser Glu Glu Gln Ile Ala Val Tyr Ser Ala Leu Ile Gln Asp Gly
465                 470                 475                 480

Met Lys Val Ile Leu Ile Glu Leu Glu Lys Ile Glu Asp Tyr Thr Val
                485                 490                 495

Met Pro Glu Ser Ile Gln Tyr Ile Lys Gln Lys His Gly Ala Ile Arg
            500                 505                 510

Trp His Gly Asp Phe Thr Glu Gln Ser Gln Cys Met Lys Thr Lys Phe
            515                 520                 525

Trp Lys Thr Val Arg Tyr His Met Pro Pro Arg Cys Arg Pro Phe
            530                 535                 540

Pro Pro Val Gln Leu Leu Gln His Thr Pro Cys Tyr Arg Thr Ala Gly
545                 550                 555                 560

Pro Glu Leu Gly Ser Arg Arg Lys Lys Cys Thr Leu Thr Thr Gly
                565                 570                 575

<210> SEQ ID NO 16
<211> LENGTH: 786
<212> TYPE: PRT
<213> ORGANISM: Homo sapiens

<400> SEQUENCE: 16

Met Thr Ser Ile Phe His Phe Ala Ile Ile Phe Met Leu Ile Leu Gln
1               5                   10                  15

Ile Arg Ile Gln Leu Ser Glu Glu Ser Glu Phe Leu Val Asp Arg Ser
                20                  25                  30

Lys Asn Gly Leu Ile His Val Pro Lys Asp Leu Ser Gln Lys Thr Thr
            35                  40                  45

Ile Leu Asn Ile Ser Gln Asn Tyr Ile Ser Glu Leu Trp Thr Ser Asp
50                  55                  60

Ile Leu Ser Leu Ser Lys Leu Arg Ile Leu Ile Ser His Asn Arg
65                  70                  75                  80

Ile Gln Tyr Leu Asp Ile Ser Val Phe Lys Phe Asn Gln Glu Leu Glu
                85                  90                  95

Tyr Leu Asp Leu Ser His Asn Lys Leu Val Lys Ile Ser Cys His Pro
            100                 105                 110

Thr Val Asn Leu Lys His Leu Asp Leu Ser Phe Asn Ala Phe Asp Ala
        115                 120                 125

Leu Pro Ile Cys Lys Glu Phe Gly Asn Met Ser Gln Leu Lys Phe Leu
130                 135                 140

Gly Leu Ser Thr Thr His Leu Glu Lys Ser Ser Val Leu Pro Ile Ala
145                 150                 155                 160

His Leu Asn Ile Ser Lys Val Leu Leu Val Leu Gly Glu Thr Tyr Gly
                165                 170                 175

Glu Lys Glu Asp Pro Glu Gly Leu Gln Asp Phe Asn Thr Glu Ser Leu
            180                 185                 190

His Ile Val Phe Pro Thr Asn Lys Glu Phe His Phe Ile Leu Asp Val
        195                 200                 205

Ser Val Lys Thr Val Ala Asn Leu Glu Leu Ser Asn Ile Lys Cys Val
210                 215                 220

Leu Glu Asp Asn Lys Cys Ser Tyr Phe Leu Ser Ile Leu Ala Lys Leu
225                 230                 235                 240

Gln Thr Asn Pro Lys Leu Ser Asn Leu Thr Leu Asn Asn Ile Glu Thr
                245                 250                 255

Thr Trp Asn Ser Phe Ile Arg Ile Leu Gln Leu Val Trp His Thr Thr
            260                 265                 270
```

-continued

```
Val Trp Tyr Phe Ser Ile Ser Asn Val Lys Leu Gln Gly Gln Leu Asp
        275                 280                 285

Phe Arg Asp Phe Asp Tyr Ser Gly Thr Ser Leu Lys Ala Leu Ser Ile
    290                 295                 300

His Gln Val Val Ser Asp Val Phe Gly Phe Pro Gln Ser Tyr Ile Tyr
305                 310                 315                 320

Glu Ile Phe Ser Asn Met Asn Ile Lys Asn Phe Thr Val Ser Gly Thr
                325                 330                 335

Arg Met Val His Met Leu Cys Pro Ser Lys Ile Ser Pro Phe Leu His
            340                 345                 350

Leu Asp Phe Ser Asn Asn Leu Leu Thr Asp Thr Val Phe Glu Asn Cys
            355                 360                 365

Gly His Leu Thr Glu Leu Glu Thr Leu Ile Leu Gln Met Asn Gln Leu
        370                 375                 380

Lys Glu Leu Ser Lys Ile Ala Glu Met Thr Thr Gln Met Lys Ser Leu
385                 390                 395                 400

Gln Gln Leu Asp Ile Ser Gln Asn Ser Val Ser Tyr Asp Glu Lys Lys
                405                 410                 415

Gly Asp Cys Ser Trp Thr Lys Ser Leu Leu Ser Leu Asn Met Ser Ser
            420                 425                 430

Asn Ile Leu Thr Asp Thr Ile Phe Arg Cys Leu Pro Pro Arg Ile Lys
        435                 440                 445

Val Leu Asp Leu His Ser Asn Lys Ile Lys Ser Ile Pro Lys Gln Val
    450                 455                 460

Val Lys Leu Glu Ala Leu Gln Glu Leu Asn Val Ala Phe Asn Ser Leu
465                 470                 475                 480

Thr Asp Leu Pro Gly Cys Gly Ser Phe Ser Ser Leu Ser Val Leu Ile
                485                 490                 495

Ile Asp His Asn Ser Val Ser His Pro Ser Ala Asp Phe Phe Gln Ser
            500                 505                 510

Cys Gln Lys Met Arg Ser Ile Lys Ala Gly Asp Asn Pro Phe Gln Cys
        515                 520                 525

Thr Cys Glu Leu Gly Glu Phe Val Lys Asn Ile Asp Gln Val Ser Ser
    530                 535                 540

Glu Val Leu Glu Gly Trp Pro Asp Ser Tyr Lys Cys Asp Tyr Pro Glu
545                 550                 555                 560

Ser Tyr Arg Gly Thr Leu Leu Lys Asp Phe His Met Ser Glu Leu Ser
                565                 570                 575

Cys Asn Ile Thr Leu Leu Ile Val Thr Ile Val Ala Thr Met Leu Val
            580                 585                 590

Leu Ala Val Thr Val Thr Ser Leu Cys Ser Tyr Leu Asp Leu Pro Trp
        595                 600                 605

Tyr Leu Arg Met Val Cys Gln Trp Thr Gln Thr Arg Arg Arg Ala Arg
    610                 615                 620

Asn Ile Pro Leu Glu Glu Leu Gln Arg Asn Leu Gln Phe His Ala Phe
625                 630                 635                 640

Ile Ser Tyr Ser Gly His Asp Ser Phe Trp Val Lys Asn Glu Leu Leu
                645                 650                 655

Pro Asn Leu Glu Lys Glu Gly Met Gln Ile Cys Leu His Glu Arg Asn
            660                 665                 670

Phe Val Pro Gly Lys Ser Ile Val Glu Asn Ile Ile Thr Cys Ile Glu
        675                 680                 685
```

```
Lys Ser Tyr Lys Ser Ile Phe Val Leu Ser Pro Asn Phe Val Gln Ser
        690                 695                 700

Glu Trp Cys His Tyr Glu Leu Tyr Phe Ala His His Asn Leu Phe His
705                 710                 715                 720

Glu Gly Ser Asn Ser Leu Ile Leu Ile Leu Leu Glu Pro Ile Pro Gln
                725                 730                 735

Tyr Ser Ile Pro Ser Ser Tyr His Lys Leu Lys Ser Leu Met Ala Arg
            740                 745                 750

Arg Thr Tyr Leu Glu Trp Pro Lys Glu Lys Ser Lys Arg Gly Leu Phe
                755                 760                 765

Trp Ala Asn Leu Arg Ala Ala Ile Asn Ile Lys Leu Thr Glu Gln Ala
770                 775                 780

Lys Lys
785

<210> SEQ ID NO 17
<211> LENGTH: 784
<212> TYPE: PRT
<213> ORGANISM: Homo sapiens

<400> SEQUENCE: 17

Met Pro His Thr Leu Trp Met Val Trp Val Leu Gly Val Ile Ile Ser
1               5                   10                  15

Leu Ser Lys Glu Glu Ser Ser Asn Gln Ala Ser Leu Ser Cys Asp Arg
            20                  25                  30

Asn Gly Ile Cys Lys Gly Ser Ser Gly Ser Leu Asn Ser Ile Pro Ser
        35                  40                  45

Gly Leu Thr Glu Ala Val Lys Ser Leu Asp Leu Ser Asn Asn Arg Ile
50                  55                  60

Thr Tyr Ile Ser Asn Ser Asp Leu Gln Arg Cys Val Asn Leu Gln Ala
65                  70                  75                  80

Leu Val Leu Thr Ser Asn Gly Ile Asn Thr Ile Glu Glu Asp Ser Phe
                85                  90                  95

Ser Ser Leu Gly Ser Leu Glu His Leu Asp Leu Ser Tyr Asn Tyr Leu
            100                 105                 110

Ser Asn Leu Ser Ser Ser Trp Phe Lys Pro Leu Ser Ser Leu Thr Phe
        115                 120                 125

Leu Asn Leu Leu Gly Asn Pro Tyr Lys Thr Leu Gly Glu Thr Ser Leu
130                 135                 140

Phe Ser His Leu Thr Lys Leu Gln Ile Leu Arg Val Gly Asn Met Asp
145                 150                 155                 160

Thr Phe Thr Lys Ile Gln Arg Lys Asp Phe Ala Gly Leu Thr Phe Leu
                165                 170                 175

Glu Glu Leu Glu Ile Asp Ala Ser Asp Leu Gln Ser Tyr Glu Pro Lys
            180                 185                 190

Ser Leu Lys Ser Ile Gln Asn Val Ser His Leu Ile Leu His Met Lys
        195                 200                 205

Gln His Ile Leu Leu Leu Glu Ile Phe Val Asp Val Thr Ser Ser Val
210                 215                 220

Glu Cys Leu Glu Leu Arg Asp Thr Asp Leu Asp Thr Phe His Phe Ser
225                 230                 235                 240

Glu Leu Ser Thr Gly Glu Thr Asn Ser Leu Ile Lys Lys Phe Thr Phe
                245                 250                 255

Arg Asn Val Lys Ile Thr Asp Glu Ser Leu Phe Gln Val Met Lys Leu
            260                 265                 270
```

```
Leu Asn Gln Ile Ser Gly Leu Leu Glu Leu Glu Phe Asp Asp Cys Thr
        275                 280                 285

Leu Asn Gly Val Gly Asn Phe Arg Ala Ser Asp Asn Asp Arg Val Ile
290                 295                 300

Asp Pro Gly Lys Val Glu Thr Leu Thr Ile Arg Arg Leu His Ile Pro
305                 310                 315                 320

Arg Phe Tyr Leu Phe Tyr Asp Leu Ser Thr Leu Tyr Ser Leu Thr Glu
                325                 330                 335

Arg Val Lys Arg Ile Thr Val Glu Asn Ser Lys Val Phe Leu Val Pro
            340                 345                 350

Cys Leu Leu Ser Gln His Leu Lys Ser Leu Glu Tyr Leu Asp Leu Ser
        355                 360                 365

Glu Asn Leu Met Val Glu Glu Tyr Leu Lys Asn Ser Ala Cys Glu Asp
370                 375                 380

Ala Trp Pro Ser Leu Gln Thr Leu Ile Leu Arg Gln Asn His Leu Ala
385                 390                 395                 400

Ser Leu Glu Lys Thr Gly Glu Thr Leu Leu Thr Leu Lys Asn Leu Thr
                405                 410                 415

Asn Ile Asp Ile Ser Lys Asn Ser Phe His Ser Met Pro Glu Thr Cys
            420                 425                 430

Gln Trp Pro Glu Lys Met Lys Tyr Leu Asn Leu Ser Ser Thr Arg Ile
        435                 440                 445

His Ser Val Thr Gly Cys Ile Pro Lys Thr Leu Glu Ile Leu Asp Val
    450                 455                 460

Ser Asn Asn Asn Leu Asn Leu Phe Ser Leu Asn Leu Pro Gln Leu Lys
465                 470                 475                 480

Glu Leu Tyr Ile Ser Arg Asn Lys Leu Met Thr Leu Pro Asp Ala Ser
                485                 490                 495

Leu Leu Pro Met Leu Leu Val Leu Lys Ile Ser Arg Asn Ala Ile Thr
            500                 505                 510

Thr Phe Ser Lys Glu Gln Leu Asp Ser Phe His Thr Leu Lys Thr Leu
        515                 520                 525

Glu Ala Gly Gly Asn Asn Phe Ile Cys Ser Cys Glu Phe Leu Ser Phe
    530                 535                 540

Thr Gln Glu Gln Gln Ala Leu Ala Lys Val Leu Ile Asp Trp Pro Ala
545                 550                 555                 560

Asn Tyr Leu Cys Asp Ser Pro Ser His Val Arg Gly Gln Gln Val Gln
                565                 570                 575

Asp Val Arg Leu Ser Val Ser Glu Cys His Arg Thr Ala Leu Val Ser
            580                 585                 590

Gly Met Cys Cys Ala Leu Phe Leu Leu Ile Leu Leu Thr Gly Val Leu
        595                 600                 605

Cys His Arg Phe His Gly Leu Trp Tyr Met Lys Met Met Trp Ala Trp
    610                 615                 620

Leu Gln Ala Lys Arg Lys Pro Arg Lys Ala Pro Ser Arg Asn Ile Cys
625                 630                 635                 640

Tyr Asp Ala Phe Val Ser Tyr Ser Glu Arg Asp Ala Tyr Trp Val Glu
                645                 650                 655

Asn Leu Met Val Gln Glu Leu Glu Asn Phe Asn Pro Pro Phe Lys Leu
            660                 665                 670

Cys Leu His Lys Arg Asp Phe Ile Pro Gly Lys Trp Ile Ile Asp Asn
        675                 680                 685
```

```
Ile Ile Asp Ser Ile Glu Lys Ser His Lys Thr Val Phe Val Leu Ser
    690                 695                 700

Glu Asn Phe Val Lys Ser Glu Trp Cys Lys Tyr Glu Leu Asp Phe Ser
705                 710                 715                 720

His Phe Arg Leu Phe Asp Glu Asn Asn Asp Ala Ala Ile Leu Ile Leu
                725                 730                 735

Leu Glu Pro Ile Glu Lys Lys Ala Ile Pro Gln Arg Phe Cys Lys Leu
            740                 745                 750

Arg Lys Ile Met Asn Thr Lys Thr Tyr Leu Glu Trp Pro Met Asp Glu
                755                 760                 765

Ala Gln Arg Glu Gly Phe Trp Val Asn Leu Arg Ala Ala Ile Lys Ser
770                 775                 780
```

<210> SEQ ID NO 18
<211> LENGTH: 904
<212> TYPE: PRT
<213> ORGANISM: Homo sapiens

<400> SEQUENCE: 18

```
Met Arg Gln Thr Leu Pro Cys Ile Tyr Phe Trp Gly Gly Leu Leu Pro
1               5                   10                  15

Phe Gly Met Leu Cys Ala Ser Ser Thr Thr Lys Cys Thr Val Ser His
                20                  25                  30

Glu Val Ala Asp Cys Ser His Leu Lys Leu Thr Gln Val Pro Asp Asp
            35                  40                  45

Leu Pro Thr Asn Ile Thr Val Leu Asn Leu Thr His Asn Gln Leu Arg
        50                  55                  60

Arg Leu Pro Ala Ala Asn Phe Thr Arg Tyr Ser Gln Leu Thr Ser Leu
65                  70                  75                  80

Asp Val Gly Phe Asn Thr Ile Ser Lys Leu Glu Pro Glu Leu Cys Gln
                85                  90                  95

Lys Leu Pro Met Leu Lys Val Leu Asn Leu Gln His Asn Glu Leu Ser
                100                 105                 110

Gln Leu Ser Asp Lys Thr Phe Ala Phe Cys Thr Asn Leu Thr Glu Leu
            115                 120                 125

His Leu Met Ser Asn Ser Ile Gln Lys Ile Lys Asn Asn Pro Phe Val
        130                 135                 140

Lys Gln Lys Asn Leu Ile Thr Leu Asp Leu Ser His Asn Gly Leu Ser
145                 150                 155                 160

Ser Thr Lys Leu Gly Thr Gln Val Gln Leu Glu Asn Leu Gln Glu Leu
                165                 170                 175

Leu Leu Ser Asn Asn Lys Ile Gln Ala Leu Lys Ser Glu Glu Leu Asp
            180                 185                 190

Ile Phe Ala Asn Ser Ser Leu Lys Lys Leu Glu Leu Ser Ser Asn Gln
        195                 200                 205

Ile Lys Glu Phe Ser Pro Gly Cys Phe His Ala Ile Gly Arg Leu Phe
    210                 215                 220

Gly Leu Phe Leu Asn Asn Val Gln Leu Gly Pro Ser Leu Thr Glu Lys
225                 230                 235                 240

Leu Cys Leu Glu Leu Ala Asn Thr Ser Ile Arg Asn Leu Ser Leu Ser
                245                 250                 255

Asn Ser Gln Leu Ser Thr Thr Ser Asn Thr Thr Phe Leu Gly Leu Lys
            260                 265                 270

Trp Thr Asn Leu Thr Met Leu Asp Leu Ser Tyr Asn Asn Leu Asn Val
        275                 280                 285
```

```
Val Gly Asn Asp Ser Phe Ala Trp Leu Pro Gln Leu Glu Tyr Phe Phe
            290                 295                 300
Leu Glu Tyr Asn Asn Ile Gln His Leu Phe Ser His Ser Leu His Gly
305                 310                 315                 320
Leu Phe Asn Val Arg Tyr Leu Asn Leu Lys Arg Ser Phe Thr Lys Gln
                325                 330                 335
Ser Ile Ser Leu Ala Ser Leu Pro Lys Ile Asp Asp Phe Ser Phe Gln
            340                 345                 350
Trp Leu Lys Cys Leu Glu His Leu Asn Met Glu Asp Asn Asp Ile Pro
            355                 360                 365
Gly Ile Lys Ser Asn Met Phe Thr Gly Leu Ile Asn Leu Lys Tyr Leu
            370                 375                 380
Ser Leu Ser Asn Ser Phe Thr Ser Leu Arg Thr Leu Thr Asn Glu Thr
385                 390                 395                 400
Phe Val Ser Leu Ala His Ser Pro Leu His Ile Leu Asn Leu Thr Lys
                405                 410                 415
Asn Lys Ile Ser Lys Ile Glu Ser Asp Ala Phe Ser Trp Leu Gly His
            420                 425                 430
Leu Glu Val Leu Asp Leu Gly Leu Asn Glu Ile Gly Gln Glu Leu Thr
            435                 440                 445
Gly Gln Glu Trp Arg Gly Leu Glu Asn Ile Phe Glu Ile Tyr Leu Ser
450                 455                 460
Tyr Asn Lys Tyr Leu Gln Leu Thr Arg Asn Ser Phe Ala Leu Val Pro
465                 470                 475                 480
Ser Leu Gln Arg Leu Met Leu Arg Arg Val Ala Leu Lys Asn Val Asp
                485                 490                 495
Ser Ser Pro Ser Pro Phe Gln Pro Leu Arg Asn Leu Thr Ile Leu Asp
            500                 505                 510
Leu Ser Asn Asn Asn Ile Ala Asn Ile Asn Asp Asp Met Leu Glu Gly
            515                 520                 525
Leu Glu Lys Leu Glu Ile Leu Asp Leu Gln His Asn Asn Leu Ala Arg
            530                 535                 540
Leu Trp Lys His Ala Asn Pro Gly Gly Pro Ile Tyr Phe Leu Lys Gly
545                 550                 555                 560
Leu Ser His Leu His Ile Leu Asn Leu Glu Ser Asn Gly Phe Asp Glu
                565                 570                 575
Ile Pro Val Glu Val Phe Lys Asp Leu Phe Glu Leu Lys Ile Ile Asp
                580                 585                 590
Leu Gly Leu Asn Asn Leu Asn Thr Leu Pro Ala Ser Val Phe Asn Asn
            595                 600                 605
Gln Val Ser Leu Lys Ser Leu Asn Leu Gln Lys Asn Leu Ile Thr Ser
610                 615                 620
Val Glu Lys Lys Val Phe Gly Pro Ala Phe Arg Asn Leu Thr Glu Leu
625                 630                 635                 640
Asp Met Arg Phe Asn Pro Phe Asp Cys Thr Cys Glu Ser Ile Ala Trp
                645                 650                 655
Phe Val Asn Trp Ile Asn Glu Thr His Thr Asn Ile Pro Glu Leu Ser
                660                 665                 670
Ser His Tyr Leu Cys Asn Thr Pro Pro His Tyr His Gly Phe Pro Val
            675                 680                 685
Arg Leu Phe Asp Thr Ser Ser Cys Lys Asp Ser Ala Pro Phe Glu Leu
            690                 695                 700
```

```
Phe Phe Met Ile Asn Thr Ser Ile Leu Leu Ile Phe Ile Phe Ile Val
705                 710                 715                 720

Leu Leu Ile His Phe Glu Gly Trp Arg Ile Ser Phe Tyr Trp Asn Val
            725                 730                 735

Ser Val His Arg Val Leu Gly Phe Lys Glu Ile Asp Arg Gln Thr Glu
            740                 745                 750

Gln Phe Glu Tyr Ala Ala Tyr Ile Ile His Ala Tyr Lys Asp Lys Asp
            755                 760                 765

Trp Val Trp Glu His Phe Ser Ser Met Glu Lys Glu Asp Gln Ser Leu
            770                 775                 780

Lys Phe Cys Leu Glu Glu Arg Asp Phe Glu Ala Gly Val Phe Glu Leu
785                 790                 795                 800

Glu Ala Ile Val Asn Ser Ile Lys Arg Ser Arg Lys Ile Ile Phe Val
                    805                 810                 815

Ile Thr His His Leu Leu Lys Asp Pro Leu Cys Lys Arg Phe Lys Val
                    820                 825                 830

His His Ala Val Gln Gln Ala Ile Glu Gln Asn Leu Asp Ser Ile Ile
                    835                 840                 845

Leu Val Phe Leu Glu Glu Ile Pro Asp Tyr Lys Leu Asn His Ala Leu
850                 855                 860

Cys Leu Arg Arg Gly Met Phe Lys Ser His Cys Ile Leu Asn Trp Pro
865                 870                 875                 880

Val Gln Lys Glu Arg Ile Gly Ala Phe Arg His Lys Leu Gln Val Ala
                    885                 890                 895

Leu Gly Ser Lys Asn Ser Val His
            900

<210> SEQ ID NO 19
<211> LENGTH: 839
<212> TYPE: PRT
<213> ORGANISM: Homo sapiens

<400> SEQUENCE: 19

Met Met Ser Ala Ser Arg Leu Ala Gly Thr Leu Ile Pro Ala Met Ala
1               5                   10                  15

Phe Leu Ser Cys Val Arg Pro Glu Ser Trp Glu Pro Cys Val Glu Val
            20                  25                  30

Val Pro Asn Ile Thr Tyr Gln Cys Met Glu Leu Asn Phe Tyr Lys Ile
            35                  40                  45

Pro Asp Asn Leu Pro Phe Ser Thr Lys Asn Leu Asp Leu Ser Phe Asn
50                  55                  60

Pro Leu Arg His Leu Gly Ser Tyr Ser Phe Phe Ser Phe Pro Glu Leu
65                  70                  75                  80

Gln Val Leu Asp Leu Ser Arg Cys Glu Ile Gln Thr Ile Glu Asp Gly
            85                  90                  95

Ala Tyr Gln Ser Leu Ser His Leu Ser Thr Leu Ile Leu Thr Gly Asn
            100                 105                 110

Pro Ile Gln Ser Leu Ala Leu Gly Ala Phe Ser Gly Leu Ser Ser Leu
            115                 120                 125

Gln Lys Leu Val Ala Val Glu Thr Asn Leu Ala Ser Leu Glu Asn Phe
130                 135                 140

Pro Ile Gly His Leu Lys Thr Leu Lys Glu Leu Asn Val Ala His Asn
145                 150                 155                 160

Leu Ile Gln Ser Phe Lys Leu Pro Glu Tyr Phe Ser Asn Leu Thr Asn
            165                 170                 175
```

```
Leu Glu His Leu Asp Leu Ser Ser Asn Lys Ile Gln Ser Ile Tyr Cys
            180                 185                 190

Thr Asp Leu Arg Val Leu His Gln Met Pro Leu Leu Asn Leu Ser Leu
            195                 200                 205

Asp Leu Ser Leu Asn Pro Met Asn Phe Ile Gln Pro Gly Ala Phe Lys
210                 215                 220

Glu Ile Arg Leu His Lys Leu Thr Leu Arg Asn Asn Phe Asp Ser Leu
225                 230                 235                 240

Asn Val Met Lys Thr Cys Ile Gln Gly Leu Ala Gly Leu Glu Val His
                245                 250                 255

Arg Leu Val Leu Gly Glu Phe Arg Asn Glu Gly Asn Leu Glu Lys Phe
            260                 265                 270

Asp Lys Ser Ala Leu Glu Gly Leu Cys Asn Leu Thr Ile Glu Glu Phe
            275                 280                 285

Arg Leu Ala Tyr Leu Asp Tyr Tyr Leu Asp Asp Ile Ile Asp Leu Phe
            290                 295                 300

Asn Cys Leu Thr Asn Val Ser Ser Phe Ser Leu Val Ser Val Thr Ile
305                 310                 315                 320

Glu Arg Val Lys Asp Phe Ser Tyr Asn Phe Gly Trp Gln His Leu Glu
                325                 330                 335

Leu Val Asn Cys Lys Phe Gly Gln Phe Pro Thr Leu Lys Leu Lys Ser
            340                 345                 350

Leu Lys Arg Leu Thr Phe Thr Ser Asn Lys Gly Gly Asn Ala Phe Ser
            355                 360                 365

Glu Val Asp Leu Pro Ser Leu Glu Phe Leu Asp Leu Ser Arg Asn Gly
            370                 375                 380

Leu Ser Phe Lys Gly Cys Cys Ser Gln Ser Asp Phe Gly Thr Thr Ser
385                 390                 395                 400

Leu Lys Tyr Leu Asp Leu Ser Phe Asn Gly Val Ile Thr Met Ser Ser
                405                 410                 415

Asn Phe Leu Gly Leu Glu Gln Leu Glu His Leu Asp Phe Gln His Ser
            420                 425                 430

Asn Leu Lys Gln Met Ser Glu Phe Ser Val Phe Leu Ser Leu Arg Asn
            435                 440                 445

Leu Ile Tyr Leu Asp Ile Ser His Thr His Thr Arg Val Ala Phe Asn
450                 455                 460

Gly Ile Phe Asn Gly Leu Ser Ser Leu Glu Val Leu Lys Met Ala Gly
465                 470                 475                 480

Asn Ser Phe Gln Glu Asn Phe Leu Pro Asp Ile Phe Thr Glu Leu Arg
                485                 490                 495

Asn Leu Thr Phe Leu Asp Leu Ser Gln Cys Gln Leu Glu Gln Leu Ser
            500                 505                 510

Pro Thr Ala Phe Asn Ser Leu Ser Ser Leu Gln Val Leu Asn Met Ser
            515                 520                 525

His Asn Asn Phe Phe Ser Leu Asp Thr Phe Pro Tyr Lys Cys Leu Asn
            530                 535                 540

Ser Leu Gln Val Leu Asp Tyr Ser Leu Asn His Ile Met Thr Ser Lys
545                 550                 555                 560

Lys Gln Glu Leu Gln His Phe Pro Ser Ser Leu Ala Phe Leu Asn Leu
                565                 570                 575

Thr Gln Asn Asp Phe Ala Cys Thr Cys Glu His Gln Ser Phe Leu Gln
            580                 585                 590
```

```
Trp Ile Lys Asp Gln Arg Gln Leu Val Glu Val Glu Arg Met Glu
        595                 600                 605

Cys Ala Thr Pro Ser Asp Lys Gln Gly Met Pro Val Leu Ser Leu Asn
610                 615                 620

Ile Thr Cys Gln Met Asn Lys Thr Ile Ile Gly Val Ser Val Leu Ser
625                 630                 635                 640

Val Leu Val Val Ser Val Ala Val Leu Val Tyr Lys Phe Tyr Phe
                645                 650                 655

His Leu Met Leu Leu Ala Gly Cys Ile Lys Tyr Gly Arg Gly Glu Asn
                660                 665                 670

Ile Tyr Asp Ala Phe Val Ile Tyr Ser Ser Gln Asp Glu Asp Trp Val
        675                 680                 685

Arg Asn Glu Leu Val Lys Asn Leu Glu Glu Gly Val Pro Pro Phe Gln
690                 695                 700

Leu Cys Leu His Tyr Arg Asp Phe Ile Pro Gly Val Ala Ile Ala Ala
705                 710                 715                 720

Asn Ile Ile His Glu Gly Phe His Lys Ser Arg Lys Val Ile Val Val
                725                 730                 735

Val Ser Gln His Phe Ile Gln Ser Arg Trp Cys Ile Phe Glu Tyr Glu
                740                 745                 750

Ile Ala Gln Thr Trp Gln Phe Leu Ser Ser Arg Ala Gly Ile Ile Phe
        755                 760                 765

Ile Val Leu Gln Lys Val Glu Lys Thr Leu Leu Arg Gln Gln Val Glu
770                 775                 780

Leu Tyr Arg Leu Leu Ser Arg Asn Thr Tyr Leu Glu Trp Glu Asp Ser
785                 790                 795                 800

Val Leu Gly Arg His Ile Phe Trp Arg Arg Leu Arg Lys Ala Leu Leu
                805                 810                 815

Asp Gly Lys Ser Trp Asn Pro Glu Gly Thr Val Gly Thr Gly Cys Asn
        820                 825                 830

Trp Gln Glu Ala Thr Ser Ile
        835

<210> SEQ ID NO 20
<211> LENGTH: 858
<212> TYPE: PRT
<213> ORGANISM: Homo sapiens

<400> SEQUENCE: 20

Met Gly Asp His Leu Asp Leu Leu Leu Gly Val Val Leu Met Ala Gly
1               5                   10                  15

Pro Val Phe Gly Ile Pro Ser Cys Ser Phe Asp Gly Arg Ile Ala Phe
                20                  25                  30

Tyr Arg Phe Cys Asn Leu Thr Gln Val Pro Gln Val Leu Asn Thr Thr
        35                  40                  45

Glu Arg Leu Leu Leu Ser Phe Asn Tyr Ile Arg Thr Val Thr Ala Ser
    50                  55                  60

Ser Phe Pro Phe Leu Glu Gln Leu Gln Leu Leu Glu Leu Gly Ser Gln
65                  70                  75                  80

Tyr Thr Pro Leu Thr Ile Asp Lys Glu Ala Phe Arg Asn Leu Pro Asn
                85                  90                  95

Leu Arg Ile Leu Asp Leu Gly Ser Ser Lys Ile Tyr Phe Leu His Pro
            100                 105                 110

Asp Ala Phe Gln Gly Leu Phe His Leu Phe Glu Leu Arg Leu Tyr Phe
        115                 120                 125
```

-continued

```
Cys Gly Leu Ser Asp Ala Val Leu Lys Asp Gly Tyr Phe Arg Asn Leu
    130             135             140
Lys Ala Leu Thr Arg Leu Asp Leu Ser Lys Asn Gln Ile Arg Ser Leu
145             150             155             160
Tyr Leu His Pro Ser Phe Gly Lys Leu Asn Ser Leu Lys Ser Ile Asp
                165             170             175
Phe Ser Ser Asn Gln Ile Phe Leu Val Cys Glu His Glu Leu Glu Pro
            180             185             190
Leu Gln Gly Lys Thr Leu Ser Phe Phe Ser Leu Ala Ala Asn Ser Leu
        195             200             205
Tyr Ser Arg Val Ser Val Asp Trp Gly Lys Cys Met Asn Pro Phe Arg
    210             215             220
Asn Met Val Leu Glu Ile Leu Asp Val Ser Gly Asn Gly Trp Thr Val
225             230             235             240
Asp Ile Thr Gly Asn Phe Ser Asn Ala Ile Ser Lys Ser Gln Ala Phe
                245             250             255
Ser Leu Ile Leu Ala His His Ile Met Gly Ala Gly Phe Gly Phe His
            260             265             270
Asn Ile Lys Asp Pro Asp Gln Asn Thr Phe Ala Gly Leu Ala Arg Ser
        275             280             285
Ser Val Arg His Leu Asp Leu Ser His Gly Phe Val Phe Ser Leu Asn
    290             295             300
Ser Arg Val Phe Glu Thr Leu Lys Asp Leu Lys Val Leu Asn Leu Ala
305             310             315             320
Tyr Asn Lys Ile Asn Lys Ile Ala Asp Glu Ala Phe Tyr Gly Leu Asp
                325             330             335
Asn Leu Gln Val Leu Asn Leu Ser Tyr Asn Leu Leu Gly Glu Leu Tyr
            340             345             350
Ser Ser Asn Phe Tyr Gly Leu Pro Lys Val Ala Tyr Ile Asp Leu Gln
        355             360             365
Lys Asn His Ile Ala Ile Ile Gln Asp Gln Thr Phe Lys Phe Leu Glu
    370             375             380
Lys Leu Gln Thr Leu Asp Leu Arg Asp Asn Ala Leu Thr Thr Ile His
385             390             395             400
Phe Ile Pro Ser Ile Pro Asp Ile Phe Leu Ser Gly Asn Lys Leu Val
                405             410             415
Thr Leu Pro Lys Ile Asn Leu Thr Ala Asn Leu Ile His Leu Ser Glu
            420             425             430
Asn Arg Leu Glu Asn Leu Asp Ile Leu Tyr Phe Leu Leu Arg Val Pro
        435             440             445
His Leu Gln Ile Leu Ile Leu Asn Gln Asn Arg Phe Ser Ser Cys Ser
    450             455             460
Gly Asp Gln Thr Pro Ser Glu Asn Pro Ser Leu Glu Gln Leu Phe Leu
465             470             475             480
Gly Glu Asn Met Leu Gln Leu Ala Trp Glu Thr Glu Leu Cys Trp Asp
                485             490             495
Val Phe Glu Gly Leu Ser His Leu Gln Val Leu Tyr Leu Asn His Asn
            500             505             510
Tyr Leu Asn Ser Leu Pro Pro Gly Val Phe Ser His Leu Thr Ala Leu
        515             520             525
Arg Gly Leu Ser Leu Asn Ser Asn Arg Leu Thr Val Leu Ser His Asn
    530             535             540
```

Asp Leu Pro Ala Asn Leu Glu Ile Leu Asp Ile Ser Arg Asn Gln Leu
545                 550                 555                 560

Leu Ala Pro Asn Pro Asp Val Phe Val Ser Leu Ser Val Leu Asp Ile
            565                 570                 575

Thr His Asn Lys Phe Ile Cys Glu Cys Glu Leu Ser Thr Phe Ile Asn
                580                 585                 590

Trp Leu Asn His Thr Asn Val Thr Ile Ala Gly Pro Pro Ala Asp Ile
            595                 600                 605

Tyr Cys Val Tyr Pro Asp Ser Phe Ser Gly Val Ser Leu Phe Ser Leu
        610                 615                 620

Ser Thr Glu Gly Cys Asp Glu Glu Val Leu Lys Ser Leu Lys Phe
625                 630                 635                 640

Ser Leu Phe Ile Val Cys Thr Val Thr Leu Thr Leu Phe Leu Met Thr
                645                 650                 655

Ile Leu Thr Val Thr Lys Phe Arg Gly Phe Cys Phe Ile Cys Tyr Lys
            660                 665                 670

Thr Ala Gln Arg Leu Val Phe Lys Asp His Pro Gln Gly Thr Glu Pro
        675                 680                 685

Asp Met Tyr Lys Tyr Asp Ala Tyr Leu Cys Phe Ser Ser Lys Asp Phe
690                 695                 700

Thr Trp Val Gln Asn Ala Leu Leu Lys His Leu Asp Thr Gln Tyr Ser
705                 710                 715                 720

Asp Gln Asn Arg Phe Asn Leu Cys Phe Glu Glu Arg Asp Phe Val Pro
                725                 730                 735

Gly Glu Asn Arg Ile Ala Asn Ile Gln Asp Ala Ile Trp Asn Ser Arg
            740                 745                 750

Lys Ile Val Cys Leu Val Ser Arg His Phe Leu Arg Asp Gly Trp Cys
        755                 760                 765

Leu Glu Ala Phe Ser Tyr Ala Gln Gly Arg Cys Leu Ser Asp Leu Asn
770                 775                 780

Ser Ala Leu Ile Met Val Val Gly Ser Leu Ser Gln Tyr Gln Leu
785                 790                 795                 800

Met Lys His Gln Ser Ile Arg Gly Phe Val Gln Lys Gln Gln Tyr Leu
                805                 810                 815

Arg Trp Pro Glu Asp Phe Gln Asp Val Gly Trp Phe Leu His Lys Leu
            820                 825                 830

Ser Gln Gln Ile Leu Lys Lys Glu Lys Lys Lys Asp Asn Asn
        835                 840                 845

Ile Pro Leu Gln Thr Val Ala Thr Ile Ser
    850                 855

<210> SEQ ID NO 21
<211> LENGTH: 796
<212> TYPE: PRT
<213> ORGANISM: Homo sapiens

<400> SEQUENCE: 21

Met Thr Lys Asp Lys Glu Pro Ile Val Lys Ser Phe His Phe Val Cys
1               5                   10                  15

Leu Met Ile Ile Ile Val Gly Thr Arg Ile Gln Phe Ser Asp Gly Asn
            20                  25                  30

Glu Phe Ala Val Asp Lys Ser Lys Arg Gly Leu Ile His Val Pro Lys
        35                  40                  45

Asp Leu Pro Leu Lys Thr Lys Val Leu Asp Met Ser Gln Asn Tyr Ile
    50                  55                  60

```
Ala Glu Leu Gln Val Ser Asp Met Ser Phe Leu Ser Glu Leu Thr Val
 65                  70                  75                  80

Leu Arg Leu Ser His Asn Arg Ile Gln Leu Leu Asp Leu Ser Val Phe
             85                  90                  95

Lys Phe Asn Gln Asp Leu Glu Tyr Leu Asp Leu Ser His Asn Gln Leu
                100                 105                 110

Gln Lys Ile Ser Cys His Pro Ile Val Ser Phe Arg His Leu Asp Leu
            115                 120                 125

Ser Phe Asn Asp Phe Lys Ala Leu Pro Ile Cys Lys Glu Phe Gly Asn
130                 135                 140

Leu Ser Gln Leu Asn Phe Leu Gly Leu Ser Ala Met Lys Leu Gln Lys
145                 150                 155                 160

Leu Asp Leu Leu Pro Ile Ala His Leu His Leu Ser Tyr Ile Leu Leu
                165                 170                 175

Asp Leu Arg Asn Tyr Tyr Ile Lys Glu Asn Glu Thr Glu Ser Leu Gln
                180                 185                 190

Ile Leu Asn Ala Lys Thr Leu His Leu Val Phe His Pro Thr Ser Leu
            195                 200                 205

Phe Ala Ile Gln Val Asn Ile Ser Val Asn Thr Leu Gly Cys Leu Gln
210                 215                 220

Leu Thr Asn Ile Lys Leu Asn Asp Asp Asn Cys Gln Val Phe Ile Lys
225                 230                 235                 240

Phe Leu Ser Glu Leu Thr Arg Gly Ser Thr Leu Leu Asn Phe Thr Leu
                245                 250                 255

Asn His Ile Glu Thr Thr Trp Lys Cys Leu Val Arg Val Phe Gln Phe
            260                 265                 270

Leu Trp Pro Lys Pro Val Glu Tyr Leu Asn Ile Tyr Asn Leu Thr Ile
            275                 280                 285

Ile Glu Ser Ile Arg Glu Glu Asp Phe Thr Tyr Ser Lys Thr Thr Leu
            290                 295                 300

Lys Ala Leu Thr Ile Glu His Ile Thr Asn Gln Val Phe Leu Phe Ser
305                 310                 315                 320

Gln Thr Ala Leu Tyr Thr Val Phe Ser Glu Met Asn Ile Met Met Leu
                325                 330                 335

Thr Ile Ser Asp Thr Pro Phe Ile His Met Leu Cys Pro His Ala Pro
                340                 345                 350

Ser Thr Phe Lys Phe Leu Asn Phe Thr Gln Asn Val Phe Thr Asp Ser
            355                 360                 365

Ile Phe Glu Lys Cys Ser Thr Leu Val Lys Leu Glu Thr Leu Ile Leu
            370                 375                 380

Gln Lys Asn Gly Leu Lys Asp Leu Phe Lys Val Gly Leu Met Thr Lys
385                 390                 395                 400

Asp Met Pro Ser Leu Glu Ile Leu Asp Val Ser Trp Asn Ser Leu Glu
                405                 410                 415

Ser Gly Arg His Lys Glu Asn Cys Thr Trp Val Glu Ser Ile Val Val
                420                 425                 430

Leu Asn Leu Ser Ser Asn Met Leu Thr Asp Ser Val Phe Arg Cys Leu
            435                 440                 445

Pro Pro Arg Ile Lys Val Leu Asp Leu His Ser Asn Lys Ile Lys Ser
            450                 455                 460

Val Pro Lys Gln Val Val Lys Leu Glu Ala Leu Gln Glu Leu Asn Val
465                 470                 475                 480
```

```
Ala Phe Asn Ser Leu Thr Asp Leu Pro Gly Cys Gly Ser Phe Ser Ser
                485                 490                 495

Leu Ser Val Leu Ile Ile Asp His Asn Ser Val Ser His Pro Ser Ala
            500                 505                 510

Asp Phe Phe Gln Ser Cys Gln Lys Met Arg Ser Ile Lys Ala Gly Asp
            515                 520                 525

Asn Pro Phe Gln Cys Thr Cys Glu Leu Arg Glu Phe Val Lys Asn Ile
        530                 535                 540

Asp Gln Val Ser Ser Glu Val Leu Glu Gly Trp Pro Asp Ser Tyr Lys
545                 550                 555                 560

Cys Asp Tyr Pro Glu Ser Tyr Arg Gly Ser Pro Leu Lys Asp Phe His
                565                 570                 575

Met Ser Glu Leu Ser Cys Asn Ile Thr Leu Leu Ile Val Thr Ile Gly
            580                 585                 590

Ala Thr Met Leu Val Leu Ala Val Thr Val Thr Ser Leu Cys Ile Tyr
            595                 600                 605

Leu Asp Leu Pro Trp Tyr Leu Arg Met Val Cys Gln Trp Thr Gln Thr
        610                 615                 620

Arg Arg Arg Ala Arg Asn Ile Pro Leu Glu Glu Leu Gln Arg Asn Leu
625                 630                 635                 640

Gln Phe His Ala Phe Ile Ser Tyr Ser Glu His Asp Ser Ala Trp Val
                645                 650                 655

Lys Ser Glu Leu Val Pro Tyr Leu Glu Lys Glu Asp Ile Gln Ile Cys
            660                 665                 670

Leu His Glu Arg Asn Phe Val Pro Gly Lys Ser Ile Val Glu Asn Ile
            675                 680                 685

Ile Asn Cys Ile Glu Lys Ser Tyr Lys Ser Ile Phe Val Leu Ser Pro
690                 695                 700

Asn Phe Val Gln Ser Glu Trp Cys His Tyr Glu Leu Tyr Phe Ala His
705                 710                 715                 720

His Asn Leu Phe His Glu Gly Ser Asn Asn Leu Ile Leu Ile Leu Leu
                725                 730                 735

Glu Pro Ile Pro Gln Asn Ser Ile Pro Asn Lys Tyr His Lys Leu Lys
            740                 745                 750

Ala Leu Met Thr Gln Arg Thr Tyr Leu Gln Trp Pro Lys Glu Lys Ser
            755                 760                 765

Lys Arg Gly Leu Phe Trp Ala Asn Ile Arg Ala Ala Phe Asn Met Lys
        770                 775                 780

Leu Thr Leu Val Thr Glu Asn Asn Asp Val Lys Ser
785                 790                 795

<210> SEQ ID NO 22
<211> LENGTH: 1049
<212> TYPE: PRT
<213> ORGANISM: Homo sapiens

<400> SEQUENCE: 22

Met Val Phe Pro Met Trp Thr Leu Lys Arg Gln Ile Leu Ile Leu Phe
1               5                   10                  15

Asn Ile Ile Leu Ile Ser Lys Leu Leu Gly Ala Arg Trp Phe Pro Lys
            20                  25                  30

Thr Leu Pro Cys Asp Val Thr Leu Asp Val Pro Lys Asn His Val Ile
        35                  40                  45

Val Asp Cys Thr Asp Lys His Leu Thr Glu Ile Pro Gly Gly Ile Pro
    50                  55                  60
```

-continued

```
Thr Asn Thr Thr Asn Leu Thr Leu Thr Ile Asn His Ile Pro Asp Ile
 65                  70                  75                  80

Ser Pro Ala Ser Phe His Arg Leu Asp His Leu Val Glu Ile Asp Phe
             85                  90                  95

Arg Cys Asn Cys Val Pro Ile Pro Leu Gly Ser Lys Asn Asn Met Cys
            100                 105                 110

Ile Lys Arg Leu Gln Ile Lys Pro Arg Ser Phe Ser Gly Leu Thr Tyr
            115                 120                 125

Leu Lys Ser Leu Tyr Leu Asp Gly Asn Gln Leu Leu Glu Ile Pro Gln
            130                 135                 140

Gly Leu Pro Pro Ser Leu Gln Leu Leu Ser Leu Glu Ala Asn Asn Ile
145                 150                 155                 160

Phe Ser Ile Arg Lys Glu Asn Leu Thr Glu Leu Ala Asn Ile Glu Ile
            165                 170                 175

Leu Tyr Leu Gly Gln Asn Cys Tyr Tyr Arg Asn Pro Cys Tyr Val Ser
            180                 185                 190

Tyr Ser Ile Glu Lys Asp Ala Phe Leu Asn Leu Thr Lys Leu Lys Val
            195                 200                 205

Leu Ser Leu Lys Asp Asn Asn Val Thr Ala Val Pro Thr Val Leu Pro
            210                 215                 220

Ser Thr Leu Thr Glu Leu Tyr Leu Tyr Asn Asn Met Ile Ala Lys Ile
225                 230                 235                 240

Gln Glu Asp Asp Phe Asn Asn Leu Asn Gln Leu Gln Ile Leu Asp Leu
                245                 250                 255

Ser Gly Asn Cys Pro Arg Cys Tyr Asn Ala Pro Phe Pro Cys Ala Pro
            260                 265                 270

Cys Lys Asn Asn Ser Pro Leu Gln Ile Pro Val Asn Ala Phe Asp Ala
            275                 280                 285

Leu Thr Glu Leu Lys Val Leu Arg Leu His Ser Asn Ser Leu Gln His
            290                 295                 300

Val Pro Pro Arg Trp Phe Lys Asn Ile Asn Lys Leu Gln Glu Leu Asp
305                 310                 315                 320

Leu Ser Gln Asn Phe Leu Ala Lys Glu Ile Gly Asp Ala Lys Phe Leu
                325                 330                 335

His Phe Leu Pro Ser Leu Ile Gln Leu Asp Leu Ser Phe Asn Phe Glu
                340                 345                 350

Leu Gln Val Tyr Arg Ala Ser Met Asn Leu Ser Gln Ala Phe Ser Ser
            355                 360                 365

Leu Lys Ser Leu Lys Ile Leu Arg Ile Arg Gly Tyr Val Phe Lys Glu
            370                 375                 380

Leu Lys Ser Phe Asn Leu Ser Pro Leu His Asn Leu Gln Asn Leu Glu
385                 390                 395                 400

Val Leu Asp Leu Gly Thr Asn Phe Ile Lys Ile Ala Asn Leu Ser Met
                405                 410                 415

Phe Lys Gln Phe Lys Arg Leu Lys Val Ile Asp Leu Ser Val Asn Lys
            420                 425                 430

Ile Ser Pro Ser Gly Asp Ser Ser Glu Val Gly Phe Cys Ser Asn Ala
            435                 440                 445

Arg Thr Ser Val Glu Ser Tyr Glu Pro Gln Val Leu Glu Gln Leu His
            450                 455                 460

Tyr Phe Arg Tyr Asp Lys Tyr Ala Arg Ser Cys Arg Phe Lys Asn Lys
465                 470                 475                 480
```

-continued

Glu Ala Ser Phe Met Ser Val Asn Glu Ser Cys Tyr Lys Tyr Gly Gln
                485                 490                 495

Thr Leu Asp Leu Ser Lys Asn Ser Ile Phe Val Lys Ser Ser Asp
            500                 505                 510

Phe Gln His Leu Ser Phe Leu Lys Cys Leu Asn Leu Ser Gly Asn Leu
            515                 520                 525

Ile Ser Gln Thr Leu Asn Gly Ser Glu Phe Gln Pro Leu Ala Glu Leu
            530                 535                 540

Arg Tyr Leu Asp Phe Ser Asn Asn Arg Leu Asp Leu Leu His Ser Thr
545                 550                 555                 560

Ala Phe Glu Glu Leu His Lys Leu Glu Val Leu Asp Ile Ser Ser Asn
                565                 570                 575

Ser His Tyr Phe Gln Ser Glu Gly Ile Thr His Met Leu Asn Phe Thr
            580                 585                 590

Lys Asn Leu Lys Val Leu Gln Lys Leu Met Met Asn Asp Asn Asp Ile
            595                 600                 605

Ser Ser Ser Thr Ser Arg Thr Met Glu Ser Glu Ser Leu Arg Thr Leu
            610                 615                 620

Glu Phe Arg Gly Asn His Leu Asp Val Leu Trp Arg Glu Gly Asp Asn
625                 630                 635                 640

Arg Tyr Leu Gln Leu Phe Lys Asn Leu Leu Lys Leu Glu Glu Leu Asp
                645                 650                 655

Ile Ser Lys Asn Ser Leu Ser Phe Leu Pro Ser Gly Val Phe Asp Gly
            660                 665                 670

Met Pro Pro Asn Leu Lys Asn Leu Ser Leu Ala Lys Asn Gly Leu Lys
            675                 680                 685

Ser Phe Ser Trp Lys Lys Leu Gln Cys Leu Lys Asn Leu Glu Thr Leu
            690                 695                 700

Asp Leu Ser His Asn Gln Leu Thr Thr Val Pro Glu Arg Leu Ser Asn
705                 710                 715                 720

Cys Ser Arg Ser Leu Lys Asn Leu Ile Leu Lys Asn Asn Gln Ile Arg
                725                 730                 735

Ser Leu Thr Lys Tyr Phe Leu Gln Asp Ala Phe Gln Leu Arg Tyr Leu
            740                 745                 750

Asp Leu Ser Ser Asn Lys Ile Gln Met Ile Gln Lys Thr Ser Phe Pro
            755                 760                 765

Glu Asn Val Leu Asn Asn Leu Lys Met Leu Leu Leu His His Asn Arg
            770                 775                 780

Phe Leu Cys Thr Cys Asp Ala Val Trp Phe Val Trp Trp Val Asn His
785                 790                 795                 800

Thr Glu Val Thr Ile Pro Tyr Leu Ala Thr Asp Val Thr Cys Val Gly
                805                 810                 815

Pro Gly Ala His Lys Gly Gln Ser Val Ile Ser Leu Asp Leu Tyr Thr
            820                 825                 830

Cys Glu Leu Asp Leu Thr Asn Leu Ile Leu Phe Ser Leu Ser Ile Ser
            835                 840                 845

Val Ser Leu Phe Leu Met Val Met Met Thr Ala Ser His Leu Tyr Phe
            850                 855                 860

Trp Asp Val Trp Tyr Ile Tyr His Phe Cys Lys Ala Lys Ile Lys Gly
865                 870                 875                 880

Tyr Gln Arg Leu Ile Ser Pro Asp Cys Cys Tyr Asp Ala Phe Ile Val
                885                 890                 895

Tyr Asp Thr Lys Asp Pro Ala Val Thr Glu Trp Val Leu Ala Glu Leu
            900                 905                 910

Val Ala Lys Leu Glu Asp Pro Arg Glu Lys His Phe Asn Leu Cys Leu
        915                 920                 925

Glu Glu Arg Asp Trp Leu Pro Gly Gln Pro Val Leu Glu Asn Leu Ser
    930                 935                 940

Gln Ser Ile Gln Leu Ser Lys Lys Thr Val Phe Val Met Thr Asp Lys
945                 950                 955                 960

Tyr Ala Lys Thr Glu Asn Phe Lys Ile Ala Phe Tyr Leu Ser His Gln
                965                 970                 975

Arg Leu Met Asp Glu Lys Val Asp Val Ile Leu Ile Phe Leu Glu
            980                 985                 990

Lys Pro Phe Gln Lys Ser Lys Phe  Leu Gln Leu Arg Lys  Arg Leu Cys
        995                 1000                1005

Gly Ser  Ser Val Leu Glu Trp  Pro Thr Asn Pro Gln  Ala His Pro
    1010                1015                1020

Tyr Phe  Trp Gln Cys Leu Lys  Asn Ala Leu Ala Thr  Asp Asn His
    1025                1030                1035

Val Ala  Tyr Ser Gln Val Phe  Lys Glu Thr Val
    1040                1045

<210> SEQ ID NO 23
<211> LENGTH: 1041
<212> TYPE: PRT
<213> ORGANISM: Homo sapiens

<400> SEQUENCE: 23

Met Glu Asn Met Phe Leu Gln Ser Ser Met Leu Thr Cys Ile Phe Leu
1               5                   10                  15

Leu Ile Ser Gly Ser Cys Glu Leu Cys Ala Glu Glu Asn Phe Ser Arg
            20                  25                  30

Ser Tyr Pro Cys Asp Glu Lys Lys Gln Asn Asp Ser Val Ile Ala Glu
        35                  40                  45

Cys Ser Asn Arg Arg Leu Gln Glu Val Pro Gln Thr Val Gly Lys Tyr
    50                  55                  60

Val Thr Glu Leu Asp Leu Ser Asp Asn Phe Ile Thr His Ile Thr Asn
65                  70                  75                  80

Glu Ser Phe Gln Gly Leu Gln Asn Leu Thr Lys Ile Asn Leu Asn His
                85                  90                  95

Asn Pro Asn Val Gln His Gln Asn Gly Asn Pro Gly Ile Gln Ser Asn
            100                 105                 110

Gly Leu Asn Ile Thr Asp Gly Ala Phe Leu Asn Leu Lys Asn Leu Arg
        115                 120                 125

Glu Leu Leu Leu Glu Asp Asn Gln Leu Pro Gln Ile Pro Ser Gly Leu
    130                 135                 140

Pro Glu Ser Leu Thr Glu Leu Ser Leu Ile Gln Asn Asn Ile Tyr Asn
145                 150                 155                 160

Ile Thr Lys Glu Gly Ile Ser Arg Leu Ile Asn Leu Lys Asn Leu Tyr
                165                 170                 175

Leu Ala Trp Asn Cys Tyr Phe Asn Lys Val Cys Glu Lys Thr Asn Ile
            180                 185                 190

Glu Asp Gly Val Phe Glu Thr Leu Thr Asn Leu Glu Leu Leu Ser Leu
        195                 200                 205

Ser Phe Asn Ser Leu Ser His Val Pro Pro Lys Leu Pro Ser Ser Leu
210                 215                 220

Arg Lys Leu Phe Leu Ser Asn Thr Gln Ile Lys Tyr Ile Ser Glu Glu
225                 230                 235                 240

Asp Phe Lys Gly Leu Ile Asn Leu Thr Leu Leu Asp Leu Ser Gly Asn
                245                 250                 255

Cys Pro Arg Cys Phe Asn Ala Pro Phe Pro Cys Val Pro Cys Asp Gly
            260                 265                 270

Gly Ala Ser Ile Asn Ile Asp Arg Phe Ala Phe Gln Asn Leu Thr Gln
        275                 280                 285

Leu Arg Tyr Leu Asn Leu Ser Ser Thr Ser Leu Arg Lys Ile Asn Ala
    290                 295                 300

Ala Trp Phe Lys Asn Met Pro His Leu Lys Val Leu Asp Leu Glu Phe
305                 310                 315                 320

Asn Tyr Leu Val Gly Glu Ile Ala Ser Gly Ala Phe Leu Thr Met Leu
                325                 330                 335

Pro Arg Leu Glu Ile Leu Asp Leu Ser Phe Asn Tyr Ile Lys Gly Ser
            340                 345                 350

Tyr Pro Gln His Ile Asn Ile Ser Arg Asn Phe Ser Lys Leu Leu Ser
        355                 360                 365

Leu Arg Ala Leu His Leu Arg Gly Tyr Val Phe Gln Glu Leu Arg Glu
    370                 375                 380

Asp Asp Phe Gln Pro Leu Met Gln Leu Pro Asn Leu Ser Thr Ile Asn
385                 390                 395                 400

Leu Gly Ile Asn Phe Ile Lys Gln Ile Asp Phe Lys Leu Phe Gln Asn
                405                 410                 415

Phe Ser Asn Leu Glu Ile Ile Tyr Leu Ser Glu Asn Arg Ile Ser Pro
            420                 425                 430

Leu Val Lys Asp Thr Arg Gln Ser Tyr Ala Asn Ser Ser Ser Phe Gln
        435                 440                 445

Arg His Ile Arg Lys Arg Arg Ser Thr Asp Phe Glu Phe Asp Pro His
    450                 455                 460

Ser Asn Phe Tyr His Phe Thr Arg Pro Leu Ile Lys Pro Gln Cys Ala
465                 470                 475                 480

Ala Tyr Gly Lys Ala Leu Asp Leu Ser Leu Asn Ser Ile Phe Phe Ile
                485                 490                 495

Gly Pro Asn Gln Phe Glu Asn Leu Pro Asp Ile Ala Cys Leu Asn Leu
            500                 505                 510

Ser Ala Asn Ser Asn Ala Gln Val Leu Ser Gly Thr Glu Phe Ser Ala
        515                 520                 525

Ile Pro His Val Lys Tyr Leu Asp Leu Thr Asn Asn Arg Leu Asp Phe
    530                 535                 540

Asp Asn Ala Ser Ala Leu Thr Glu Leu Ser Asp Leu Glu Val Leu Asp
545                 550                 555                 560

Leu Ser Tyr Asn Ser His Tyr Phe Arg Ile Ala Gly Val Thr His His
                565                 570                 575

Leu Glu Phe Ile Gln Asn Phe Thr Asn Leu Lys Val Leu Asn Leu Ser
            580                 585                 590

His Asn Asn Ile Tyr Thr Leu Thr Asp Lys Tyr Asn Leu Glu Ser Lys
        595                 600                 605

Ser Leu Val Glu Leu Val Phe Ser Gly Asn Arg Leu Asp Ile Leu Trp
610                 615                 620

-continued

```
Asn Asp Asp Asp Asn Arg Tyr Ile Ser Ile Phe Lys Gly Leu Lys Asn
625                 630                 635                 640

Leu Thr Arg Leu Asp Leu Ser Leu Asn Arg Leu Lys His Ile Pro Asn
            645                 650                 655

Glu Ala Phe Leu Asn Leu Pro Ala Ser Leu Thr Glu Leu His Ile Asn
            660                 665                 670

Asp Asn Met Leu Lys Phe Phe Asn Trp Thr Leu Leu Gln Gln Phe Pro
        675                 680                 685

Arg Leu Glu Leu Leu Asp Leu Arg Gly Asn Lys Leu Leu Phe Leu Thr
    690                 695                 700

Asp Ser Leu Ser Asp Phe Thr Ser Ser Leu Arg Thr Leu Leu Leu Ser
705                 710                 715                 720

His Asn Arg Ile Ser His Leu Pro Ser Gly Phe Leu Ser Glu Val Ser
                725                 730                 735

Ser Leu Lys His Leu Asp Leu Ser Ser Asn Leu Leu Lys Thr Ile Asn
            740                 745                 750

Lys Ser Ala Leu Glu Thr Lys Thr Thr Thr Lys Leu Ser Met Leu Glu
755                 760                 765

Leu His Gly Asn Pro Phe Glu Cys Thr Cys Asp Ile Gly Asp Phe Arg
770                 775                 780

Arg Trp Met Asp Glu His Leu Asn Val Lys Ile Pro Arg Leu Val Asp
785                 790                 795                 800

Val Ile Cys Ala Ser Pro Gly Asp Gln Arg Gly Lys Ser Ile Val Ser
                805                 810                 815

Leu Glu Leu Thr Thr Cys Val Ser Asp Val Thr Ala Val Ile Leu Phe
            820                 825                 830

Phe Phe Thr Phe Phe Ile Thr Thr Met Val Met Leu Ala Ala Leu Ala
            835                 840                 845

His His Leu Phe Tyr Trp Asp Val Trp Phe Ile Tyr Asn Val Cys Leu
850                 855                 860

Ala Lys Val Lys Gly Tyr Arg Ser Leu Ser Thr Ser Gln Thr Phe Tyr
865                 870                 875                 880

Asp Ala Tyr Ile Ser Tyr Asp Thr Lys Asp Ala Ser Val Thr Asp Trp
            885                 890                 895

Val Ile Asn Glu Leu Arg Tyr His Leu Glu Glu Ser Arg Asp Lys Asn
            900                 905                 910

Val Leu Leu Cys Leu Glu Glu Arg Asp Trp Asp Pro Gly Leu Ala Ile
        915                 920                 925

Ile Asp Asn Leu Met Gln Ser Ile Asn Gln Ser Lys Lys Thr Val Phe
930                 935                 940

Val Leu Thr Lys Lys Tyr Ala Lys Ser Trp Asn Phe Lys Thr Ala Phe
945                 950                 955                 960

Tyr Leu Ala Leu Gln Arg Leu Met Asp Glu Asn Met Asp Val Ile Ile
            965                 970                 975

Phe Ile Leu Leu Glu Pro Val Leu Gln His Ser Gln Tyr Leu Arg Leu
            980                 985                 990

Arg Gln Arg Ile Cys Lys Ser Ser Ile Leu Gln Trp Pro Asp Asn Pro
        995                 1000                1005

Lys Ala Glu Gly Leu Phe Trp Gln Thr Leu Arg Asn Val Val Leu
    1010                1015                1020
```

<210> SEQ ID NO 24
<211> LENGTH: 1032
<212> TYPE: PRT
<213> ORGANISM: Homo sapiens

<400> SEQUENCE: 24

```
Thr Glu Asn Asp Ser Arg Tyr Asn Asn Met Tyr Val Asp Ser Ile
    1025                1030                1035
Lys Gln Tyr
    1040

Met Gly Phe Cys Arg Ser Ala Leu His Pro Leu Ser Leu Val Gln
1               5                   10                  15
Ala Ile Met Leu Ala Met Thr Leu Ala Leu Gly Thr Leu Pro Ala Phe
            20                  25                  30
Leu Pro Cys Glu Leu Gln Pro His Gly Leu Val Asn Cys Asn Trp Leu
            35                  40                  45
Phe Leu Lys Ser Val Pro His Phe Ser Met Ala Ala Pro Arg Gly Asn
    50                  55                  60
Val Thr Ser Leu Ser Leu Ser Ser Asn Arg Ile His His Leu His Asp
65                  70                  75                  80
Ser Asp Phe Ala His Leu Pro Ser Leu Arg His Leu Asn Leu Lys Trp
                85                  90                  95
Asn Cys Pro Pro Val Gly Leu Ser Pro Met His Phe Pro Cys His Met
            100                 105                 110
Thr Ile Glu Pro Ser Thr Phe Leu Ala Val Pro Thr Leu Glu Glu Leu
        115                 120                 125
Asn Leu Ser Tyr Asn Asn Ile Met Thr Val Pro Ala Leu Pro Lys Ser
    130                 135                 140
Leu Ile Ser Leu Ser Leu Ser His Thr Asn Ile Leu Met Leu Asp Ser
145                 150                 155                 160
Ala Ser Leu Ala Gly Leu His Ala Leu Arg Phe Leu Phe Met Asp Gly
                165                 170                 175
Asn Cys Tyr Tyr Lys Asn Pro Cys Arg Gln Ala Leu Glu Val Ala Pro
            180                 185                 190
Gly Ala Leu Leu Gly Leu Gly Asn Leu Thr His Leu Ser Leu Lys Tyr
        195                 200                 205
Asn Asn Leu Thr Val Val Pro Arg Asn Leu Pro Ser Ser Leu Glu Tyr
    210                 215                 220
Leu Leu Leu Ser Tyr Asn Arg Ile Val Lys Leu Ala Pro Glu Asp Leu
225                 230                 235                 240
Ala Asn Leu Thr Ala Leu Arg Val Leu Asp Val Gly Gly Asn Cys Arg
                245                 250                 255
Arg Cys Asp His Ala Pro Asn Pro Cys Met Glu Cys Pro Arg His Phe
            260                 265                 270
Pro Gln Leu His Pro Asp Thr Phe Ser His Leu Ser Arg Leu Glu Gly
        275                 280                 285
Leu Val Leu Lys Asp Ser Ser Leu Ser Trp Leu Asn Ala Ser Trp Phe
    290                 295                 300
Arg Gly Leu Gly Asn Leu Arg Val Leu Asp Leu Ser Glu Asn Phe Leu
305                 310                 315                 320
Tyr Lys Cys Ile Thr Lys Thr Lys Ala Phe Gln Gly Leu Thr Gln Leu
                325                 330                 335
```

Arg Lys Leu Asn Leu Ser Phe Asn Tyr Gln Lys Arg Val Ser Phe Ala
              340                 345                 350

His Leu Ser Leu Ala Pro Ser Phe Gly Ser Leu Val Ala Leu Lys Glu
              355                 360                 365

Leu Asp Met His Gly Ile Phe Phe Arg Ser Leu Asp Glu Thr Thr Leu
              370                 375                 380

Arg Pro Leu Ala Arg Leu Pro Met Leu Gln Thr Leu Arg Leu Gln Met
385                 390                 395                 400

Asn Phe Ile Asn Gln Ala Gln Leu Gly Ile Phe Arg Ala Phe Pro Gly
              405                 410                 415

Leu Arg Tyr Val Asp Leu Ser Asp Asn Arg Ile Ser Gly Ala Ser Glu
              420                 425                 430

Leu Thr Ala Thr Met Gly Glu Ala Asp Gly Gly Glu Lys Val Trp Leu
              435                 440                 445

Gln Pro Gly Asp Leu Ala Pro Ala Pro Val Asp Thr Pro Ser Ser Glu
              450                 455                 460

Asp Phe Arg Pro Asn Cys Ser Thr Leu Asn Phe Thr Leu Asp Leu Ser
465                 470                 475                 480

Arg Asn Asn Leu Val Thr Val Gln Pro Glu Met Phe Ala Gln Leu Ser
              485                 490                 495

His Leu Gln Cys Leu Arg Leu Ser His Asn Cys Ile Ser Gln Ala Val
              500                 505                 510

Asn Gly Ser Gln Phe Leu Pro Leu Thr Gly Leu Gln Val Leu Asp Leu
              515                 520                 525

Ser His Asn Lys Leu Asp Leu Tyr His Glu His Ser Phe Thr Glu Leu
              530                 535                 540

Pro Arg Leu Glu Ala Leu Asp Leu Ser Tyr Asn Ser Gln Pro Phe Gly
545                 550                 555                 560

Met Gln Gly Val Gly His Asn Phe Ser Phe Val Ala His Leu Arg Thr
              565                 570                 575

Leu Arg His Leu Ser Leu Ala His Asn Asn Ile His Ser Gln Val Ser
              580                 585                 590

Gln Gln Leu Cys Ser Thr Ser Leu Arg Ala Leu Asp Phe Ser Gly Asn
              595                 600                 605

Ala Leu Gly His Met Trp Ala Glu Gly Asp Leu Tyr Leu His Phe Phe
              610                 615                 620

Gln Gly Leu Ser Gly Leu Ile Trp Leu Asp Leu Ser Gln Asn Arg Leu
625                 630                 635                 640

His Thr Leu Leu Pro Gln Thr Leu Arg Asn Leu Pro Lys Ser Leu Gln
              645                 650                 655

Val Leu Arg Leu Arg Asp Asn Tyr Leu Ala Phe Phe Lys Trp Trp Ser
              660                 665                 670

Leu His Phe Leu Pro Lys Leu Glu Val Leu Asp Leu Ala Gly Asn Gln
              675                 680                 685

Leu Lys Ala Leu Thr Asn Gly Ser Leu Pro Ala Gly Thr Arg Leu Arg
              690                 695                 700

Arg Leu Asp Val Ser Cys Asn Ser Ile Ser Phe Val Ala Pro Gly Phe
705                 710                 715                 720

Phe Ser Lys Ala Lys Glu Leu Arg Glu Leu Asn Leu Ser Ala Asn Ala
              725                 730                 735

Leu Lys Thr Val Asp His Ser Trp Phe Gly Pro Leu Ala Ser Ala Leu
              740                 745                 750

-continued

```
Gln Ile Leu Asp Val Ser Ala Asn Pro Leu His Cys Ala Cys Gly Ala
            755                 760                 765

Ala Phe Met Asp Phe Leu Leu Glu Val Gln Ala Val Pro Gly Leu
770                 775                 780

Pro Ser Arg Val Lys Cys Gly Ser Pro Gly Gln Leu Gln Gly Leu Ser
785                 790                 795                 800

Ile Phe Ala Gln Asp Leu Arg Leu Cys Leu Asp Glu Ala Leu Ser Trp
                805                 810                 815

Asp Cys Phe Ala Leu Ser Leu Leu Ala Val Ala Leu Gly Leu Gly Val
                820                 825                 830

Pro Met Leu His His Leu Cys Gly Trp Asp Leu Trp Tyr Cys Phe His
                835                 840                 845

Leu Cys Leu Ala Trp Leu Pro Trp Arg Gly Arg Gln Ser Gly Arg Asp
            850                 855                 860

Glu Asp Ala Leu Pro Tyr Asp Ala Phe Val Val Phe Asp Lys Thr Gln
865                 870                 875                 880

Ser Ala Val Ala Asp Trp Val Tyr Asn Glu Leu Arg Gly Gln Leu Glu
                885                 890                 895

Glu Cys Arg Gly Arg Trp Ala Leu Arg Leu Cys Leu Glu Glu Arg Asp
            900                 905                 910

Trp Leu Pro Gly Lys Thr Leu Phe Glu Asn Leu Trp Ala Ser Val Tyr
            915                 920                 925

Gly Ser Arg Lys Thr Leu Phe Val Leu Ala His Thr Asp Arg Val Ser
            930                 935                 940

Gly Leu Leu Arg Ala Ser Phe Leu Leu Ala Gln Gln Arg Leu Leu Glu
945                 950                 955                 960

Asp Arg Lys Asp Val Val Val Leu Val Ile Leu Ser Pro Asp Gly Arg
                965                 970                 975

Arg Ser Arg Tyr Val Arg Leu Arg Gln Arg Leu Cys Arg Gln Ser Val
            980                 985                 990

Leu Leu Trp Pro His Gln Pro Ser Gly Gln Arg Ser Phe Trp Ala Gln
            995                1000                1005

Leu Gly Met Ala Leu Thr Arg Asp Asn His His Phe Tyr Asn Arg
            1010                1015                1020

Asn Phe Cys Gln Gly Pro Thr Ala Glu
            1025                1030

<210> SEQ ID NO 25
<211> LENGTH: 811
<212> TYPE: PRT
<213> ORGANISM: Homo sapiens

<400> SEQUENCE: 25

Met Arg Leu Ile Arg Asn Ile Tyr Ile Phe Cys Ser Ile Val Met Thr
1               5                   10                  15

Ala Glu Gly Asp Ala Pro Glu Leu Pro Glu Glu Arg Glu Leu Met Thr
                20                  25                  30

Asn Cys Ser Asn Met Ser Leu Arg Lys Val Pro Ala Asp Leu Thr Pro
            35                  40                  45

Ala Thr Thr Thr Leu Asp Leu Ser Tyr Asn Leu Leu Phe Gln Leu Gln
        50                  55                  60

Ser Ser Asp Phe His Ser Val Ser Lys Leu Arg Val Leu Ile Leu Cys
65                  70                  75                  80

His Asn Arg Ile Gln Gln Leu Asp Leu Lys Thr Phe Glu Phe Asn Lys
                85                  90                  95
```

-continued

```
Glu Leu Arg Tyr Leu Asp Leu Ser Asn Asn Arg Leu Lys Ser Val Thr
            100                 105                 110

Trp Tyr Leu Leu Ala Gly Leu Arg Tyr Leu Asp Leu Ser Phe Asn Asp
            115                 120                 125

Phe Asp Thr Met Pro Ile Cys Glu Glu Ala Gly Asn Met Ser His Leu
            130                 135                 140

Glu Ile Leu Gly Leu Ser Gly Ala Lys Ile Gln Lys Ser Asp Phe Gln
145                 150                 155                 160

Lys Ile Ala His Leu His Leu Asn Thr Val Phe Leu Gly Phe Arg Thr
                165                 170                 175

Leu Pro His Tyr Glu Glu Gly Ser Leu Pro Ile Leu Asn Thr Thr Lys
            180                 185                 190

Leu His Ile Val Leu Pro Met Asp Thr Asn Phe Trp Val Leu Leu Arg
            195                 200                 205

Asp Gly Ile Lys Thr Ser Lys Ile Leu Glu Met Thr Asn Ile Asp Gly
            210                 215                 220

Lys Ser Gln Phe Val Ser Tyr Glu Met Gln Arg Asn Leu Ser Leu Glu
225                 230                 235                 240

Asn Ala Lys Thr Ser Val Leu Leu Asn Lys Val Asp Leu Leu Trp
                245                 250                 255

Asp Asp Leu Phe Leu Ile Leu Gln Phe Val Trp His Thr Ser Val Glu
            260                 265                 270

His Phe Gln Ile Arg Asn Val Thr Phe Gly Gly Lys Ala Tyr Leu Asp
            275                 280                 285

His Asn Ser Phe Asp Tyr Ser Asn Thr Val Met Arg Thr Ile Lys Leu
            290                 295                 300

Glu His Val His Phe Arg Val Phe Tyr Ile Gln Gln Asp Lys Ile Tyr
305                 310                 315                 320

Leu Leu Leu Thr Lys Met Asp Ile Glu Asn Leu Thr Ile Ser Asn Ala
                325                 330                 335

Gln Met Pro His Met Leu Phe Pro Asn Tyr Pro Thr Lys Phe Gln Tyr
            340                 345                 350

Leu Asn Phe Ala Asn Asn Ile Leu Thr Asp Glu Leu Phe Lys Arg Thr
            355                 360                 365

Ile Gln Leu Pro His Leu Lys Thr Leu Ile Leu Asn Gly Asn Lys Leu
370                 375                 380

Glu Thr Leu Ser Leu Val Ser Cys Phe Ala Asn Asn Thr Pro Leu Glu
385                 390                 395                 400

His Leu Asp Leu Ser Gln Asn Leu Leu Gln His Lys Asn Asp Glu Asn
                405                 410                 415

Cys Ser Trp Pro Glu Thr Val Val Asn Met Asn Leu Ser Tyr Asn Lys
            420                 425                 430

Leu Ser Asp Ser Val Phe Arg Cys Leu Pro Lys Ser Ile Gln Ile Leu
            435                 440                 445

Asp Leu Asn Asn Asn Gln Ile Gln Thr Val Pro Lys Glu Thr Ile His
            450                 455                 460

Leu Met Ala Leu Arg Glu Leu Asn Ile Ala Phe Asn Phe Leu Thr Asp
465                 470                 475                 480

Leu Pro Gly Cys Ser His Phe Ser Arg Leu Ser Val Leu Asn Ile Glu
                485                 490                 495

Met Asn Phe Ile Leu Ser Pro Ser Leu Asp Phe Val Gln Ser Cys Gln
            500                 505                 510
```

```
Glu Val Lys Thr Leu Asn Ala Gly Arg Asn Pro Phe Arg Cys Thr Cys
            515                 520                 525

Glu Leu Lys Asn Phe Ile Gln Leu Glu Thr Tyr Ser Glu Val Met Met
        530                 535                 540

Val Gly Trp Ser Asp Ser Tyr Thr Cys Glu Tyr Pro Leu Asn Leu Arg
545                 550                 555                 560

Gly Thr Arg Leu Lys Asp Val His Leu His Glu Leu Ser Cys Asn Thr
                565                 570                 575

Ala Leu Leu Ile Val Thr Ile Val Ile Met Leu Val Leu Gly Leu
            580                 585                 590

Ala Val Ala Phe Cys Cys Leu His Phe Asp Leu Pro Trp Tyr Leu Arg
        595                 600                 605

Met Leu Gly Gln Cys Thr Gln Thr Trp His Arg Val Arg Lys Thr Thr
610                 615                 620

Gln Glu Gln Leu Lys Arg Asn Val Arg Phe His Ala Phe Ile Ser Tyr
625                 630                 635                 640

Ser Glu His Asp Ser Leu Trp Val Lys Asn Glu Leu Ile Pro Asn Leu
                645                 650                 655

Glu Lys Glu Asp Gly Ser Ile Leu Ile Cys Leu Tyr Glu Ser Tyr Phe
            660                 665                 670

Asp Pro Gly Lys Ser Ile Ser Glu Asn Ile Val Ser Phe Ile Glu Lys
        675                 680                 685

Ser Tyr Lys Ser Ile Phe Val Leu Ser Pro Asn Phe Val Gln Asn Glu
        690                 695                 700

Trp Cys His Tyr Glu Phe Tyr Phe Ala His His Asn Leu Phe His Glu
705                 710                 715                 720

Asn Ser Asp His Ile Ile Leu Ile Leu Leu Glu Pro Ile Pro Phe Tyr
                725                 730                 735

Cys Ile Pro Thr Arg Tyr His Lys Leu Lys Ala Leu Leu Glu Lys Lys
            740                 745                 750

Ala Tyr Leu Glu Trp Pro Lys Asp Arg Arg Lys Cys Gly Leu Phe Trp
        755                 760                 765

Ala Asn Leu Arg Ala Ala Ile Asn Val Asn Val Leu Ala Thr Arg Glu
        770                 775                 780

Met Tyr Glu Leu Gln Thr Phe Thr Glu Leu Asn Glu Glu Ser Arg Gly
785                 790                 795                 800

Ser Thr Ile Ser Leu Met Arg Thr Asp Cys Leu
                805                 810
```

<210> SEQ ID NO 26
<211> LENGTH: 243
<212> TYPE: PRT
<213> ORGANISM: Artificial Sequence
<220> FEATURE:
<223> OTHER INFORMATION: Made in Lab - Synthesized fusion protein

<400> SEQUENCE: 26

```
Met Glu Ala Ala Val Ala Ala Pro Arg Pro Arg Leu Leu Leu Leu Val
1               5                   10                  15

Leu Ala Ala Ala Ala Ala Ala Ala Ala Leu Leu Pro Gly Ala Thr
            20                  25                  30

Ala Leu Gln Cys Phe Cys His Leu Cys Thr Lys Asp Asn Phe Thr Cys
        35                  40                  45

Val Thr Asp Gly Leu Cys Phe Val Ser Val Thr Glu Thr Thr Asp Lys
    50                  55                  60
```

```
Val Ile His Asn Ser Met Cys Ile Ala Glu Ile Asp Leu Ile Pro Arg
 65                  70                  75                  80

Asp Arg Pro Phe Val Cys Ala Pro Ser Ser Lys Thr Gly Ser Val Thr
                 85                  90                  95

Thr Thr Tyr Cys Cys Asn Gln Asp His Cys Asn Lys Ile Glu Leu Pro
            100                 105                 110

Thr Thr Val Lys Ser Ser Pro Gly Leu Gly Pro Val Glu Leu Trp Leu
        115                 120                 125

Ile Phe Phe Ala Ser Leu Gly Ser Phe Leu Ser Ile Leu Leu Val Gly
130                 135                 140

Val Leu Gly Tyr Leu Gly Leu Asn Arg Ala Ala Arg His Leu Cys Pro
145                 150                 155                 160

Pro Leu Pro Thr Pro Cys Ala Ser Ser Ala Ile Glu Phe Pro Gly Gly
                165                 170                 175

Lys Glu Thr Trp Gln Trp Ile Asn Pro Val Asp Phe Gln Glu Glu Ala
            180                 185                 190

Ser Leu Gln Glu Ala Leu Val Val Glu Met Ser Trp Asp Lys Gly Glu
        195                 200                 205

Arg Thr Glu Pro Leu Glu Lys Thr Glu Leu Pro Glu Gly Ala Pro Glu
210                 215                 220

Leu Ala Leu Asp Thr Glu Leu Ser Leu Glu Asp Gly Asp Arg Cys Lys
225                 230                 235                 240

Ala Lys Met

<210> SEQ ID NO 27
<211> LENGTH: 406
<212> TYPE: PRT
<213> ORGANISM: Artificial Sequence
<220> FEATURE:
<223> OTHER INFORMATION: Made in Lab - synthesized fusion protein

<400> SEQUENCE: 27

Met Gly Arg Gly Leu Leu Arg Gly Leu Trp Pro Leu His Ile Val Leu
 1               5                  10                  15

Trp Thr Arg Ile Ala Ser Thr Ile Pro Pro His Val Gln Lys Ser Val
                20                  25                  30

Asn Asn Asp Met Ile Val Thr Asp Asn Asn Gly Ala Val Lys Phe Pro
            35                  40                  45

Gln Leu Cys Lys Phe Cys Asp Val Arg Phe Ser Thr Cys Asp Asn Gln
        50                  55                  60

Lys Ser Cys Met Ser Asn Cys Ser Ile Thr Ser Ile Cys Glu Lys Pro
 65                  70                  75                  80

Gln Glu Val Cys Val Ala Val Trp Arg Lys Asn Asp Glu Asn Ile Thr
                 85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
130                 135                 140

Asp Asn Ile Ile Phe Ser Glu Glu Tyr Asn Thr Ser Asn Pro Asp Leu
145                 150                 155                 160

Leu Leu Val Ile Phe Gln Trp Met Ala Phe Val Ala Pro Ser Ile Cys
                165                 170                 175
```

```
Ile Ala Ile Ile Met Val Gly Ile Phe Ser Thr His Tyr Phe Gln Gln
                180                 185                 190

Lys Val Phe Val Leu Ala Ala Leu Arg Pro Gln Trp Cys Ser Arg
            195                 200                 205

Glu Ile Pro Asp Pro Ala Asn Ser Thr Cys Ala Lys Lys Tyr Pro Ile
210                 215                 220

Ala Glu Glu Lys Thr Gln Leu Pro Leu Asp Arg Leu Leu Ile Asp Trp
225                 230                 235                 240

Pro Thr Pro Glu Asp Pro Glu Pro Leu Val Ile Ser Glu Val Leu His
                245                 250                 255

Gln Val Thr Pro Val Phe Arg His Pro Pro Cys Ser Asn Trp Pro Gln
            260                 265                 270

Arg Glu Lys Gly Ile Gln Gly His Gln Ala Ser Glu Lys Asp Met Met
            275                 280                 285

His Ser Ala Ser Ser Pro Pro Pro Arg Ala Leu Gln Ala Glu Ser
            290                 295                 300

Arg Gln Leu Val Asp Leu Tyr Lys Val Leu Glu Ser Arg Gly Ser Asp
305                 310                 315                 320

Pro Lys Pro Glu Asn Pro Ala Cys Pro Trp Thr Val Leu Pro Ala Gly
                325                 330                 335

Asp Leu Pro Thr His Asp Gly Tyr Leu Pro Ser Asn Ile Asp Asp Leu
                340                 345                 350

Pro Ser His Glu Ala Pro Leu Ala Asp Ser Leu Glu Glu Leu Glu Pro
            355                 360                 365

Gln His Ile Ser Leu Ser Val Phe Pro Ser Ser Ser Leu His Pro Leu
            370                 375                 380

Thr Phe Ser Cys Gly Asp Lys Leu Thr Leu Asp Gln Leu Lys Met Arg
385                 390                 395                 400

Cys Asp Ser Leu Met Leu
                405

<210> SEQ ID NO 28
<211> LENGTH: 671
<212> TYPE: PRT
<213> ORGANISM: Artificial Sequence
<220> FEATURE:
<223> OTHER INFORMATION: Made in Lab - Synthesized fusion protein

<400> SEQUENCE: 28

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
                20                  25                  30

Asn Asn Asp Met Ile Val Thr Asp Asn Asn Gly Ala Val Lys Phe Pro
            35                  40                  45

Gln Leu Cys Lys Phe Cys Asp Val Arg Phe Ser Thr Cys Asp Asn Gln
        50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125
```

```
Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Trp Met Ala Phe Val Ala Pro Ser Ile Cys
                165                 170                 175

Ile Ala Ile Ile Met Val Gly Ile Phe Ser Thr His Tyr Phe Gln Gln
            180                 185                 190

Lys Val Phe Val Leu Leu Ala Ala Leu Arg Pro Gln Trp Cys Ser Arg
        195                 200                 205

Glu Ile Pro Asp Pro Ala Asn Ser Thr Cys Ala Lys Lys Tyr Pro Ile
    210                 215                 220

Ala Glu Glu Lys Thr Gln Leu Pro Leu Asp Arg Leu Leu Ile Asp Trp
225                 230                 235                 240

Pro Thr Pro Glu Asp Pro Glu Pro Leu Val Ile Ser Glu Val Leu His
                245                 250                 255

Gln Val Thr Pro Val Phe Arg His Pro Pro Cys Ser Asn Trp Pro Gln
            260                 265                 270

Arg Glu Lys Gly Ile Gln Gly His Gln Ala Ser Glu Lys Asp Met Met
        275                 280                 285

His Ser Ala Ser Ser Pro Pro Pro Arg Ala Leu Gln Ala Glu Ser
    290                 295                 300

Arg Gln Leu Val Asp Leu Tyr Lys Val Leu Glu Ser Arg Gly Ser Asp
305                 310                 315                 320

Pro Lys Pro Glu Asn Pro Ala Cys Pro Trp Thr Val Leu Pro Ala Gly
                325                 330                 335

Asp Leu Pro Thr His Asp Gly Tyr Leu Pro Ser Asn Ile Asp Asp Leu
            340                 345                 350

Pro Ser His Glu Ala Pro Leu Ala Asp Ser Leu Glu Glu Leu Glu Pro
        355                 360                 365

Gln His Ile Ser Leu Ser Val Phe Pro Ser Ser Ser Leu His Pro Leu
    370                 375                 380

Thr Phe Ser Cys Gly Asp Lys Leu Thr Leu Asp Gln Leu Lys Met Arg
385                 390                 395                 400

Cys Asp Ser Leu Met Leu Gly Ser Gly Ala Thr Asn Phe Ser Leu Leu
                405                 410                 415

Lys Gln Ala Gly Asp Val Glu Glu Asn Pro Gly Pro Met Glu Ala Ala
            420                 425                 430

Val Ala Ala Pro Arg Pro Arg Leu Leu Leu Val Leu Ala Ala Ala
        435                 440                 445

Ala Ala Ala Ala Ala Leu Leu Pro Gly Ala Thr Ala Leu Gln Cys
    450                 455                 460

Phe Cys His Leu Cys Thr Lys Asp Asn Phe Thr Cys Val Thr Asp Gly
465                 470                 475                 480

Leu Cys Phe Val Ser Val Thr Glu Thr Thr Asp Lys Val Ile His Asn
                485                 490                 495

Ser Met Cys Ile Ala Glu Ile Asp Leu Ile Pro Arg Asp Arg Pro Phe
            500                 505                 510

Val Cys Ala Pro Ser Ser Lys Thr Gly Ser Val Thr Thr Thr Tyr Cys
        515                 520                 525

Cys Asn Gln Asp His Cys Asn Lys Ile Glu Leu Pro Thr Thr Val Lys
530                 535                 540
```

Ser Ser Pro Gly Leu Gly Pro Val Glu Leu Trp Leu Ile Phe Phe Ala
545                 550                 555                 560

Ser Leu Gly Ser Phe Leu Ser Ile Leu Leu Val Gly Val Leu Gly Tyr
            565                 570                 575

Leu Gly Leu Asn Arg Ala Ala Arg His Leu Cys Pro Pro Leu Pro Thr
            580                 585                 590

Pro Cys Ala Ser Ser Ala Ile Glu Phe Pro Gly Gly Lys Glu Thr Trp
            595                 600                 605

Gln Trp Ile Asn Pro Val Asp Phe Gln Glu Glu Ala Ser Leu Gln Glu
            610                 615                 620

Ala Leu Val Val Glu Met Ser Trp Asp Lys Gly Glu Arg Thr Glu Pro
625                 630                 635                 640

Leu Glu Lys Thr Glu Leu Pro Glu Gly Ala Pro Glu Leu Ala Leu Asp
            645                 650                 655

Thr Glu Leu Ser Leu Glu Asp Gly Asp Arg Cys Lys Ala Lys Met
            660                 665                 670

<210> SEQ ID NO 29
<211> LENGTH: 1183
<212> TYPE: PRT
<213> ORGANISM: Artificial Sequence
<220> FEATURE:
<223> OTHER INFORMATION: Made in Lab - Synthesized fusion protein

<400> SEQUENCE: 29

Met Ala Leu Pro Val Thr Ala Leu Leu Leu Pro Leu Ala Leu Leu Leu
1               5                   10                  15

His Ala Ala Arg Pro Gln Ser Ala Leu Thr Gln Pro Pro Ser Ala Ser
            20                  25                  30

Gly Thr Pro Gly Gln Arg Val Thr Ile Ser Cys Ser Gly Ser Ser Ser
            35                  40                  45

Asn Ile Gly Ser Asn Tyr Val Tyr Trp Tyr Gln Gln Leu Pro Gly Thr
50                  55                  60

Ala Pro Lys Leu Leu Ile Tyr Arg Asn Asn Gln Arg Pro Ser Gly Val
65                  70                  75                  80

Pro Asp Arg Phe Ser Gly Ser Lys Ser Gly Thr Ser Ala Ser Leu Ala
            85                  90                  95

Ile Ser Gly Leu Arg Ser Glu Asp Glu Ala Asp Tyr Tyr Cys Ala Ala
            100                 105                 110

Trp Asp Asp Ser Leu Ser Gly Tyr Val Phe Gly Thr Gly Thr Lys Val
            115                 120                 125

Thr Val Leu Gly Gly Gly Gly Ser Gly Gly Gly Ser Gly Gly
            130                 135                 140

Gly Gly Ser Gln Met Gln Leu Val Gln Ser Gly Ala Glu Val Lys Lys
145                 150                 155                 160

Pro Gly Ala Ser Val Lys Val Ser Cys Lys Ala Ser Gly Tyr Thr Phe
            165                 170                 175

Ser Arg Tyr Tyr Ile His Trp Val Arg Gln Ala Pro Gly Gln Gly Leu
            180                 185                 190

Glu Trp Met Gly Leu Ile Asn Pro Gly Gly Gly Ser Thr Asn Tyr Ala
            195                 200                 205

Gln Lys Phe Gln Gly Arg Val Thr Met Thr Arg Asp Thr Ser Thr Asn
            210                 215                 220

Thr Val Tyr Leu Glu Leu Ser Ser Leu Arg Ser Asp Asp Thr Ala Val
225                 230                 235                 240

Tyr Tyr Cys Ala Arg Asp Tyr Gly Thr Ile Asp Ala Arg Arg Phe Asp
                245                 250                 255

Phe Trp Gly Gln Gly Thr Leu Val Thr Val Ser Ser Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg Gly Ser Gly Glu Gly
                485                 490                 495

Arg Gly Ser Leu Leu Thr Cys Gly Asp Val Glu Glu Asn Pro Gly Pro
            500                 505                 510

Met Gly Arg Gly Leu Leu Arg Gly Leu Trp Pro Leu His Ile Val Leu
        515                 520                 525

Trp Thr Arg Ile Ala Ser Thr Ile Pro Pro His Val Gln Lys Ser Val
    530                 535                 540

Asn Asn Asp Met Ile Val Thr Asp Asn Asn Gly Ala Val Lys Phe Pro
545                 550                 555                 560

Gln Leu Cys Lys Phe Cys Asp Val Arg Phe Ser Thr Cys Asp Asn Gln
                565                 570                 575

Lys Ser Cys Met Ser Asn Cys Ser Ile Thr Ser Ile Cys Glu Lys Pro
            580                 585                 590

Gln Glu Val Cys Val Ala Val Trp Arg Lys Asn Asp Glu Asn Ile Thr
        595                 600                 605

Leu Glu Thr Val Cys His Asp Pro Lys Leu Pro Tyr His Asp Phe Ile
    610                 615                 620

Leu Glu Asp Ala Ala Ser Pro Lys Cys Ile Met Lys Glu Lys Lys Lys
625                 630                 635                 640

Pro Gly Glu Thr Phe Phe Met Cys Ser Cys Ser Ser Asp Glu Cys Asn
                645                 650                 655

```
Asp Asn Ile Ile Phe Ser Glu Glu Tyr Asn Thr Ser Asn Pro Asp Leu
            660                 665                 670

Leu Leu Val Ile Phe Gln Trp Met Ala Phe Val Ala Pro Ser Ile Cys
        675                 680                 685

Ile Ala Ile Ile Met Val Gly Ile Phe Ser Thr His Tyr Phe Gln Gln
    690                 695                 700

Lys Val Phe Val Leu Leu Ala Ala Leu Arg Pro Gln Trp Cys Ser Arg
705                 710                 715                 720

Glu Ile Pro Asp Pro Ala Asn Ser Thr Cys Ala Lys Lys Tyr Pro Ile
                725                 730                 735

Ala Glu Glu Lys Thr Gln Leu Pro Leu Asp Arg Leu Leu Ile Asp Trp
            740                 745                 750

Pro Thr Pro Glu Asp Pro Glu Pro Leu Val Ile Ser Glu Val Leu His
        755                 760                 765

Gln Val Thr Pro Val Phe Arg His Pro Pro Cys Ser Asn Trp Pro Gln
    770                 775                 780

Arg Glu Lys Gly Ile Gln Gly His Gln Ala Ser Glu Lys Asp Met Met
785                 790                 795                 800

His Ser Ala Ser Ser Pro Pro Pro Arg Ala Leu Gln Ala Glu Ser
                805                 810                 815

Arg Gln Leu Val Asp Leu Tyr Lys Val Leu Glu Ser Arg Gly Ser Asp
            820                 825                 830

Pro Lys Pro Glu Asn Pro Ala Cys Pro Trp Thr Val Leu Pro Ala Gly
        835                 840                 845

Asp Leu Pro Thr His Asp Gly Tyr Leu Pro Ser Asn Ile Asp Asp Leu
    850                 855                 860

Pro Ser His Glu Ala Pro Leu Ala Asp Ser Leu Glu Glu Leu Glu Pro
865                 870                 875                 880

Gln His Ile Ser Leu Ser Val Phe Pro Ser Ser Ser Leu His Pro Leu
                885                 890                 895

Thr Phe Ser Cys Gly Asp Lys Leu Thr Leu Asp Gln Leu Lys Met Arg
            900                 905                 910

Cys Asp Ser Leu Met Leu Gly Ser Gly Ala Thr Asn Phe Ser Leu Leu
        915                 920                 925

Lys Gln Ala Gly Asp Val Glu Glu Asn Pro Gly Pro Met Glu Ala Ala
    930                 935                 940

Val Ala Ala Pro Arg Pro Arg Leu Leu Leu Leu Val Leu Ala Ala Ala
945                 950                 955                 960

Ala Ala Ala Ala Ala Leu Leu Pro Gly Ala Thr Ala Leu Gln Cys
                965                 970                 975

Phe Cys His Leu Cys Thr Lys Asp Asn Phe Thr Cys Val Thr Asp Gly
            980                 985                 990

Leu Cys Phe Val Ser Val Thr Glu  Thr Thr Asp Lys Val Ile His Asn
        995                 1000                1005

Ser Met Cys Ile Ala Glu Ile Asp Leu Ile Pro Arg Asp Arg Pro
                1010                1015                1020

Phe Val Cys Ala Pro Ser Ser Lys Thr Gly Ser Val Thr Thr Thr
            1025                1030                1035

Tyr Cys Cys Asn Gln Asp His Cys Asn Lys Ile Glu Leu Pro Thr
            1040                1045                1050

Thr Val Lys Ser Ser Pro Gly Leu Gly Pro Val Glu Leu Trp Leu
            1055                1060                1065
```

```
Ile Phe Phe Ala Ser Leu Gly Ser Phe Leu Ser Ile Leu Leu Val
    1070                1075                1080

Gly Val Leu Gly Tyr Leu Gly Leu Asn Arg Ala Ala Arg His Leu
    1085                1090                1095

Cys Pro Pro Leu Pro Thr Pro Cys Ala Ser Ser Ala Ile Glu Phe
    1100                1105                1110

Pro Gly Gly Lys Glu Thr Trp Gln Trp Ile Asn Pro Val Asp Phe
    1115                1120                1125

Gln Glu Glu Ala Ser Leu Gln Glu Ala Leu Val Val Glu Met Ser
    1130                1135                1140

Trp Asp Lys Gly Glu Arg Thr Glu Pro Leu Glu Lys Thr Glu Leu
    1145                1150                1155

Pro Glu Gly Ala Pro Glu Leu Ala Leu Asp Thr Glu Leu Ser Leu
    1160                1165                1170

Glu Asp Gly Asp Arg Cys Lys Ala Lys Met
    1175                1180

<210> SEQ ID NO 30
<211> LENGTH: 937
<212> TYPE: PRT
<213> ORGANISM: Artificial Sequence
<220> FEATURE:
<223> OTHER INFORMATION: Made in Lab - Synthesized fusion protein
<220> FEATURE:
<221> NAME/KEY: misc_feature
<222> LOCATION: (22)..(22)
<223> OTHER INFORMATION: Xaa can be any naturally occurring amino acid

<400> SEQUENCE: 30

Met Ala Leu Pro Val Thr Ala Leu Leu Leu Pro Leu Ala Leu Leu
1               5                   10                  15

His Ala Ala Arg Pro Xaa Thr Thr Thr Pro Ala Pro Arg Pro Pro Thr
                20                  25                  30

Pro Ala Pro Thr Ile Ala Ser Gln Pro Leu Ser Leu Arg Pro Glu Ala
            35                  40                  45

Cys Arg Pro Ala Ala Gly Gly Ala Val His Thr Arg Gly Leu Asp Phe
    50                  55                  60

Ala Cys Asp Ile Tyr Ile Trp Ala Pro Leu Ala Gly Thr Cys Gly Val
65                  70                  75                  80

Leu Leu Leu Ser Leu Val Ile Thr Leu Tyr Cys Lys Arg Gly Arg Lys
                85                  90                  95

Lys Leu Leu Tyr Ile Phe Lys Gln Pro Phe Met Arg Pro Val Gln Thr
                100                 105                 110

Thr Gln Glu Glu Asp Gly Cys Ser Cys Arg Phe Pro Glu Glu Glu Glu
            115                 120                 125

Gly Gly Cys Glu Leu Arg Val Lys Phe Ser Arg Ser Ala Asp Ala Pro
    130                 135                 140

Ala Tyr Gln Gln Gly Gln Asn Gln Leu Tyr Asn Glu Leu Asn Leu Gly
145                 150                 155                 160

Arg Arg Glu Glu Tyr Asp Val Leu Asp Lys Arg Arg Gly Arg Asp Pro
                165                 170                 175

Glu Met Gly Gly Lys Pro Arg Arg Lys Asn Pro Gln Glu Gly Leu Tyr
                180                 185                 190

Asn Glu Leu Gln Lys Asp Lys Met Ala Glu Ala Tyr Ser Glu Ile Gly
            195                 200                 205

Met Lys Gly Glu Arg Arg Arg Gly Lys Gly His Asp Gly Leu Tyr Gln
    210                 215                 220
```

```
Gly Leu Ser Thr Ala Thr Lys Asp Thr Tyr Asp Ala Leu His Met Gln
225                 230                 235                 240

Ala Leu Pro Pro Arg Gly Ser Gly Glu Gly Arg Gly Ser Leu Leu Thr
            245                 250                 255

Cys Gly Asp Val Glu Glu Asn Pro Gly Pro Met Gly Arg Gly Leu Leu
                260                 265                 270

Arg Gly Leu Trp Pro Leu His Ile Val Leu Trp Thr Arg Ile Ala Ser
        275                 280                 285

Thr Ile Pro Pro His Val Gln Lys Ser Val Asn Asn Asp Met Ile Val
        290                 295                 300

Thr Asp Asn Asn Gly Ala Val Lys Phe Pro Gln Leu Cys Lys Phe Cys
305                 310                 315                 320

Asp Val Arg Phe Ser Thr Cys Asp Asn Gln Lys Ser Cys Met Ser Asn
                325                 330                 335

Cys Ser Ile Thr Ser Ile Cys Glu Lys Pro Gln Glu Val Cys Val Ala
            340                 345                 350

Val Trp Arg Lys Asn Asp Glu Asn Ile Thr Leu Glu Thr Val Cys His
        355                 360                 365

Asp Pro Lys Leu Pro Tyr His Asp Phe Ile Leu Glu Asp Ala Ala Ser
    370                 375                 380

Pro Lys Cys Ile Met Lys Glu Lys Lys Pro Gly Glu Thr Phe Phe
385                 390                 395                 400

Met Cys Ser Cys Ser Ser Asp Glu Cys Asn Asp Asn Ile Ile Phe Ser
                405                 410                 415

Glu Glu Tyr Asn Thr Ser Asn Pro Asp Leu Leu Leu Val Ile Phe Gln
            420                 425                 430

Trp Met Ala Phe Val Ala Pro Ser Ile Cys Ile Ala Ile Ile Met Val
        435                 440                 445

Gly Ile Phe Ser Thr His Tyr Phe Gln Gln Lys Val Phe Val Leu Leu
    450                 455                 460

Ala Ala Leu Arg Pro Gln Trp Cys Ser Arg Glu Ile Pro Asp Pro Ala
465                 470                 475                 480

Asn Ser Thr Cys Ala Lys Lys Tyr Pro Ile Ala Glu Glu Lys Thr Gln
                485                 490                 495

Leu Pro Leu Asp Arg Leu Leu Ile Asp Trp Pro Thr Pro Glu Asp Pro
            500                 505                 510

Glu Pro Leu Val Ile Ser Glu Val Leu His Gln Val Thr Pro Val Phe
        515                 520                 525

Arg His Pro Pro Cys Ser Asn Trp Pro Gln Arg Glu Lys Gly Ile Gln
    530                 535                 540

Gly His Gln Ala Ser Glu Lys Asp Met Met His Ser Ala Ser Ser Pro
545                 550                 555                 560

Pro Pro Pro Arg Ala Leu Gln Ala Glu Ser Arg Gln Leu Val Asp Leu
                565                 570                 575

Tyr Lys Val Leu Glu Ser Arg Gly Ser Asp Pro Lys Pro Glu Asn Pro
            580                 585                 590

Ala Cys Pro Trp Thr Val Leu Pro Ala Gly Asp Leu Pro Thr His Asp
        595                 600                 605

Gly Tyr Leu Pro Ser Asn Ile Asp Asp Leu Pro Ser His Glu Ala Pro
    610                 615                 620

Leu Ala Asp Ser Leu Glu Glu Leu Glu Pro Gln His Ile Ser Leu Ser
625                 630                 635                 640
```

```
Val Phe Pro Ser Ser Ser Leu His Pro Leu Thr Phe Ser Cys Gly Asp
            645                 650                 655

Lys Leu Thr Leu Asp Gln Leu Lys Met Arg Cys Asp Ser Leu Met Leu
            660                 665                 670

Gly Ser Gly Ala Thr Asn Phe Ser Leu Leu Lys Gln Ala Gly Asp Val
            675                 680                 685

Glu Glu Asn Pro Gly Pro Met Glu Ala Val Ala Ala Pro Arg Pro
            690                 695                 700

Arg Leu Leu Leu Leu Val Leu Ala Ala Ala Ala Ala Ala Ala Ala
705                 710                 715                 720

Leu Leu Pro Gly Ala Thr Ala Leu Gln Cys Phe Cys His Leu Cys Thr
            725                 730                 735

Lys Asp Asn Phe Thr Cys Val Thr Asp Gly Leu Cys Phe Val Ser Val
            740                 745                 750

Thr Glu Thr Thr Asp Lys Val Ile His Asn Ser Met Cys Ile Ala Glu
            755                 760                 765

Ile Asp Leu Ile Pro Arg Asp Arg Pro Phe Val Cys Ala Pro Ser Ser
            770                 775                 780

Lys Thr Gly Ser Val Thr Thr Thr Tyr Cys Cys Asn Gln Asp His Cys
785                 790                 795                 800

Asn Lys Ile Glu Leu Pro Thr Thr Val Lys Ser Ser Pro Gly Leu Gly
            805                 810                 815

Pro Val Glu Leu Trp Leu Ile Phe Phe Ala Ser Leu Gly Ser Phe Leu
            820                 825                 830

Ser Ile Leu Leu Val Gly Val Leu Gly Tyr Leu Gly Leu Asn Arg Ala
            835                 840                 845

Ala Arg His Leu Cys Pro Pro Leu Pro Thr Pro Cys Ala Ser Ser Ala
850                 855                 860

Ile Glu Phe Pro Gly Gly Lys Glu Thr Trp Gln Trp Ile Asn Pro Val
865                 870                 875                 880

Asp Phe Gln Glu Glu Ala Ser Leu Gln Glu Ala Leu Val Val Glu Met
            885                 890                 895

Ser Trp Asp Lys Gly Glu Arg Thr Glu Pro Leu Glu Lys Thr Glu Leu
            900                 905                 910

Pro Glu Gly Ala Pro Glu Leu Ala Leu Asp Thr Glu Leu Ser Leu Glu
            915                 920                 925

Asp Gly Asp Arg Cys Lys Ala Lys Met
            930                 935
```

<210> SEQ ID NO 31
<211> LENGTH: 233
<212> TYPE: PRT
<213> ORGANISM: Artificial Sequence
<220> FEATURE:
<223> OTHER INFORMATION: Made in Lab - Synthesized fusion protein

<400> SEQUENCE: 31

```
Met Glu Ala Ala Val Ala Ala Pro Arg Pro Arg Leu Leu Leu Leu Val
1               5                   10                  15

Leu Ala Ala Ala Ala Ala Ala Ala Ala Ala Leu Leu Pro Gly Ala Thr
                20                  25                  30

Ala Leu Gln Cys Phe Cys His Leu Cys Thr Lys Asp Asn Phe Thr Cys
                35                  40                  45

Val Thr Asp Gly Leu Cys Phe Val Ser Val Thr Glu Thr Thr Asp Lys
            50                  55                  60
```

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Val Lys Ser Ser Pro Gly Leu Gly Pro Val Glu Leu Val Val
            115                 120                 125

Ile Ser Val Gly Ser Met Gly Leu Ile Ile Ser Leu Leu Cys Val Tyr
130                 135                 140

Phe Trp Leu Glu Arg Thr Met Pro Arg Ile Pro Thr Leu Lys Asn Leu
145                 150                 155                 160

Glu Asp Leu Val Thr Glu Tyr His Gly Asn Phe Ser Ala Trp Ser Gly
                165                 170                 175

Val Ser Lys Gly Leu Ala Glu Ser Leu Gln Pro Asp Tyr Ser Glu Arg
                180                 185                 190

Leu Cys Leu Val Ser Glu Ile Pro Pro Lys Gly Gly Ala Leu Gly Glu
            195                 200                 205

Gly Pro Gly Ala Ser Pro Cys Asn Gln His Ser Pro Tyr Trp Ala Pro
210                 215                 220

Pro Cys Tyr Thr Leu Lys Pro Glu Thr
225                 230

<210> SEQ ID NO 32
<211> LENGTH: 386
<212> TYPE: PRT
<213> ORGANISM: Artificial Sequence
<220> FEATURE:
<223> OTHER INFORMATION: Made in Lab - Synthesized fusion protein

<400> SEQUENCE: 32

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
                20                  25                  30

Asn Asn Asp Met Ile Val Thr Asp Asn Asn Gly Ala Val Lys Phe Pro
            35                  40                  45

Gln Leu Cys Lys Phe Cys Asp Val Arg Phe Ser Thr Cys Asp Asn Gln
        50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
            115                 120                 125

Pro Gly Glu Thr Phe Phe Met Cys Ser Cys Ser Ser Asp Glu Cys Asn
130                 135                 140

Asp Asn Ile Ile Phe Ser Glu Glu Tyr Asn Thr Ser Asn Pro Asp Leu
145                 150                 155                 160

Leu Leu Val Ile Phe Gln Pro Ile Leu Leu Thr Ile Ser Ile Leu Ser
            165                 170                 175

Phe Phe Ser Val Ala Leu Leu Val Ile Leu Ala Cys Val Leu Trp Lys
            180                 185                 190

```
Lys Arg Ile Lys Pro Ile Val Trp Pro Ser Leu Pro Asp His Lys Lys
            195                 200                 205

Thr Leu Glu His Leu Cys Lys Lys Pro Arg Lys Asn Leu Asn Val Ser
        210                 215                 220

Phe Asn Pro Glu Ser Phe Leu Asp Cys Gln Ile His Arg Val Asp Asp
225                 230                 235                 240

Ile Gln Ala Arg Asp Glu Val Glu Gly Phe Leu Gln Asp Thr Phe Pro
                245                 250                 255

Gln Gln Leu Glu Ser Glu Lys Gln Arg Leu Gly Gly Asp Val Gln
            260                 265                 270

Ser Pro Asn Cys Pro Ser Glu Asp Val Val Ile Thr Pro Glu Ser Phe
        275                 280                 285

Gly Arg Asp Ser Ser Leu Thr Cys Leu Ala Gly Asn Val Ser Ala Cys
290                 295                 300

Asp Ala Pro Ile Leu Ser Ser Ser Arg Ser Leu Asp Cys Arg Glu Ser
305                 310                 315                 320

Gly Lys Asn Gly Pro His Val Tyr Gln Asp Leu Leu Leu Ser Leu Gly
                325                 330                 335

Thr Thr Asn Ser Thr Leu Pro Pro Phe Ser Leu Gln Ser Gly Ile
            340                 345                 350

Leu Thr Leu Asn Pro Val Ala Gln Gly Gln Pro Ile Leu Thr Ser Leu
            355                 360                 365

Gly Ser Asn Gln Glu Glu Ala Tyr Val Thr Met Ser Ser Phe Tyr Gln
        370                 375                 380

Asn Gln
385

<210> SEQ ID NO 33
<211> LENGTH: 641
<212> TYPE: PRT
<213> ORGANISM: Artificial Sequence
<220> FEATURE:
<223> OTHER INFORMATION: Made in Lab - Synthesized fusion protein

<400> SEQUENCE: 33

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160
```

-continued

```
Leu Leu Val Ile Phe Gln Pro Ile Leu Leu Thr Ile Ser Ile Leu Ser
                165                 170                 175
Phe Phe Ser Val Ala Leu Leu Val Ile Leu Ala Cys Val Leu Trp Lys
            180                 185                 190
Lys Arg Ile Lys Pro Ile Val Trp Pro Ser Leu Pro Asp His Lys Lys
        195                 200                 205
Thr Leu Glu His Leu Cys Lys Lys Pro Arg Lys Asn Leu Asn Val Ser
    210                 215                 220
Phe Asn Pro Glu Ser Phe Leu Asp Cys Gln Ile His Arg Val Asp Asp
225                 230                 235                 240
Ile Gln Ala Arg Asp Glu Val Glu Gly Phe Leu Gln Asp Thr Phe Pro
                245                 250                 255
Gln Gln Leu Glu Glu Ser Glu Lys Gln Arg Leu Gly Gly Asp Val Gln
            260                 265                 270
Ser Pro Asn Cys Pro Ser Glu Asp Val Val Ile Thr Pro Glu Ser Phe
        275                 280                 285
Gly Arg Asp Ser Ser Leu Thr Cys Leu Ala Gly Asn Val Ser Ala Cys
    290                 295                 300
Asp Ala Pro Ile Leu Ser Ser Ser Arg Ser Leu Asp Cys Arg Glu Ser
305                 310                 315                 320
Gly Lys Asn Gly Pro His Val Tyr Gln Asp Leu Leu Leu Ser Leu Gly
                325                 330                 335
Thr Thr Asn Ser Thr Leu Pro Pro Pro Phe Ser Leu Gln Ser Gly Ile
            340                 345                 350
Leu Thr Leu Asn Pro Val Ala Gln Gly Gln Pro Ile Leu Thr Ser Leu
        355                 360                 365
Gly Ser Asn Gln Glu Glu Ala Tyr Val Thr Met Ser Ser Phe Tyr Gln
    370                 375                 380
Asn Gln Gly Ser Gly Ala Thr Asn Phe Ser Leu Leu Lys Gln Ala Gly
385                 390                 395                 400
Asp Val Glu Glu Asn Pro Gly Pro Met Glu Ala Ala Val Ala Ala Pro
                405                 410                 415
Arg Pro Arg Leu Leu Leu Leu Val Leu Ala Ala Ala Ala Ala Ala Ala
            420                 425                 430
Ala Ala Leu Leu Pro Gly Ala Thr Ala Leu Gln Cys Phe Cys His Leu
        435                 440                 445
Cys Thr Lys Asp Asn Phe Thr Cys Val Thr Asp Gly Leu Cys Phe Val
    450                 455                 460
Ser Val Thr Glu Thr Thr Asp Lys Val Ile His Asn Ser Met Cys Ile
465                 470                 475                 480
Ala Glu Ile Asp Leu Ile Pro Arg Asp Arg Pro Phe Val Cys Ala Pro
                485                 490                 495
Ser Ser Lys Thr Gly Ser Val Thr Thr Thr Tyr Cys Cys Asn Gln Asp
            500                 505                 510
His Cys Asn Lys Ile Glu Leu Pro Thr Thr Val Lys Ser Ser Pro Gly
        515                 520                 525
Leu Gly Pro Val Glu Leu Val Ile Ser Val Gly Ser Met Gly Leu
    530                 535                 540
Ile Ile Ser Leu Leu Cys Val Tyr Phe Trp Leu Glu Arg Thr Met Pro
545                 550                 555                 560
Arg Ile Pro Thr Leu Lys Asn Leu Glu Asp Leu Val Thr Glu Tyr His
                565                 570                 575
```

```
Gly Asn Phe Ser Ala Trp Ser Gly Val Ser Lys Gly Leu Ala Glu Ser
            580                 585                 590

Leu Gln Pro Asp Tyr Ser Glu Arg Leu Cys Leu Val Ser Glu Ile Pro
        595                 600                 605

Pro Lys Gly Gly Ala Leu Gly Glu Gly Pro Gly Ala Ser Pro Cys Asn
    610                 615                 620

Gln His Ser Pro Tyr Trp Ala Pro Pro Cys Tyr Thr Leu Lys Pro Glu
625                 630                 635                 640

Thr

<210> SEQ ID NO 34
<211> LENGTH: 1153
<212> TYPE: PRT
<213> ORGANISM: Artificial Sequence
<220> FEATURE:
<223> OTHER INFORMATION: Made in Lab - Synthesized fusion protein

<400> SEQUENCE: 34

Met Ala Leu Pro Val Thr Ala Leu Leu Leu Pro Leu Ala Leu Leu Leu
1               5                   10                  15

His Ala Ala Arg Pro Gln Ser Ala Leu Thr Gln Pro Ser Ala Ser
            20                  25                  30

Gly Thr Pro Gly Gln Arg Val Thr Ile Ser Cys Ser Gly Ser Ser Ser
        35                  40                  45

Asn Ile Gly Ser Asn Tyr Val Tyr Trp Tyr Gln Gln Leu Pro Gly Thr
    50                  55                  60

Ala Pro Lys Leu Leu Ile Tyr Arg Asn Asn Gln Arg Pro Ser Gly Val
65                  70                  75                  80

Pro Asp Arg Phe Ser Gly Ser Lys Ser Gly Thr Ser Ala Ser Leu Ala
                85                  90                  95

Ile Ser Gly Leu Arg Ser Glu Asp Glu Ala Asp Tyr Tyr Cys Ala Ala
            100                 105                 110

Trp Asp Asp Ser Leu Ser Gly Tyr Val Phe Gly Thr Gly Thr Lys Val
        115                 120                 125

Thr Val Leu Gly Gly Gly Gly Ser Gly Gly Gly Ser Gly Gly
    130                 135                 140

Gly Gly Ser Gln Met Gln Leu Val Gln Ser Gly Ala Glu Val Lys Lys
145                 150                 155                 160

Pro Gly Ala Ser Val Lys Val Ser Cys Lys Ala Ser Gly Tyr Thr Phe
                165                 170                 175

Ser Arg Tyr Tyr Ile His Trp Val Arg Gln Ala Pro Gly Gln Gly Leu
            180                 185                 190

Glu Trp Met Gly Leu Ile Asn Pro Gly Gly Gly Ser Thr Asn Tyr Ala
        195                 200                 205

Gln Lys Phe Gln Gly Arg Val Thr Met Thr Arg Asp Thr Ser Thr Asn
    210                 215                 220

Thr Val Tyr Leu Glu Leu Ser Ser Leu Arg Ser Asp Asp Thr Ala Val
225                 230                 235                 240

Tyr Tyr Cys Ala Arg Asp Tyr Gly Thr Ile Asp Ala Arg Arg Phe Asp
                245                 250                 255

Phe Trp Gly Gln Gly Thr Leu Val Thr Val Ser Ser Thr Thr Thr Pro
            260                 265                 270

Ala Pro Arg Pro Pro Thr Pro Ala Pro Thr Ile Ala Ser Gln Pro Leu
        275                 280                 285
```

```
Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Ser Leu Val Ile Thr Leu Tyr
                325                 330                 335

Cys Lys Arg Gly Arg Lys Leu Leu Tyr Ile Phe Lys Gln Pro Phe
            340                 345                 350

Met Arg Pro Val Gln Thr Thr Gln Glu Asp Gly Cys Ser Cys Arg
        355                 360                 365

Phe Pro Glu Glu Glu Gly Gly Cys Glu Leu Arg Val Lys Phe Ser
370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg Gly Ser Gly Glu Gly
                485                 490                 495

Arg Gly Ser Leu Leu Thr Cys Gly Asp Val Glu Glu Asn Pro Gly Pro
            500                 505                 510

Met Gly Arg Gly Leu Leu Arg Gly Leu Trp Pro Leu His Ile Val Leu
        515                 520                 525

Trp Thr Arg Ile Ala Ser Thr Ile Pro Pro His Val Gln Lys Ser Val
    530                 535                 540

Asn Asn Asp Met Ile Val Thr Asp Asn Asn Gly Ala Val Lys Phe Pro
545                 550                 555                 560

Gln Leu Cys Lys Phe Cys Asp Val Arg Phe Ser Thr Cys Asp Asn Gln
                565                 570                 575

Lys Ser Cys Met Ser Asn Cys Ser Ile Thr Ser Ile Cys Glu Lys Pro
            580                 585                 590

Gln Glu Val Cys Val Ala Val Trp Arg Lys Asn Asp Glu Asn Ile Thr
        595                 600                 605

Leu Glu Thr Val Cys His Asp Pro Lys Leu Pro Tyr His Asp Phe Ile
610                 615                 620

Leu Glu Asp Ala Ala Ser Pro Lys Cys Ile Met Lys Glu Lys Lys
625                 630                 635                 640

Pro Gly Glu Thr Phe Phe Met Cys Ser Cys Ser Ser Asp Glu Cys Asn
                645                 650                 655

Asp Asn Ile Ile Phe Ser Glu Glu Tyr Asn Thr Ser Asn Pro Asp Leu
            660                 665                 670

Leu Leu Val Ile Phe Gln Pro Ile Leu Leu Thr Ile Ser Ile Leu Ser
        675                 680                 685

Phe Phe Ser Val Ala Leu Leu Val Ile Leu Ala Cys Val Leu Trp Lys
690                 695                 700
```

-continued

Lys Arg Ile Lys Pro Ile Val Trp Pro Ser Leu Pro Asp His Lys Lys
705                 710                 715                 720

Thr Leu Glu His Leu Cys Lys Lys Pro Arg Lys Asn Leu Asn Val Ser
            725                 730                 735

Phe Asn Pro Glu Ser Phe Leu Asp Cys Gln Ile His Arg Val Asp Asp
        740                 745                 750

Ile Gln Ala Arg Asp Glu Val Glu Gly Phe Leu Gln Asp Thr Phe Pro
    755                 760                 765

Gln Gln Leu Glu Glu Ser Glu Lys Gln Arg Leu Gly Gly Asp Val Gln
770                 775                 780

Ser Pro Asn Cys Pro Ser Glu Asp Val Val Ile Thr Pro Glu Ser Phe
785                 790                 795                 800

Gly Arg Asp Ser Ser Leu Thr Cys Leu Ala Gly Asn Val Ser Ala Cys
            805                 810                 815

Asp Ala Pro Ile Leu Ser Ser Arg Ser Leu Asp Cys Arg Glu Ser
        820                 825                 830

Gly Lys Asn Gly Pro His Val Tyr Gln Asp Leu Leu Leu Ser Leu Gly
            835                 840                 845

Thr Thr Asn Ser Thr Leu Pro Pro Phe Ser Leu Gln Ser Gly Ile
850                 855                 860

Leu Thr Leu Asn Pro Val Ala Gln Gly Gln Pro Ile Leu Thr Ser Leu
865                 870                 875                 880

Gly Ser Asn Gln Glu Glu Ala Tyr Val Thr Met Ser Ser Phe Tyr Gln
            885                 890                 895

Asn Gln Gly Ser Gly Ala Thr Asn Phe Ser Leu Leu Lys Gln Ala Gly
            900                 905                 910

Asp Val Glu Glu Asn Pro Gly Pro Met Glu Ala Ala Val Ala Ala Pro
            915                 920                 925

Arg Pro Arg Leu Leu Leu Leu Val Leu Ala Ala Ala Ala Ala Ala
        930                 935                 940

Ala Ala Leu Leu Pro Gly Ala Thr Ala Leu Gln Cys Phe Cys His Leu
945                 950                 955                 960

Cys Thr Lys Asp Asn Phe Thr Cys Val Thr Asp Gly Leu Cys Phe Val
            965                 970                 975

Ser Val Thr Glu Thr Thr Asp Lys Val Ile His Asn Ser Met Cys Ile
            980                 985                 990

Ala Glu Ile Asp Leu Ile Pro Arg Asp Arg Pro Phe Val Cys Ala Pro
        995                 1000                1005

Ser Ser Lys Thr Gly Ser Val Thr Thr Thr Tyr Cys Cys Asn Gln
    1010                1015                1020

Asp His Cys Asn Lys Ile Glu Leu Pro Thr Thr Val Lys Ser Ser
    1025                1030                1035

Pro Gly Leu Gly Pro Val Glu Leu Val Val Ile Ser Val Gly Ser
    1040                1045                1050

Met Gly Leu Ile Ile Ser Leu Leu Cys Val Tyr Phe Trp Leu Glu
    1055                1060                1065

Arg Thr Met Pro Arg Ile Pro Thr Leu Lys Asn Leu Glu Asp Leu
    1070                1075                1080

Val Thr Glu Tyr His Gly Asn Phe Ser Ala Trp Ser Gly Val Ser
    1085                1090                1095

Lys Gly Leu Ala Glu Ser Leu Gln Pro Asp Tyr Ser Glu Arg Leu
    1100                1105                1110

```
Cys Leu Val Ser Glu Ile Pro Pro Lys Gly Gly Ala Leu Gly Glu
    1115                1120                1125

Gly Pro Gly Ala Ser Pro Cys Asn Gln His Ser Pro Tyr Trp Ala
    1130                1135                1140

Pro Pro Cys Tyr Thr Leu Lys Pro Glu Thr
    1145                1150

<210> SEQ ID NO 35
<211> LENGTH: 907
<212> TYPE: PRT
<213> ORGANISM: Artificial Sequence
<220> FEATURE:
<223> OTHER INFORMATION: Made in Lab - Synthesized fusion protein
<220> FEATURE:
<221> NAME/KEY: misc_feature
<222> LOCATION: (22)..(22)
<223> OTHER INFORMATION: Xaa can be any naturally occurring amino acid

<400> SEQUENCE: 35

Met Ala Leu Pro Val Thr Ala Leu Leu Leu Pro Leu Ala Leu Leu
1               5                   10                  15

His Ala Ala Arg Pro Xaa Thr Thr Thr Pro Ala Pro Arg Pro Pro Thr
                20                  25                  30

Pro Ala Pro Thr Ile Ala Ser Gln Pro Leu Ser Leu Arg Pro Glu Ala
            35                  40                  45

Cys Arg Pro Ala Ala Gly Gly Ala Val His Thr Arg Gly Leu Asp Phe
50                  55                  60

Ala Cys Asp Ile Tyr Ile Trp Ala Pro Leu Ala Gly Thr Cys Gly Val
65                  70                  75                  80

Leu Leu Leu Ser Leu Val Ile Thr Leu Tyr Cys Lys Arg Gly Arg Lys
                85                  90                  95

Lys Leu Leu Tyr Ile Phe Lys Gln Pro Phe Met Arg Pro Val Gln Thr
            100                 105                 110

Thr Gln Glu Glu Asp Gly Cys Ser Cys Arg Phe Pro Glu Glu Glu Glu
        115                 120                 125

Gly Gly Cys Glu Leu Arg Val Lys Phe Ser Arg Ser Ala Asp Ala Pro
130                 135                 140

Ala Tyr Gln Gln Gly Gln Asn Gln Leu Tyr Asn Glu Leu Asn Leu Gly
145                 150                 155                 160

Arg Arg Glu Glu Tyr Asp Val Leu Asp Lys Arg Gly Arg Asp Pro
                165                 170                 175

Glu Met Gly Gly Lys Pro Arg Arg Lys Asn Pro Gln Glu Gly Leu Tyr
            180                 185                 190

Asn Glu Leu Gln Lys Asp Lys Met Ala Glu Ala Tyr Ser Glu Ile Gly
        195                 200                 205

Met Lys Gly Glu Arg Arg Arg Gly Lys Gly His Asp Gly Leu Tyr Gln
210                 215                 220

Gly Leu Ser Thr Ala Thr Lys Asp Thr Tyr Asp Ala Leu His Met Gln
225                 230                 235                 240

Ala Leu Pro Pro Arg Gly Ser Gly Glu Gly Arg Gly Ser Leu Leu Thr
                245                 250                 255

Cys Gly Asp Val Glu Glu Asn Pro Gly Pro Met Gly Arg Gly Leu Leu
            260                 265                 270

Arg Gly Leu Trp Pro Leu His Ile Val Leu Trp Thr Arg Ile Ala Ser
        275                 280                 285

Thr Ile Pro Pro His Val Gln Lys Ser Val Asn Asn Asp Met Ile Val
290                 295                 300
```

```
Thr Asp Asn Asn Gly Ala Val Lys Phe Pro Gln Leu Cys Lys Phe Cys
305                 310                 315                 320

Asp Val Arg Phe Ser Thr Cys Asp Asn Gln Lys Ser Cys Met Ser Asn
                325                 330                 335

Cys Ser Ile Thr Ser Ile Cys Glu Lys Pro Gln Glu Val Cys Val Ala
            340                 345                 350

Val Trp Arg Lys Asn Asp Glu Asn Ile Thr Leu Glu Thr Val Cys His
        355                 360                 365

Asp Pro Lys Leu Pro Tyr His Asp Phe Ile Leu Glu Asp Ala Ala Ser
    370                 375                 380

Pro Lys Cys Ile Met Lys Glu Lys Lys Pro Gly Glu Thr Phe Phe
385                 390                 395                 400

Met Cys Ser Cys Ser Ser Asp Glu Cys Asn Asp Asn Ile Ile Phe Ser
                405                 410                 415

Glu Glu Tyr Asn Thr Ser Asn Pro Asp Leu Leu Val Ile Phe Gln
            420                 425                 430

Pro Ile Leu Leu Thr Ile Ser Ile Leu Ser Phe Phe Ser Val Ala Leu
        435                 440                 445

Leu Val Ile Leu Ala Cys Val Leu Trp Lys Lys Arg Ile Lys Pro Ile
450                 455                 460

Val Trp Pro Ser Leu Pro Asp His Lys Lys Thr Leu Glu His Leu Cys
465                 470                 475                 480

Lys Lys Pro Arg Lys Asn Leu Asn Val Ser Phe Asn Pro Glu Ser Phe
                485                 490                 495

Leu Asp Cys Gln Ile His Arg Val Asp Asp Ile Gln Ala Arg Asp Glu
            500                 505                 510

Val Glu Gly Phe Leu Gln Asp Thr Phe Pro Gln Gln Leu Glu Glu Ser
        515                 520                 525

Glu Lys Gln Arg Leu Gly Gly Asp Val Gln Ser Pro Asn Cys Pro Ser
    530                 535                 540

Glu Asp Val Val Ile Thr Pro Glu Ser Phe Gly Arg Asp Ser Ser Leu
545                 550                 555                 560

Thr Cys Leu Ala Gly Asn Val Ser Ala Cys Asp Ala Pro Ile Leu Ser
                565                 570                 575

Ser Ser Arg Ser Leu Asp Cys Arg Glu Ser Gly Lys Asn Gly Pro His
            580                 585                 590

Val Tyr Gln Asp Leu Leu Leu Ser Leu Gly Thr Thr Asn Ser Thr Leu
        595                 600                 605

Pro Pro Pro Phe Ser Leu Gln Ser Gly Ile Leu Thr Leu Asn Pro Val
    610                 615                 620

Ala Gln Gly Gln Pro Ile Leu Thr Ser Leu Gly Ser Asn Gln Glu Glu
625                 630                 635                 640

Ala Tyr Val Thr Met Ser Ser Phe Tyr Gln Asn Gln Gly Ser Gly Ala
                645                 650                 655

Thr Asn Phe Ser Leu Leu Lys Gln Ala Gly Asp Val Glu Glu Asn Pro
            660                 665                 670

Gly Pro Met Glu Ala Ala Val Ala Ala Pro Arg Pro Arg Leu Leu Leu
        675                 680                 685

Leu Val Leu Ala Ala Ala Ala Ala Ala Ala Ala Leu Leu Pro Gly
    690                 695                 700

Ala Thr Ala Leu Gln Cys Phe Cys His Leu Cys Thr Lys Asp Asn Phe
705                 710                 715                 720
```

```
Thr Cys Val Thr Asp Gly Leu Cys Phe Val Ser Val Thr Glu Thr Thr
                725                 730                 735
Asp Lys Val Ile His Asn Ser Met Cys Ile Ala Glu Ile Asp Leu Ile
            740                 745                 750
Pro Arg Asp Arg Pro Phe Val Cys Ala Pro Ser Ser Lys Thr Gly Ser
        755                 760                 765
Val Thr Thr Thr Tyr Cys Cys Asn Gln Asp His Cys Asn Lys Ile Glu
    770                 775                 780
Leu Pro Thr Thr Val Lys Ser Ser Pro Gly Leu Gly Pro Val Glu Leu
785                 790                 795                 800
Val Val Ile Ser Val Gly Ser Met Gly Leu Ile Ile Ser Leu Leu Cys
                805                 810                 815
Val Tyr Phe Trp Leu Glu Arg Thr Met Pro Arg Ile Pro Thr Leu Lys
            820                 825                 830
Asn Leu Glu Asp Leu Val Thr Glu Tyr His Gly Asn Phe Ser Ala Trp
        835                 840                 845
Ser Gly Val Ser Lys Gly Leu Ala Glu Ser Leu Gln Pro Asp Tyr Ser
    850                 855                 860
Glu Arg Leu Cys Leu Val Ser Glu Ile Pro Pro Lys Gly Gly Ala Leu
865                 870                 875                 880
Gly Glu Gly Pro Gly Ala Ser Pro Cys Asn Gln His Ser Pro Tyr Trp
                885                 890                 895
Ala Pro Pro Cys Tyr Thr Leu Lys Pro Glu Thr
            900                 905
```

```
<210> SEQ ID NO 36
<211> LENGTH: 3
<212> TYPE: PRT
<213> ORGANISM: Artificial Sequence
<220> FEATURE:
<223> OTHER INFORMATION: Exemplary linker sequence

<400> SEQUENCE: 36

Gly Gly Gly
1

<210> SEQ ID NO 37
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 37

Asp Gly Gly Gly Ser
1               5

<210> SEQ ID NO 38
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 38

Thr Gly Glu Lys Pro
1               5

<210> SEQ ID NO 39
<211> LENGTH: 4
<212> TYPE: PRT
```

```
<213> ORGANISM: Artificial Sequence
<220> FEATURE:
<223> OTHER INFORMATION: Exemplary linker sequence

<400> SEQUENCE: 39

Gly Gly Arg Arg
1

<210> SEQ ID NO 40
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 40

Gly Gly Gly Gly Ser
1               5

<210> SEQ ID NO 41
<211> LENGTH: 14
<212> TYPE: PRT
<213> ORGANISM: Artificial Sequence
<220> FEATURE:
<223> OTHER INFORMATION: Exemplary linker sequence

<400> SEQUENCE: 41

Glu Gly Lys Ser Ser Gly Ser Gly Ser Glu Ser Lys Val Asp
1               5                   10

<210> SEQ ID NO 42
<211> LENGTH: 18
<212> TYPE: PRT
<213> ORGANISM: Artificial Sequence
<220> FEATURE:
<223> OTHER INFORMATION: Exemplary linker sequence

<400> SEQUENCE: 42

Lys Glu Ser Gly Ser Val Ser Ser Glu Gln Leu Ala Gln Phe Arg Ser
1               5                   10                  15

Leu Asp

<210> SEQ ID NO 43
<211> LENGTH: 8
<212> TYPE: PRT
<213> ORGANISM: Artificial Sequence
<220> FEATURE:
<223> OTHER INFORMATION: Exemplary linker sequence

<400> SEQUENCE: 43

Gly Gly Arg Arg Gly Gly Gly Ser
1               5

<210> SEQ ID NO 44
<211> LENGTH: 9
<212> TYPE: PRT
<213> ORGANISM: Artificial Sequence
<220> FEATURE:
<223> OTHER INFORMATION: Exemplary linker sequence

<400> SEQUENCE: 44

Leu Arg Gln Arg Asp Gly Glu Arg Pro
1               5

<210> SEQ ID NO 45
<211> LENGTH: 12
```

```
<212> TYPE: PRT
<213> ORGANISM: Artificial Sequence
<220> FEATURE:
<223> OTHER INFORMATION: Exemplary linker sequence

<400> SEQUENCE: 45

Leu Arg Gln Lys Asp Gly Gly Gly Ser Glu Arg Pro
1               5                   10

<210> SEQ ID NO 46
<211> LENGTH: 16
<212> TYPE: PRT
<213> ORGANISM: Artificial Sequence
<220> FEATURE:
<223> OTHER INFORMATION: Exemplary linker sequence

<400> SEQUENCE: 46

Leu Arg Gln Lys Asp Gly Gly Gly Ser Gly Gly Gly Ser Glu Arg Pro
1               5                   10                  15

<210> SEQ ID NO 47
<211> LENGTH: 7
<212> TYPE: PRT
<213> ORGANISM: Artificial Sequence
<220> FEATURE:
<223> OTHER INFORMATION: Cleavage sequence by TEV protease
<220> FEATURE:
<221> NAME/KEY: misc_feature
<222> LOCATION: (2)..(3)
<223> OTHER INFORMATION: Xaa is any amino acid
<220> FEATURE:
<221> NAME/KEY: misc_feature
<222> LOCATION: (5)..(5)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa = Gly or Ser

<400> SEQUENCE: 47

Glu Xaa Xaa Tyr Xaa Gln Xaa
1               5

<210> SEQ ID NO 48
<211> LENGTH: 7
<212> TYPE: PRT
<213> ORGANISM: Artificial Sequence
<220> FEATURE:
<223> OTHER INFORMATION: Cleavage sequence by TEV protease

<400> SEQUENCE: 48

Glu Asn Leu Tyr Phe Gln Gly
1               5

<210> SEQ ID NO 49
<211> LENGTH: 7
<212> TYPE: PRT
<213> ORGANISM: Artificial Sequence
<220> FEATURE:
<223> OTHER INFORMATION: Cleavage sequence by TEV protease

<400> SEQUENCE: 49

Glu Asn Leu Tyr Phe Gln Ser
1               5

<210> SEQ ID NO 50
<211> LENGTH: 22
<212> TYPE: PRT
<213> ORGANISM: Artificial Sequence
```

<220> FEATURE:
<223> OTHER INFORMATION: Self-cleaving polypeptide comprising 2A site

<400> SEQUENCE: 50

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 51
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 51

Ala Thr Asn Phe Ser Leu Leu Lys Gln Ala Gly Asp Val Glu Glu Asn
1               5                   10                  15

Pro Gly Pro

<210> SEQ ID NO 52
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 52

Leu Leu Lys Gln Ala Gly Asp Val Glu Glu Asn Pro Gly Pro
1               5                   10

<210> SEQ ID NO 53
<211> LENGTH: 21
<212> TYPE: PRT
<213> ORGANISM: Artificial Sequence
<220> FEATURE:
<223> OTHER INFORMATION: Self-cleaving polypeptide comprising 2A site

<400> SEQUENCE: 53

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 54
<211> LENGTH: 18
<212> TYPE: PRT
<213> ORGANISM: Artificial Sequence
<220> FEATURE:
<223> OTHER INFORMATION: Self-cleaving polypeptide comprising 2A site

<400> SEQUENCE: 54

Glu Gly Arg Gly Ser Leu Leu Thr Cys Gly Asp Val Glu Glu Asn Pro
1               5                   10                  15

Gly Pro

<210> SEQ ID NO 55
<211> LENGTH: 13
<212> TYPE: PRT
<213> ORGANISM: Artificial Sequence
<220> FEATURE:
<223> OTHER INFORMATION: Self-cleaving polypeptide comprising 2A site

<400> SEQUENCE: 55

Leu Leu Thr Cys Gly Asp Val Glu Glu Asn Pro Gly Pro
1               5                   10

<210> SEQ ID NO 56
<211> LENGTH: 23
<212> TYPE: PRT
<213> ORGANISM: Artificial Sequence
<220> FEATURE:
<223> OTHER INFORMATION: Self-cleaving polypeptide comprising 2A site

<400> SEQUENCE: 56

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 57
<211> LENGTH: 20
<212> TYPE: PRT
<213> ORGANISM: Artificial Sequence
<220> FEATURE:
<223> OTHER INFORMATION: Self-cleaving polypeptide comprising 2A site

<400> SEQUENCE: 57

Gln Cys Thr Asn Tyr Ala Leu Leu Lys Leu Ala Gly Asp Val Glu Ser
1               5                   10                  15

Asn Pro Gly Pro
            20

<210> SEQ ID NO 58
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 58

Leu Leu Lys Leu Ala Gly Asp Val Glu Ser Asn Pro Gly Pro
1               5                   10

<210> SEQ ID NO 59
<211> LENGTH: 25
<212> TYPE: PRT
<213> ORGANISM: Artificial Sequence
<220> FEATURE:
<223> OTHER INFORMATION: Self-cleaving polypeptide comprising 2A site

<400> SEQUENCE: 59

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 60
<211> LENGTH: 22
<212> TYPE: PRT
<213> ORGANISM: Artificial Sequence
<220> FEATURE:
<223> OTHER INFORMATION: Self-cleaving polypeptide comprising 2A site

```
<400> SEQUENCE: 60

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 61
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 61

Leu Leu Lys Leu Ala Gly Asp Val Glu Ser Asn Pro Gly Pro
1               5                   10

<210> SEQ ID NO 62
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 62

Leu Leu Asn Phe Asp Leu Leu Lys Leu Ala Gly Asp Val Glu Ser Asn
1               5                   10                  15

Pro Gly Pro

<210> SEQ ID NO 63
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 63

Thr Leu Asn Phe Asp Leu Leu Lys Leu Ala Gly Asp Val Glu Ser Asn
1               5                   10                  15

Pro Gly Pro

<210> SEQ ID NO 64
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 64

Leu Leu Lys Leu Ala Gly Asp Val Glu Ser Asn Pro Gly Pro
1               5                   10

<210> SEQ ID NO 65
<211> LENGTH: 17
<212> TYPE: PRT
<213> ORGANISM: Artificial Sequence
<220> FEATURE:
<223> OTHER INFORMATION: Self-cleaving polypeptide comprising 2A site
```

<400> SEQUENCE: 65

Asn Phe Asp Leu Leu Lys Leu Ala Gly Asp Val Glu Ser Asn Pro Gly
1               5                   10                  15

Pro

<210> SEQ ID NO 66
<211> LENGTH: 20
<212> TYPE: PRT
<213> ORGANISM: Artificial Sequence
<220> FEATURE:
<223> OTHER INFORMATION: Self-cleaving polypeptide comprising 2A site

<400> SEQUENCE: 66

Gln Leu Leu Asn Phe Asp Leu Leu Lys Leu Ala Gly Asp Val Glu Ser
1               5                   10                  15

Asn Pro Gly Pro
            20

<210> SEQ ID NO 67
<211> LENGTH: 24
<212> TYPE: PRT
<213> ORGANISM: Artificial Sequence
<220> FEATURE:
<223> OTHER INFORMATION: Self-cleaving polypeptide comprising 2A site

<400> SEQUENCE: 67

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 68
<211> LENGTH: 40
<212> TYPE: PRT
<213> ORGANISM: Artificial Sequence
<220> FEATURE:
<223> OTHER INFORMATION: Self-cleaving polypeptide comprising 2A site

<400> SEQUENCE: 68

Val Thr Glu Leu Leu Tyr Arg Met Lys Arg Ala Glu Thr Tyr Cys Pro
1               5                   10                  15

Arg Pro Leu Leu Ala Ile His Pro Thr Glu Ala Arg His Lys Gln Lys
            20                  25                  30

Ile Val Ala Pro Val Lys Gln Thr
        35                  40

<210> SEQ ID NO 69
<211> LENGTH: 18
<212> TYPE: PRT
<213> ORGANISM: Artificial Sequence
<220> FEATURE:
<223> OTHER INFORMATION: Self-cleaving polypeptide comprising 2A site

<400> SEQUENCE: 69

Leu Asn Phe Asp Leu Leu Lys Leu Ala Gly Asp Val Glu Ser Asn Pro
1               5                   10                  15

Gly Pro

<210> SEQ ID NO 70
<211> LENGTH: 40
<212> TYPE: PRT
<213> ORGANISM: Artificial Sequence
<220> FEATURE:
<223> OTHER INFORMATION: Self-cleaving polypeptide comprising 2A site

<400> SEQUENCE: 70

Leu Leu Ala Ile His Pro Thr Glu Ala Arg His Lys Gln Lys Ile Val
1               5                   10                  15

Ala Pro Val Lys Gln Thr Leu Asn Phe Asp Leu Leu Lys Leu Ala Gly
            20                  25                  30

Asp Val Glu Ser Asn Pro Gly Pro
        35                  40

<210> SEQ ID NO 71
<211> LENGTH: 33
<212> TYPE: PRT
<213> ORGANISM: Artificial Sequence
<220> FEATURE:
<223> OTHER INFORMATION: Self-cleaving polypeptide comprising 2A site

<400> SEQUENCE: 71

Glu Ala Arg His Lys Gln Lys Ile Val Ala Pro Val Lys Gln Thr Leu
1               5                   10                  15

Asn Phe Asp Leu Leu Lys Leu Ala Gly Asp Val Glu Ser Asn Pro Gly
            20                  25                  30

Pro

<210> SEQ ID NO 72
<211> LENGTH: 10
<212> TYPE: DNA
<213> ORGANISM: Artificial Sequence
<220> FEATURE:
<223> OTHER INFORMATION: Consensus Kozak sequence

<400> SEQUENCE: 72 gccrccatgg                                                                10

<210> SEQ ID NO 73
<211> LENGTH: 4
<212> TYPE: PRT
<213> ORGANISM: Artificial Sequence
<220> FEATURE:
<223> OTHER INFORMATION: Exemplary rule for determining light chain
      CDR-L3 motif
<220> FEATURE:
<221> NAME/KEY: MISC_FEATURE
<222> LOCATION: (3)..(3)
<223> OTHER INFORMATION: Xaa is any amino acid

<400> SEQUENCE: 73

Phe Gly Xaa Gly
1

<210> SEQ ID NO 74
<211> LENGTH: 4
<212> TYPE: PRT
<213> ORGANISM: Artificial Sequence
<220> FEATURE:
<223> OTHER INFORMATION: Exemplary rule for determining heavy chain
      CDR-H1motif
<220> FEATURE:
<221> NAME/KEY: MISC_FEATURE
<222> LOCATION: (2)..(4)
<223> OTHER INFORMATION: Xaa is any amino acid

<400> SEQUENCE: 74

Cys Xaa Xaa Xaa
1

```
<210> SEQ ID NO 75
<211> LENGTH: 5
<212> TYPE: PRT
<213> ORGANISM: Artificial Sequence
<220> FEATURE:
<223> OTHER INFORMATION: Exemplary rule for determining heavy chain
      CDR-H2 motif

<400> SEQUENCE: 75

Leu Glu Trp Ile Gly
1               5

<210> SEQ ID NO 76
<211> LENGTH: 4
<212> TYPE: PRT
<213> ORGANISM: Artificial Sequence
<220> FEATURE:
<223> OTHER INFORMATION: Exemplary rule for determining heavy chain
      CDR-H3 motif
<220> FEATURE:
<221> NAME/KEY: MISC_FEATURE
<222> LOCATION: (3)..(3)
<223> OTHER INFORMATION: Xaa is any amino acid

<400> SEQUENCE: 76

Trp Gly Xaa Gly
1
```

TGFBETA SIGNAL CONVERTOR

CROSS REFERENCE TO RELATED APPLICATIONS

This application is a National Stage application under 35 U.S.C. § 371 of International Application No. PCT/US2017/062358, filed Nov. 17, 2017, which claims the benefit under 35 U.S.C. § 119(e) of U.S. Provisional Application No. 62/423,565, filed Nov. 17, 2016, and U.S. Provisional Application No. 62/467,496, filed Mar. 6, 2017, which is incorporated by reference herein in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is BLBD_080_02WO_ST25.txt. The text file is 215 KB, was created on Nov. 17, 2017, and is being submitted electronically via EFS-Web, concurrent with the filing of the specification.

BACKGROUND

Technical Field

The present disclosure relates to improved adoptive cell therapies. More particularly, the disclosure relates to improved signaling molecules, cells, and methods of using the same.

Description of the Related Art

The global burden of cancer doubled between 1975 and 2000. Cancer is the second leading cause of morbidity and mortality worldwide, with approximately 14.1 million new cases and 8.2 million cancer related deaths in 2012. The most common cancers are breast cancer, lung and bronchus cancer, prostate cancer, colon and rectum cancer, bladder cancer, melanoma of the skin, non-Hodgkin lymphoma, thyroid cancer, kidney and renal pelvis cancer, endometrial cancer, leukemia, and pancreatic cancer. The number of new cancer cases is projected to rise to 22 million within the next two decades.

The immune system has a key role in detecting and combating human cancer. The majority of transformed cells are quickly detected by immune sentinels and destroyed through the activation of antigen-specific T cells via clonally expressed T cell receptors (TCR). Accordingly, cancer can be considered an immunological disorder, a failure of immune system to mount the necessary anti-tumor response to durably suppress and eliminate the disease. In order to more effectively combat cancer, certain immunotherapy interventions developed over the last few decades have specifically focused on enhancing T cell immunity. These treatments have yielded only sporadic cases of disease remission, and have not had substantial overall success. More recent therapies that use monoclonal antibodies targeting molecules that inhibit T cell activation, such as CTLA-4 or PD-1, have shown a more substantial anti-tumor effect; however, these treatments are also associated with substantial toxicity due to systemic immune activation.

Most recently, adoptive cellular immunotherapy strategies, which are based on the isolation, modification, expansion and reinfusion of T cells, have been explored and tested in early stage clinical trials. T cells have often been the effector cells of choice for cancer immunotherapy due to their selective recognition and powerful effector mechanisms. These treatments have shown mixed rates of success, but a small number of patients have experienced durable remissions, highlighting the as-yet unrealized potential for T cell-based immunotherapies.

Successful recognition of tumor cell associated antigens by cytolytic T cells initiates targeted tumor lysis and underpins any effective cancer immunotherapy approach. Tumor-infiltrating T cells (TILs) express TCRs specifically directed to tumor-associated antigens; however, substantial numbers of TILs are limited to only a few human cancers. Engineered T cell receptors (TCRs) and chimeric antigen receptors (CARs) potentially increase the applicability of T cell-based immunotherapy to many cancers and other immune disorders.

In addition, state of the art engineered T cells are still regulated by a complex immunosuppressive tumor microenvironment that consists of cancer cells, inflammatory cells, stromal cells and cytokines. Among these components, cancer cells, inflammatory cells and suppressive cytokines adversely impact T cell phenotype and function. Collectively, the tumor microenvironment drives T cells to terminally differentiate into exhausted T cells.

T cell exhaustion is a state of T cell dysfunction in a chronic environment marked by increased expression of, or increased signaling by inhibitory receptors; reduced effector cytokine production; and a decreased ability to persist and eliminate cancer. Exhausted T cells also show loss of function in a hierarchical manner: decreased IL-2 production and ex vivo killing capacity are lost at the early stage of exhaustion, TNF-α production is lost at the intermediate stage, and IFN-γ and GzmB production are lost at the advanced stage of exhaustion. Most T cells in the tumor microenvironment differentiate into exhausted T cells and lose the ability to eliminate cancer and are eventually cleared.

Transforming growth factor beta (TGFβ) is a pleiotropic cytokine that has been implicated as an immunosuppressive signaling molecule in the tumor microenvironment. TGFβ binds to the TGFβR1 and TGFβR2 serine/threonine kinase receptor complexes, resulting in receptor-mediated phosphorylation of downstream transcription factors Smad2 and Smad3. Many tumors evade the cytostatic and anti-proliferative effects of TGFβ by acquiring mutations in the TGFβR2 receptors and/or downstream Smad signaling proteins. TGFβ suppresses key molecules involved in the effector and cytolytic activities of T cells in vitro, including IFNγ secretion.

To date, clinical trials directed to the inhibition of TGFβ signaling using neutralizing Abs or kinase inhibitors have yielded disappointing results and significant therapeutic benefits have not yet been reported.

BRIEF SUMMARY

The present disclosure generally relates, in part, to improved TGFβ signal convertors (chimeric TFGβ receptors or CTBRs), genetically modified cells, compositions, and methods of using the same.

In various embodiments, a fusion polypeptide is contemplated comprising: a first polypeptide comprising: an extracellular TFGβ1-binding domain of TGFβR2, a transmembrane domain, and an immune receptor intracellular signaling domain; a polypeptide cleavage signal; and a second polypeptide comprising an extracellular TGFβ1-binding domain of TGFβR1, a transmembrane domain, and an immune receptor intracellular signaling domain.

In additional embodiments, the immune receptor intracellular signaling domain of the first polypeptide is isolated from a cytokine receptor, an interleukin receptor, a pattern recognition receptor, or a toll-like receptor.

In particular embodiments, the immune receptor intracellular signaling domain of the second polypeptide is isolated from a cytokine receptor, an interleukin receptor, a pattern recognition receptor, or a toll-like receptor.

In some embodiments, the immune receptor intracellular signaling domain of the first polypeptide is an IL-12Rβ2 intracellular signaling domain and the immune receptor intracellular signaling domain of the second polypeptide is an IL-12Rβ1 intracellular signaling domain. In various embodiments, the transmembrane domain of the first polypeptide comprises an IL-12Rβ2 transmembrane domain. In particular embodiments, the transmembrane domain of the second polypeptide comprises an IL-12Rβ1 transmembrane domain. In particular embodiments, the fusion protein is referred to as a CTBR12 or CTBR12 signal convertor.

In certain embodiments, the immune receptor intracellular signaling domain of the first polypeptide is an IL-12Rβ1 intracellular signaling domain and the immune receptor intracellular signaling domain of the second polypeptide is an IL-12Rβ2 intracellular signaling domain. In further embodiments, the transmembrane domain of the first polypeptide comprises an IL-12Rβ1 transmembrane domain. In particular embodiments, the transmembrane domain of the second polypeptide comprises an IL-12Rβ2 transmembrane domain. In particular embodiments, the fusion protein is referred to as a CTBR12 or CTBR12 signal convertor.

In additional embodiments, the immune receptor intracellular signaling domain of the first polypeptide is an IL-7Rα intracellular signaling domain and the immune receptor intracellular signaling domain of the second polypeptide is an IL-2Rγ intracellular signaling domain. In some embodiments, the transmembrane domain of the first polypeptide comprises an IL-7Rα transmembrane domain. In particular embodiments, the transmembrane domain of the second polypeptide comprises an IL-2Rγ transmembrane domain. In particular embodiments, the fusion protein is referred to as a CTBR7 or CTBR7 signal convertor.

In various embodiments, the immune receptor intracellular signaling domain of the first polypeptide is an IL-2Rγ intracellular signaling domain and the immune receptor intracellular signaling domain of the second polypeptide is an IL-7Rα intracellular signaling domain. In further embodiments, the transmembrane domain of the first polypeptide comprises an IL-2Rγ transmembrane domain. In certain embodiments, the transmembrane domain of the second polypeptide comprises an IL-7Rα transmembrane domain. In particular embodiments, the fusion protein is referred to as a CTBR7 or CTBR7 signal convertor.

In additional embodiments, the immune receptor intracellular signaling domain of the first polypeptide is an IL-2Rβ intracellular signaling domain and the immune receptor intracellular signaling domain of the second polypeptide is an IL-2Rγ intracellular signaling domain. In various embodiments, the transmembrane domain of the first polypeptide comprises an IL-2Rβ transmembrane domain. In various embodiments, the transmembrane domain of the second polypeptide comprises an IL-2Rγ transmembrane domain. In particular embodiments, the fusion protein is referred to as a CTBR15 or CTBR15 signal convertor.

In particular embodiments, the immune receptor intracellular signaling domain of the first polypeptide is an IL-2Rγ intracellular signaling domain and the immune receptor intracellular signaling domain of the second polypeptide is an IL-2Rβ intracellular signaling domain. In some embodiments, the transmembrane domain of the first polypeptide comprises an IL-2Rγ transmembrane domain. In certain embodiments, the transmembrane domain of the second polypeptide comprises an IL-2Rβ transmembrane domain. In particular embodiments, the fusion protein is referred to as a CTBR15 or CTBR15 signal convertor.

In further embodiments, the immune receptor intracellular signaling domain of the first polypeptide is an IL-21R intracellular signaling domain and the immune receptor intracellular signaling domain of the second polypeptide is an IL-2Rγ intracellular signaling domain. In particular embodiments, the transmembrane domain of the first polypeptide comprises an IL-21R transmembrane domain. In various embodiments, the transmembrane domain of the second polypeptide comprises an IL-2Rγ transmembrane domain. In particular embodiments, the fusion protein is referred to as a CTBR21 or CTBR21 signal convertor.

In additional embodiments, the immune receptor intracellular signaling domain of the first polypeptide is an IL-2Rγ intracellular signaling domain and the immune receptor intracellular signaling domain of the second polypeptide is an IL-21R intracellular signaling domain. In certain embodiments, the transmembrane domain of the first polypeptide comprises an IL-2Rγ transmembrane domain. In further embodiments, the transmembrane domain of the second polypeptide comprises an IL-21R transmembrane domain. In particular embodiments, the fusion protein is referred to as a CTBR21 or CTBR21 signal convertor.

In various embodiments, the immune receptor intracellular signaling domain of the first polypeptide is an IL-18R1 intracellular signaling domain and the immune receptor intracellular signaling domain of the second polypeptide is an IL-18RAP intracellular signaling domain. In some embodiments, the transmembrane domain of the first polypeptide comprises an IL-18R1 transmembrane domain. In various embodiments, the transmembrane domain of the second polypeptide comprises an IL-18RAP transmembrane domain. In particular embodiments, the fusion protein is referred to as a CTBR18 or CTBR18 signal convertor.

In some embodiments, the immune receptor intracellular signaling domain of the first polypeptide is an IL-18RAP intracellular signaling domain and the immune receptor intracellular signaling domain of the second polypeptide is an IL-18R1 intracellular signaling domain. In additional embodiments, the transmembrane domain of the first polypeptide comprises an IL-18RAP transmembrane domain. In particular embodiments, the transmembrane domain of the second polypeptide comprises an IL-18R1 transmembrane domain. In particular embodiments, the fusion protein is referred to as a CTBR18 or CTBR18 signal convertor.

In certain embodiments, the immune receptor intracellular signaling domain of the first polypeptide is an IL-1R1 intracellular signaling domain and the immune receptor intracellular signaling domain of the second polypeptide is an IL-1RAP intracellular signaling domain. In further embodiments, the transmembrane domain of the first polypeptide comprises an IL-1R1 transmembrane domain. In various embodiments, the transmembrane domain of the second polypeptide comprises an IL-1RAP transmembrane domain. In particular embodiments, the fusion protein is referred to as a CTBR1 or CTBR1 signal convertor.

In certain embodiments, the immune receptor intracellular signaling domain of the first polypeptide is an IL-1RAP intracellular signaling domain and the immune receptor intracellular signaling domain of the second polypeptide is an IL-1R1 intracellular signaling domain. In various embodiments, the transmembrane domain of the first polypeptide comprises an IL-1RAP transmembrane domain. In some embodiments, the transmembrane domain of the second polypeptide comprises an IL-1R1 transmembrane domain. In particular embodiments, the fusion protein is referred to as a CTBR1 or CTBR1 signal convertor.

In additional embodiments, the immune receptor intracellular signaling domain of the first polypeptide is an IL-1RAP intracellular signaling domain and the immune receptor intracellular signaling domain of the second polypeptide is an IL-1RL2 intracellular signaling domain. In various embodiments, the transmembrane domain of the first polypeptide comprises an IL-1RAP transmembrane domain. In further embodiments, the transmembrane domain of the second polypeptide comprises an IL-1RL2 transmembrane domain. In particular embodiments, the fusion protein is referred to as a CTBR36 or CTBR36 signal convertor.

In particular embodiments, the immune receptor intracellular signaling domain of the first polypeptide is an IL-1RL2 intracellular signaling domain and the immune receptor intracellular signaling domain of the second polypeptide is an IL-1RAP intracellular signaling domain. In certain embodiments, the transmembrane domain of the first polypeptide comprises an IL-1RL2 transmembrane domain. In some embodiments, the transmembrane domain of the second polypeptide comprises an IL-1RAP transmembrane domain. In particular embodiments, the fusion protein is referred to as a CTBR36 or CTBR36 signal convertor.

In various embodiments, the immune receptor intracellular signaling domain of the first polypeptide is an IFNAR1 intracellular signaling domain and the immune receptor intracellular signaling domain of the second polypeptide is an IFNAR2 intracellular signaling domain. In further embodiments, the transmembrane domain of the first polypeptide comprises an IFNAR1 transmembrane domain. In particular embodiments, the transmembrane domain of the second polypeptide comprises an IFNAR2 transmembrane domain. In particular embodiments, the fusion protein is referred to as a CTBRIFN1 or CTBRIFN1 signal convertor.

In various embodiments, the immune receptor intracellular signaling domain of the first polypeptide is an IFNAR2 intracellular signaling domain and the immune receptor intracellular signaling domain of the second polypeptide is an IFNAR1 intracellular signaling domain. In certain embodiments, the transmembrane domain of the first polypeptide comprises an IFNAR2 transmembrane domain. In various embodiments, the transmembrane domain of the second polypeptide comprises an IFNAR1 transmembrane domain. In particular embodiments, the fusion protein is referred to as a CTBR.IFN1 or CTBR.IFN1 signal convertor.

In further embodiments, the immune receptor intracellular signaling domain of the first polypeptide is a TLR1 intracellular signaling domain and the immune receptor intracellular signaling domain of the second polypeptide is a TLR1 intracellular signaling domain. In additional embodiments, the transmembrane domain of the first polypeptide comprises a TLR1 transmembrane domain. In some embodiments, the transmembrane domain of the second polypeptide comprises a TLR1 transmembrane domain. In particular embodiments, the fusion protein is referred to as a CTBR.TLR1 or CTBR.TLR1 signal convertor.

In particular embodiments, the immune receptor intracellular signaling domain of the first polypeptide is a TLR2 intracellular signaling domain and the immune receptor intracellular signaling domain of the second polypeptide is a TLR2 intracellular signaling domain. In certain embodiments, the transmembrane domain of the first polypeptide comprises a TLR2 transmembrane domain. In further embodiments, the transmembrane domain of the second polypeptide comprises a TLR2 transmembrane domain. In particular embodiments, the fusion protein is referred to as a CTBR.TLR2 or CTBR.TLR2 signal convertor.

In various embodiments, the immune receptor intracellular signaling domain of the first polypeptide is a TLR3 intracellular signaling domain and the immune receptor intracellular signaling domain of the second polypeptide is a TLR3 intracellular signaling domain. In further embodiments, the transmembrane domain of the first polypeptide comprises a TLR3 transmembrane domain. In particular embodiments, the transmembrane domain of the second polypeptide comprises a TLR3 transmembrane domain. In particular embodiments, the fusion protein is referred to as a CTBR.TLR3 or CTBR.TLR3 signal convertor.

In various embodiments, the immune receptor intracellular signaling domain of the first polypeptide is a TLR4 intracellular signaling domain and the immune receptor intracellular signaling domain of the second polypeptide is a TLR4 intracellular signaling domain. In some embodiments, the transmembrane domain of the first polypeptide comprises a TLR4 transmembrane domain. In certain embodiments, the transmembrane domain of the second polypeptide comprises a TLR4 transmembrane domain. In particular embodiments, the fusion protein is referred to as a CTBR.TLR4 or CTBR.TLR4 signal convertor.

In additional embodiments, the immune receptor intracellular signaling domain of the first polypeptide is a TLR5 intracellular signaling domain and the immune receptor intracellular signaling domain of the second polypeptide is a TLR5 intracellular signaling domain. In particular embodiments, the transmembrane domain of the first polypeptide comprises a TLR5 transmembrane domain. In various embodiments, the transmembrane domain of the second polypeptide comprises a TLR5 transmembrane domain. In particular embodiments, the fusion protein is referred to as a CTBR.TLR5 or CTBR.TLR5 signal convertor.

In some embodiments, the immune receptor intracellular signaling domain of the first polypeptide is a TLR6 intracellular signaling domain and the immune receptor intracellular signaling domain of the second polypeptide is a TLR6 intracellular signaling domain. In further embodiments, the transmembrane domain of the first polypeptide comprises a TLR6 transmembrane domain. In particular embodiments, the transmembrane domain of the second polypeptide comprises a TLR6 transmembrane domain. In particular embodiments, the fusion protein is referred to as a CTBR.TLR6 or CTBR.TLR6 signal convertor.

In some embodiments, the immune receptor intracellular signaling domain of the first polypeptide is a TLR7 intracellular signaling domain and the immune receptor intracellular signaling domain of the second polypeptide is a TLR7 intracellular signaling domain. In various embodiments, the transmembrane domain of the first polypeptide comprises a TLR7 transmembrane domain. In further embodiments, the transmembrane domain of the second polypeptide comprises a TLR7 transmembrane domain. In particular embodiments, the fusion protein is referred to as a CTBR.TLR7 or CTBR.TLR7 signal convertor.

In certain embodiments, the immune receptor intracellular signaling domain of the first polypeptide is a TLR8 intracellular signaling domain and the immune receptor intracellular signaling domain of the second polypeptide is a TLR8 intracellular signaling domain. In particular embodiments, the transmembrane domain of the first polypeptide comprises a TLR8 transmembrane domain. In some embodiments, the transmembrane domain of the second polypeptide comprises a TLR8 transmembrane domain. In particular embodiments, the fusion protein is referred to as a CTBR.TLR8 or CTBR.TLR8 signal convertor.

In various embodiments, the immune receptor intracellular signaling domain of the first polypeptide is a TLR9 intracellular signaling domain and the immune receptor intracellular signaling domain of the second polypeptide is a TLR9 intracellular signaling domain. In further embodiments, the transmembrane domain of the first polypeptide comprises a TLR9 transmembrane domain. In additional embodiments, the transmembrane domain of the second polypeptide comprises a TLR9 transmembrane domain. In particular embodiments, the fusion protein is referred to as a CTBR.TLR9 or CTBR.TLR9 signal convertor.

In certain embodiments, the immune receptor intracellular signaling domain of the first polypeptide is a TLR10 intracellular signaling domain and the immune receptor intracellular signaling domain of the second polypeptide is a TLR10 intracellular signaling domain. In certain embodiments, the transmembrane domain of the first polypeptide comprises a TLR10 transmembrane domain. In particular embodiments, the transmembrane domain of the second polypeptide comprises a TLR10 transmembrane domain. In particular embodiments, the fusion protein is referred to as a CTBR.TLR10 or CTBR.TLR10 signal convertor.

In further embodiments, the polypeptide cleavage signal is a viral self-cleaving polypeptide.

In various embodiments, the polypeptide cleavage signal is a viral self-cleaving 2A polypeptide.

In some embodiments, the polypeptide cleavage signal is a viral self-cleaving polypeptide selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide.

In particular embodiments, a fusion polypeptide comprises: a TGFβR2 polypeptide comprising an extracellular TGFβ1-binding domain of TGFβR2, an IL-12Rβ2 transmembrane domain, and an IL-12Rβ2 intracellular signaling domain; a viral self-cleaving 2A peptide; and a TGFβR1 polypeptide comprising an extracellular TGFβ1-binding domain of TGFβR1, an IL-12Rβ1 transmembrane domain, and an IL-12Rβ1 intracellular signaling domain. In particular embodiments, the fusion protein is referred to as a CTBR12 or CTBR12 signal convertor.

In various embodiments, a fusion polypeptide comprises: a TGFβR2 polypeptide comprising an extracellular TGFβ1-binding domain of TGFβR2, an IL-12Rβ1 transmembrane domain, and an IL-12Rβ1 intracellular signaling domain; a viral self-cleaving 2A peptide; and a TGFβR1 polypeptide comprising an extracellular TGFβ1-binding domain of TGFβR1, an IL-12Rβ2 transmembrane domain, and an IL-12Rβ2 intracellular signaling domain. In particular embodiments, the fusion protein is referred to as a CTBR12 or CTBR12 signal convertor.

In additional embodiments, a fusion polypeptide comprises: a TGFβR2 polypeptide comprising an extracellular TFGβ1-binding domain of TGFβR2, an IL-7Rα transmembrane domain, and an IL-7Rα intracellular signaling domain; a viral self-cleaving 2A peptide; and a TGFβR1 polypeptide comprising an extracellular TFGβ1-binding domain of TGFβR1, an IL-2Rγ transmembrane domain, and an IL-2Rγ intracellular signaling domain. In particular embodiments, the fusion protein is referred to as a CTBR7 or CTBR7 signal convertor.

In particular embodiments, a fusion polypeptide comprises: a TGFβR2 polypeptide comprising an extracellular TFGβ1-binding domain of TGFβR2, an IL-2Rγ transmembrane domain, and an IL-2Rγ intracellular signaling domain; a viral self-cleaving 2A peptide; and a TGFβR1 polypeptide comprising an extracellular TFGβ1-binding domain of TGFβR1, an IL-7Rα transmembrane domain, and an IL-7Rα intracellular signaling domain. In particular embodiments, the fusion protein is referred to as a CTBR7 or CTBR7 signal convertor.

In certain embodiments, a fusion polypeptide comprises: a TGFβR2 polypeptide comprising an extracellular TFGβ1-binding domain of TGFβR2, an IL-2Rβ transmembrane domain, and an IL-2Rβ intracellular signaling domain; a viral self-cleaving 2A peptide; and a TGFβR1 polypeptide comprising an extracellular TFGβ1-binding domain of TGFβR1, an IL-2Rγ transmembrane domain, and an IL-2Rγ intracellular signaling domain. In particular embodiments, the fusion protein is referred to as a CTBR15 or CTBR15 signal convertor.

In various embodiments, a fusion polypeptide comprises: a TGFβR2 polypeptide comprising an extracellular TFGβ1-binding domain of TGFβR2, an IL-2Rγ transmembrane domain, and an IL-2Rγ intracellular signaling domain; a viral self-cleaving 2A peptide; and a TGFβR1 polypeptide comprising an extracellular TFGβ1-binding domain of TGFβR1, an IL-2Rβ transmembrane domain, and an IL-2Rβ intracellular signaling domain. In particular embodiments, the fusion protein is referred to as a CTBR15 or CTBR15 signal convertor.

In some embodiments, a fusion polypeptide comprises: a TGFβR2 polypeptide comprising an extracellular TFGβ1-binding domain of TGFβR2, an IL-21R transmembrane domain, and an IL-21R intracellular signaling domain; a viral self-cleaving 2A peptide; and a TGFβR1 polypeptide comprising an extracellular TFGβ1-binding domain of TGFβR1, an IL-2Rγ transmembrane domain, and an IL-2Rγ intracellular signaling domain. In particular embodiments, the fusion protein is referred to as a CTBR21 or CTBR21 signal convertor.

In certain embodiments, a fusion polypeptide comprises: a TGFβR2 polypeptide comprising an extracellular TFGβ1-binding domain of TGFβR2, an IL-2Rγ transmembrane domain, and an IL-2Rγ intracellular signaling domain; a viral self-cleaving 2A peptide; and a TGFβR1 polypeptide comprising an extracellular TFGβ1-binding domain of TGFβR1, an IL-21R transmembrane domain, and an IL-21R intracellular signaling domain. In particular embodiments, the fusion protein is referred to as a CTBR21 or CTBR21 signal convertor.

In various embodiments, a fusion polypeptide comprises: a TGFβR2 polypeptide comprising an extracellular TGFβ1-binding domain of TGFβR2, an IL-18R1 transmembrane domain, and an IL-18R1 intracellular signaling domain; a viral self-cleaving 2A peptide; and a TGFβR1 polypeptide comprising an extracellular TGFβ1-binding domain of TGFβR1, an IL-18RAP transmembrane domain, and an IL-18RAP intracellular signaling domain. In particular embodiments, the fusion protein is referred to as a CTBR18 or CTBR18 signal convertor.

In additional embodiments, a fusion polypeptide comprises: a TGFβR2 polypeptide comprising an extracellular TFGβ1-binding domain of TGFβR2, an IL-18RAP transmembrane domain, and an IL-18RAP intracellular signaling domain; a viral self-cleaving 2A peptide; and a TGFβR1 polypeptide comprising an extracellular TGFβ1-binding domain of TGFβR1, an IL-18R1 transmembrane domain, and an IL-18R1 intracellular signaling domain. In particular embodiments, the fusion protein is referred to as a CTBR18 or CTBR18 signal convertor.

In particular embodiments, a fusion polypeptide comprises: a TGFβR2 polypeptide comprising an extracellular TFGβ1-binding domain of TGFβR2, an IL-1R1 transmembrane domain, and an IL-1R1 intracellular signaling domain; a viral self-cleaving 2A peptide; and a TGFβR1 polypeptide comprising an extracellular TFGβ1-binding domain of TGFβR1, an IL-1RAP transmembrane domain, and an IL-1RAP intracellular signaling domain. In particular embodiments, the fusion protein is referred to as a CTBR36 or CTBR36 signal convertor.

In certain embodiments, a fusion polypeptide comprises: a TGFβR2 polypeptide comprising an extracellular TGFβ1-binding domain of TGFβR2, an IL-1RAP transmembrane domain, and an IL-1RAP intracellular signaling domain; a viral self-cleaving 2A peptide; and a TGFβR1 polypeptide comprising an extracellular TGFβ1-binding domain of TGFβR1, an IL-1R1 transmembrane domain, and an IL-1R1 intracellular signaling domain. In particular embodiments, the fusion protein is referred to as a CTBR36 or CTBR36 signal convertor.

In various embodiments, a fusion polypeptide comprises: a TGFβR2 polypeptide comprising an extracellular TFGβ1-binding domain of TGFβR2, an IFNAR1 transmembrane domain, and an IFNAR1 intracellular signaling domain; a viral self-cleaving 2A peptide; and a TGFβR1 polypeptide comprising an extracellular TGFβ1-binding domain of TGFβR1, an IFNAR2 transmembrane domain, and an IFNAR2 intracellular signaling domain. In particular embodiments, the fusion protein is referred to as a CTBR.IFN1 or CTBR.IFN1 signal convertor.

In some embodiments, a fusion polypeptide comprises: a TGFβR2 polypeptide comprising an extracellular TFGβ1-binding domain of TGFβR2, an IFNAR2 transmembrane domain, and an IFNAR2 intracellular signaling domain; a viral self-cleaving 2A peptide; and a TGFβR1 polypeptide comprising an extracellular TGFβ1-binding domain of TGFβR1, an IFNAR1 transmembrane domain, and an IFNAR1 intracellular signaling domain.

In further embodiments, a fusion polypeptide comprises: a TGFβR2 polypeptide comprising an extracellular TFGβ1-binding domain of TGFβR2, a TLR1 transmembrane domain, and a TLR1 intracellular signaling domain; a viral self-cleaving 2A peptide; and a TGFβR1 polypeptide comprising an extracellular TFGβ1-binding domain of TGFβR1, a TLR1 transmembrane domain, and a TLR1 intracellular signaling domain. In particular embodiments, the fusion protein is referred to as a CTBR.TLR1 or CTBR.TLR1 signal convertor.

In particular embodiments, a fusion polypeptide comprises: a TGFβR2 polypeptide comprising an extracellular TFGβ1-binding domain of TGFβR2, a TLR2 transmembrane domain, and a TLR2 intracellular signaling domain; a viral self-cleaving 2A peptide; and a TGFβR1 polypeptide comprising an extracellular TFGβ1-binding domain of TGFβR1, a TLR2 transmembrane domain, and a TLR2 intracellular signaling domain. In particular embodiments, the fusion protein is referred to as a CTBR.TLR2 or CTBR.TLR2 signal convertor.

In various embodiments, a fusion polypeptide comprises: a TGFβR2 polypeptide comprising an extracellular TFGβ1-binding domain of TGFβR2, a TLR3 transmembrane domain, and a TLR3 intracellular signaling domain; a viral self-cleaving 2A peptide; and a TGFβR1 polypeptide comprising an extracellular TFGβ1-binding domain of TGFβR1, a TLR3 transmembrane domain, and a TLR3 intracellular signaling domain. In particular embodiments, the fusion protein is referred to as a CTBR.TLR3 or CTBR.TLR3 signal convertor.

In certain embodiments, a fusion polypeptide comprises: a TGFβR2 polypeptide comprising an extracellular TFGβ1-binding domain of TGFβR2, a TLR4 transmembrane domain, and a TLR4 intracellular signaling domain; a viral self-cleaving 2A peptide; and a TGFβR1 polypeptide comprising an extracellular TFGβ1-binding domain of TGFβR1, a TLR4 transmembrane domain, and a TLR4 intracellular signaling domain. In particular embodiments, the fusion protein is referred to as a CTBR.TLR4 or CTBR.TLR4 signal convertor.

In additional embodiments, a fusion polypeptide comprises: a TGFβR2 polypeptide comprising an extracellular TFGβ1-binding domain of TGFβR2, a TLR5 transmembrane domain, and a TLR5 intracellular signaling domain; a viral self-cleaving 2A peptide; and a TGFβR1 polypeptide comprising an extracellular TFGβ1-binding domain of TGFβR1, a TLR5 transmembrane domain, and a TLR5 intracellular signaling domain. In particular embodiments, the fusion protein is referred to as a CTBR.TLR5 or CTBR.TLR5 signal convertor.

In various embodiments, a fusion polypeptide comprises: a TGFβR2 polypeptide comprising an extracellular TFGβ1-binding domain of TGFβR2, a TLR6 transmembrane domain, and a TLR6 intracellular signaling domain; a viral self-cleaving 2A peptide; and a TGFβR1 polypeptide comprising an extracellular TFGβ1-binding domain of TGFβR1, a TLR6 transmembrane domain, and a TLR6 intracellular signaling domain. In particular embodiments, the fusion protein is referred to as a CTBR.TLR6 or CTBR.TLR6 signal convertor.

In some embodiments, a fusion polypeptide comprises: a TGFβR2 polypeptide comprising an extracellular TFGβ1-binding domain of TGFβR2, a TLR7 transmembrane domain, and a TLR7 intracellular signaling domain; a viral self-cleaving 2A peptide; and a TGFβR1 polypeptide comprising an extracellular TFGβ1-binding domain of TGFβR1, a TLR7 transmembrane domain, and a TLR7 intracellular signaling domain. In particular embodiments, the fusion protein is referred to as a CTBR.TLR7 or CTBR.TLR7 signal convertor.

In particular embodiments, a fusion polypeptide comprises: a TGFβR2 polypeptide comprising an extracellular TFGβ1-binding domain of TGFβR2, a TLR8 transmembrane domain, and a TLR8 intracellular signaling domain; a viral self-cleaving 2A peptide; and a TGFβR1 polypeptide comprising an extracellular TFGβ1-binding domain of TGFβR1, a TLR8 transmembrane domain, and a TLR8 intracellular signaling domain. In particular embodiments, the fusion protein is referred to as a CTBR.TLR8 or CTBR.TLR8 signal convertor.

In additional embodiments, a fusion polypeptide comprises: a TGFβR2 polypeptide comprising an extracellular TFGβ1-binding domain of TGFβR2, a TLR9 transmembrane domain, and a TLR9 intracellular signaling domain; a viral self-cleaving 2A peptide; and a TGFβR1 polypeptide comprising an extracellular TFGβ1-binding domain of TGFβR1, a TLR9 transmembrane domain, and a TLR9 intracellular signaling domain. In particular embodiments, the fusion protein is referred to as a CTBR.TLR9 or CTBR.TLR9 signal convertor.

In various embodiments, a fusion polypeptide comprises: a TGFβR2 polypeptide comprising an extracellular TFGβ1-binding domain of TGFβR2, a TLR10 transmembrane domain, and a TLR10 intracellular signaling domain; a viral self-cleaving 2A peptide; and a TGFβR1 polypeptide comprising an extracellular TFGβ1-binding domain of TGFβR1, a TLR10 transmembrane domain, and a TLR10 intracellular signaling domain. In particular embodiments, the fusion protein is referred to as a CTBR.TLR10 or CTBR.TLR10 signal convertor.

In some embodiments, the viral self-cleaving 2A polypeptide is selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide.

In further embodiments, a fusion polypeptide contemplated herein further comprises an engineered antigen receptor and a second viral self-cleaving 2A polypeptide.

In certain embodiments, the second viral self-cleaving 2A polypeptide is selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide.

In particular embodiments, the engineered antigen receptor is selected from the group consisting of: an engineered T cell receptor (TCR), a chimeric antigen receptor (CAR), a DARIC receptor or components thereof, and a chimeric cytokine receptor; optionally, wherein the engineered antigen receptor recognizes an antigen selected from the group consisting of: alpha folate receptor, 5T4, αvβ6 integrin, BCMA, B7-H3, B7-H6, CAIX, CD16, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, VEGFR2, and WT-1.

In further embodiments, a fusion polypeptide comprises an amino acid sequence set forth in any one of SEQ ID NOs: 26 to 35.

In various embodiments, a polynucleotide encoding a fusion polypeptide contemplated herein is provided.

In additional embodiments, a vector comprising a polynucleotide or a fusion polynucleotide contemplated herein is provided.

In particular embodiments, a cell comprising a fusion polypeptide, a polynucleotide, or a vector contemplated herein is provided.

In further embodiments, the cell is a hematopoietic cell.
In certain embodiments, the cell is a T cell.
In various embodiments, the cell is a CD3+, CD4+, and/or CD8+ cell.
In some embodiments, the cell is an immune effector cell.

In additional embodiments, the cell is a cytotoxic T lymphocytes (CTLs), a tumor infiltrating lymphocytes (TILs), or a helper T cells.

In further embodiments, the cell is a natural killer (NK) cell or natural killer T (NKT) cell.

In particular embodiments, the source of the cell is peripheral blood mononuclear cells, bone marrow, lymph nodes tissue, cord blood, thymus issue, tissue from a site of infection, ascites, pleural effusion, spleen tissue, or tumors.

In some embodiments, a cell comprising a fusion polypeptide contemplated herein further comprises an engineered antigen receptor.

In various embodiments, the engineered antigen receptor is selected from the group consisting of: an engineered T cell receptor (TCR), a chimeric antigen receptor (CAR), a DARIC receptor or components thereof, and a chimeric cytokine receptor.

In additional embodiments, a composition comprising a fusion polypeptide, a polynucleotide, a vector, or a cell contemplated herein is provided.

In particular embodiments, a pharmaceutical composition comprising a pharmaceutically acceptable carrier and a fusion polypeptide, a polynucleotide, a vector, or a cell contemplated herein is provided.

In certain embodiments, a method of treating a subject in need thereof comprises administering the subject an effective amount of a composition or pharmaceutical composition contemplated herein.

In some embodiments, a method of treating, preventing, or ameliorating at least one symptom of a cancer, infectious disease, autoimmune disease, inflammatory disease, and immunodeficiency, or condition associated therewith, comprises administering to the subject an effective amount of a composition or pharmaceutical composition contemplated herein.

In additional embodiments, a method of treating a solid cancer comprises administering to the subject an effective amount of a composition or pharmaceutical composition contemplated herein.

In various embodiments, the solid cancer comprises liver cancer, pancreatic cancer, lung cancer, breast cancer, ovarian cancer, prostate cancer, testicular cancer, bladder cancer, brain cancer, sarcoma, head and neck cancer, bone cancer, thyroid cancer, kidney cancer, or skin cancer.

In particular embodiments, the solid cancer is a pancreatic cancer, a lung cancer, or a breast cancer.

In certain embodiments, a method of treating a hematological malignancy comprises administering to the subject an effective amount of a composition or pharmaceutical composition contemplated herein is provided.

In various embodiments, the hematological malignancy is a leukemia, lymphoma, or multiple myeloma.

BRIEF DESCRIPTION OF SEVERAL VIEWS OF THE DRAWINGS

FIG. 3 shows phospho-SMAD2/3 expression in primary human T cells transduced with an anti-ROR1 CAR alone and in combination with the TGFβ DNR, TGFβ R2 subunit, and the CTBR12 signal convertor and treated with TGFβ1 compared to untreated cells.

FIG. 15 also shows phospho-SMAD2/3 expression in primary human T cells transduced with an anti-EGFR CAR alone and in combination with the TGFβ DNR, the CTBR12 signal convertor, and the CTBR7 signal convertor and treated with TGFβ1 (bottom panel) compared to untreated cells.

FIG. 20 shows a cartoon of polypeptides encoding a T cell receptor (TCR) that recognizes NY-ESO1 (A2), an NY-ESO1 TCR and a TGFβ dominant negative receptor (NY-ESO1.DNR); an NY-ESO1 TCR and CTBR7 signal convertor (NY-ESO1.CTBR7), and an NY-ESO1 TCR and CTBR12 signal convertor (NY-ESO1.CTBR12).

FIG. 22 also shows phospho-STAT4 expression in primary human T cells transduced with an NY-ESO1.CTBR12 and treated with either IL-12 or TGFβ1 (bottom panel).

FIG. 23 shows IFNγ secretion from primary human T cells transduced with an NY-ESO1 TCR, NY-ESO1.DNR, NY-ESO1.CTBR7, and NY-ESO1.CTBR12 cultured with A2(+).NY-ESO1(+) cell lines in the presence or absence of TGFβ1.

BRIEF DESCRIPTION OF THE SEQUENCE IDENTIFIERS

Figure 1:
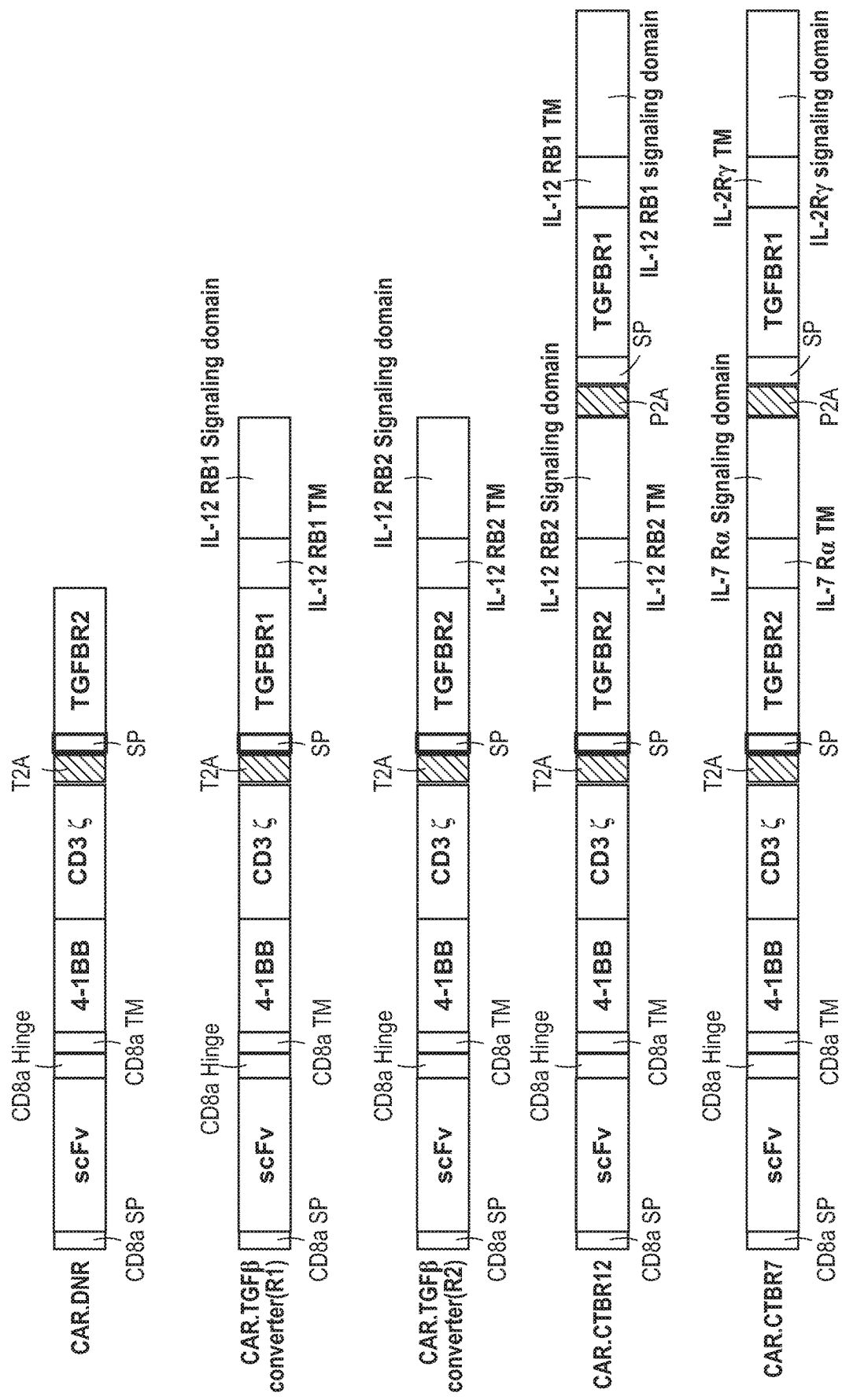
FIG. 1 shows a cartoon of polypeptides encoding a chimeric antigen receptor (CAR) and TGFβ dominant negative receptor (CAR.DNR); a CAR and a TGFβR2 subunit (R2); a CAR and CTBR12 signal convertor (CAR.CTBR12), and a CAR and CTBR7 signal convertor (CAR. CTBR7).

SEQ ID NO: 1 sets forth the polypeptide sequence of human TGFβR1.

SEQ ID NO: 2 sets forth the polypeptide sequence of human TGFβR2.

SEQ ID NO: 3 sets forth the polypeptide sequence of human IL-12Rβ1 (CD212).

SEQ ID NO: 4 sets forth the polypeptide sequence of human IL-12Rβ2.

SEQ ID NO: 5 sets forth the polypeptide sequence of human IL-7Rα (CD127).

SEQ ID NO: 6 sets forth the polypeptide sequence of human IL-2Rγ (CD132).

SEQ ID NO: 7 sets forth the polypeptide sequence of human IL-2Rβ (CD122).

SEQ ID NO: 8 sets forth the polypeptide sequence of human IL-21R (CD360).

SEQ ID NO: 9 sets forth the polypeptide sequence of human IL-18R1 (CD218a).

SEQ ID NO: 10 sets forth the polypeptide sequence of human IL-18RAP (CD218b).

SEQ ID NO: 11 sets forth the polypeptide sequence of human IL-1R1 (CD121a).

SEQ ID NO: 12 sets forth the polypeptide sequence of human IL-1RAP.

SEQ ID NO: 13 sets forth the polypeptide sequence of human IFNAR1.

SEQ ID NO: 14 sets forth the polypeptide sequence of human IFNAR2.

SEQ ID NO: 15 sets forth the polypeptide sequence of human IL-1RL2.

SEQ ID NO: 16 sets forth the polypeptide sequence of human TLR1 (CD281).

SEQ ID NO: 17 sets forth the polypeptide sequence of human TLR2 (CD282).

SEQ ID NO: 18 sets forth the polypeptide sequence of human TLR3 (CD283).

SEQ ID NO: 19 sets forth the polypeptide sequence of human TLR4 (CD284).

SEQ ID NO: 20 sets forth the polypeptide sequence of human TLR5 (CD285).

SEQ ID NO: 21 sets forth the polypeptide sequence of human TLR6 (CD286).

SEQ ID NO: 22 sets forth the polypeptide sequence of human TLR7 (CD287).

SEQ ID NO: 23 sets forth the polypeptide sequence of human TLR8 (CD288).

SEQ ID NO: 24 sets forth the polypeptide sequence of human TLR9 (CD289).

SEQ ID NO: 25 sets forth the polypeptide sequence of human TLR10 (CD290).

SEQ ID NO: 26 sets forth the polypeptide sequence of a fusion protein comprising the extracellular domain of human TGFβR1 and the transmembrane and intracellular domain of human IL-12Rβ1.

SEQ ID NO: 27 sets forth the polypeptide sequence of a fusion protein comprising the extracellular domain of human TGFβR2 and the transmembrane and intracellular domain of human IL-12Rβ2.

SEQ ID NO: 28 sets forth the polypeptide sequence of a fusion protein comprising the extracellular domain of human TGFβR2 and the transmembrane and intracellular domain of human IL-12Rβ2, a polypeptide cleavage sequence, and the extracellular domain of human TGFβR1 and the transmembrane and intracellular domain of human IL-12Rβ1.

SEQ ID NO: 29 sets forth the polypeptide sequence of a fusion protein comprising a chimeric antigen receptor, a polypeptide cleavage sequence, the extracellular domain of human TGFβR2 and the transmembrane and intracellular domain of human IL-12Rβ2, a polypeptide cleavage sequence, and the extracellular domain of human TGFβR1 and the transmembrane and intracellular domain of human IL-12Rβ1.

SEQ ID NO: 30 sets forth the polypeptide sequence of a fusion protein comprising a chimeric antigen receptor, a polypeptide cleavage sequence, the extracellular domain of human TGFβR2 and the transmembrane and intracellular domain of human IL-12Rβ2, a polypeptide cleavage sequence, and the extracellular domain of human TGFβR1 and the transmembrane and intracellular domain of human IL-12Rβ1. X represents any scFv sequence.

SEQ ID NO: 31 sets forth the polypeptide sequence of a fusion protein comprising the extracellular domain of human TGFβR1 and the transmembrane and intracellular domain of human IL-2Rγ.

SEQ ID NO: 32 sets forth the polypeptide sequence of a fusion protein comprising the extracellular domain of human TGFβR2 and the transmembrane and intracellular domain of human IL-7Rα.

SEQ ID NO: 33 sets forth the polypeptide sequence of a fusion protein comprising the extracellular domain of human TGFβR2 and the transmembrane and intracellular domain of human IL-7Rα, a polypeptide cleavage sequence, and the extracellular domain of human TGFβR1 and the transmembrane and intracellular domain of human IL-2Rγ.

SEQ ID NO: 34 sets forth the polypeptide sequence of a fusion protein comprising a chimeric antigen receptor, a polypeptide cleavage sequence, the extracellular domain of human TGFβR2 and the transmembrane and intracellular domain of human IL-7Rα, a polypeptide cleavage sequence, and the extracellular domain of human TGFβR1 and the transmembrane and intracellular domain of human IL-2Rγ.

SEQ ID NO: 35 sets forth the polypeptide sequence of a fusion protein comprising a chimeric antigen receptor, a polypeptide cleavage sequence, the extracellular domain of human TGFβR2 and the transmembrane and intracellular domain of human IL-7Rα, a polypeptide cleavage sequence, and the extracellular domain of human TGFβR1 and the transmembrane and intracellular domain of human IL-2Rγ.

SEQ ID NOs: 36-46 set forth the amino acid sequences of various linkers.

SEQ ID NOs: 47-71 set forth the amino acid sequences of protease cleavage sites and self-cleaving polypeptide cleavage sites.

DETAILED DESCRIPTION

A. Overview

Chimeric antigen receptor expressing T cells (CAR T cells) have demonstrated significant anti-tumor activity in hematologic malignancies. Activity in solid tumor indications, however, has been limited in part due to the immunosuppressive solid tumor microenvironment (TME). The overproduction of immunosuppressive cytokines, including TGFβ, by tumor cells and tumor-infiltrating lymphocytes contributes to an immunosuppressive tumor microenvironment. TGFβ inhibits T cell function via a variety of mechanisms. TGFβ is frequently associated with tumor metastasis and invasion, inhibiting the function of immune cells, and poor prognosis in patients with cancer. TGFβ signaling through TGFβR2 in tumor-specific CTLs dampens their function and frequency in the tumor, and blocking TGFβ signaling on CD8$^+$ T cells with monoclonal antibodies results in more rapid tumor surveillance and the presence of many more CTLs at the tumor site. To date, strategies to inhibit TGFβ in a clinical setting have not resulted in significant therapeutic benefits.

The present disclosure generally relates to polypeptides that convert an immunosuppressive TGFβ signal to an immunostimulatory signal and to cells expressing the polypeptides. Without wishing to be bound by any particular theory, the polypeptides contemplated herein are TGFβ signal convertors that comprise the TGFβ binding domains of TGFβR1 and TGFβR2, that when linked to immunostimulatory endodomains and co-expressed in immune effector cells, can convert TGFβ exposure from an immunosuppressive signal to an immunostimulatory one that stimulates immune effector cell activity and function. Coexpression of TGFβ signal convertor polypeptides in immune effector cells renders the cells resistant to the immunosuppressive impacts of TGFβ, e.g., by restoring or increasing proinflammatory cytokine secretion. In particular preferred embodiments, the TGFβ signal convertor polypeptide is referred to as a chimeric TGFβ receptor or CTBR.

In various embodiments, the present disclosure contemplates, in part, polypeptides that convert an immunosuppressive TGFβ signal to an immunostimulatory signal mediated through or by one or more intracellular domains of one or more immune receptors.

In various embodiments, the present disclosure contemplates, in part, polypeptides that convert an immunosuppressive TGFβ signal to an immunostimulatory signal mediated through or by one or more intracellular domains of one or more cytokine receptors.

In various embodiments, the present disclosure contemplates, in part, polypeptides that convert an immunosuppressive TGFβ signal to an immunostimulatory signal mediated through or by one or more intracellular domains of one or more interleukin receptors.

In various embodiments, the present disclosure contemplates, in part, polypeptides that convert an immunosuppressive TGFβ signal to an immunostimulatory signal mediated through or by one or more intracellular domains of one or more pattern recognition receptors.

In various embodiments, the present disclosure contemplates, in part, polypeptides that convert an immunosuppressive TGFβ signal to an immunostimulatory signal mediated through or by one or more intracellular domains of one or more toll-like receptors.

In particular embodiments, the present disclosure contemplates, in part, a polypeptide comprising a TGFβR1 extracellular domain that binds TGFβ, a transmembrane domain and one or more intracellular domains of one or more immune receptors; and a polypeptide comprising a TGFβR2 extracellular domain that binds TGFβ, a transmembrane domain and one or more intracellular domains of one or more immune receptors. In one embodiment, the polypeptides are linked to each other by a polypeptide cleavage signal, e.g., a 2A polypeptide cleavage signal.

In particular embodiments, the present disclosure contemplates, in part, an immune effector cell, e.g., CAR T cell, that expresses a polypeptide comprising a TGFβR1 extracellular domain that binds TGFβ, a transmembrane domain and one or more intracellular domains of one or more immune receptors; and a polypeptide comprising a TGFβR2 extracellular domain that binds TGFβ, a transmembrane domain and one or more intracellular domains of one or more immune receptors.

In particular embodiments, the transmembrane domains and intracellular signaling domains are isolated from an IL-12 receptor, an IL-7 receptor, an IL-15 receptor, an IL-21 receptor, an IL-2 receptor, an IL-1 receptor, an IL-18 receptor, an IL-36 receptor, a type I IFN receptor, a TLR1 receptor, a TLR2 receptor, a TLR3 receptor, a TLR4 receptor, a TLR5 receptor, a TLR6 receptor, a TLR7 receptor, a TLR8 receptor, a TLR9 receptor, or a TLR10 receptor.

In particular embodiments, the transmembrane domains and intracellular signaling domains are isolated from IL-12Rβ2, IL-7Rα, IL-2Rγ, IL-2Rβ, IL-21R, IL-18R1, IL-18RAP, IL-1R1, IL-1RAP, IFNAR1, IFNAR2, IL-1RL2, TLR1, TLR2, TLR3, TLR4, TLR5, TLR6, TLR7, TLR8, TLR9, or TLR10.

The practice of the particular embodiments will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., *Molecular Cloning: A Laboratory Manual* (3rd Edition, 2001); Sambrook, et al., *Molecular Cloning: A Laboratory Manual* (2nd Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford, 1985); Anand, *Techniques for the Analysis of Complex Genomes*, (Academic Press, New York, 1992); *Transcription and Translation* (B. Hames & S. Higgins, Eds., 1984); Perbal, *A Practical Guide to Molecular Cloning* (1984); Harlow and Lane, *Antibodies*, (Cold Spring Harbor Laboratory Press, Cold Spring Harbor, N.Y., 1998) *Current Protocols in Immunology* Q. E. Coligan, A. M. Kruisbeek, D. H. Margulies, E. M. Shevach and W. Strober, eds., 1991); *Annual Review of Immunology*; as well as monographs in journals such as *Advances in Immunology*.

B. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of particular embodiments, preferred embodiments of compositions, methods and materials are described herein. For the purposes of the present disclosure, the following terms are defined below.

The articles "a," "an," and "the" are used herein to refer to one or to more than one (i.e., to at least one, or to one or more) of the grammatical object of the article. By way of example, "an element" means one element or one or more elements.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are present that materially affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment. Thus, the appearances of the foregoing phrases in various places throughout this specification are not necessarily all referring to the same embodiment. Furthermore, the particular features, structures, or characteristics may be combined in any suitable manner in one or more embodiments. It is also understood that the positive recitation of a feature in one embodiment, serves as a basis for excluding the feature in a particular embodiment.

An "antigen (Ag)" refers to a compound, composition, or substance that can stimulate the production of antibodies or a T cell response in an animal, including compositions (such as one that includes a cancer-specific protein) that are injected or absorbed into an animal. Exemplary antigens include but are not limited to lipids, carbohydrates, polysaccharides, glycoproteins, peptides, or nucleic acids. An antigen reacts with the products of specific humoral or cellular immunity, including those induced by heterologous antigens, such as the disclosed antigens.

A "target antigen" or "target antigen of interest" is an antigen that a binding domain contemplated herein, is designed to bind. In particular embodiments, the target antigen is selected from the group consisting of: alpha folate receptor, 5T4, $\alpha v\beta 6$ integrin, BCMA, B7-H3, B7-H6, CAIX, CD16, CD19, CD20, CD22, CD30, CD33, CD37, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FR$\alpha$, GD2, GD3, Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11R$\alpha$, IL-13R$\alpha$2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, STn, TAG72, TEMs, VEGFR2, and WT-1.

In one embodiment, the antigen is an MHC-peptide complex, such as a class I MHC-peptide complex or a class II MHC-peptide complex.

As used herein, the terms, "binding domain," "extracellular domain," "antigen binding domain," "extracellular binding domain," "extracellular antigen binding domain," "antigen-specific binding domain," and "extracellular antigen specific binding domain," are used interchangeably and provide a polypeptide with the ability to specifically bind to the target antigen of interest. The binding domain may be derived either from a natural, synthetic, semi-synthetic, or recombinant source. Illustrative examples of binding domains include, but are not limited to antibodies and antigen binding fragments thereof, FN3 domains and DARPins.

The terms "specific binding affinity" or "specifically binds" or "specifically bound" or "specific binding" or "specifically targets" as used herein, describe binding of an antibody or antigen binding fragment thereof to a target antigen at greater binding affinity than background binding. A binding domain "specifically binds" to a target antigen, if it binds to or associates with the antigen with an affinity or $K_a$ (i.e., an equilibrium association constant of a particular binding interaction with units of 1/M) of, for example, greater than or equal to about $10^5$ M$^{-1}$. In certain embodiments, a binding domain (or a fusion protein thereof) binds to a target with a $K_a$ greater than or equal to about $10^6$ M$^{-1}$, $10^7$ M$^{-1}$, $10^8$ M$^{-1}$, $10^9$ M$^{-1}$, $10^{10}$ M$^{-1}$, $10^{11}$ M$^{-1}$, $10^{12}$ M$^{-1}$, or $10^{13}$ M$^{-1}$. "High affinity" binding domains (or single chain fusion proteins thereof) refers to those binding domains with a $K_a$ of at least $10^7$ M$^{-1}$, at least $10^8$ M$^{-1}$, at least $10^9$ M$^{-1}$, at least $10^{10}$ M$^{-1}$, at least $10^{11}$ M$^{-1}$, at least $10^{12}$ M$^{-1}$, at least $10^{13}$ M$^{-1}$, or greater.

Alternatively, affinity may be defined as an equilibrium dissociation constant ($K_d$) of a particular binding interaction with units of M (e.g., $10^{-5}$ M to $10^{-13}$ M, or less). Affinities of binding domain polypeptides can be readily determined using conventional techniques, e.g., by competitive ELISA (enzyme-linked immunosorbent assay), or by binding association, or displacement assays using labeled ligands, or using a surface-plasmon resonance device such as the Biacore T100, which is available from Biacore, Inc., Piscataway, N.J., or optical biosensor technology such as the EPIC system or EnSpire that are available from Corning and Perkin Elmer respectively (see also, e.g., Scatchard et al. (1949) Ann. N.Y. Acad. Sci. 51:660; and U.S. Pat. Nos. 5,283,173; 5,468,614, or the equivalent).

In one embodiment, the affinity of specific binding is about 2 times greater than background binding, about 5 times greater than background binding, about 10 times greater than background binding, about 20 times greater than background binding, about 50 times greater than background binding, about 100 times greater than background binding, or about 1000 times greater than background binding or more.

An "antibody" refers to a binding agent that is a polypeptide comprising at least a light chain or heavy chain immunoglobulin variable region which specifically recognizes and binds an epitope of an antigen, such as a lipid, carbohydrate, polysaccharide, glycoprotein, peptide, or nucleic acid containing an antigenic determinant, such as those recognized by an immune cell.

An "epitope" or "antigenic determinant" refers to the region of an antigen to which a binding agent binds.

Antibodies include antigen binding fragments thereof, such as Camel Ig, Ig NAR, Fab fragments, Fab' fragments, F(ab)'$_2$ fragments, F(ab)'$_3$ fragments, Fv, single chain Fv proteins ("scFv"), bis-scFv, (scFv)$_2$, minibodies, diabodies, triabodies, tetrabodies, disulfide stabilized Fv proteins ("dsFv"), and single-domain antibody (sdAb, Nanobody) and portions of full length antibodies responsible for antigen binding. The term also includes genetically engineered forms such as chimeric antibodies (for example, humanized murine antibodies), heteroconjugate antibodies (such as, bispecific antibodies) and antigen binding fragments thereof. See also, Pierce Catalog and Handbook, 1994-1995 (Pierce Chemical Co., Rockford, Ill.); Kuby, J., Immunology, 3rd Ed., W. H. Freeman & Co., New York, 1997.

As would be understood by the skilled person and as described elsewhere herein, a complete antibody comprises two heavy chains and two light chains. Each heavy chain consists of a variable region and a first, second, and third constant region, while each light chain consists of a variable region and a constant region. Mammalian heavy chains are classified as $\alpha$, $\delta$, $\epsilon$, $\gamma$, and $\mu$. Mammalian light chains are classified as $\lambda$ or $\kappa$. Immunoglobulins comprising the $\alpha$, $\delta$, $\epsilon$, $\gamma$, and $\mu$ heavy chains are classified as immunoglobulin (Ig)A, IgD, IgE, IgG, and IgM. The complete antibody forms a "Y" shape. The stem of the Y consists of the second and third constant regions (and for IgE and IgM, the fourth constant region) of two heavy chains bound together and disulfide bonds (inter-chain) are formed in the hinge. Heavy chains γ, α and δ have a constant region composed of three tandem (in a line) Ig domains, and a hinge region for added flexibility; heavy chains μ and ε have a constant region composed of four immunoglobulin domains. The second and third constant regions are referred to as "CH2 domain" and "CH3 domain", respectively. Each arm of the Y includes the variable region and first constant region of a single heavy chain bound to the variable and constant regions of a single light chain. The variable regions of the light and heavy chains are responsible for antigen binding.

Light and heavy chain variable regions contain a "framework" region interrupted by three hypervariable regions, also called "complementarity-determining regions" or "CDRs." The CDRs can be defined or identified by conventional methods, such as by sequence according to Kabat et al. (Wu, T T and Kabat, E. A., *J Exp Med.* 132(2):211-50, (1970); Borden, P. and Kabat E. A., *PNAS,* 84: 2440-2443 (1987); (see, Kabat et al., *Sequences of Proteins of Immunological Interest,* U.S. Department of Health and Human Services, 1991, which is hereby incorporated by reference), or by structure according to Chothia et al (Chothia, C. and Lesk, A. M., *J Mol. Biol.,* 196(4): 901-917 (1987), Chothia, C. et al, *Nature,* 342: 877-883 (1989)).

Illustrative examples of rules for predicting light chain CDRs include: CDR-L1 starts at about residue 24, is preceded by a Cys, is about 10-17 residues, and is followed by a Trp (typically Trp-Tyr-Gln, but also, Trp-Leu-Gln, Trp-Phe-Gln, Trp-Tyr-Leu); CDR-L2 starts about 16 residues after the end of CDR-L1, is generally preceded by Ile-Tyr, but also, Val-Tyr, Ile-Lys, Ile-Phe, and is 7 residues; and CDR-L3 starts about 33 residues after the end of CDR-L2, is preceded by a Cys, is 7-11 residues, and is followed by Phe-Gly-XXX-Gly (XXX is any amino acid) [SEQ ID NO:73].

Illustrative examples of rules for predicting heavy chain CDRs include: CDR-H1 starts at about residue 26, is preceded by Cys-XXX-XXX-XXX (SEQ ID NO:74), is 10-12 residues and is followed by a Trp (typically Trp-Val, but also, Trp-Ile, Trp-Ala); CDR-H2 starts about 15 residues after the end of CDR-H1, is generally preceded by Leu-Glu-Trp-Ile-Gly (SEQ ID NO:75), or a number of variations, is 16-19 residues, and is followed by Lys/Arg-Leu/Ile/Val/Phe/Thr/Ala-Thr/Ser/Ile/Ala; and CDR-H3 starts about 33 residues after the end of CDR-H2, is preceded by Cys-XXX-XXX (typically Cys-Ala-Arg), is 3 to 25 residues, and is followed by Trp-Gly-XXX-Gly (SEQ ID NO:76).

In one embodiment, light chain CDRs and the heavy chain CDRs are determined according to the Kabat method In one embodiment, light chain CDRs and the heavy chain CDR2 and CDR3 are determined according to the Kabat method, and heavy chain CDR1 is determined according to the AbM method, which is a comprise between the Kabat and Clothia methods, see e.g., Whitelegg N & Rees A R, *Protein Eng.* 2000 December; 13(12):819-24 and *Methods Mol Biol.* 2004; 248:51-91. Programs for predicting CDRs are publicly available, e.g., AbYsis (www.bioinf.org.uk/abysis/).

The sequences of the framework regions of different light or heavy chains are relatively conserved within a species, such as humans. The framework region of an antibody, that is the combined framework regions of the constituent light and heavy chains, serves to position and align the CDRs in three-dimensional space. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, the CDRs located in the variable domain of the heavy chain of the antibody are referred to as CDRH1, CDRH2, and CDRH3, whereas the CDRs located in the variable domain of the light chain of the antibody are referred to as CDRL1, CDRL2, and CDRL3. Antibodies with different specificities (i.e., different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_L$" or "VL" refer to the variable region of an immunoglobulin light chain, including that of an antibody, Fv, scFv, dsFv, Fab, or other antibody fragment as disclosed herein.

References to "$V_H$" or "VH" refer to the variable region of an immunoglobulin heavy chain, including that of an antibody, Fv, scFv, dsFv, Fab, or other antibody fragment as disclosed herein.

A "monoclonal antibody" is an antibody produced by a single clone of B lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a mouse. In particular preferred embodiments, an antigen-specific binding domain is a chimeric antibody or antigen binding fragment thereof.

In particular embodiments, the antibody is a human antibody (such as a human monoclonal antibody) or antigen binding fragment thereof that specifically binds to a target antigen. Human antibodies can be constructed by combining Fv clone variable domain sequence(s) selected from human-derived phage display libraries with known human constant domain sequences(s) as described above. Alternatively, human monoclonal antibodies may be made by the hybridoma method. Human myeloma and mouse-human heteromyeloma cell lines for the production of human monoclonal antibodies have been described, for example, by Kozbor J. Immunol., 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991). In addition, transgenic animals (e.g., mice) can be used to produce a full repertoire of human antibodies in the absence of endogenous immunoglobulin production. See, e.g., Jakobovits et al., *PNAS USA,* 90: 2551 (1993); Jakobovits et al., *Nature,* 362: 255 (1993); Bruggermann et al., *Year in Immunol.,* 7: 33 (1993). Gene shuffling can also be used to derive human antibodies from non-human, e.g., rodent antibodies, where the human antibody has similar affinities and specificities to the starting non-human antibody. See PCT WO 93/06213 published Apr. 1, 1993. Unlike traditional humanization of non-human antibodies by CDR grafting, this technique provides completely human antibodies, which have no FR or CDR residues of non-human origin.

A "humanized" antibody is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. Humanized or other monoclonal antibodies can have additional conservative amino acid substitutions, which have substantially no effect on antigen binding or other immunoglobulin functions. Humanized antibodies can be constructed by means of genetic engineering (see for example, U.S. Pat. No. 5,585,089).

"Camel Ig" or "camelid VHH" as used herein refers to the smallest known antigen-binding unit of a heavy chain antibody (Koch-Nolte, et al, *FASEB J.*, 21: 3490-3498 (2007)). A "heavy chain antibody" or a "camelid antibody" refers to an antibody that contains two VH domains and no light chains (Riechmann L. et al, *J. Immunol. Methods* 231:25-38 (1999); WO94/04678; WO94/25591; U.S. Pat. No. 6,005,079).

"IgNAR" of "immunoglobulin new antigen receptor" refers to class of antibodies from the shark immune repertoire that consist of homodimers of one variable new antigen receptor (VNAR) domain and five constant new antigen receptor (CNAR) domains. IgNARs represent some of the smallest known immunoglobulin-based protein scaffolds and are highly stable and possess efficient binding characteristics. The inherent stability can be attributed to both (i) the underlying Ig scaffold, which presents a considerable number of charged and hydrophilic surface exposed residues compared to the conventional antibody VH and VL domains found in murine antibodies; and (ii) stabilizing structural features in the complementary determining region (CDR) loops including inter-loop disulfide bridges, and patterns of intra-loop hydrogen bonds.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three hypervariable regions (HVRs) of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *PNAS USA* 90: 6444-6448 (1993). Triabodies and tetrabodies are also described in Hudson et al., *Nat. Med.* 9:129-134 (2003).

"Single domain antibody" or "sdAb" or "nanobody" refers to an antibody fragment that consists of the variable region of an antibody heavy chain (VH domain) or the variable region of an antibody light chain (VL domain) (Holt, L., et al, *Trends in Biotechnology*, 21(11): 484-490).

"Single-chain Fv" or "scFv" antibody fragments comprise the VH and VL domains of antibody, wherein these domains are present in a single polypeptide chain and in either orientation (e.g., VL-VH or VH-VL). Generally, the scFv polypeptide further comprises a polypeptide linker between the VH and VL domains which enables the scFv to form the desired structure for antigen binding. For a review of scFv, see, e.g., Pluckthün, in *The Pharmacology of Monoclonal Antibodies*, vol. 113, Rosenburg and Moore eds., (Springer-Verlag, New York, 1994), pp. 269-315.

Single chain antibodies may be cloned from the V region genes of a hybridoma specific for a desired target. The production of such hybridomas has become routine. A technique which can be used for cloning the variable region heavy chain ($V_H$) and variable region light chain ($V_L$) has been described, for example, in Orlandi et al., *PNAS*, 1989; 86: 3833-3837.

A "linker" refers to a plurality of amino acid residues between the various polypeptide domains, e.g., between VH and VL domains, added for appropriate spacing and conformation of the molecule. In particular embodiments, the linker is a variable region linking sequence. A "variable region linking sequence," is an amino acid sequence that connects the VH and VL domains and provides a spacer function compatible with interaction of the two sub-binding domains so that the resulting polypeptide retains a specific binding affinity to the same target molecule as an antibody that comprises the same light and heavy chain variable regions. In particular embodiments, a linker separates one or more heavy or light chain variable domains, hinge domains, multimerization domains, transmembrane domains, co-stimulatory domains, and/or primary signaling domains.

Illustrated examples of linkers suitable for use in particular embodiments contemplated herein include, but are not limited to the following amino acid sequences: GGG; DGGGS (SEQ ID NO: 36); TGEKP (SEQ ID NO: 37) (see, e.g., Liu et al., PNAS 5525-5530 (1997)); GGRR (SEQ ID NO: 38) (Pomerantz et al. 1995, supra); (GGGGS)$_n$ wherein n=1, 2, 3, 4 or 5 (SEQ ID NO: 39) (Kim et al., PNAS 93, 1156-1160 (1996.); EGKSSGSGSESKVD (SEQ ID NO:

40) (Chaudhary et al., 1990, Proc. Natl. Acad. Sci. U.S.A. 87:1066-1070); KESGSVSSEQLAQFRSLD (SEQ ID NO: 41) (Bird et al., 1988, Science 242:423-426), GGRRGGGS (SEQ ID NO: 42); LRQRDGERP (SEQ ID NO: 43); LRQKDGGGSERP (SEQ ID NO: 44); LRQKD(GGGS)$_2$ERP (SEQ ID NO: 45). Alternatively, flexible linkers can be rationally designed using a computer program capable of modeling both DNA-binding sites and the peptides themselves (Desjarlais & Berg, PNAS 90:2256-2260 (1993), PNAS 91:11099-11103 (1994) or by phage display methods. In one embodiment, the linker comprises the following amino acid sequence: GSTSGSGKPGSGEGSTKG (SEQ ID NO: 46) (Cooper et al., Blood, 101(4): 1637-1644 (2003)).

A "spacer domain," refers to a polypeptide that separates two domains. In one embodiment, a spacer domain moves an antigen binding domain away from the effector cell surface to enable proper cell/cell contact, antigen binding and activation (Patel et al., Gene Therapy, 1999; 6: 412-419). In particular embodiments, a spacer domain separates one or more heavy or light chain variable domains, multimerization domains, transmembrane domains, co-stimulatory domains, and/or primary signaling domains. The spacer domain may be derived either from a natural, synthetic, semi-synthetic, or recombinant source. In certain embodiments, a spacer domain is a portion of an immunoglobulin, including, but not limited to, one or more heavy chain constant regions, e.g., CH2 and CH3. The spacer domain can include the amino acid sequence of a naturally occurring immunoglobulin hinge region or an altered immunoglobulin hinge region.

A "hinge domain," refers to a polypeptide that plays a role in positioning the antigen binding domain away from the effector cell surface to enable proper cell/cell contact, antigen binding and activation. In particular embodiments, polypeptides may comprise one or more hinge domains between the binding domain and the multimerization domain, between the binding domain and the transmembrane domain (TM), or between the multimerization domain and the transmembrane domain. The hinge domain may be derived either from a natural, synthetic, semi-synthetic, or recombinant source. The hinge domain can include the amino acid sequence of a naturally occurring immunoglobulin hinge region or an altered immunoglobulin hinge region.

An "altered hinge region" refers to (a) a naturally occurring hinge region with up to 30% amino acid changes (e.g., up to 25%, 20%, 15%, 10%, or 5% amino acid substitutions or deletions), (b) a portion of a naturally occurring hinge region that is at least 10 amino acids (e.g., at least 12, 13, 14 or 15 amino acids) in length with up to 30% amino acid changes (e.g., up to 25%, 20%, 15%, 10%, or 5% amino acid substitutions or deletions), or (c) a portion of a naturally occurring hinge region that comprises the core hinge region (which may be 4, 5, 6, 7, 8, 9, 10, 11, 12, 13, 14, or 15, or at least 4, 5, 6, 7, 8, 9, 10, 11, 12, 13, 14, or 15 amino acids in length). In certain embodiments, one or more cysteine residues in a naturally occurring immunoglobulin hinge region may be substituted by one or more other amino acid residues (e.g., one or more serine residues). An altered immunoglobulin hinge region may alternatively or additionally have a proline residue of a wild type immunoglobulin hinge region substituted by another amino acid residue (e.g., a serine residue).

A "multimerization domain," as used herein, refers to a polypeptide that preferentially interacts or associates with another different polypeptide directly or via a bridging molecule, wherein the interaction of different multimerization domains substantially contributes to or efficiently promotes multimerization (i.e., the formation of a dimer, trimer, or multipartite complex, which may be a homodimer, heterodimer, homotrimer, heterotrimer, homomultimer, heteromultimer). A multimerization domain may be derived either from a natural, synthetic, semi-synthetic, or recombinant source.

Illustrative examples of multimerization domains suitable for use in particular embodiments contemplated herein include an FKBP polypeptide, an FRB polypeptide, a calcineurin polypeptide, a cyclophilin polypeptide, a bacterial DHFR polypeptide, a PYL1 polypeptide, an ABI1 polypeptide, a GIB1 polypeptide, a GAI polypeptide, or variants thereof.

A "bridging factor" refers to a molecule that associates with and that is disposed between two or more multimerization domains. In particular embodiments, multimerization domains substantially contribute to or efficiently promote formation of a polypeptide complex only in the presence of a bridging factor. In particular embodiments, multimerization domains do not contribute to or do not efficiently promote formation of a polypeptide complex in the absence of a bridging factor. Illustrative examples of bridging factors suitable for use in particular embodiments contemplated herein include, but are not limited to rapamycin (sirolimus) or a rapalog thereof, coumermycin or a derivative thereof, gibberellin or a derivative thereof, abscisic acid (ABA) or a derivative thereof, methotrexate or a derivative thereof, cyclosporin A or a derivative thereof, FKCsA or a derivative thereof, trimethoprim (Tmp)-synthetic ligand for FKBP (SLF) or a derivative thereof, or any combination thereof.

Rapamycin analogs (rapalogs) include, but are not limited to those disclosed in U.S. Pat. No. 6,649,595, which rapalog structures are incorporated herein by reference in their entirety. In certain embodiments, a bridging factor is a rapalog with substantially reduced immunosuppressive effect as compared to rapamycin. In a preferred embodiment, the rapalog is AP21967 derivatives (also known as C-16-(S)-7-methylindolerapamycin, IC$_{50}$=10 nM, a chemically modified non-immunosuppressive rapamycin analogue).

A "substantially reduced immunosuppressive effect" refers to at least less than 0.1 to 0.005 times the immunosuppressive effect observed or expected for the same dose measured either clinically or in an appropriate in vitro (e.g., inhibition of T cell proliferation) or in vivo surrogate of human immunosuppressive activity.

As used herein, "anchor domain" refers to an amino acid sequence or other molecule that promotes tethering, anchoring or association of a dimerizable receptor to a cell surface. Exemplary anchor domains include an amino acid sequence with a structure that is stable in a cell membrane or an amino acid sequence that promotes the addition of a glycolipid (also known as glycosyl phosphatidylinositols or GPIs), or the like. In certain embodiments, an anchor domain is a hydrophobic domain (e.g., transmembrane domain) or a GPI signal sequence. In some embodiments, a nucleic acid molecule encoding a polypeptide contemplated herein comprises an anchor domain, optionally wherein the anchor domain is a GPI molecule.

A "transmembrane domain" or "TM domain" is a domain that anchors a polypeptide to the plasma membrane of a cell. The TM domain may be derived either from a natural, synthetic, semi-synthetic, or recombinant source.

An "intracellular signaling domain" refers to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal.

The term "effector function" or "effector cell function" refers to a specialized function of an immune effector cell. Effector function includes, but is not limited to, activation, cytokine production, proliferation and cytotoxic activity, including the release of cytotoxic factors, or other cellular responses elicited with antigen binding to the receptor expressed on the immune effector cell.

It is known that signals generated through the TCR alone are insufficient for full activation of the T cell and that a secondary or co-stimulatory signal is also required. Thus, T cell activation can be said to be mediated by two distinct classes of intracellular signaling domains: primary signaling domains that initiate antigen-dependent primary activation through the TCR (e.g., a TCR/CD3 complex) and co-stimulatory signaling domains that act in an antigen-independent manner to provide a secondary or co-stimulatory signal.

A "primary signaling domain" refers to a signaling domain that regulates the primary activation of the TCR complex either in a stimulatory way, or in an inhibitory way. Primary signaling domains that act in a stimulatory manner may contain signaling motifs which are known as immunoreceptor tyrosine-based activation motifs or ITAMs. Illustrative examples of ITAM containing primary signaling domains that are suitable for use in particular embodiments include, but are not limited to those derived from FcRγ, FcRβ, CD3γ, CD3δ, CD3ε, CD3ζ, CD22, CD79a, CD79b, and CD66d.

As used herein, the term, "co-stimulatory signaling domain," or "co-stimulatory domain" refers to an intracellular signaling domain of a co-stimulatory molecule. Co-stimulatory molecules are cell surface molecules other than antigen receptors or Fc receptors that provide a second signal required for efficient activation and function of T lymphocytes upon binding to antigen. Illustrative examples of such co-stimulatory molecules from which co-stimulatory domains may be isolated include, but are not limited to: TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70.

An "immune disorder" refers to a disease that evokes a response from the immune system. In particular embodiments, the term "immune disorder" refers to a cancer, an autoimmune disease, or an immunodeficiency. In one embodiment, immune disorders encompasse infectious disease.

As used herein, the term "cancer" relates generally to a class of diseases or conditions in which abnormal cells divide without control and can invade nearby tissues.

As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor.

As used herein, the term "benign" or "non-malignant" refers to tumors that may grow larger but do not spread to other parts of the body. Benign tumors are self-limited and typically do not invade or metastasize.

A "cancer cell" refers to an individual cell of a cancerous growth or tissue. Cancer cells include both solid cancers and liquid cancers. A "tumor" or "tumor cell" refers generally to a swelling or lesion formed by an abnormal growth of cells, which may be benign, pre-malignant, or malignant. Most cancers form tumors, but liquid cancers, e.g., leukemia, do not necessarily form tumors. For those cancers that form tumors, the terms cancer (cell) and tumor (cell) are used interchangeably. The amount of a tumor in an individual is the "tumor burden" which can be measured as the number, volume, or weight of the tumor.

The term "relapse" refers to the diagnosis of return, or signs and symptoms of return, of a cancer after a period of improvement or remission.

"Remission," is also referred to as "clinical remission," and includes both partial and complete remission. In partial remission, some, but not all, signs and symptoms of cancer have disappeared. In complete remission, all signs and symptoms of cancer have disappeared, although cancer still may be in the body.

"Refractory" refers to a cancer that is resistant to, or non-responsive to, therapy with a particular therapeutic agent. A cancer can be refractory from the onset of treatment (i.e., non-responsive to initial exposure to the therapeutic agent), or as a result of developing resistance to the therapeutic agent, either over the course of a first treatment period or during a subsequent treatment period.

"Antigen negative" refers to a cell that does not express antigen or expresses a negligible amount of antigen that is undetectable. In one embodiment, antigen negative cells do not bind receptors directed to the antigen. In one embodiment, antigen negative cells do not substantially bind receptors directed to the antigen.

An "autoimmune disease" refers to a disease in which the body produces an immunogenic (i.e., immune system) response to some constituent of its own tissue. In other words, the immune system loses its ability to recognize some tissue or system within the body as "self" and targets and attacks it as if it were foreign. Autoimmune diseases can be classified into those in which predominantly one organ is affected (e.g., hemolytic anemia and anti-immune thyroiditis), and those in which the autoimmune disease process is diffused through many tissues (e.g., systemic lupus erythematosus). For example, multiple sclerosis is thought to be caused by T cells attacking the sheaths that surround the nerve fibers of the brain and spinal cord. This results in loss of coordination, weakness, and blurred vision. Autoimmune diseases are known in the art and include, for instance, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, psoriasis, and the like.

An "immunodeficiency" means the state of a patient whose immune system has been compromised by disease or by administration of chemicals. This condition makes the system deficient in the number and type of blood cells needed to defend against a foreign substance. Immunodeficiency conditions or diseases are known in the art and include, for example, AIDS (acquired immunodeficiency syndrome), SCID (severe combined immunodeficiency disease), selective IgA deficiency, common variable immunodeficiency, X-linked agammaglobulinemia, chronic granulomatous disease, hyper-IgM syndrome, and diabetes.

An "infectious disease" refers to a disease that can be transmitted from person to person or from organism to organism, and is caused by a microbial or viral agent (e.g., common cold). Infectious diseases are known in the art and include, for example, hepatitis, sexually transmitted diseases (e.g., Chlamydia, gonorrhea), tuberculosis, HIV/AIDS, diphtheria, hepatitis B, hepatitis C, cholera, and influenza.

As used herein, the terms "individual" and "subject" are often used interchangeably and refer to any animal that exhibits a symptom of cancer or other immune disorder that can be treated with the compositions and methods contemplated elsewhere herein. Suitable subjects (e.g., patients) include laboratory animals (such as mouse, rat, rabbit, or guinea pig), farm animals, and domestic animals or pets (such as a cat or dog). Non-human primates and, preferably, human patients, are included. Typical subjects include human patients that have, have been diagnosed with, or are at risk or having, cancer or another immune disorder.

As used herein, the term "patient" refers to a subject that has been diagnosed with cancer or another immune disorder that can be treated with the compositions and methods disclosed elsewhere herein.

As used herein "treatment" or "treating," includes any beneficial or desirable effect on the symptoms or pathology of a disease or pathological condition, and may include even minimal reductions in one or more measurable markers of the disease or condition being treated. Treatment can involve optionally either the reduction of the disease or condition, or the delaying of the progression of the disease or condition, e.g., delaying tumor outgrowth. "Treatment" does not necessarily indicate complete eradication or cure of the disease or condition, or associated symptoms thereof.

As used herein, "prevent," and similar words such as "prevented," "preventing" etc., indicate an approach for preventing, inhibiting, or reducing the likelihood of the occurrence or recurrence of, a disease or condition. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

As used herein, the phrase "ameliorating at least one symptom of" refers to decreasing one or more symptoms of the disease or condition for which the subject is being treated. In particular embodiments, the disease or condition being treated is a cancer, wherein the one or more symptoms ameliorated include, but are not limited to, weakness, fatigue, shortness of breath, easy bruising and bleeding, frequent infections, enlarged lymph nodes, distended or painful abdomen (due to enlarged abdominal organs), bone or joint pain, fractures, unplanned weight loss, poor appetite, night sweats, persistent mild fever, and decreased urination (due to impaired kidney function).

By "enhance" or "promote," or "increase" or "expand" refers generally to the ability of a composition contemplated herein to produce, elicit, or cause a greater physiological response (i.e., downstream effects) compared to the response caused by either vehicle or a control molecule/composition. A measurable physiological response may include an increase in T cell expansion, activation, persistence, cytokine secretion, and/or an increase in cancer cell killing ability, among others apparent from the understanding in the art and the description herein. An "increased" or "enhanced" amount is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7, 1.8, etc.) the response produced by vehicle or a control composition.

By "decrease" or "lower," or "lessen," or "reduce," or "abate" refers generally to the ability of composition contemplated herein to produce, elicit, or cause a lesser physiological response (i.e., downstream effects) compared to the response caused by either vehicle or a control molecule/composition. A "decrease" or "reduced" amount is typically a "statistically significant" amount, and may include an decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7, 1.8, etc.) the response (reference response) produced by vehicle, a control composition, or the response in a particular cell lineage.

By "maintain," or "preserve," or "maintenance," or "no change," or "no substantial change," or "no substantial decrease" refers generally to the ability of a composition contemplated herein to produce, elicit, or cause a substantially similar or comparable physiological response (i.e., downstream effects) in a cell, as compared to the response caused by either vehicle, a control molecule/composition, or the response in a particular cell lineage. A comparable response is one that is not significantly different or measurable different from the reference response

C. TGFβ Signal Convertors (Chimeric TFGβ Receptors)

In particular embodiments, a TGFβ signal convertor that transduces an immunostimulatory signal upon exposure to TGFβ, including but not limited to TGFβ1, is contemplated. As used herein, the term "TGFβ signal convertor" refers to one or more non-naturally occurring polypeptides that converts TGFβ immunosuppressive signals from the tumor microenvironment to immunostimulatory signals in a T cell, e.g., stimulating immune effector cell activity and function, increasing production and/or secretion of proinflammatory cytokines. In particular embodiments, the term "TGFβ signal convertor" is used interchangeably with the term "chimeric TGFβ receptor(s)" or "CTBR" or "CTBR signal convertor."

In particular embodiments, the CTBR signal convertor is a polypeptide comprising an extracellular TGFβ-binding domain of TGFβR2, a transmembrane domain, an intracellular signaling domain of an immune receptor including, but not limited to a cytokine receptor, an interleukin receptor, a pattern recognition receptor, and a toll-like receptor; a polypeptide cleavage signal; and an extracellular TGFβ-binding domain of TGFβR1, a transmembrane domain, and an intracellular signaling domain of an immune receptor including, but not limited to a cytokine receptor, an interleukin receptor, a pattern recognition receptor, and a toll-like receptor.

In particular embodiments, the CTBR signal convertor is a fusion polypeptide that comprises a first polypeptide comprising an extracellular TGFβ-binding domain of TGFβR2, a transmembrane domain, an intracellular signaling domain of an immune receptor including, but not limited to a cytokine receptor, an interleukin receptor, a pattern recognition receptor, and a toll-like receptor; a polypeptide cleavage signal; and a second polypeptide comprising an extracellular TGFβ-binding domain of TGFβR1, a transmembrane domain, and an intracellular signaling domain of an immune receptor including, but not limited to a cytokine receptor, an interleukin receptor, a pattern recognition receptor, and a toll-like receptor.

In other particular embodiments, the CTBR signal convertor is a complex of polypeptides comprising a polypeptide comprising an extracellular TGFβ-binding domain of TGFβR2, a transmembrane domain, and an intracellular signaling domain of an immune receptor including, but not limited to a cytokine receptor, an interleukin receptor, a pattern recognition receptor, and a toll-like receptor; and a polypeptide comprising an extracellular TGFβ-binding domain of TGFβR1, a transmembrane domain, and an intracellular signaling domain of an immune receptor including, but not limited to a cytokine receptor, an interleukin receptor, a pattern recognition receptor, and a toll-like receptor.

As used herein, the term "immune receptor" refers to a receptor that is expressed on the surface of an immune cell that modulates an immune response upon binding its cognate ligand. Immune receptors suitable for use in particular embodiments include, but are not limited to: cytokine receptors, interleukin receptors, pattern recognition receptors, and toll-like receptors, wherein signaling through the immune receptor stimulates an immune response.

Illustrative examples of immune receptor transmembrane and intracellular signaling domains that can be used in particular embodiments contemplated herein include, but are not limited to transmembrane and intracellular signaling domains isolated from an IL-12 receptor, an IL-7 receptor, an IL-15 receptor, an IL-21 receptor, an IL-2 receptor, an IL-1 receptor, an IL-18 receptor, an IL-36 receptor, a type I IFN receptor, a TLR1 receptor, a TLR2 receptor, a TLR3 receptor, a TLR4 receptor, a TLR5 receptor, a TLR6 receptor, a TLR7 receptor, a TLR8 receptor, a TLR5 receptor, or a TLR10 receptor.

Further illustrative examples of immune receptor transmembrane and intracellular signaling domains that can be used in particular embodiments contemplated herein include, but are not limited to transmembrane and intracellular signaling domains isolated from IL-12Rβ2, IL-7Rα, IL-2Rγ, IL-2Rβ, IL-21R, IL-18R1, IL-18RAP, IL-1R1, IL-1RAP, IFNAR1, IFNAR2, IL-1RL2, TLR1, TLR2, TLR3, TLR4, TLR5, TLR6, TLR7, TLR8, TLR5, or TLR10.

Illustrative examples of cytokine receptor transmembrane and intracellular signaling domains that can be used in particular embodiments contemplated herein include, but are not limited to transmembrane and intracellular signaling domains isolated from IL-12Rβ2, IL-7Rα, IL-2Rγ, IL-2Rβ, IL-21R, IL-18R1, IL-18RAP, IL-1R1, IL-1RAP, IFNAR1, IFNAR2, and IL-1RL2.

Illustrative examples of interleukin receptor transmembrane and intracellular signaling domains that can be used in particular embodiments contemplated herein include, but are not limited to transmembrane and intracellular signaling domains isolated from IL-12Rβ2, IL-7Rα, IL-2Rγ, IL-2Rβ, IL-21R, IL-18R1, IL-18RAP, IL-1R1, IL-1RAP, and IL-1RL2.

Illustrative examples of toll-like receptor transmembrane and intracellular signaling domains that can be used in particular embodiments contemplated herein include, but are not limited to transmembrane and intracellular signaling domains isolated from TLR1, TLR2, TLR3, TLR4, TLR5, TLR6, TLR7, TLR8, TLR9, and TLR10.

1. CTBR12 Signal Convertor

Interleukin-12 (IL-12) is a cytokine that promotes T cell function and activity by, in part, increasing IFNγ expression, increasing T cell proliferation, and potentiating IL-12 signaling. IL-12 binds interleukin 12 receptor, beta 1 (IL-12Rβ1, also known as CD212) and interleukin 12 receptor, beta 2 (IL-12Rβ2).

IL-12 signaling through IL-12Rβ1 and IL-12Rβ2 results in STAT5, STAT4, and STAT5 phosphorylation. Phosphorylated STAT5/STAT4 translocates to the nucleus and binds the IFNγ promoter to increase IFNγ expression. Phosphorylated STAT4 also recruits Jun oncogene (c-Jun) to IFNγ promoter to increase IFNγ expression, and potentiates IL-12 signaling by increasing transcription of IL-12Rβ2. STAT5 phosphorylation increases T cell proliferation.

IL-12 signaling also increases expression of interleukin 2 receptor, alpha (IL-2R) by recruiting STAT4 and c-Jun to the promoter of IL-2R, thereby enhancing T cell proliferation.

In various embodiments, one or more immune effector cells, including immune effector cells expressing an engineered antigen receptor, are modified by introducing one or more polynucleotides or vectors encoding a CTBR12 signal convertor. In various embodiments, one or more immune effector cells are modified by introducing one or more polynucleotides or vectors encoding a CTBR12 signal convertor and an engineered antigen receptor.

In particular embodiments, the CTBR12 signal convertor converts an immunosuppressive TGFβ signal to an IL-12-mediated immunostimulatory signal. In particular embodiments a CTBR12 signal convertor contemplated herein comprises: an extracellular TGFβ1-binding domain of TGFβR1, a transmembrane domain, and an IL-12Rβ1 intracellular signaling domain; a polypeptide cleavage signal; and an extracellular TFGβ1-binding domain of TGFβR2, a transmembrane domain, and an IL-12Rβ2 intracellular signaling domain. In particular embodiments a CTBR 12 signal convertor contemplated herein comprises: an extracellular TFGβ1-binding domain of TGFβR1, a transmembrane domain, and an IL-12Rβ2 intracellular signaling domain; a polypeptide cleavage signal; and an extracellular TFGβ1-binding domain of TGFβR2, a transmembrane domain, and an IL-12Rβ1 intracellular signaling domain.

In particular embodiments a CTBR12 signal convertor contemplated herein comprises a fusion polypeptide comprising: a first polypeptide comprising an extracellular TFGβ1-binding domain of TGFβR1, a transmembrane domain, and an IL-12Rβ1 intracellular signaling domain; a polypeptide cleavage signal; and a second polypeptide comprising an extracellular TFGβ1-binding domain of TGFβR2, a transmembrane domain, and an IL-12Rβ2 intracellular signaling domain. In particular embodiments a CTBR12 signal convertor contemplated herein comprises a fusion polypeptide comprising: a first polypeptide comprising an extracellular TFGβ1-binding domain of TGFβR1, a transmembrane domain, and an IL-12Rβ2 intracellular signaling domain; a polypeptide cleavage signal; and a second polypeptide comprising an extracellular TFGβ1-binding domain of TGFβR2, a transmembrane domain, and an IL-12Rβ1 intracellular signaling domain.

In particular embodiments, the CTBR12 signal convertor is a complex of polypeptides comprising a first polypeptide comprising a polypeptide comprising an extracellular TGFβ1-binding domain of TGFβR1, a transmembrane domain, and an IL-12Rβ1 intracellular signaling domain; and a polypeptide comprising an extracellular TFGβ1-binding domain of TGFβR2, a transmembrane domain, and an IL-12Rβ2 intracellular signaling domain. In particular embodiments, the CTBR12 signal convertor is a complex of polypeptides comprising a first polypeptide comprising a polypeptide comprising an extracellular TFGβ1-binding domain of TGFβR1, a transmembrane domain, and an IL-12Rβ2 intracellular signaling domain; and a polypeptide comprising an extracellular TGFβ1-binding domain of TGFβR2, a transmembrane domain, and an IL-12Rβ1 intracellular signaling domain.

In certain embodiments, a polypeptide comprises a transmembrane domain of TGFβR1 or TGFβR2. In certain embodiments, a polypeptide comprises a transmembrane domain of IL-12Rβ1 or IL-12Rβ2. In one embodiment, a polypeptide comprises an extracellular TFGβ1-binding domain of TGFβR1 and an IL-12Rβ1 transmembrane domain and intracellular signaling domain. In one embodiment, a polypeptide comprises an extracellular TFGβ1-binding domain of TGFβR2 and an IL-12Rβ2 transmembrane domain and intracellular signaling domain. In one embodiment, a polypeptide comprises an extracellular TFGβ1-binding domain of TGFβR1 and an IL-12Rβ2 transmembrane domain and intracellular signaling domain. In one embodiment, a polypeptide comprises an extracellular TFGβ1-binding domain of TGFβR2 and an IL-12Rβ1 transmembrane domain and intracellular signaling domain.

In particular embodiments, the polypeptide cleavage signal is a viral self-cleaving polypeptide; more preferably, a viral self-cleaving 2A polypeptide; and more preferably a viral self-cleaving polypeptide selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide. In one embodiment, the polypeptide cleavage signal is a P2A or T2A viral self-cleaving polypeptide.

2. CTBR7 Signal Convertor

Interleukin-7 (IL-7) is a cytokine that promotes T cell function and activity by, in part, improving T cell precursor survival and proliferation. IL-7 binds interleukin 7 receptor alpha (IL-7Rα, also known as CD127) and interleukin 2 receptor, common gamma chain (IL-2Rγ, also known as CD132 and γc). IL-7 signaling activates the JAK/STAT, PI-3K, and Src kinase pathways and results in transcription of anti-apoptotic genes and genes that promote proliferation of T cell precursors.

In various embodiments, one or more immune effector cells, including immune effector cells expressing an engineered antigen receptor, are modified by introducing one or more polynucleotides or vectors encoding a CTBR7 signal convertor. In various embodiments, one or more immune effector cells are modified by introducing one or more polynucleotides or vectors encoding a CTBR7 signal convertor and an engineered antigen receptor.

In particular embodiments, the TGFβ signal convertor converts an immunosuppressive TGFβ signal to an IL-7-mediated immunostimulatory signal. In particular embodiments, a CTBR7 signal convertor contemplated herein comprises: an extracellular TGFβ1-binding domain of TGFβR1, a transmembrane domain, and an IL-7Rα intracellular signaling domain; a polypeptide cleavage signal; and an extracellular TGFβ1-binding domain of TGFβR2, a transmembrane domain, and an IL-2Rγ intracellular signaling domain. In particular embodiments, a CTBR7 signal convertor contemplated herein comprises: an extracellular TFGβ1-binding domain of TGFβR1, a transmembrane domain, and an IL-2Rγ intracellular signaling domain; a polypeptide cleavage signal; and an extracellular TFGβ1-binding domain of TGFβR2, a transmembrane domain, and an IL-7Rα intracellular signaling domain.

In particular embodiments a CTBR7 signal convertor contemplated herein comprises a fusion polypeptide comprising: a first polypeptide comprising an extracellular TFGβ1-binding domain of TGFβR1, a transmembrane domain, and an IL-7Rα intracellular signaling domain; a polypeptide cleavage signal; and a second polypeptide comprising an extracellular TFGβ1-binding domain of TGFβR2, a transmembrane domain, and an IL-2Rγ intracellular signaling domain. In particular embodiments, a CTBR7 signal convertor contemplated herein comprises a fusion polypeptide comprising: a first polypeptide comprising an extracellular TFGβ1-binding domain of TGFβR1, a transmembrane domain, and an IL-2Rγ intracellular signaling domain; a polypeptide cleavage signal; and a second polypeptide comprising an extracellular TFGβ1-binding domain of TGFβR2, a transmembrane domain, and an IL-7Rα intracellular signaling domain.

In particular embodiments, the CTBR7 signal convertor is a complex of polypeptides comprising a first polypeptide comprising a polypeptide comprising an extracellular TGFβ1-binding domain of TGFβR1, a transmembrane domain, and an IL-7Rα intracellular signaling domain; and a polypeptide comprising an extracellular TGFβ1-binding domain of TGFβR2, a transmembrane domain, and an IL-2Rγ intracellular signaling domain. In particular embodiments, the CTBR7 signal convertor is a complex of polypeptides comprising a first polypeptide comprising a polypeptide comprising an extracellular TFGβ1-binding domain of TGFβR1, a transmembrane domain, and an IL-2Rγ intracellular signaling domain; and a polypeptide comprising an extracellular TGFβ1-binding domain of TGFβR2, a transmembrane domain, and an IL-7Rα intracellular signaling domain.

In certain embodiments, a polypeptide comprises a transmembrane domain of TGFβR1 or TGFβR2. In certain embodiments, a polypeptide comprises a transmembrane domain of IL-7Rα or IL-2Rγ. In one embodiment, a polypeptide comprises an extracellular TFGβ1-binding domain of TGFβR1 and an IL-7Rα transmembrane domain and intracellular signaling domain. In one embodiment, a polypeptide comprises an extracellular TFGβ1-binding domain of TGFβR2 and an IL-2Rγ transmembrane domain and intracellular signaling domain. In one embodiment, a polypeptide comprises an extracellular TFGβ1-binding domain of TGFβR1 and an IL-2Rγ transmembrane domain and intracellular signaling domain. In one embodiment, a polypeptide comprises an extracellular TFGβ1-binding domain of TGFβR2 and an IL-7Rα transmembrane domain and intracellular signaling domain.

In particular embodiments, the polypeptide cleavage signal is a viral self-cleaving polypeptide; more preferably, a viral self-cleaving 2A polypeptide; and more preferably a viral self-cleaving polypeptide selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide. In one embodiment, the polypeptide cleavage signal is a P2A or T2A viral self-cleaving polypeptide.

3. CTBR15 Signal Convertor

Interleukin-15 (IL-15) is a cytokine that promotes T cell function and activity by, in part, improving T cell precursor survival and proliferation. IL-15 binds with high affinity to IL-15Rα (also known as CD215), which then associates with a complex comprising IL-2Rβ (also known as IL-15Rβ and CD122) and IL-2Rγ (also known as CD132 and γc), expressed either on the same cell (cis-presentation) or on a different cell (trans-presentation). IL-15 signaling activates the JAK/STAT, PI-3K, and Src kinase pathways and results in transcription of anti-apoptotic genes and genes that promote proliferation of T cell precursors.

In various embodiments, one or more immune effector cells, including immune effector cells expressing an engineered antigen receptor, are modified by introducing one or more polynucleotides or vectors encoding a CTBR15 signal convertor, and optionally, a polynucleotide or vector encoding an IL-15Rα polypeptide. In various embodiments, one or more immune effector cells are modified by introducing one or more polynucleotides or vectors encoding a CTBR15 signal convertor and an engineered antigen receptor, and optionally, a polynucleotide or vector encoding an IL-15Rα polypeptide.

In particular embodiments, the TGFβ signal convertor converts an immunosuppressive TGFβ signal to an IL-15-mediated immunostimulatory signal. In particular embodiments, a CTBR15 signal convertor contemplated herein comprises: an extracellular TFGβ1-binding domain of TGFβR1, a transmembrane domain, and an IL-2Rβ intracellular signaling domain; a polypeptide cleavage signal; and an extracellular TGFβ1-binding domain of TGFβR2, a transmembrane domain, and an IL-2Rγ intracellular signaling domain. In particular embodiments, a CTBR15 signal convertor contemplated herein comprises: an extracellular TFGβ1-binding domain of TGFβR1, a transmembrane domain, and an IL-2Rγ intracellular signaling domain; a polypeptide cleavage signal; and an extracellular TFGβ1-binding domain of TGFβR2, a transmembrane domain, and an IL-2Rβ intracellular signaling domain.

In particular embodiments a CTBR15 signal convertor contemplated herein comprises a fusion polypeptide comprising: a first polypeptide comprising an extracellular TFGβ1-binding domain of TGFβR1, a transmembrane domain, and an IL-2Rβ intracellular signaling domain; a polypeptide cleavage signal; and a second polypeptide comprising an extracellular TFGβ1-binding domain of TGFβR2, a transmembrane domain, and an IL-2Rγ intracellular signaling domain. In particular embodiments, a CTBR15 signal convertor contemplated herein comprises a fusion polypeptide comprising: a first polypeptide comprising an extracellular TFGβ1-binding domain of TGFβR1, a transmembrane domain, and an IL-2Rγ intracellular signaling domain; a polypeptide cleavage signal; and a second polypeptide comprising an extracellular TFGβ1-binding domain of TGFβR2, a transmembrane domain, and an IL-2Rβ intracellular signaling domain.

In particular embodiments, the CTBR15 signal convertor is a complex of polypeptides comprising a first polypeptide comprising a polypeptide comprising an extracellular TFGβ1-binding domain of TGFβR1, a transmembrane domain, and an IL-2Rβ intracellular signaling domain; and a polypeptide comprising an extracellular TGFβ1-binding domain of TGFβR2, a transmembrane domain, and an IL-2Rγ intracellular signaling domain. In particular embodiments, the CTBR15 signal convertor is a complex of polypeptides comprising a first polypeptide comprising a polypeptide comprising an extracellular TFGβ1-binding domain of TGFβR1, a transmembrane domain, and an IL-2Rγ intracellular signaling domain; and a polypeptide comprising an extracellular TGFβ1-binding domain of TGFβR2, a transmembrane domain, and an IL-2Rβ intracellular signaling domain.

In certain embodiments, a polypeptide comprises a transmembrane domain of TGFβR1 or TGFβR2. In certain embodiments, a polypeptide comprises a transmembrane domain of IL-2Rβ or IL-2Rγ. In one embodiment, a polypeptide comprises an extracellular TFGβ1-binding domain of TGFβR1 and an IL-2Rβ transmembrane domain and intracellular signaling domain. In one embodiment, a polypeptide comprises an extracellular TFGβ1-binding domain of TGFβR2 and an IL-2Rγ transmembrane domain and intracellular signaling domain. In one embodiment, a polypeptide comprises an extracellular TFGβ1-binding domain of TGFβR1 and an IL-2Rγ transmembrane domain and intracellular signaling domain. In one embodiment, a polypeptide comprises an extracellular TFGβ1-binding domain of TGFβR2 and an IL-2Rβ transmembrane domain and intracellular signaling domain.

In particular embodiments, the polypeptide cleavage signal is a viral self-cleaving polypeptide; more preferably, a viral self-cleaving 2A polypeptide; and more preferably a viral self-cleaving polypeptide selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide. In one embodiment, the polypeptide cleavage signal is a P2A or T2A viral self-cleaving polypeptide.

4. CTBR21 Signal Convertor

Interleukin-21 (IL-21) is a cytokine that promotes T cell function and activity by, in part, improving T cell precursor survival and proliferation. IL-21 binds to interleukin 21 receptor (IL-21R, also known as CD360) and IL-2Rγ (also known as CD132 and γc). IL-21 signaling activates the JAK/STAT, PI-3K, and Src kinase pathways and results in transcription of anti-apoptotic genes and genes that promote proliferation of T cell precursors.

In various embodiments, one or more immune effector cells, including immune effector cells expressing an engineered antigen receptor, are modified by introducing one or more polynucleotides or vectors encoding a CTBR21 signal convertor. In various embodiments, one or more immune effector cells are modified by introducing one or more polynucleotides or vectors encoding a CTBR21 signal convertor and an engineered antigen receptor.

In particular embodiments, the TGFβ signal convertor converts an immunosuppressive TGFβ signal to an IL-21-mediated immunostimulatory signal. In particular embodiments, a CTBR21 signal convertor contemplated herein comprises: an extracellular TGFβ1-binding domain of TGFβR1, a transmembrane domain, and an IL-21R intracellular signaling domain; a polypeptide cleavage signal; and an extracellular TGFβ1-binding domain of TGFβR2, a transmembrane domain, and an IL-2Rγ intracellular signaling domain. In particular embodiments, a CTBR21 signal convertor contemplated herein comprises: an extracellular TFGβ1-binding domain of TGFβR1, a transmembrane domain, and an IL-2Rγ intracellular signaling domain; a polypeptide cleavage signal; and an extracellular TFGβ1-binding domain of TGFβR2, a transmembrane domain, and an IL-21R intracellular signaling domain.

In particular embodiments a CTBR21 signal convertor contemplated herein comprises a fusion polypeptide comprising: a first polypeptide comprising an extracellular TFGβ1-binding domain of TGFβR1, a transmembrane domain, and an IL-21R intracellular signaling domain; a polypeptide cleavage signal; and a second polypeptide comprising an extracellular TFGβ1-binding domain of TGFβR2, a transmembrane domain, and an IL-2Rγ intracellular signaling domain. In particular embodiments, a CTBR21 signal convertor contemplated herein comprises a fusion polypeptide comprising: a first polypeptide comprising an extracellular TFGβ1-binding domain of TGFβR1, a transmembrane domain, and an IL-2Rγ intracellular signaling domain; a polypeptide cleavage signal; and a second polypeptide comprising an extracellular TFGβ1-binding domain of TGFβR2, a transmembrane domain, and an IL-21R intracellular signaling domain.

In particular embodiments, the CTBR21 signal convertor is a complex of polypeptides comprising a first polypeptide comprising a polypeptide comprising an extracellular TGFβ1-binding domain of TGFβR1, a transmembrane domain, and an IL-21R intracellular signaling domain; and a polypeptide comprising an extracellular TGFβ1-binding domain of TGFβR2, a transmembrane domain, and an IL-2Rγ intracellular signaling domain. In particular embodiments, the CTBR21 signal convertor is a complex of polypeptides comprising a first polypeptide comprising a polypeptide comprising an extracellular TFGβ1-binding domain of TGFβR1, a transmembrane domain, and an IL-2Rγ intracellular signaling domain; and a polypeptide comprising an extracellular TGFβ1-binding domain of TGFβR2, a transmembrane domain, and an IL-21R intracellular signaling domain.

In certain embodiments, a polypeptide comprises a transmembrane domain of TGFβR1 or TGFβR2. In certain embodiments, a polypeptide comprises a transmembrane domain of IL-21R or IL-2Rγ. In one embodiment, a polypeptide comprises an extracellular TFGβ1-binding domain of TGFβR1 and an IL-21R transmembrane domain and intracellular signaling domain. In one embodiment, a polypeptide comprises an extracellular TFGβ1-binding domain of TGFβR2 and an IL-2Rγ transmembrane domain and intracellular signaling domain. In one embodiment, a polypeptide comprises an extracellular TFGβ1-binding domain of TGFβR1 and an IL-2Rγ transmembrane domain and intracellular signaling domain. In one embodiment, a polypeptide comprises an extracellular TFGβ1-binding domain of TGFβR2 and an IL-21R transmembrane domain and intracellular signaling domain.

In particular embodiments, the polypeptide cleavage signal is a viral self-cleaving polypeptide; more preferably, a viral self-cleaving 2A polypeptide; and more preferably a viral self-cleaving polypeptide selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide. In one embodiment, the polypeptide cleavage signal is a P2A or T2A viral self-cleaving polypeptide.

5. CTBR18 Signal Convertor

Interleukin-18 (IL-18) is a cytokine that promotes T cell function and activity by, in part, increasing IFNγ expression, increasing T cell proliferation, and protecting against activation induced cell death (AICD). IL-18 binds interleukin 18 receptor 1, (IL-18R1, also known as CD218a) and interleukin 18 receptor accessory protein (IL-18RAP, CD218b).

IL-18 signaling through IL-18R1 and IL-18RAP results in activation through the MyD88 adaptor protein and IRAK4 phosphorylation. Phosphorylation of IRAK4 and subsequent phosphorylation of IRAK1/2 ultimately leads to activation of NF-kappa B and AP-1 transcription factors to increase IFNγ expression and increase sensitivity to IL-12. The transcriptional program induced by IL-18 also increases T cell proliferation and protects against AICD.

In various embodiments, one or more immune effector cells, including immune effector cells expressing an engineered antigen receptor, are modified by introducing one or more polynucleotides or vectors encoding a CTBR18 signal convertor. In various embodiments, one or more immune effector cells are modified by introducing one or more polynucleotides or vectors encoding a CTBR18 signal convertor and an engineered antigen receptor.

In particular embodiments, the TGFβ signal convertor converts an immunosuppressive TGFβ signal to an IL-18-mediated immunostimulatory signal. In particular embodiments, a CTBR18 signal convertor contemplated herein comprises: an extracellular TFGβ1-binding domain of TGFβR1, a transmembrane domain, and an IL-18RAP intracellular signaling domain; a polypeptide cleavage signal; and an extracellular TFGβ1-binding domain of TGFβR2, a transmembrane domain, and an IL-18R1 intracellular signaling domain. In particular embodiments, a CTBR18 signal convertor contemplated herein comprises: an extracellular TFGβ1-binding domain of TGFβR1, a transmembrane domain, and an IL-18R1 intracellular signaling domain; a polypeptide cleavage signal; and an extracellular TFGβ1-binding domain of TGFβR2, a transmembrane domain, and an IL-18RAP intracellular signaling domain.

In particular embodiments, a CTBR18 signal convertor contemplated herein comprises a fusion polypeptide comprising: a first polypeptide comprising an extracellular TFGβ1-binding domain of TGFβR1, a transmembrane domain, and an IL-18R1 intracellular signaling domain; a polypeptide cleavage signal; and a second polypeptide comprising an extracellular TFGβ1-binding domain of TGFβR2, a transmembrane domain, and an IL-18RAP intracellular signaling domain. In particular embodiments, a CTBR18 signal convertor contemplated herein comprises a fusion polypeptide comprising: a first polypeptide comprising an extracellular TFGβ1-binding domain of TGFβR1, a transmembrane domain, and an IL-18RAP intracellular signaling domain; a polypeptide cleavage signal; and a second polypeptide comprising an extracellular TFGβ1-binding domain of TGFβR2, a transmembrane domain, and an IL-18R1 intracellular signaling domain.

In particular embodiments, the CTBR18 signal convertor is a complex of polypeptides comprising a first polypeptide comprising a polypeptide comprising an extracellular TFGβ1-binding domain of TGFβR1, a transmembrane domain, and an IL-18RAP intracellular signaling domain; and a polypeptide comprising an extracellular TFGβ1-binding domain of TGFβR2, a transmembrane domain, and an IL-18R1 intracellular signaling domain. In particular embodiments, the CTBR18 signal convertor is a complex of polypeptides comprising a first polypeptide comprising a polypeptide comprising an extracellular TFGβ1-binding domain of TGFβR1, a transmembrane domain, and an IL-18R1 intracellular signaling domain; and a polypeptide comprising an extracellular TFGβ1-binding domain of TGFβR2, a transmembrane domain, and an IL-18RAP intracellular signaling domain.

In certain embodiments, a polypeptide comprises a transmembrane domain of TGFβR1 or TGFβR2. In certain embodiments, a polypeptide comprises a transmembrane domain of IL-18R1 or IL-18RAP. In one embodiment, a polypeptide comprises an extracellular TFGβ1-binding domain of TGFβR1 and an IL-18RAP transmembrane domain and intracellular signaling domain. In one embodiment, a polypeptide comprises an extracellular TFGβ1-binding domain of TGFβR2 and an IL-18R1 transmembrane domain and intracellular signaling domain. In one embodiment, a polypeptide comprises an extracellular TFGβ1-binding domain of TGFβR1 and an IL-18R1 transmembrane domain and intracellular signaling domain. In one embodiment, a polypeptide comprises an extracellular TFGβ1-binding domain of TGFβR2 and an IL-18RAP transmembrane domain and intracellular signaling domain.

In particular embodiments, the polypeptide cleavage signal is a viral self-cleaving polypeptide; more preferably, a viral self-cleaving 2A polypeptide; and more preferably a viral self-cleaving polypeptide selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide. In one embodiment, the polypeptide cleavage signal is a P2A or T2A viral self-cleaving polypeptide.

6. CTBR1 Signal Convertor

Interleukin-1 (IL-1) is a cytokine that promotes T cell function and activity by, in part, increasing IFNγ expression, increasing T cell proliferation, and potentiating protecting against activation induced cell death (AICD). IL-1 binds interleukin 1 receptor 1, (IL-1R1, also known as CD121a) and interleukin 1 receptor accessory protein (IL-1RAP).

IL-1 signaling through IL-1R1 and IL-1RAP results in activation through the MyD88 adaptor protein and IRAK4 phosphorylation. Phosphorylation of IRAK4 and subsequent phosphorylation of IRAK1/2 ultimately leads to activation of NF-kappa B and AP-1 transcription factors to increase IFNγ expression and increase sensitivity to IL-12. The transcriptional program induced by IL-1 also increases T cell proliferation and protects against AICD.

In various embodiments, one or more immune effector cells, including immune effector cells expressing an engineered antigen receptor, are modified by introducing one or more polynucleotides or vectors encoding a CTBR1 signal convertor. In various embodiments, one or more immune effector cells are modified by introducing one or more polynucleotides or vectors encoding a CTBR1 signal convertor and an engineered antigen receptor.

In particular embodiments, the TGFβ signal convertor converts an immunosuppressive TGFβ signal to an IL-1-mediated immunostimulatory signal. In particular embodiments, a CTBR1 signal convertor contemplated herein comprises: an extracellular TFGβ1-binding domain of TGFβR1, a transmembrane domain, and an IL-1RAP intracellular signaling domain; a polypeptide cleavage signal; and an extracellular TFGβ1-binding domain of TGFβR2, a transmembrane domain, and an IL-1R1 intracellular signaling domain. In particular embodiments, a CTBR1 signal convertor contemplated herein comprises: an extracellular TFGβ1-binding domain of TGFβR1, a transmembrane domain, and an IL-1R1 intracellular signaling domain; a polypeptide cleavage signal; and an extracellular TFGβ1-binding domain of TGFβR2, a transmembrane domain, and an IL-1RAP intracellular signaling domain.

In particular embodiments, a CTBR1 signal convertor contemplated herein comprises a fusion polypeptide comprising: a first polypeptide comprising an extracellular TFGβ1-binding domain of TGFβR1, a transmembrane domain, and an IL-1R1 intracellular signaling domain; a polypeptide cleavage signal; and a second polypeptide comprising an extracellular TFGβ1-binding domain of TGFβR2, a transmembrane domain, and an IL-1RAP intracellular signaling domain. In particular embodiments, a CTBR1 signal convertor contemplated herein comprises a fusion polypeptide comprising: a first polypeptide comprising an extracellular TFGβ1-binding domain of TGFβR1, a transmembrane domain, and an IL-1RAP intracellular signaling domain; a polypeptide cleavage signal; and a second polypeptide comprising an extracellular TFGβ1-binding domain of TGFβR2, a transmembrane domain, and an IL-1R1 intracellular signaling domain.

In particular embodiments, the CTBR1 signal convertor is a complex of polypeptides comprising a first polypeptide comprising a polypeptide comprising an extracellular TFGβ1-binding domain of TGFβR1, a transmembrane domain, and an IL-1RAP intracellular signaling domain; and a polypeptide comprising an extracellular TFGβ1-binding domain of TGFβR2, a transmembrane domain, and an IL-1R1 intracellular signaling domain. In particular embodiments, the CTBR1 signal convertor is a complex of polypeptides comprising a first polypeptide comprising a polypeptide comprising an extracellular TGFβ1-binding domain of TGFβR1, a transmembrane domain, and an IL-1R1 intracellular signaling domain; and a polypeptide comprising an extracellular TGFβ1-binding domain of TGFβR2, a transmembrane domain, and an IL-1RAP intracellular signaling domain.

In certain embodiments, a polypeptide comprises a transmembrane domain of TGFβR1 or TGFβR2. In certain embodiments, a polypeptide comprises a transmembrane domain of IL-1R1 or IL-1RAP. In one embodiment, a polypeptide comprises an extracellular TFGβ1-binding domain of TGFβR1 and an IL-1RAP transmembrane domain and intracellular signaling domain. In one embodiment, a polypeptide comprises an extracellular TFGβ1-binding domain of TGFβR2 and an IL-1R1 transmembrane domain and intracellular signaling domain. In one embodiment, a polypeptide comprises an extracellular TGFβ1-binding domain of TGFβR1 and an IL-1R1 transmembrane domain and intracellular signaling domain. In one embodiment, a polypeptide comprises an extracellular TFGβ1-binding domain of TGFβR2 and an IL-1RAP transmembrane domain and intracellular signaling domain.

In particular embodiments, the polypeptide cleavage signal is a viral self-cleaving polypeptide; more preferably, a viral self-cleaving 2A polypeptide; and more preferably a viral self-cleaving polypeptide selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide. In one embodiment, the polypeptide cleavage signal is a P2A or T2A viral self-cleaving polypeptide.

7. CTBR.TLR Signal Convertor

Toll like receptors (TLR1 through TLR10) are pattern recognition receptors that detect invading pathogens and activate the innate and adaptive immune responses. Activation of TLRs by various ligands leads to induction of a pro-inflammatory transcriptional program and expression of multiple inflammatory cytokines.

TLR signaling occurs via homodimerization of TLR signaling domains leading to activation through the MyD88 adaptor protein and IRAK4 phosphorylation. Phosphorylation of IRAK4 and subsequent phosphorylation of IRAK1/2 ultimately leads to activation of NF-kappa B and AP-1 transcription factors to increase inflammatory cytokine production and induce proliferation. TLR activation can also lead to the activation of IRF3 and IRF7 transcription factors.

In various embodiments, one or more immune effector cells, including immune effector cells expressing an engineered antigen receptor, are modified by introducing one or more polynucleotides or vectors encoding a CTBR.TLR signal convertor. In various embodiments, one or more immune effector cells are modified by introducing one or more polynucleotides or vectors encoding a CTBR.TLR signal convertor and an engineered antigen receptor.

In particular embodiments, the TGFβ signal convertor converts an immunosuppressive TGFβ signal to a TLR-mediated immunostimulatory signal. In particular embodiments, a CTBR.TLR signal convertor contemplated herein comprises: an extracellular TFGβ1-binding domain of TGFβR1, a transmembrane domain, and a TLR intracellular signaling domain; a polypeptide cleavage signal; and an extracellular TGFβ1-binding domain of TGFβR2, a transmembrane domain, and an identical TLR signaling domain.

In particular embodiments, a CTBR.TLR signal convertor contemplated herein comprises a fusion polypeptide comprising: a first polypeptide comprising an extracellular TFGβ1-binding domain of TGFβR1, a transmembrane domain, and a TLR intracellular signaling domain; a polypeptide cleavage signal; and a second polypeptide comprising an extracellular TFGβ1-binding domain of TGFβR2, a transmembrane domain, and an identical TLR signaling domain.

In particular embodiments, the CTBR.TLR signal convertor is a complex of polypeptides comprising a first polypeptide comprising a polypeptide comprising an extracellular TFGβ1-binding domain of TGFβR1, a transmembrane domain, and a TLR intracellular signaling domain; and a polypeptide comprising an extracellular TGFβ1-binding domain of TGFβR2, a transmembrane domain, and an identical TLR intracellular signaling domain.

In certain embodiments, a polypeptide comprises a transmembrane domain of TGFβR1 or TGFβR2. In certain embodiments, a polypeptide comprises a transmembrane domain of a TLR. In one embodiment, a polypeptide comprises an extracellular TGFβ1-binding domain of TGFβR1 and a TLR transmembrane domain and intracellular signaling domain. In one embodiment, a polypeptide comprises an extracellular TFGβ1-binding domain of TGFβR2 and a TLR transmembrane domain and intracellular signaling domain.

In particular embodiments, the polypeptide cleavage signal is a viral self-cleaving polypeptide; more preferably, a viral self-cleaving 2A polypeptide; and more preferably a viral self-cleaving polypeptide selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide. In one embodiment, the polypeptide cleavage signal is a P2A or T2A viral self-cleaving polypeptide.

D. Engineered Antigen Receptors

In particular embodiments, a polypeptide comprises an engineered antigen receptor, a polypeptide cleavage signal and a CTBR. In other particular embodiments, a polynucleotide or vector encoding a CTBR is introduced into an immune effector cell that comprises an engineered antigen receptor. Without wishing to be bound by any particular theory, it is contemplated in particular embodiments, that any mechanism known in the art may be used to introduce and co-express an engineered antigen receptor and a CTBR in the same immune effector cell or population of cells to increase the resistance of the immune effector cells to the TME and potentiate and increase the efficiency, potency, and durability of the immune effector cell response.

In particular embodiments, immune effector cells contemplated herein comprise an engineered antigen receptor and a CTBR. In particular embodiments, the engineered antigen receptor is an engineered T cell receptor (TCR), a chimeric antigen receptor (CAR), a DARIC receptor or components thereof, or a zetakine.

1. Engineered TCRs

In particular embodiments, immune effector cells contemplated herein comprise an engineered TCR and a CTBR signal convertor. In one embodiment, T cells are engineered by introducing a polynucleotide or vector encoding an engineered TCR and a CTBR signal convertor separated by one or more polypeptide cleavage signals. In one embodiment, T cells are engineered by introducing a polynucleotide or vector encoding an engineered TCR and a polynucleotide or vector encoding a CTBR signal convertor. In one embodiment, T cells are engineered to express an engineered TCR are further engineered by introducing a polynucleotide or vector encoding a CTBR signal convertor.

Naturally occurring T cell receptors comprise two subunits, an alpha chain and a beta chain subunit, each of which is a unique protein produced by recombination event in each T cell's genome. Libraries of TCRs may be screened for their selectivity to particular target antigens. In this manner, natural TCRs, which have a high-avidity and reactivity toward target antigens may be selected, cloned, and subsequently introduced into a population of T cells used for adoptive immunotherapy.

In one embodiment, T cells are modified by introducing a TCR subunit has the ability to form TCRs that confer specificity to T cells for tumor cells expressing a target antigen. In particular embodiments, the subunits have one or more amino acid substitutions, deletions, insertions, or modifications compared to the naturally occurring subunit, so long as the subunits retain the ability to form TCRs and confer upon transfected T cells the ability to home to target cells, and participate in immunologically-relevant cytokine signaling. The engineered TCRs preferably also bind target cells displaying the relevant tumor-associated peptide with high avidity, and optionally mediate efficient killing of target cells presenting the relevant peptide in vivo.

The nucleic acids encoding engineered TCRs are preferably isolated from their natural context in a (naturally-occurring) chromosome of a T cell, and can be incorporated into suitable vectors as described elsewhere herein. Both the nucleic acids and the vectors comprising them can be transferred into a cell, preferably a T cell in particular embodiments. The modified T cells are then able to express one or more chains of a TCR encoded by the transduced nucleic acid or nucleic acids. In preferred embodiments, the engineered TCR is an exogenous TCR because it is introduced into T cells that do not normally express the particular TCR. The essential aspect of the engineered TCRs is that it has high avidity for a tumor antigen presented by a major histocompatibility complex (MHC) or similar immunological component. In contrast to engineered TCRs, CARs are engineered to bind target antigens in an MHC independent manner.

The TCR can be expressed with additional polypeptides attached to the amino-terminal or carboxyl-terminal portion of the alpha chain or beta chain of a TCR so long as the attached additional polypeptide does not interfere with the ability of the alpha chain or beta chain to form a functional T cell receptor and the MHC dependent antigen recognition.

Antigens that are recognized by the engineered TCRs contemplated in particular embodiments include, but are not limited to cancer antigens, including antigens on both hematological cancers and solid tumors. Illustrative antigens include, but are not limited to alpha folate receptor, alpha folate receptor, 5T4, αvβ6 integrin, BCMA, B7-H3, B7-H6, CAIX, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, VEGFR2, and WT-1.

2. Chimeric Antigen Receptors

In various embodiments, immune effector cells express CARs that redirect cytotoxicity toward tumor cells. CARs are molecules that combine antibody-based specificity for a target antigen (e.g., tumor antigen) with a T cell receptor-activating intracellular domain to generate a chimeric protein that exhibits a specific anti-tumor cellular immune activity. As used herein, the term, "chimeric," describes being composed of parts of different proteins or DNAs from different origins.

In particular embodiments, immune effector cells contemplated herein comprise CAR and a CTBR signal convertor. In one embodiment, T cells are engineered by introducing a polynucleotide or vector encoding a CAR and a CTBR signal convertor separated by one or more polypeptide cleavage signals. In one embodiment, T cells are engineered by introducing a polynucleotide or vector encoding a CAR and a polynucleotide or vector encoding a CTBR signal convertor. In one embodiment, T cells are engineered to express a CAR are further engineered by introducing a polynucleotide or vector encoding a CTBR signal convertor.

In various embodiments, a CAR comprises an extracellular domain that binds to a specific target antigen (also referred to as a binding domain or antigen-specific binding domain), a transmembrane domain and an intracellular signaling domain. The main characteristic of CARs is their ability to redirect immune effector cell specificity, thereby triggering proliferation, cytokine production, phagocytosis or production of molecules that can mediate cell death of the target antigen expressing cell in a major histocompatibility (MEW) independent manner, exploiting the cell specific targeting abilities of monoclonal antibodies, soluble ligands or cell specific coreceptors.

In particular embodiments, CARs comprise an extracellular binding domain that specifically binds to a target polypeptide, e.g., target antigen, expressed on tumor cell. As used herein, the terms, "binding domain," "extracellular domain," "extracellular binding domain," "antigen binding domain," "antigen-specific binding domain," and "extracellular antigen specific binding domain," are used interchangeably and provide a chimeric receptor, e.g., a CAR or DARIC, with the ability to specifically bind to the target antigen of interest. A binding domain may comprise any protein, polypeptide, oligopeptide, or peptide that possesses the ability to specifically recognize and bind to a biological molecule (e.g., a cell surface receptor or tumor protein, lipid, polysaccharide, or other cell surface target molecule, or component thereof). A binding domain includes any naturally occurring, synthetic, semi-synthetic, or recombinantly produced binding partner for a biological molecule of interest.

In particular embodiments, the extracellular binding domain comprises an antibody or antigen binding fragment thereof.

An "antibody" refers to a binding agent that is a polypeptide comprising at least a light chain or heavy chain immunoglobulin variable region which specifically recognizes and binds an epitope of a target antigen, such as a peptide, lipid, polysaccharide, or nucleic acid containing an antigenic determinant, such as those recognized by an immune cell. Antibodies include antigen binding fragments, e.g., Camel Ig (a camelid antibody or VHH fragment thereof), Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), and single-domain antibody (sdAb, Nanobody) or other antibody fragments thereof. The term also includes genetically engineered forms such as chimeric antibodies (for example, humanized murine antibodies), heteroconjugate antibodies (such as, bispecific antibodies) and antigen binding fragments thereof. See also, Pierce Catalog and Handbook, 1994-1995 (Pierce Chemical Co., Rockford, Ill.); Kuby, J., Immunology, 3rd Ed., W. H. Freeman & Co., New York, 1997.

In one preferred embodiment, the binding domain is an scFv.

In another preferred embodiment, the binding domain is a camelid antibody.

In particular embodiments, the CAR comprises an extracellular domain that binds an antigen selected from the group consisting of: alpha folate receptor, 5T4, αvβ6 integrin, BCMA, B7-H3, B7-H6, CAIX, CD16, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, VEGFR2, and WT-1.

In particular embodiments, the CARs comprise an extracellular binding domain, e.g., antibody or antigen binding fragment thereof that binds an antigen, wherein the antigen is an MHC-peptide complex, such as a class I MHC-peptide complex or a class II MHC-peptide complex.

In certain embodiments, the CARs comprise linker residues between the various domains. A "variable region linking sequence," is an amino acid sequence that connects a heavy chain variable region to a light chain variable region and provides a spacer function compatible with interaction of the two sub-binding domains so that the resulting polypeptide retains a specific binding affinity to the same target molecule as an antibody that comprises the same light and heavy chain variable regions. In particular embodiments, CARs comprise one, two, three, four, or five or more linkers. In particular embodiments, the length of a linker is about 1 to about 25 amino acids, about 5 to about 20 amino acids, or about 10 to about 20 amino acids, or any intervening length of amino acids. In some embodiments, the linker is 1, 2, 3, 4, 5, 6, 7, 8, 9, 10, 11, 12, 13, 14, 15, 16, 17, 18, 19, 20, 21, 22, 23, 24, 25, or more amino acids long.

In particular embodiments, the binding domain of the CAR is followed by one or more "spacer domains," which refers to the region that moves the antigen binding domain away from the effector cell surface to enable proper cell/cell contact, antigen binding and activation (Patel et al., Gene Therapy, 1999; 6: 412-419). The spacer domain may be derived either from a natural, synthetic, semi-synthetic, or recombinant source. In certain embodiments, a spacer domain is a portion of an immunoglobulin, including, but not limited to, one or more heavy chain constant regions, e.g., CH2 and CH3. The spacer domain can include the amino acid sequence of a naturally occurring immunoglobulin hinge region or an altered immunoglobulin hinge region.

In one embodiment, the spacer domain comprises the CH2 and CH3 of IgG1, IgG4, or IgD.

In one embodiment, the binding domain of the CAR is linked to one or more "hinge domains," which plays a role in positioning the antigen binding domain away from the effector cell surface to enable proper cell/cell contact, antigen binding and activation. A CAR generally comprises one or more hinge domains between the binding domain and the transmembrane domain (TM). The hinge domain may be derived either from a natural, synthetic, semi-synthetic, or recombinant source. The hinge domain can include the amino acid sequence of a naturally occurring immunoglobulin hinge region or an altered immunoglobulin hinge region.

Illustrative hinge domains suitable for use in the CARs described herein include the hinge region derived from the extracellular regions of type 1 membrane proteins such as CD8α, and CD4, which may be wild-type hinge regions from these molecules or may be altered. In another embodiment, the hinge domain comprises a CD8α hinge region.

In one embodiment, the hinge is a PD-1 hinge or CD152 hinge.

The "transmembrane domain" is the portion of the CAR that fuses the extracellular binding portion and intracellular signaling domain and anchors the CAR to the plasma membrane of the immune effector cell. The TM domain may be derived either from a natural, synthetic, semi-synthetic, or recombinant source.

Illustrative TM domains may be derived from (i.e., comprise at least the transmembrane region(s) of the alpha or beta chain of the T-cell receptor, CD3δ, CD3ε, CD3γ, CD3ζ, CD4, CD5, CD8α, CD9, CD 16, CD22, CD27, CD28, CD33, CD37, CD45, CD64, CD80, CD86, CD 134, CD137, CD152, CD154, AMN, and PD-1.

In one embodiment, a CAR comprises a TM domain derived from CD8α. In another embodiment, a CAR contemplated herein comprises a TM domain derived from CD8α and a short oligo- or polypeptide linker, preferably between 1, 2, 3, 4, 5, 6, 7, 8, 9, or 10 amino acids in length that links the TM domain and the intracellular signaling domain of the CAR. A glycine-serine linker provides a particularly suitable linker.

In particular embodiments, a CAR comprises an intracellular signaling domain. An "intracellular signaling domain," refers to the part of a CAR that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain.

The term "effector function" refers to a specialized function of the cell. Effector function of the T cell, for example, may be cytolytic activity or help or activity including the secretion of a cytokine. Thus, the term "intracellular signaling domain" refers to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal.

It is known that signals generated through the TCR alone are insufficient for full activation of the T cell and that a secondary or costimulatory signal is also required. Thus, T cell activation can be said to be mediated by two distinct classes of intracellular signaling domains: primary signaling domains that initiate antigen-dependent primary activation through the TCR (e.g., a TCR/CD3 complex) and costimulatory signaling domains that act in an antigen-independent manner to provide a secondary or costimulatory signal. In preferred embodiments, a CAR comprises an intracellular signaling domain that comprises one or more "costimulatory signaling domains" and a "primary signaling domain."

Primary signaling domains regulate primary activation of the TCR complex either in a stimulatory way, or in an inhibitory way. Primary signaling domains that act in a stimulatory manner may contain signaling motifs which are known as immunoreceptor tyrosine-based activation motifs or ITAMs.

Illustrative examples of ITAM containing primary signaling domains suitable for use in CARs contemplated in particular embodiments include those derived from FcRγ, FcRβ, CD3γ, CD3δ, CD3ε, CD3ζ, CD22, CD79a, CD79b, and CD66d. In particular preferred embodiments, a CAR comprises a CD3ζ primary signaling domain and one or more costimulatory signaling domains. The intracellular primary signaling and costimulatory signaling domains may be linked in any order in tandem to the carboxyl terminus of the transmembrane domain.

In particular embodiments, a CAR comprises one or more costimulatory signaling domains to enhance the efficacy and expansion of T cells expressing CAR receptors. As used herein, the term, "costimulatory signaling domain," or "costimulatory domain", refers to an intracellular signaling domain of a costimulatory molecule.

Illustrative examples of such costimulatory molecules suitable for use in CARs contemplated in particular embodiments include TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70. In one embodiment, a CAR comprises one or more costimulatory signaling domains selected from the group consisting of CD28, CD137, and CD134, and a CD3ζ primary signaling domain.

In various embodiments, the CAR comprises: an extracellular domain that binds an antigen selected from the group consisting of: BCMA, CD19, CSPG4, PSCA, ROR1, and TAG72; a transmembrane domain isolated from a polypeptide selected from the group consisting of: CD4, CD8α, CD154, and PD-1; one or more intracellular costimulatory signaling domains isolated from a polypeptide selected from the group consisting of:

CD28, CD134, and CD137; and a signaling domain isolated from a polypeptide selected from the group consisting of: FcRγ, FcRβ, CD3γ, CD3δ, CD3ε, CD3ζ, CD22, CD79a, CD79b, and CD66d.

3. DARIC

In particular embodiments, immune effector cells comprise one or more chains of a DARIC receptor. As used herein, the term "DARIC receptor" refers to a multi-chain engineered antigen receptor.

In particular embodiments, immune effector cells contemplated herein comprise one or more chains of a DARIC receptor and a CTBR signal convertor. In one embodiment, T cells are engineered by introducing a polynucleotide or vector encoding one or more chains of a DARIC receptor and a CTBR signal convertor separated by one or more polypeptide cleavage signals. In one embodiment, T cells are engineered by introducing a polynucleotide or vector encoding one or more chains of a DARIC receptor and a polynucleotide or vector encoding a CTBR signal convertor. In one embodiment, T cells are engineered to express one or more chains of a DARIC receptor are further engineered by introducing a polynucleotide or vector encoding a CTBR signal convertor.

Illustrative examples of DARIC architectures and components are disclosed in PCT Publication No. WO2015/017214 and U.S. Patent Publication No. 20150266973, each of which is incorporated here by reference in its entirety.

In one embodiment, a donor repair template comprises the following DARIC components: a signaling polypeptide comprising a first multimerization domain, a first transmembrane domain, and one or more intracellular co-stimulatory signaling domains and/or primary signaling domains; and a binding polypeptide comprising a binding domain, a second multimerization domain, and optionally a second transmembrane domain. A functional DARIC comprises a bridging factor that promotes the formation of a DARIC receptor complex on the cell surface with the bridging factor associated with and disposed between the multimerization domains of the signaling polypeptide and the binding polypeptide.

In particular embodiments, the first and second multimerization domains associate with a bridging factor selected from the group consisting of: rapamycin or a rapalog thereof, coumermycin or a derivative thereof, gibberellin or a derivative thereof, abscisic acid (ABA) or a derivative thereof, methotrexate or a derivative thereof, cyclosporin A or a derivative thereof, FKCsA or a derivative thereof, trimethoprim (Tmp)-synthetic ligand for FKBP (SLF) or a derivative thereof, and any combination thereof.

Illustrative examples of rapamycin analogs (rapalogs) include those disclosed in U.S. Pat. No. 6,649,595, which rapalog structures are incorporated herein by reference in their entirety. In certain embodiments, a bridging factor is a rapalog with substantially reduced immunosuppressive effect as compared to rapamycin. A "substantially reduced immunosuppressive effect" refers to a rapalog having at least less than 0.1 to 0.005 times the immunosuppressive effect observed or expected for an equimolar amount of rapamycin, as measured either clinically or in an appropriate in vitro (e.g., inhibition of T cell proliferation) or in vivo surrogate of human immunosuppressive activity. In one embodiment, "substantially reduced immunosuppressive effect" refers to a rapalog having an EC50 value in such an in vitro assay that is at least 10 to 250 times larger than the EC50 value observed for rapamycin in the same assay.

Other illustrative examples of rapalogs include, but are not limited to everolimus, novolimus, pimecrolimus, ridaforolimus, tacrolimus, temsirolimus, umirolimus, and zotarolimus.

In certain embodiments, multimerization domains will associate with a bridging factor being a rapamycin or rapalog thereof. For example, the first and second multimerization domains are a pair selected from FKBP and FRB. FRB domains are polypeptide regions (protein "domains") that are capable of forming a tripartite complex with an FKBP protein and rapamycin or rapalog thereof. FRB domains are present in a number of naturally occurring proteins, including mTOR proteins (also referred to in the literature as FRAP, RAPT 1, or RAFT) from human and other species; yeast proteins including Tor1 and Tor2; and a Candida FRAP homolog. Information concerning the nucleotide sequences, cloning, and other aspects of these proteins is already known in the art. For example, a protein sequence accession number for a human mTOR is GenBank Accession No. L34075.1 (Brown et al., Nature 369:756, 1994).

FRB domains suitable for use in particular embodiments contemplated herein generally contain at least about 85 to about 100 amino acid residues. In certain embodiments, an FRB amino acid sequence for use in fusion proteins of this disclosure will comprise a 93 amino acid sequence Ile-2021 through Lys-2113 and a mutation of T2098L, based the amino acid sequence of GenBank Accession No. L34075.1. An FRB domain for use in DARICs contemplated in particular embodiments will be capable of binding to a complex of an FKBP protein bound to rapamycin or a rapalog thereof. In certain embodiments, a peptide sequence of an FRB domain comprises (a) a naturally occurring peptide sequence spanning at least the indicated 93 amino acid region of human mTOR or corresponding regions of homologous proteins; (b) a variant of a naturally occurring FRB in which up to about ten amino acids, or about 1 to about 5 amino acids or about 1 to about 3 amino acids, or in some embodiments just one amino acid, of the naturally-occurring peptide have been deleted, inserted, or substituted; or (c) a peptide encoded by a nucleic acid molecule capable of selectively hybridizing to a DNA molecule encoding a naturally occurring FRB domain or by a DNA sequence which would be capable, but for the degeneracy of the genetic code, of selectively hybridizing to a DNA molecule encoding a naturally occurring FRB domain.

FKBPs (FK506 binding proteins) are the cytosolic receptors for macrolides, such as FK506, FK520 and rapamycin, and are highly conserved across species lines. FKBPs are proteins or protein domains that are capable of binding to rapamycin or to a rapalog thereof and further forming a tripartite complex with an FRB-containing protein or fusion protein. An FKBP domain may also be referred to as a "rapamycin binding domain." Information concerning the nucleotide sequences, cloning, and other aspects of various FKBP species is known in the art (see, e.g., Staendart et al., Nature 346:671, 1990 (human FKBP12); Kay, Biochem. J. 314:361, 1996). Homologous FKBP proteins in other mammalian species, in yeast, and in other organisms are also known in the art and may be used in the fusion proteins disclosed herein. An FKBP domain contemplated in particular embodiments will be capable of binding to rapamycin or a rapalog thereof and participating in a tripartite complex with an FRB-containing protein (as may be determined by any means, direct or indirect, for detecting such binding).

Illustrative examples of FKBP domains suitable for use in a DARIC contemplated in particular embodiments include, but are not limited to: a naturally occurring FKBP peptide sequence, preferably isolated from the human FKBP12 protein (GenBank Accession No. AAA58476.1) or a peptide sequence isolated therefrom, from another human FKBP, from a murine or other mammalian FKBP, or from some other animal, yeast or fungal FKBP; a variant of a naturally occurring FKBP sequence in which up to about ten amino acids, or about 1 to about 5 amino acids or about 1 to about 3 amino acids, or in some embodiments just one amino acid, of the naturally-occurring peptide have been deleted, inserted, or substituted; or a peptide sequence encoded by a nucleic acid molecule capable of selectively hybridizing to a DNA molecule encoding a naturally occurring FKBP or by a DNA sequence which would be capable, but for the degeneracy of the genetic code, of selectively hybridizing to a DNA molecule encoding a naturally occurring FKBP.

Other illustrative examples of multimerization domain pairs suitable for use in a DARIC contemplated in particular embodiments include, but are not limited to include from FKBP and FRB, FKBP and calcineurin, FKBP and cyclophilin, FKBP and bacterial DHFR, calcineurin and cyclophilin, PYL1 and ABI1, or GIB1 and GAI, or variants thereof.

In yet other embodiments, an anti-bridging factor blocks the association of a signaling polypeptide and a binding polypeptide with the bridging factor. For example, cyclosporin or FK506 could be used as anti-bridging factors to titrate out rapamycin and, therefore, stop signaling since only one multimerization domain is bound. In certain embodiments, an anti-bridging factor (e.g., cyclosporine, FK506) is an immunosuppressive agent. For example, an immunosuppressive anti-bridging factor may be used to block or minimize the function of the DARIC components contemplated in particular embodiments and at the same time inhibit or block an unwanted or pathological inflammatory response in a clinical setting.

In one embodiment, the first multimerization domain comprises FRB T2098L, the second multimerization domain comprises FKBP12, and the bridging factor is rapalog AP21967.

In another embodiment, the first multimerization domain comprises FRB, the second multimerization domain comprises FKBP12, and the bridging factor is Rapamycin, temsirolimus or everolimus.

In particular embodiments, a signaling polypeptide a first transmembrane domain and a binding polypeptide comprises a second transmembrane domain or GPI anchor. Illustrative examples of the first and second transmembrane domains are isolated from a polypeptide independently selected from the group consisting of: CD3δ, CD3ε, CD3γ, CD3ζ, CD4, CD5, CD8α, CD9, CD 16, CD22, CD27, CD28, CD33, CD37, CD45, CD64, CD80, CD86, CD 134, CD137, CD152, CD154, AMN, and PD-1.

In one embodiment, a signaling polypeptide comprises one or more intracellular co-stimulatory signaling domains and/or primary signaling domains.

Illustrative examples of primary signaling domains suitable for use in DARIC signaling components contemplated in particular embodiments include those derived from FcRγ, FcRβ, CD3γ, CD3δ, CD3ε, CD3ζ, CD22, CD79a, CD79b, and CD66d. In particular preferred embodiments, a DARIC signaling component comprises a CD3ζ primary signaling domain and one or more costimulatory signaling domains. The intracellular primary signaling and costimulatory signaling domains may be linked in any order in tandem to the carboxyl terminus of the transmembrane domain.

Illustrative examples of such costimulatory molecules suitable for use in DARIC signaling components contemplated in particular embodiments include TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70. In one embodiment, a DARIC signaling component comprises one or more costimulatory signaling domains selected from the group consisting of CD28, CD137, and CD134, and a CD3ζ primary signaling domain.

In particular embodiments, a DARIC binding component comprises a binding domain. In one embodiment, the binding domain is an antibody or antigen binding fragment thereof.

The antibody or antigen binding fragment thereof comprises at least a light chain or heavy chain immunoglobulin variable region which specifically recognizes and binds an epitope of a target antigen, such as a peptide, lipid, polysaccharide, or nucleic acid containing an antigenic determinant, such as those recognized by an immune cell. Antibodies include antigen binding fragments, e.g., Camel Ig (a camelid antibody or VHH fragment thereof), Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), and single-domain antibody (sdAb, Nanobody) or other antibody fragments thereof. The term also includes genetically engineered forms such as chimeric antibodies (for example, humanized murine antibodies), heteroconjugate antibodies (such as, bispecific antibodies) and antigen binding fragments thereof. See also, Pierce Catalog and Handbook, 1994-1995 (Pierce Chemical Co., Rockford, Ill.); Kuby, J., Immunology, 3rd Ed., W. H. Freeman & Co., New York, 1997.

In one preferred embodiment, the binding domain is an scFv.

In another preferred embodiment, the binding domain is a camelid antibody.

In particular embodiments, the DARIC binding component comprises an extracellular domain that binds an antigen selected from the group consisting of: alpha folate receptor, 5T4, αvβ6 integrin, BCMA, B7-H3, B7-H6, CAIX, CD16, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, VEGFR2, and WT-1.

In one embodiment, the DARIC binding component comprises an extracellular domain, e.g., antibody or antigen binding fragment thereof that binds an MHC-peptide complex, such as a class I MHC-peptide complex or class II MHC-peptide complex.

In particular embodiments, the DARIC components contemplated herein comprise a linker or spacer that connects two proteins, polypeptides, peptides, domains, regions, or motifs. In certain embodiments, a linker comprises about two to about 35 amino acids, or about four to about 20 amino acids or about eight to about 15 amino acids or 15 to about 25 amino acids. In other embodiments, a spacer may have a particular structure, such as an antibody CH2CH3 domain, hinge domain or the like. In one embodiment, a spacer comprises the CH2 and CH3 domains of IgG1, IgG4, or IgD.

In particular embodiments, the DARIC components contemplated herein comprise one or more "hinge domains," which plays a role in positioning the domains to enable proper cell/cell contact, antigen binding and activation. A DARIC may comprise one or more hinge domains between the binding domain and the multimerization domain and/or the transmembrane domain (TM) or between the multimerization domain and the transmembrane domain. The hinge domain may be derived either from a natural, synthetic, semi-synthetic, or recombinant source. The hinge domain can include the amino acid sequence of a naturally occurring immunoglobulin hinge region or an altered immunoglobulin hinge region. In particular embodiment, the hinge is a CD8α hinge or a CD4 hinge.

In one embodiment, a DARIC comprises a signaling polypeptide comprises a first multimerization domain of FRB T2098L, a CD8 transmembrane domain, a 4-1BB costimulatory domain, and a CD3ζ primary signaling domain; the binding polypeptide comprises an scFv that binds CD19, a second multimerization domain of FKBP12 and a CD4 transmembrane domain; and the bridging factor is rapalog AP21967.

In one embodiment, a DARIC comprises a signaling polypeptide comprises a first multimerization domain of FRB, a CD8 transmembrane domain, a 4-1BB costimulatory domain, and a CD3ζ primary signaling domain; the binding polypeptide comprises an scFv that binds CD19, a second multimerization domain of FKBP12 and a CD4 transmembrane domain; and the bridging factor is Rapamycin, temsirolimus or everolimus.

4. Zetakines

In various embodiments, immune effector cells comprise chimeric cytokine receptor that redirect cytotoxicity toward tumor cells. Zetakines are chimeric transmembrane immunoreceptors that comprise an extracellular domain comprising a soluble receptor ligand linked to a support region capable of tethering the extracellular domain to a cell surface, a transmembrane region and an intracellular signaling domain. Zetakines, when expressed on the surface of T lymphocytes, direct T cell activity to those cells expressing a receptor for which the soluble receptor ligand is specific. Zetakine chimeric immunoreceptors redirect the antigen specificity of T cells, with application to treatment of a variety of cancers, particularly via the autocrine/paracrine cytokine systems utilized by human malignancy.

In particular embodiments, immune effector cells contemplated herein comprise one or more chains of a zetakine receptor and a CTBR signal convertor. In one embodiment, T cells are engineered by introducing a polynucleotide or vector encoding one or more chains of a zetakine receptor and a CTBR signal convertor separated by one or more polypeptide cleavage signals. In one embodiment, T cells are engineered by introducing a polynucleotide or vector encoding one or more chains of a zetakine receptor and a polynucleotide or vector encoding a CTBR signal convertor. In one embodiment, T cells are engineered to express one or more chains of a zetakine receptor are further engineered by introducing a polynucleotide or vector encoding a CTBR signal convertor.

In particular embodiments, the zetakine comprises an immunosuppressive cytokine or cytokine receptor binding variant thereof, a linker, a transmembrane domain, and an intracellular signaling domain.

In particular embodiments, the cytokine or cytokine receptor binding variant thereof is selected from the group consisting of: interleukin-4 (IL-4), interleukin-6 (IL-6), interleukin-8 (IL-8), interleukin-10 (IL-10), and interleukin-13 (IL-13).

In certain embodiments, the linker comprises a CH2CH3 domain, hinge domain, or the like. In one embodiment, a linker comprises the CH2 and CH3 domains of IgG1, IgG4, or IgD. In one embodiment, a linker comprises a CD8α or CD4 hinge domain.

In particular embodiments, the transmembrane domain is selected from the group consisting of: the alpha or beta chain of the T-cell receptor, CD3δ, CD3ε, CD3γ, CD3ζ, CD4, CD5, CD8α, CD9, CD 16, CD22, CD27, CD28, CD33, CD37, CD45, CD64, CD80, CD86, CD 134, CD137, CD152, CD154, AMN, and PD-1.

In particular embodiments, the intracellular signaling domain is selected from the group consisting of: an ITAM containing primary signaling domain and/or a costimulatory domain.

In particular embodiments, the intracellular signaling domain is selected from the group consisting of: FcRγ, FcRβ, CD3γ, CD3δ, CD3ε, CD3ζ, CD22, CD79a, CD79b, and CD66d.

In particular embodiments, the intracellular signaling domain is selected from the group consisting of: TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70.

In one embodiment, a chimeric cytokine receptor comprises one or more costimulatory signaling domains selected from the group consisting of CD28, CD137, and CD134, and a CD3ζ primary signaling domain.

E. Polypeptides

Various polypeptides are contemplated herein, including, but not limited to, TGFβ signal convertor polypeptides, CTBRs, engineered TCRs, CARs, DARICs, zetakines, fusion proteins comprising the foregoing polypeptides and fragments thereof. In preferred embodiments, a polypeptide comprises an amino acid sequence set forth in any one of SEQ ID NOs: 1-71. "Polypeptide," "peptide" and "protein" are used interchangeably, unless specified to the contrary, and according to conventional meaning, i.e., as a sequence of amino acids. In one embodiment, a "polypeptide" includes fusion polypeptides and other variants. Polypeptides can be prepared using any of a variety of well-known recombinant and/or synthetic techniques. Polypeptides are not limited to a specific length, e.g., they may comprise a full-length protein sequence, a fragment of a full length protein, or a fusion protein, and may include post-translational modifications of the polypeptide, for example, glycosylations, acetylations, phosphorylations and the like, as well as other modifications known in the art, both naturally occurring and non-naturally occurring.

An "isolated peptide" or an "isolated polypeptide" and the like, as used herein, refer to in vitro isolation and/or purification of a peptide or polypeptide molecule from a cellular environment, and from association with other components of the cell, i.e., it is not significantly associated with in vivo substances.

Polypeptides include "polypeptide variants." Polypeptide variants may differ from a naturally occurring polypeptide in one or more substitutions, deletions, additions and/or insertions. Such variants may be naturally occurring or may be synthetically generated, for example, by modifying one or more of the above polypeptide sequences. For example, in particular embodiments, it may be desirable to improve the binding affinity and/or other biological properties of a polypeptide by introducing one or more substitutions, deletions, additions and/or insertions the polypeptide. In particular embodiments, polypeptides include polypeptides having at least about 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 86%, 97%, 98%, or 99% amino acid identity to any of the reference sequences contemplated herein, typically where the variant maintains at least one biological activity of the reference sequence.

Polypeptides variants include biologically active "polypeptide fragments." Illustrative examples of biologically active polypeptide fragments include DNA binding domains, nuclease domains, and the like. As used herein, the term "biologically active fragment" or "minimal biologically active fragment" refers to a polypeptide fragment that retains at least 100%, at least 90%, at least 80%, at least 70%, at least 60%, at least 50%, at least 40%, at least 30%, at least 20%, at least 10%, or at least 5% of the naturally occurring polypeptide activity. In certain embodiments, a polypeptide fragment can comprise an amino acid chain at least 5 to about 1700 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, 450, 500, 550, 600, 650, 700, 750, 800, 850, 900, 950, 1000, 1100, 1200, 1300, 1400, 1500, 1600, 1700 or more amino acids long.

In particular embodiments, the polypeptides set forth herein may comprise one or more amino acids denoted as "X." "X" if present in an amino acid SEQ ID NO, refers to any one or more amino acids. In particular embodiments, SEQ ID NOs denoting a fusion protein comprise a sequence of continuous X residues that cumulatively represent any amino acid sequence.

As noted above, polypeptides may be altered in various ways including amino acid substitutions, deletions, truncations, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985, *Proc. Natl. Acad. Sci. USA*. 82: 488-492), Kunkel et al., (1987, *Methods in Enzymol*, 154: 367-382), U.S. Pat. No. 4,873,192, Watson, J. D. et al., (*Molecular Biology of the Gene*, Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) *Atlas of Protein Sequence and Structure (Natl. Biomed. Res. Found*, Washington, D.C.).

In certain embodiments, a polypeptide variant comprises one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypep-tides contemplated in particular embodiments and still obtain a functional molecule that encodes a variant or derivative polypeptide with desirable characteristics. When it is desired to alter the amino acid sequence of a polypeptide to create an equivalent, or even an improved, variant polypeptide, one skilled in the art, for example, can change one or more of the codons of the encoding DNA sequence, e.g., according to Table 1.

TABLE 1

Amino Acid Codons

| Amino Acid | One letter code | Three letter code | Codons | | | | | |
|---|---|---|---|---|---|---|---|---|
| Alanine | A | Ala | GCA | GCC | GCG | | GCU | |
| Cysteine | C | Cys | UGC | | | UGU | | |
| Aspartic acid | D | Asp | GAC | | | GAU | | |
| Glutamic acid | E | Glu | GAA | | | GAG | | |
| Phenylalanine | F | Phe | UUC | | | UUU | | |
| Glycine | G | Gly | GGA | GGC | GGG | | GGU | |
| Histidine | H | His | CAC | | | CAU | | |
| Isoleucine | I | Iso | AUA | AUC | | AUU | | |
| Lysine | K | Lys | AAA | | | AAG | | |
| Leucine | L | Leu | UUA | UUG | CUA | CUC | CUG | CUU |
| Methionine | M | Met | | | AUG | | | |
| Asparagine | N | Asn | AAC | | | AAU | | |
| Proline | P | Pro | CCA | CCC | CCG | | CCU | |
| Glutamine | Q | Gln | CAA | | | CAG | | |
| Arginine | R | Arg | AGA | AGG | CGA | CGC | CGG | CGU |
| Serine | S | Ser | AGC | AGU | UCA | UCC | UCG | UCU |
| Threonine | T | Thr | ACA | ACC | ACG | | ACU | |
| Valine | V | Val | GUA | GUC | GUG | | GUU | |
| Tryptophan | W | Trp | | | UGG | | | |
| Tyrosine | Y | Tyr | UAC | | | UAU | | |

Guidance in determining which amino acid residues can be substituted, inserted, or deleted without abolishing biological activity can be found using computer programs well known in the art, such as DNASTAR, DNA Strider, Geneious, Mac Vector, or Vector NTI software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. Co., p. 224).

In one embodiment, where expression of two or more polypeptides is desired, the polynucleotide sequences encoding them can be separated by an IRES sequence as disclosed elsewhere herein.

Polypeptides contemplated in particular embodiments include fusion polypeptides. In particular embodiments, fusion polypeptides and polynucleotides encoding fusion polypeptides are provided. Fusion polypeptides and fusion proteins refer to a polypeptide having at least two, three, four, five, six, seven, eight, nine, or ten polypeptide segments.

In another embodiment, two or more polypeptides can be expressed as a fusion protein that comprises one or more self-cleaving polypeptide sequences as disclosed elsewhere herein.

Fusion polypeptides can comprise one or more polypeptide domains or segments including, but are not limited to signal peptides, cell permeable peptide domains (CPP), DNA binding domains, nuclease domains, etc., epitope tags (e.g., maltose binding protein ("MBP"), glutathione S transferase (GST), HIS6, MYC, FLAG, V5, VSV-G, and HA), polypeptide linkers, and polypeptide cleavage signals. Fusion polypeptides are typically linked C-terminus to N-terminus, although they can also be linked C-terminus to C-terminus, N-terminus to N-terminus, or N-terminus to C-terminus. In particular embodiments, the polypeptides of the fusion protein can be in any order. Fusion polypeptides or fusion proteins can also include conservatively modified variants, polymorphic variants, alleles, mutants, subsequences, and interspecies homologs, so long as the desired activity of the fusion polypeptide is preserved. Fusion polypeptides may be produced by chemical synthetic methods or by chemical linkage between the two moieties or may generally be prepared using other standard techniques. Ligated DNA sequences comprising the fusion polypeptide are operably linked to suitable transcriptional or translational control elements as disclosed elsewhere herein.

Fusion polypeptides may optionally comprise a linker that can be used to link the one or more polypeptides or domains within a polypeptide. A peptide linker sequence may be employed to separate any two or more polypeptide components by a distance sufficient to ensure that each polypeptide folds into its appropriate secondary and tertiary structures so as to allow the polypeptide domains to exert their desired functions. Such a peptide linker sequence is incorporated into the fusion polypeptide using standard techniques in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. Nos. 4,935,233 and 4,751,180. Linker sequences are not required when a particular fusion polypeptide segment contains non-essential N-terminal amino acid regions that can be used to separate the functional domains and prevent steric interference. Preferred linkers are typically flexible amino acid subsequences which are synthesized as part of a recombinant fusion protein. Linker polypeptides can be between 1 and 200 amino acids in length, between 1 and 100 amino acids in length, or between 1 and 50 amino acids in length, including all integer values in between.

Exemplary polypeptide cleavage signals include polypeptide cleavage recognition sites such as protease cleavage sites, nuclease cleavage sites (e.g., rare restriction enzyme recognition sites, self-cleaving ribozyme recognition sites), and self-cleaving viral oligopeptides (see deFelipe and Ryan, 2004. *Traffic*, 5(8); 616-26).

Suitable protease cleavages sites and self-cleaving peptides are known to the skilled person (see, e.g., in Ryan et al., 1997. *J. Gener. Virol.* 78, 699-722; Scymczak et al. (2004) Nature Biotech. 5, 589-594). Exemplary protease cleavage sites include, but are not limited to the cleavage sites of potyvirus NIa proteases (e.g., tobacco etch virus protease), potyvirus HC proteases, potyvirus P1 (P35) proteases, byovirus NIa proteases, byovirus RNA-2-encoded proteases, aphthovirus L proteases, enterovirus 2A proteases, rhinovirus 2A proteases, picorna 3C proteases, comovirus 24K proteases, nepovirus 24K proteases, RTSV (rice tungro spherical virus) 3C-like protease, PYVF (parsnip yellow fleck virus) 3C-like protease, heparin, thrombin, factor Xa and enterokinase. Due to its high cleavage stringency, TEV (tobacco etch virus) protease cleavage sites are preferred in one embodiment, e.g., EXXYXQ(G/S) (SEQ ID NO: 47), for example, ENLYFQG (SEQ ID NO: 48) and ENLYFQS (SEQ ID NO: 49), wherein X represents any amino acid (cleavage by TEV occurs between Q and G or Q and S).

In certain embodiments, the self-cleaving polypeptide site comprises a 2A or 2A-like site, sequence or domain (Donnelly et al., 2001. *J. Gen. Virol.* 82:1027-1041). In a particular embodiment, the viral 2A peptide is an aphthovirus 2A peptide, a potyvirus 2A peptide, or a cardiovirus 2A peptide.

In one embodiment, the viral 2A peptide is selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide.

Illustrative examples of 2A sites are provided in Table 2.

TABLE 2

| | |
|---|---|
| SEQ ID NO: 50 | GSGATNFSLLKQAGDVEENPGP |
| SEQ ID NO: 51 | ATNFSLLKQAGDVEENPGP |
| SEQ ID NO: 52 | LLKQAGDVEENPGP |
| SEQ ID NO: 53 | GSGEGRGSLLTCGDVEENPGP |
| SEQ ID NO: 54 | EGRGSLLTCGDVEENPGP |
| SEQ ID NO: 55 | LLTCGDVEENPGP |
| SEQ ID NO: 56 | GSGQCTNYALLKLAGDVESNPGP |
| SEQ ID NO: 57 | QCTNYALLKLAGDVESNPGP |
| SEQ ID NO: 58 | LLKLAGDVESNPGP |
| SEQ ID NO: 59 | GSGVKQTLNFDLLKLAGDVESNPGP |
| SEQ ID NO: 60 | VKQTLNFDLLKLAGDVESNPGP |
| SEQ ID NO: 61 | LLKLAGDVESNPGP |

TABLE 2-continued

| SEQ ID NO: 62 | LLNFDLLKLAGDVESNPGP |
| --- | --- |
| SEQ ID NO: 63 | TLNFDLLKLAGDVESNPGP |
| SEQ ID NO: 64 | LLKLAGDVESNPGP |
| SEQ ID NO: 65 | NFDLLKLAGDVESNPGP |
| SEQ ID NO: 66 | QLLNFDLLKLAGDVESNPGP |
| SEQ ID NO: 67 | APVKQTLNFDLLKLAGDVESNPGP |
| SEQ ID NO: 68 | VTELLYRMKRAETYCPRPLLAIHPTEARHKQKIVAPVKQT |
| SEQ ID NO: 69 | LNFDLLKLAGDVESNPGP |
| SEQ ID NO: 70 | LLAIHPTEARHKQKIVAPVKQTLNFDLLKLAGDVESNPGP |
| SEQ ID NO: 71 | EARHKQKIVAPVKQTLNFDLLKLAGDVESNPGP |

In preferred embodiments, a polypeptide comprises a CTBR signal convertor polypeptide.

F. Polynucleotides

In particular embodiments, polynucleotides encoding TGFβ signal convertor polypeptides, CTBRs, engineered TCRs, CARs, DARICs, zetakines, fusion proteins comprising the foregoing polypeptides and fragments thereof are provided. As used herein, the terms "polynucleotide" or "nucleic acid" refer to deoxyribonucleic acid (DNA), ribonucleic acid (RNA) and DNA/RNA hybrids. Polynucleotides may be single-stranded or double-stranded and either recombinant, synthetic, or isolated. Polynucleotides include, but are not limited to: pre-messenger RNA (pre-mRNA), messenger RNA (mRNA), RNA, short interfering RNA (siRNA), short hairpin RNA (shRNA), microRNA (miRNA), ribozymes, genomic RNA (gRNA), plus strand RNA (RNA(+)), minus strand RNA (RNA(−)), tracrRNA, crRNA, single guide RNA (sgRNA), synthetic RNA, synthetic mRNA, genomic DNA (gDNA), PCR amplified DNA, complementary DNA (cDNA), synthetic DNA, or recombinant DNA. Polynucleotides refer to a polymeric form of nucleotides of at least 5, at least 10, at least 15, at least 20, at least 25, at least 30, at least 40, at least 50, at least 100, at least 200, at least 300, at least 400, at least 500, at least 1000, at least 5000, at least 10000, or at least 15000 or more nucleotides in length, either ribonucleotides or deoxyribonucleotides or a modified form of either type of nucleotide, as well as all intermediate lengths. It will be readily understood that "intermediate lengths," in this context, means any length between the quoted values, such as 6, 7, 8, 9, etc., 101, 102, 103, etc.; 151, 152, 153, etc.; 201, 202, 203, etc. In particular embodiments, polynucleotides or variants have at least or about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a reference sequence.

In particular embodiments, polynucleotides may be codon-optimized. As used herein, the term "codon-optimized" refers to substituting codons in a polynucleotide encoding a polypeptide in order to increase the expression, stability and/or activity of the polypeptide. Factors that influence codon optimization include, but are not limited to one or more of: (i) variation of codon biases between two or more organisms or genes or synthetically constructed bias tables, (ii) variation in the degree of codon bias within an organism, gene, or set of genes, (iii) systematic variation of codons including context, (iv) variation of codons according to their decoding tRNAs, (v) variation of codons according to GC %, either overall or in one position of the triplet, (vi) variation in degree of similarity to a reference sequence for example a naturally occurring sequence, (vii) variation in the codon frequency cutoff, (viii) structural properties of mRNAs transcribed from the DNA sequence, (ix) prior knowledge about the function of the DNA sequences upon which design of the codon substitution set is to be based, (x) systematic variation of codon sets for each amino acid, and/or (xi) isolated removal of spurious translation initiation sites.

As used herein the term "nucleotide" refers to a heterocyclic nitrogenous base in N-glycosidic linkage with a phosphorylated sugar. Nucleotides are understood to include natural bases, and a wide variety of art-recognized modified bases. Such bases are generally located at the 1' position of a nucleotide sugar moiety. Nucleotides generally comprise a base, sugar and a phosphate group. In ribonucleic acid (RNA), the sugar is a ribose, and in deoxyribonucleic acid (DNA) the sugar is a deoxyribose, i.e., a sugar lacking a hydroxyl group that is present in ribose. Exemplary natural nitrogenous bases include the purines, adenosine (A) and guanidine (G), and the pyrimidines, cytidine (C) and thymidine (T) (or in the context of RNA, uracil (U)). The C-1 atom of deoxyribose is bonded to N-1 of a pyrimidine or N-9 of a purine. Nucleotides are usually mono, di- or triphosphates. The nucleotides can be unmodified or modified at the sugar, phosphate and/or base moiety, (also referred to interchangeably as nucleotide analogs, nucleotide derivatives, modified nucleotides, non-natural nucleotides, and non-standard nucleotides; see for example, WO 92/07065 and WO 93/15187). Examples of modified nucleic acid bases are summarized by Limbach et al., (1994, Nucleic Acids Res. 22, 2183-2196).

A nucleotide may also be regarded as a phosphate ester of a nucleoside, with esterification occurring on the hydroxyl group attached to C-5 of the sugar. As used herein, the term "nucleoside" refers to a heterocyclic nitrogenous base in N-glycosidic linkage with a sugar. Nucleosides are recognized in the art to include natural bases, and also to include well known modified bases. Such bases are generally located at the position of a nucleoside sugar moiety. Nucleosides generally comprise a base and sugar group. The nucleosides can be unmodified or modified at the sugar, and/or base moiety, (also referred to interchangeably as nucleoside analogs, nucleoside derivatives, modified nucleosides, non-natural nucleosides, or non-standard nucleosides). As also noted above, examples of modified nucleic acid bases are summarized by Limbach et al., (1994, Nucleic Acids Res. 22, 2183-2196).

Illustrative examples of polynucleotides include, but are not limited to polynucleotides encoding SEQ ID NOs: 1-71.

In various illustrative embodiments, polynucleotides contemplated herein include, but are not limited to polynucleotides encoding TGFβ signal convertors, CTBR signal convertors, engineered antigen receptors, fusion polypeptides, and expression vectors, viral vectors, and transfer plasmids comprising polynucleotides contemplated herein.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion, substitution, or modification of at least one nucleotide. Accordingly, the terms "polynucleotide variant" and "variant" include polynucleotides in which one or more nucleotides have been added or deleted, or modified, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide.

In one embodiment, a polynucleotide comprises a nucleotide sequence that hybridizes to a target nucleic acid sequence under stringent conditions. To hybridize under "stringent conditions" describes hybridization protocols in which nucleotide sequences at least 60% identical to each other remain hybridized. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 86%, 97%, 98%, or 99% sequence identity to any of the reference sequences described herein, typically where the polypeptide variant maintains at least one biological activity of the reference polypeptide.

Terms used to describe sequence relationships between two or more polynucleotides or polypeptides include "reference sequence," "comparison window," "sequence identity," "percentage of sequence identity," and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., *Current Protocols in Molecular Biology*, John Wiley & Sons Inc, 1994-1998, Chapter 15.

As used herein, "isolated polynucleotide" refers to a polynucleotide that has been purified from the sequences which flank it in a naturally-occurring state, e.g., a DNA fragment that has been removed from the sequences that are normally adjacent to the fragment. An "isolated polynucleotide" also refers to a complementary DNA (cDNA), a recombinant DNA, or other polynucleotide that does not exist in nature and that has been made by the hand of man.

In various embodiments, a polynucleotide comprises an mRNA encoding a polypeptide contemplated herein. In certain embodiments, the mRNA comprises a cap, one or more nucleotides, and a poly(A) tail.

Terms that describe the orientation of polynucleotides include: 5' (normally the end of the polynucleotide having a free phosphate group) and 3' (normally the end of the polynucleotide having a free hydroxyl (OH) group). Polynucleotide sequences can be annotated in the 5' to 3' orientation or the 3' to 5' orientation. For DNA and mRNA, the 5' to 3' strand is designated the "sense," "plus," or "coding" strand because its sequence is identical to the sequence of the premessenger (premRNA) [except for uracil (U) in RNA, instead of thymine (T) in DNA]. For DNA and mRNA, the complementary 3' to 5' strand which is the strand transcribed by the RNA polymerase is designated as "template," "antisense," "minus," or "non-coding" strand. As used herein, the term "reverse orientation" refers to a 5' to 3' sequence written in the 3' to 5' orientation or a 3' to 5' sequence written in the 5' to 3' orientation.

The terms "complementary" and "complementarity" refer to polynucleotides (i.e., a sequence of nucleotides) related by the base-pairing rules. For example, the complementary strand of the DNA sequence 5' A G T C A T G 3' is 3' T C A G T A C 5'. The latter sequence is often written as the reverse complement with the 5' end on the left and the 3' end on the right, 5' C A T G A C T 3'. A sequence that is equal to its reverse complement is said to be a palindromic sequence. Complementarity can be "partial," in which only some of the nucleic acids' bases are matched according to the base pairing rules. Or, there can be "complete" or "total" complementarity between the nucleic acids.

Moreover, it will be appreciated by those of ordinary skill in the art that, as a result of the degeneracy of the genetic code, there are many nucleotide sequences that encode a polypeptide, or fragment of variant thereof, as described herein. Some of these polynucleotides bear minimal homology to the nucleotide sequence of any native gene. Nonetheless, polynucleotides that vary due to differences in codon usage are specifically contemplated in particular embodiments, for example polynucleotides that are optimized for human and/or primate codon selection. In particular embodiments, the polynucleotides are codon optimized for expression and/or stability. Further, alleles of the genes comprising the polynucleotide sequences provided herein may also be used. Alleles are endogenous genes that are altered as a result of one or more mutations, such as deletions, additions and/or substitutions of nucleotides.

The term "nucleic acid cassette" or "expression cassette" as used herein refers to genetic sequences within the vector which can express an RNA, and subsequently a polypeptide. In one embodiment, the nucleic acid cassette contains a gene(s)-of-interest, e.g., a polynucleotide(s)-of-interest. In another embodiment, the nucleic acid cassette contains one or more expression control sequences, e.g., a promoter, enhancer, poly(A) sequence, and a gene(s)-of-interest, e.g., a polynucleotide(s)-of-interest. Vectors may comprise 1, 2, 3, 4, 5, 6, 7, 8, 9 or 10 or more nucleic acid cassettes. The nucleic acid cassette is positionally and sequentially oriented within the vector such that the nucleic acid in the cassette can be transcribed into RNA, and when necessary, translated into a protein or a polypeptide, undergo appropriate post-translational modifications required for activity in the transformed cell, and be translocated to the appropriate compartment for biological activity by targeting to appropriate intracellular compartments or secretion into extracellular compartments. Preferably, the cassette has its 3' and 5' ends adapted for ready insertion into a vector, e.g., it has restriction endonuclease sites at each end. In a preferred embodiment, the nucleic acid cassette contains the sequence of a therapeutic gene used to treat, prevent, or ameliorate a genetic disorder. The cassette can be removed and inserted into a plasmid or viral vector as a single unit.

Polynucleotides include polynucleotide(s)-of-interest. As used herein, the term "polynucleotide-of-interest" refers to a polynucleotide encoding a polypeptide or fusion polypeptide or a polynucleotide that serves as a template for the transcription of an inhibitory polynucleotide, as contemplated herein.

The polynucleotides contemplated herein, regardless of the length of the coding sequence itself, may be combined with other DNA sequences, such as promoters and/or enhancers, untranslated regions (UTRs), signal sequences, Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, epitope tags, as disclosed elsewhere herein or as known in the art, such that their overall length may vary considerably. It is therefore contemplated that a polynucleotide fragment of almost any length may be employed, with the total length preferably being limited by the ease of preparation and use in the intended recombinant DNA protocol.

Polynucleotides can be prepared, manipulated, expressed and/or delivered using any of a variety of well-established techniques known and available in the art. In order to express a desired polypeptide, a nucleotide sequence encoding the polypeptide, can be inserted into appropriate vector.

Illustrative examples of vectors include, but are not limited to plasmid, autonomously replicating sequences, and transposable elements, e.g., Sleeping Beauty, PiggyBac.

Additional Illustrative examples of vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses.

Illustrative examples of viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40).

Illustrative examples of expression vectors include, but are not limited to pClneo vectors (Promega) for expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells. In particular embodiments, coding sequences of polypeptides disclosed herein can be ligated into such expression vectors for the expression of the polypeptides in mammalian cells.

In particular embodiments, the vector is an episomal vector or a vector that is maintained extrachromosomally. As used herein, the term "episomal" refers to a vector that is able to replicate without integration into host's chromosomal DNA and without gradual loss from a dividing host cell also meaning that said vector replicates extrachromosomally or episomally.

"Expression control sequences," "control elements," or "regulatory sequences" present in an expression vector are those non-translated regions of the vector—origin of replication, selection cassettes, promoters, enhancers, translation initiation signals (Shine Dalgarno sequence or Kozak sequence) introns, a polyadenylation sequence, 5' and 3' untranslated regions—which interact with host cellular proteins to carry out transcription and translation. Such elements may vary in their strength and specificity. Depending on the vector system and host utilized, any number of suitable transcription and translation elements, including ubiquitous promoters and inducible promoters may be used.

In particular embodiments, a polynucleotide comprises a vector, including but not limited to expression vectors and viral vectors. A vector may comprise one or more exogenous, endogenous, or heterologous control sequences such as promoters and/or enhancers. An "endogenous control sequence" is one which is naturally linked with a given gene in the genome. An "exogenous control sequence" is one which is placed in juxtaposition to a gene by means of genetic manipulation (i.e., molecular biological techniques) such that transcription of that gene is directed by the linked enhancer/promoter. A "heterologous control sequence" is an exogenous sequence that is from a different species than the cell being genetically manipulated. A "synthetic" control sequence may comprise elements of one more endogenous and/or exogenous sequences, and/or sequences determined in vitro or in silico that provide optimal promoter and/or enhancer activity for the particular therapy.

The term "promoter" as used herein refers to a recognition site of a polynucleotide (DNA or RNA) to which an RNA polymerase binds. An RNA polymerase initiates and transcribes polynucleotides operably linked to the promoter. In particular embodiments, promoters operative in mammalian cells comprise an AT-rich region located approximately 25 to 30 bases upstream from the site where transcription is initiated and/or another sequence found 70 to 80 bases upstream from the start of transcription, a CNCAAT region where N may be any nucleotide.

The term "enhancer" refers to a segment of DNA which contains sequences capable of providing enhanced transcription and in some instances can function independent of their orientation relative to another control sequence. An enhancer can function cooperatively or additively with promoters and/or other enhancer elements. The term "promoter/enhancer" refers to a segment of DNA which contains sequences capable of providing both promoter and enhancer functions.

The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer) and a second polynucleotide sequence, e.g., a polynucleotide-of-interest, wherein the expression control sequence directs transcription of the nucleic acid corresponding to the second sequence.

As used herein, the term "constitutive expression control sequence" refers to a promoter, enhancer, or promoter/enhancer that continually or continuously allows for transcription of an operably linked sequence. A constitutive expression control sequence may be a "ubiquitous" promoter, enhancer, or promoter/enhancer that allows expression in a wide variety of cell and tissue types or a "cell specific," "cell type specific," "cell lineage specific," or "tissue specific" promoter, enhancer, or promoter/enhancer that allows expression in a restricted variety of cell and tissue types, respectively.

Illustrative ubiquitous expression control sequences suitable for use in particular embodiments include, but are not limited to, a cytomegalovirus (CMV) immediate early promoter, a viral simian virus 40 (SV40) (e.g., early or late), a Moloney murine leukemia virus (MoMLV) LTR promoter, a Rous sarcoma virus (RSV) LTR, a herpes simplex virus (HSV) (thymidine kinase) promoter, H5, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus (Irions et al., Nature Biotechnology 25, 1477-1482 (2007)), a Ubiquitin C promoter (UBC), a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, d1587rev primer-binding site substituted (MND) promoter (Challita et al., J Virol. 69(2):748-55 (1995)).

In one embodiment, a vector comprises an MND promoter.

In one embodiment, a vector comprises an EF1a promoter comprising the first intron of the human EF1a gene.

In one embodiment, a vector comprises an EF1a promoter that lacks the first intron of the human EF1a gene.

In a particular embodiment, it may be desirable to use a cell, cell type, cell lineage or tissue specific expression control sequence to achieve cell type specific, lineage specific, or tissue specific expression of a desired polynucleotide sequence (e.g., to express a particular nucleic acid encoding a polypeptide in only a subset of cell types, cell lineages, or tissues or during specific stages of development).

In a particular embodiment, it may be desirable to express a polynucleotide a T cell specific promoter.

As used herein, "conditional expression" may refer to any type of conditional expression including, but not limited to, inducible expression; repressible expression; expression in cells or tissues having a particular physiological, biological, or disease state, etc. This definition is not intended to exclude cell type or tissue specific expression. Certain embodiments provide conditional expression of a polynucleotide-of-interest, e.g., expression is controlled by subjecting a cell, tissue, organism, etc., to a treatment or condition that causes the polynucleotide to be expressed or that causes an increase or decrease in expression of the polynucleotide encoded by the polynucleotide-of-interest.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, Gene, 323:67), the cumate inducible gene switch (WO 2002/088346), tetracycline-dependent regulatory systems, etc. Inducer agents include, but are not limited to glucocorticoids, estrogens, mifepristone (RU486), metals, interferons, small molecules, cumate, tetracycline, doxycycline, and variants thereof.

Conditional expression can also be achieved by using a site specific DNA recombinase. According to certain embodiments the vector comprises at least one (typically two) site(s) for recombination mediated by a site specific recombinase. As used herein, the terms "recombinase" or "site specific recombinase" include excisive or integrative proteins, enzymes, co-factors or associated proteins that are involved in recombination reactions involving one or more recombination sites (e.g., two, three, four, five, seven, ten, twelve, fifteen, twenty, thirty, fifty, etc.), which may be wild-type proteins (see Landy, Current Opinion in Biotechnology 3:699-707 (1993)), or mutants, derivatives (e.g., fusion proteins containing the recombination protein sequences or fragments thereof), fragments, and variants thereof. Illustrative examples of recombinases suitable for use in particular embodiments include, but are not limited to: Cre, Int, IHF, Xis, Flp, Fis, Hin, Gin, ΦC31, Cin, Tn3 resolvase, TndX, XerC, XerD, TnpX, Hjc, Gin, SpCCE1, and ParA.

The polynucleotides may comprise one or more recombination sites for any of a wide variety of site specific recombinases. It is to be understood that the target site for a site specific recombinase is in addition to any site(s) required for integration of a vector, e.g., a retroviral vector or lentiviral vector. As used herein, the terms "recombination sequence," "recombination site," or "site specific recombination site" refer to a particular nucleic acid sequence to which a recombinase recognizes and binds.

For example, one recombination site for Cre recombinase is loxP which is a 34 base pair sequence comprising two 13 base pair inverted repeats (serving as the recombinase binding sites) flanking an 8 base pair core sequence (see FIG. 1 of Sauer, B., Current Opinion in Biotechnology 5:521-527 (1994)). Other exemplary loxP sites include, but are not limited to: lox511 (Hoess et al., 1996; Bethke and Sauer, 1997), lox5171 (Lee and Saito, 1998), lox2272 (Lee and Saito, 1998), m2 (Langer et al., 2002), lox71 (Albert et al., 1995), and lox66 (Albert et al., 1995).

Suitable recognition sites for the FLP recombinase include, but are not limited to: FRT (McLeod, et al., 1996), $F_1$, $F_2$, $F_3$ (Schlake and Bode, 1994), $F_4$, $F_5$ (Schlake and Bode, 1994), FRT(LE) (Senecoff et al., 1988), FRT(RE) (Senecoff et al., 1988).

Other examples of recognition sequences are the attB, attP, attL, and attR sequences, which are recognized by the recombinase enzyme λ Integrase, e.g., phi-c31. The φC31 SSR mediates recombination only between the heterotypic sites attB (34 bp in length) and attP (39 bp in length) (Groth et al., 2000). attB and attP, named for the attachment sites for the phage integrase on the bacterial and phage genomes, respectively, both contain imperfect inverted repeats that are likely bound by φC31 homodimers (Groth et al., 2000). The product sites, attL and attR, are effectively inert to further φC31-mediated recombination (Belteki et al., 2003), making the reaction irreversible. For catalyzing insertions, it has been found that attB-bearing DNA inserts into a genomic attP site more readily than an attP site into a genomic attB site (Thyagaraj an et al., 2001; Belteki et al., 2003). Thus, typical strategies position by homologous recombination an attP-bearing "docking site" into a defined locus, which is then partnered with an attB-bearing incoming sequence for insertion.

As used herein, an "internal ribosome entry site" or "IRES" refers to an element that promotes direct internal ribosome entry to the initiation codon, such as ATG, of a cistron (a protein encoding region), thereby leading to the cap-independent translation of the gene. See, e.g., Jackson et al., 1990. *Trends Biochem Sci* 15(12):477-83) and Jackson and Kaminski. 1995. RNA 1(10):985-1000. Examples of IRES generally employed by those of skill in the art include those described in U.S. Pat. No. 6,692,736. Further examples of "IRES" known in the art include, but are not limited to IRES obtainable from picornavirus (Jackson et al., 1990) and IRES obtainable from viral or cellular mRNA sources, such as for example, immunoglobulin heavy-chain binding protein (BiP), the vascular endothelial growth factor (VEGF) (Huez et al. 1998. *Mol. Cell. Biol.* 18(11):6178-6190), the fibroblast growth factor 2 (FGF-2), and insulin-like growth factor (IGFII), the translational initiation factor eIF4G and yeast transcription factors TFIID and HAP4, the encephelomycarditis virus (EMCV) which is commercially available from Novagen (Duke et al., 1992. J. Virol 66(3): 1602-9) and the VEGF IRES (Huez et al., 1998. Mol Cell Biol 18(11):6178-90). IRES have also been reported in viral genomes of Picornaviridae, Dicistroviridae and Flaviviridae species and in HCV, Friend murine leukemia virus (FrMLV) and Moloney murine leukemia virus (MoMLV).

In one embodiment, the IRES used in polynucleotides contemplated herein is an EMCV IRES.

In particular embodiments, the polynucleotides comprise polynucleotides that have a consensus Kozak sequence and that encode a desired polypeptide. As used herein, the term "Kozak sequence" refers to a short nucleotide sequence that greatly facilitates the initial binding of mRNA to the small subunit of the ribosome and increases translation. The consensus Kozak sequence is (GCC)RCCATGG (SEQ ID NO:72), where R is a purine (A or G) (Kozak, 1986. *Cell.* 44(2):283-92, and Kozak, 1987. *Nucleic Acids Res.* 15(20): 8125-48).

Elements directing the efficient termination and polyadenylation of the heterologous nucleic acid transcripts increases heterologous gene expression. Transcription termination signals are generally found downstream of the polyadenylation signal. In particular embodiments, vectors comprise a polyadenylation sequence 3' of a polynucleotide encoding a polypeptide to be expressed. The term "polyA site" or "polyA sequence" as used herein denotes a DNA sequence which directs both the termination and polyadenylation of the nascent RNA transcript by RNA polymerase II. Polyadenylation sequences can promote mRNA stability by addition of a polyA tail to the 3' end of the coding sequence and thus, contribute to increased translational efficiency. Cleavage and polyadenylation is directed by a poly(A) sequence in the RNA. The core poly(A) sequence for mammalian pre-mRNAs has two recognition elements flanking a cleavage-polyadenylation site. Typically, an almost invariant AAUAAA hexamer lies 20-50 nucleotides upstream of a more variable element rich in U or GU residues. Cleavage of the nascent transcript occurs between these two elements and is coupled to the addition of up to 250 adenosines to the 5' cleavage product. In particular embodiments, the core poly(A) sequence is an ideal polyA sequence (e.g., AATAAA, ATTAAA, AGTAAA). In particular embodiments, the poly(A) sequence is an SV40 polyA sequence, a bovine growth hormone polyA sequence (BGHpA), a rabbit β-globin polyA sequence (rβgpA), or another suitable heterologous or endogenous polyA sequence known in the art.

In some embodiments, a polynucleotide or cell harboring the polynucleotide utilizes a suicide gene, including an inducible suicide gene to reduce the risk of direct toxicity and/or uncontrolled proliferation. In specific embodiments, the suicide gene is not immunogenic to the host harboring the polynucleotide or cell. A certain example of a suicide gene that may be used is caspase-9 or caspase-8 or cytosine deaminase. Caspase-9 can be activated using a specific chemical inducer of dimerization (CID).

In certain embodiments, polynucleotides comprise gene segments that cause the immune effector cells, e.g., T cells, to be susceptible to negative selection in vivo. By "negative selection" is meant that the infused cell can be eliminated as a result of a change in the in vivo condition of the individual. The negative selectable phenotype may result from the insertion of a gene that confers sensitivity to an administered agent, for example, a compound. Negative selectable genes are known in the art, and include, inter alia the following: the Herpes simplex virus type I thymidine kinase (HSV-I TK) gene (Wigler et al., *Cell* 11:223, 1977) which confers ganciclovir sensitivity; the cellular hypoxanthine phosphribosyltransferase (HPRT) gene, the cellular adenine phosphoribosyltransferase (APRT) gene, and bacterial cytosine deaminase, (Mullen et al., *Proc. Natl. Acad. Sci. USA.* 89:33 (1992)).

In some embodiments, genetically modified immune effector cells, such as T cells, comprise a polynucleotide further comprising a positive marker that enables the selection of cells of the negative selectable phenotype in vitro. The positive selectable marker may be a gene which, upon being introduced into the host cell expresses a dominant phenotype permitting positive selection of cells carrying the gene. Genes of this type are known in the art, and include, inter alia, hygromycin-B phosphotransferase gene (hph) which confers resistance to hygromycin B, the amino glycoside phosphotransferase gene (neo or aph) from Tn5 which codes for resistance to the antibiotic G418, the dihydrofolate reductase (DHFR) gene, the adenosine deaminase gene (ADA), and the multi-drug resistance (MDR) gene.

In one embodiment, the positive selectable marker and the negative selectable element are linked such that loss of the negative selectable element necessarily also is accompanied by loss of the positive selectable marker. In a particular embodiment, the positive and negative selectable markers are fused so that loss of one obligatorily leads to loss of the other. An example of a fused polynucleotide that yields as an expression product a polypeptide that confers both the desired positive and negative selection features described above is a hygromycin phosphotransferase thymidine kinase fusion gene (HyTK). Expression of this gene yields a polypeptide that confers hygromycin B resistance for positive selection in vitro, and ganciclovir sensitivity for negative selection in vivo. See also the publications of PCT US91/08442 and PCT/US94/05601, by S. D. Lupton, describing the use of bifunctional selectable fusion genes derived from fusing a dominant positive selectable markers with negative selectable markers.

Preferred positive selectable markers are derived from genes selected from the group consisting of hph, nco, and gpt, and preferred negative selectable markers are derived from genes selected from the group consisting of cytosine deaminase, HSV-I TK, VZV TK, HPRT, APRT and gpt. Exemplary bifunctional selectable fusion genes contemplated in particular embodiments include, but are not limited to genes wherein the positive selectable marker is derived from hph or neo, and the negative selectable marker is derived from cytosine deaminase or a TK gene or selectable marker.

In particular embodiments, polynucleotides encoding one or more polypeptides, or fusion polypeptides may be introduced into immune effector cells, e.g., T cells, by both non-viral and viral methods. In particular embodiments, delivery of one or more polynucleotides may be provided by the same method or by different methods, and/or by the same vector or by different vectors.

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. In particular embodiments, non-viral vectors are used to deliver one or more polynucleotides contemplated herein to a T cell.

Illustrative examples of non-viral vectors include, but are not limited to plasmids (e.g., DNA plasmids or RNA plasmids), transposons, cosmids, and bacterial artificial chromosomes.

Illustrative methods of non-viral delivery of polynucleotides contemplated in particular embodiments include, but are not limited to: electroporation, sonoporation, lipofection, microinjection, biolistics, virosomes, liposomes, immunoliposomes, nanoparticles, polycation or lipid:nucleic acid conjugates, naked DNA, artificial virions, DEAE-dextran-mediated transfer, gene gun, and heat-shock.

Illustrative examples of polynucleotide delivery systems suitable for use in particular embodiments contemplated in particular embodiments include, but are not limited to those provided by Amaxa Biosystems, Maxcyte, Inc., BTX Molecular Delivery Systems, and Copernicus Therapeutics Inc. Lipofection reagents are sold commercially (e.g., Transfectam™ and Lipofectin™). Cationic and neutral lipids that are suitable for efficient receptor-recognition lipofection of polynucleotides have been described in the literature. See e.g., Liu et al. (2003) *Gene Therapy.* 10:180-187; and Balazs et al. (2011) *Journal of Drug Delivery.* 2011:1-12. Antibody-targeted, bacterially derived, non-living nanocell-based delivery is also contemplated in particular embodiments.

Viral vectors comprising polynucleotides contemplated in particular embodiments can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., mobilized peripheral blood, lymphocytes, bone marrow aspirates, tissue biopsy, etc.) or universal donor hematopoietic stem cells, followed by reimplantation of the cells into a patient.

In one embodiment, viral vectors comprising nuclease variants and/or donor repair templates are administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Illustrative examples of viral vector systems suitable for use in particular embodiments contemplated in particular embodiments include, but are not limited to adeno-associated virus (AAV), retrovirus, herpes simplex virus, adenovirus, and vaccinia virus vectors.

In various embodiments, one or more polynucleotides are introduced into an immune effector cell, e.g., T cell, by transducing the cell with a recombinant adeno-associated virus (rAAV), comprising the one or more polynucleotides.

AAV is a small (~26 nm) replication-defective, primarily episomal, non-enveloped virus. AAV can infect both dividing and non-dividing cells and may incorporate its genome into that of the host cell. Recombinant AAV (rAAV) are typically composed of, at a minimum, a transgene and its regulatory sequences, and 5' and 3' AAV inverted terminal repeats (ITRs). The ITR sequences are about 145 bp in length. In particular embodiments, the rAAV comprises ITRs and capsid sequences isolated from AAV1, AAV2, AAV3, AAV4, AAV5, AAV6, AAV7, AAV8, AAV9, or AAV10.

In some embodiments, a chimeric rAAV is used the ITR sequences are isolated from one AAV serotype and the capsid sequences are isolated from a different AAV serotype. For example, a rAAV with ITR sequences derived from AAV2 and capsid sequences derived from AAV6 is referred to as AAV2/AAV6. In particular embodiments, the rAAV vector may comprise ITRs from AAV2, and capsid proteins from any one of AAV1, AAV2, AAV3, AAV4, AAV5, AAV6, AAV7, AAV8, AAV9, or AAV10. In a preferred embodiment, the rAAV comprises ITR sequences derived from AAV2 and capsid sequences derived from AAV6. In a preferred embodiment, the rAAV comprises ITR sequences derived from AAV2 and capsid sequences derived from AAV2.

In some embodiments, engineering and selection methods can be applied to AAV capsids to make them more likely to transduce cells of interest.

Construction of rAAV vectors, production, and purification thereof have been disclosed, e.g., in U.S. Pat. Nos.

9,169,494; 9,169,492; 9,012,224; 8,889,641; 8,809,058; and 8,784,799, each of which is incorporated by reference herein, in its entirety.

In various embodiments, one or more polynucleotides are introduced into an immune effector cell, e.g., T cell, by transducing the cell with a retrovirus, e.g., lentivirus, comprising the one or more polynucleotides.

As used herein, the term "retrovirus" refers to an RNA virus that reverse transcribes its genomic RNA into a linear double-stranded DNA copy and subsequently covalently integrates its genomic DNA into a host genome. Illustrative retroviruses suitable for use in particular embodiments, include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), Spumavirus, Friend murine leukemia virus, Murine Stem Cell Virus (MSCV) and Rous Sarcoma Virus (RSV)) and lentivirus.

As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV based vector backbones (i.e., HIV cis-acting sequence elements) are preferred.

In various embodiments, a lentiviral vector contemplated herein comprises one or more LTRs, and one or more, or all, of the following accessory elements: a cPPT/FLAP, a Psi (T) packaging signal, an export element, poly (A) sequences, and may optionally comprise a WPRE or HPRE, an insulator element, a selectable marker, and a cell suicide gene, as discussed elsewhere herein.

In particular embodiments, lentiviral vectors contemplated herein may be integrative or non-integrating or integration defective lentivirus. As used herein, the term "integration defective lentivirus" or "IDLV" refers to a lentivirus having an integrase that lacks the capacity to integrate the viral genome into the genome of the host cells. Integration-incompetent viral vectors have been described in patent application WO 2006/010834, which is herein incorporated by reference in its entirety.

Illustrative mutations in the HIV-1 pol gene suitable to reduce integrase activity include, but are not limited to: H12N, H12C, H16C, H16V, S81 R, D41A, K42A, H51A, Q53C, D55V, D64E, D64V, E69A, K71A, E85A, E87A, D116N, D1161, D116A, N120G, N1201, N120E, E152G, E152A, D35E, K156E, K156A, E157A, K159E, K159A, K160A, R166A, D167A, E170A, H171A, K173A, K186Q, K186T, K188T, E198A, R199c, R199T, R199A, D202A, K211A, Q214L, Q216L, Q221 L, W235F, W235E, K236S, K236A, K246A, G247W, D253A, R262A, R263A and K264H.

The term "long terminal repeat (LTR)" refers to domains of base pairs located at the ends of retroviral DNAs which, in their natural sequence context, are direct repeats and contain U3, R and U5 regions.

As used herein, the term "FLAP element" or "cPPT/FLAP" refers to a nucleic acid whose sequence includes the central polypurine tract and central termination sequences (cPPT and CTS) of a retrovirus, e.g., HIV-1 or HIV-2. Suitable FLAP elements are described in U.S. Pat. No. 6,682,907 and in Zennou, et al., 2000, Cell, 101:173.

As used herein, the term "packaging signal" or "packaging sequence" refers to psi [Ψ] sequences located within the retroviral genome which are required for insertion of the viral RNA into the viral capsid or particle, see e.g., Clever et al., 1995. J. of Virology, Vol. 69, No. 4; pp. 2101-2109.

The term "export element" refers to a cis-acting post-transcriptional regulatory element which regulates the transport of an RNA transcript from the nucleus to the cytoplasm of a cell. Examples of RNA export elements include, but are not limited to, the human immunodeficiency virus (HIV) rev response element (RRE) (see e.g., Cullen et al., 1991.1 Virol. 65: 1053; and Cullen et al., 1991. Cell 58: 423), and the hepatitis B virus post-transcriptional regulatory element (HPRE).

In particular embodiments, expression of heterologous sequences in viral vectors is increased by incorporating posttranscriptional regulatory elements, efficient polyadenylation sites, and optionally, transcription termination signals into the vectors. A variety of posttranscriptional regulatory elements can increase expression of a heterologous nucleic acid at the protein, e.g., woodchuck hepatitis virus posttranscriptional regulatory element (WPRE; Zufferey et al., 1999, J. Virol., 73:2886); the posttranscriptional regulatory element present in hepatitis B virus (HPRE) (Huang et al., Mol. Cell. Biol., 5:3864); and the like (Liu et al., 1995, Genes Dev., 9:1766).

Lentiviral vectors preferably contain several safety enhancements as a result of modifying the LTRs. "Self-inactivating" (SIN) vectors refers to replication-defective vectors, e.g., retroviral or lentiviral vectors, in which the right (3') LTR enhancer-promoter region, known as the U3 region, has been modified (e.g., by deletion or substitution) to prevent viral transcription beyond the first round of viral replication. Self-inactivation is preferably achieved through in the introduction of a deletion in the U3 region of the 3' LTR of the vector DNA, i.e., the DNA used to produce the vector RNA. Thus, during reverse transcription, this deletion is transferred to the 5' LTR of the proviral DNA. In particular embodiments, it is desirable to eliminate enough of the U3 sequence to greatly diminish or abolish altogether the transcriptional activity of the LTR, thereby greatly diminishing or abolishing the production of full-length vector RNA in transduced cells. In the case of HIV based lentivectors, it has been discovered that such vectors tolerate significant U3 deletions, including the removal of the LTR TATA box (e.g., deletions from −418 to −18), without significant reductions in vector titers.

An additional safety enhancement is provided by replacing the U3 region of the 5' LTR with a heterologous promoter to drive transcription of the viral genome during production of viral particles. Examples of heterologous promoters which can be used include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters.

The terms "pseudotype" or "pseudotyping" as used herein, refer to a virus whose viral envelope proteins have been substituted with those of another virus possessing preferable characteristics. For example, HIV can be pseudo-typed with vesicular stomatitis virus G-protein (VSV-G) envelope proteins, which allows HIV to infect a wider range of cells because HIV envelope proteins (encoded by the env gene) normally target the virus to $CD4^+$ presenting cells.

In certain embodiments, lentiviral vectors are produced according to known methods. See e.g., Kutner et al., *BMC Biotechnol.* 2009; 9:10. doi: 10.1186/1472-6750-9-10; Kutner et al. *Nat. Protoc.* 2009; 4(4):495-505. doi: 10.1038/nprot. 2009.22.

According to certain specific embodiments contemplated herein, most or all of the viral vector backbone sequences are derived from a lentivirus, e.g., HIV-1. However, it is to be understood that many different sources of retroviral and/or lentiviral sequences can be used, or combined and numerous substitutions and alterations in certain of the lentiviral sequences may be accommodated without impairing the ability of a transfer vector to perform the functions described herein. Moreover, a variety of lentiviral vectors are known in the art, see Naldini et al., (1996a, 1996b, and 1998); Zufferey et al., (1997); Dull et al., 1998, U.S. Pat. Nos. 6,013,516; and 5,994,136, many of which may be adapted to produce a viral vector or transfer plasmid contemplated herein.

In various embodiments, one or more polynucleotides are introduced into an immune effector cell, by transducing the cell with an adenovirus comprising the one or more polynucleotides.

Adenoviral based vectors are capable of very high transduction efficiency in many cell types and do not require cell division. With such vectors, high titer and high levels of expression have been obtained. This vector can be produced in large quantities in a relatively simple system. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity.

Generation and propagation of the current adenovirus vectors, which are replication deficient, may utilize a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones & Shenk, 1978), the current adenovirus vectors, with the help of 293 cells, carry foreign DNA in either the E1, the D3 or both regions (Graham & Prevec, 1991). Adenovirus vectors have been used in eukaryotic gene expression (Levrero et al., 1991; Gomez-Foix et al., 1992) and vaccine development (Grunhaus & Horwitz, 1992; Graham & Prevec, 1992). Studies in administering recombinant adenovirus to different tissues include trachea instillation (Rosenfeld et al., 1991; Rosenfeld et al., 1992), muscle injection (Ragot et al., 1993), peripheral intravenous injections (Herz & Gerard, 1993) and stereotactic inoculation into the brain (Le Gal La Salle et al., 1993). An example of the use of an Ad vector in a clinical trial involved polynucleotide therapy for antitumor immunization with intramuscular injection (Sterman et al., *Hum. Gene Ther.* 7:1083-9 (1998)).

In various embodiments, one or more polynucleotides are introduced into an immune effector cell by transducing the cell with a herpes simplex virus, e.g., HSV-1, HSV-2, comprising the one or more polynucleotides.

The mature HSV virion consists of an enveloped icosahedral capsid with a viral genome consisting of a linear double-stranded DNA molecule that is 152 kb. In one embodiment, the HSV based viral vector is deficient in one or more essential or non-essential HSV genes. In one embodiment, the HSV based viral vector is replication deficient. Most replication deficient HSV vectors contain a deletion to remove one or more intermediate-early, early, or late HSV genes to prevent replication. For example, the HSV vector may be deficient in an immediate early gene selected from the group consisting of: ICP4, ICP22, ICP27, ICP47, and a combination thereof. Advantages of the HSV vector are its ability to enter a latent stage that can result in long-term DNA expression and its large viral DNA genome that can accommodate exogenous DNA inserts of up to 25 kb. HSV-based vectors are described in, for example, U.S. Pat. Nos. 5,837,532, 5,846,782, and 5,804,413, and International Patent Applications WO 91/02788, WO 96/04394, WO 98/15637, and WO 99/06583, each of which are incorporated by reference herein in its entirety.

G. Genetically Modified Cells

In various embodiments, cells are modified to express TGFβ signal convertor polypeptides, CTBRs, engineered TCRs, CARs, DARICs, zetakines, and fusion proteins contemplated herein, for use in the treatment of cancer. Cells may be non-genetically modified to express the polypeptides contemplated herein, or in particular preferred embodiments, cells may be genetically modified to express the polypeptides contemplated herein. As used herein, the term "genetically engineered" or "genetically modified" refers to the addition of extra genetic material in the form of DNA or RNA into the total genetic material in a cell. The terms, "genetically modified cells," "modified cells," and "redirected cells," are used interchangeably in particular embodiments.

In particular embodiments, the CTBR signal convertor polypeptides contemplated herein are introduced and expressed in immune effector cells to improve the resistance of the cells to the immunosuppressive signals in the TME mediated by TGFβ. In particular embodiments, CTBR signal convertor polypeptides are introduced and expressed in immune effector cells that have been redirected to a target cell by virtue of co-expressing an engineered antigen receptor in the cell.

An "immune effector cell," is any cell of the immune system that has one or more effector functions (e.g., cytotoxic cell killing activity, secretion of cytokines, induction of ADCC and/or CDC). The illustrative immune effector cells contemplated herein are T lymphocytes, in particular cytotoxic T cells (CTLs; CD8+ T cells), TILs, and helper T cells (HTLs; CD4+ T cells. In one embodiment, immune effector cells include natural killer (NK) cells. In one embodiment, immune effector cells include natural killer T (NKT) cells. Immune effector cells can be autologous/autogeneic ("self") or non-autologous ("non-self," e.g., allogeneic, syngeneic or xenogeneic).

"Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In preferred embodiments, the cells are autologous.

Illustrative immune effector cells suitable for introducing the CTBR signal convertor polypeptides contemplated herein include T lymphocytes. The terms "T cell" or "T lymphocyte" are art-recognized and are intended to include thymocytes, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a helper T cell (HTL; $CD4^+$ T cell) $CD4^+$ T cell, a cytotoxic T cell (CTL; $CD8^+$ T cell), $CD4^+CD8^+$ T cell, $CD4^+CD8^+$ T cell, or any other subset of T cells. Other illustrative populations of T cells suitable for use in particular embodiments include naïve T cells and memory T cells.

As would be understood by the skilled person, other cells may also be used as immune effector cells with CTBR signal convertor polypeptides contemplated herein. In particular, immune effector cells also include NK cells, NKT cells, neutrophils, and macrophages. Immune effector cells also include progenitors of effector cells wherein such progenitor cells can be induced to differentiate into an immune effector cells in vivo or in vitro. Thus, in particular embodiments, immune effector cell includes progenitors of immune effectors cells such as hematopoietic stem cells (HSCs) contained within the $CD34^+$ population of cells derived from cord blood, bone marrow or mobilized peripheral blood which upon administration in a subject differentiate into mature immune effector cells, or which can be induced in vitro to differentiate into mature immune effector cells.

As used herein, immune effector cells genetically engineered to contain a specific chimeric receptor may be referred to as, "antigen specific redirected immune effector cells."

The term, "$CD34^+$ cell," as used herein refers to a cell expressing the CD34 protein on its cell surface. "CD34," as used herein refers to a cell surface glycoprotein (e.g., sialomucin protein) that often acts as a cell-cell adhesion factor and is involved in T cell entrance into lymph nodes. The $CD34^!$ cell population contains hematopoietic stem cells (HSC), which upon administration to a patient differentiate and contribute to all hematopoietic lineages, including T cells, NK cells, NKT cells, neutrophils and cells of the monocyte/macrophage lineage.

Methods for making the immune effector cells which express a TGFβ signal convertor polypeptide contemplated herein are provided in particular embodiments. In one embodiment, the method comprises transfecting or transducing immune effector cells isolated from an individual such that the immune effector cells express one or more TGFβ signal convertor polypeptides as contemplated herein. In one embodiment, the method comprises transfecting or transducing immune effector cells isolated from an individual such that the immune effector cells express one or more TGFβ signal convertor polypeptides and engineered antigen receptors contemplated herein. In certain embodiments, the immune effector cells are isolated from an individual and genetically modified without further manipulation in vitro. Such cells can then be directly re-administered into the individual. In further embodiments, the immune effector cells are first activated and stimulated to proliferate in vitro prior to being genetically modified. In this regard, the immune effector cells may be cultured before and/or after being genetically modified.

In particular embodiments, prior to in vitro manipulation or genetic modification of the immune effector cells described herein, the source of cells is obtained from a subject. In particular embodiments, the modified immune effector cells comprise T cells.

T cells can be obtained from a number of sources including, but not limited to, peripheral blood mononuclear cells, bone marrow, lymph nodes tissue, cord blood, thymus issue, tissue from a site of infection, ascites, pleural effusion, spleen tissue, and tumors. In certain embodiments, T cells can be obtained from a unit of blood collected from a subject using any number of techniques known to the skilled person, such as sedimentation, e.g., FICOLL™ separation.

In other embodiments, an isolated or purified population of T cells is used. In some embodiments, after isolation of PBMC, both cytotoxic and helper T lymphocytes can be sorted into naïve, memory, and effector T cell subpopulations either before or after activation, expansion, and/or genetic modification.

In one embodiment, an isolated or purified population of T cells expresses one or more of the markers including, but not limited to a $CD3^+$, $CD4^+$, $CD8^+$, or a combination thereof.

In certain embodiments, the T cells are isolated from an individual and first activated and stimulated to proliferate in vitro prior to being modified to express a TGFβ signal convertor polypeptide.

In order to achieve sufficient therapeutic doses of T cell compositions, T cells are often subjected to one or more rounds of stimulation, activation and/or expansion. T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; and 6,867,041, each of which is incorporated herein by reference in its entirety. In particular embodiments, T cells are activated and expanded for about 6 hours, about 12 hours, about 18 hours or about 24 hours prior to introduction of vectors or polynucleotides encoding the TGFβ signal convertor polypeptides. Optionally in combination with an engineered antigen receptor contemplated herein.

In one embodiment, T cells are activated at the same time that they are modified.

In various embodiments, a method of generating an immune effector cell comprises activating a population of cells comprising T cells and expanding the population of T cells. T cell activation can be accomplished by providing a primary stimulation signal through the T cell TCR/CD3 complex and by providing a secondary costimulation signal through an accessory molecule, e.g., CD28.

The TCR/CD3 complex may be stimulated by contacting the T cell with a suitable CD3 binding agent, e.g., a CD3 ligand or an anti-CD3 monoclonal antibody. Illustrative examples of CD3 antibodies include, but are not limited to, OKT3, G19-4, BC3, and 64.1.

In addition to the primary stimulation signal provided through the TCR/CD3 complex, induction of T cell responses requires a second, costimulatory signal. In particular embodiments, a CD28 binding agent can be used to provide a costimulatory signal. Illustrative examples of CD28 binding agents include but are not limited to: natural CD 28 ligands, e.g., a natural ligand for CD28 (e.g., a member of the B7 family of proteins, such as B7-1(CD80) and B7-2 (CD86); and anti-CD28 monoclonal antibody or fragment thereof capable of crosslinking the CD28 molecule, e.g., monoclonal antibodies 9.3, B-T3, XR-CD28, KOLT-2, 15E8, 248.23.2, and EX5.3D10.

In one embodiment, the molecule providing the primary stimulation signal, for example a molecule which provides stimulation through the TCR/CD3 complex and the costimulatory molecule are coupled to the same surface.

In certain embodiments, binding agents that provide stimulatory and costimulatory signals are localized on the surface of a cell. This can be accomplished by transfecting or transducing a cell with a nucleic acid encoding the binding agent in a form suitable for its expression on the cell surface or alternatively by coupling a binding agent to the cell surface.

In another embodiment, the molecule providing the primary stimulation signal, for example a molecule which provides stimulation through the TCR/CD3 complex and the costimulatory molecule are displayed on antigen presenting cells.

In one embodiment, the molecule providing the primary stimulation signal, for example a molecule which provides stimulation through the TCR/CD3 complex and the costimulatory molecule are provided on separate surfaces.

In a certain embodiment, one of the binding agents that provides stimulatory and costimulatory signals is soluble (provided in solution) and the other agent(s) is provided on one or more surfaces.

In a particular embodiment, the binding agents that provide stimulatory and costimulatory signals are both provided in a soluble form (provided in solution).

In various embodiments, the methods for making T cells contemplated herein comprise activating T cells with anti-CD3 and anti-CD28 antibodies.

In one embodiment, expanding T cells activated by the methods contemplated herein further comprises culturing a population of cells comprising T cells for several hours (about 3 hours) to about 7 days to about 28 days or any hourly integer value in between. In another embodiment, the T cell composition may be cultured for 14 days. In a particular embodiment, T cells are cultured for about 21 days. In another embodiment, the T cell compositions are cultured for about 2-3 days. Several cycles of stimulation/activation/expansion may also be desired such that culture time of T cells can be 60 days or more.

In particular embodiments, conditions appropriate for T cell culture include an appropriate media (e.g., Minimal Essential Media or RPMI Media 1640 or, X-vivo 15, (Lonza)) and one or more factors necessary for proliferation and viability including, but not limited to serum (e.g., fetal bovine or human serum), interleukin-2 (IL-2), insulin, IFN-$\gamma$, IL-4, IL-7, IL-21, GM-CSF, IL-10, IL-12, IL-15, TGF$\beta$, and TNF-$\alpha$ or any other additives suitable for the growth of cells known to the skilled artisan.

Further illustrative examples of cell culture media include, but are not limited to RPMI 1640, Clicks, AIM-V, DMEM, MEM, a-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells.

Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2).

In particular embodiments, PBMCs or isolated T cells are contacted with a stimulatory agent and costimulatory agent, such as anti-CD3 and anti-CD28 antibodies, generally attached to a bead or other surface, in a culture medium with appropriate cytokines, such as IL-2, IL-7, and/or IL-15.

In other embodiments, artificial APC (aAPC) made by engineering K562, U937, 721.221, T2, and C1R cells to direct the stable expression and secretion, of a variety of costimulatory molecules and cytokines. In a particular embodiment K32 or U32 aAPCs are used to direct the display of one or more antibody-based stimulatory molecules on the AAPC cell surface. Populations of T cells can be expanded by aAPCs expressing a variety of costimulatory molecules including, but not limited to, CD137L (4-1BBL), CD134L (OX40L), and/or CD80 or CD86. Finally, the aAPCs provide an efficient platform to expand genetically modified T cells and to maintain CD28 expression on CD8 T cells. aAPCs provided in WO 03/057171 and US2003/0147869 are hereby incorporated by reference in their entirety.

In a particular embodiment, polynucleotide encoding a TGF$\beta$ signal convertor and an engineered antigen receptor are introduced into the population of T cells. In a particular embodiment, polynucleotide encoding a TGF$\beta$ signal convertor is introduced into a population of T cells that express an engineered antigen receptor. The polynucleotides may be introduced into the T cells by microinjection, transfection, lipofection, heat-shock, electroporation, transduction, gene gun, microinjection, DEAE-dextran-mediated transfer, and the like.

In a preferred embodiment, polynucleotides are introduced into a T cell by viral transduction.

Illustrative examples of viral vector systems suitable for introducing a polynucleotide into an immune effector cell or CD34$^+$ cell include, but are not limited to adeno-associated virus (AAV), retrovirus, herpes simplex virus, adenovirus, vaccinia virus vectors for gene transfer.

In one embodiment, polynucleotides are introduced into a T cell by AAV transduction.

In one embodiment, polynucleotides are introduced into a T cell by retroviral transduction.

In one embodiment, polynucleotides are introduced into a T cell by lentiviral transduction.

In one embodiment, polynucleotides are introduced into a T cell by adenovirus transduction.

In one embodiment, polynucleotides are introduced into a T cell by herpes simplex virus transduction.

In one embodiment, polynucleotides are introduced into a T cell by vaccinia virus transduction.

H. Compositions and Formulations

The compositions contemplated herein may comprise one or more polypeptides, polynucleotides, vectors comprising same, genetically modified immune effector cells, etc. Compositions include, but are not limited to pharmaceutical compositions. A "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the ability of the composition to deliver the intended therapy.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" refers to a diluent, adjuvant, excipient, or vehicle with which the polypeptides, polynucleotides, vectors comprising same, or genetically modified immune effector cells are administered. Illustrative examples of pharmaceutical carriers can be sterile liquids, such as cell culture media, water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients in particular embodiments, include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Except insofar as any conventional media or agent is incompatible with the active ingredient, its use in the therapeutic compositions is contemplated. Supplementary active ingredients can also be incorporated into the compositions.

In one embodiment, a composition comprising a pharmaceutically acceptable carrier is suitable for administration to a subject. In particular embodiments, a composition comprising a carrier is suitable for parenteral administration, e.g., intravascular (intravenous or intraarterial), intraperitoneal or intramuscular administration. In particular embodiments, a composition comprising a pharmaceutically acceptable carrier is suitable for intraventricular, intraspinal, or intrathecal administration. Pharmaceutically acceptable carriers include sterile aqueous solutions, cell culture media, or dispersions. The use of such media and agents for pharmaceutically active substances is well known in the art. Except insofar as any conventional media or agent is incompatible with the polypeptides, polynucleotides, vectors comprising same, or genetically modified immune effector cells, use thereof in the pharmaceutical compositions is contemplated.

In particular embodiments, compositions contemplated herein comprise genetically modified T cells and a pharmaceutically acceptable carrier. A composition comprising a cell-based composition contemplated herein can be administered separately by enteral or parenteral administration methods or in combination with other suitable compounds to effect the desired treatment goals.

The pharmaceutically acceptable carrier must be of sufficiently high purity and of sufficiently low toxicity to render it suitable for administration to the human subject being treated. It further should maintain or increase the stability of the composition. The pharmaceutically acceptable carrier can be liquid or solid and is selected, with the planned manner of administration in mind, to provide for the desired bulk, consistency, etc., when combined with other components of the composition. For example, the pharmaceutically acceptable carrier can be, without limitation, a binding agent (e.g., pregelatinized maize starch, polyvinylpyrrolidone or hydroxypropyl methylcellulose, etc.), a filler (e.g., lactose and other sugars, microcrystalline cellulose, pectin, gelatin, calcium sulfate, ethyl cellulose, polyacrylates, calcium hydrogen phosphate, etc.), a lubricant (e.g., magnesium stearate, talc, silica, colloidal silicon dioxide, stearic acid, metallic stearates, hydrogenated vegetable oils, corn starch, polyethylene glycols, sodium benzoate, sodium acetate, etc.), a disintegrant (e.g., starch, sodium starch glycolate, etc.), or a wetting agent (e.g., sodium lauryl sulfate, etc.). Other suitable pharmaceutically acceptable carriers for the compositions contemplated herein include, but are not limited to, water, salt solutions, alcohols, polyethylene glycols, gelatins, amyloses, magnesium stearates, talcs, silicic acids, viscous paraffins, hydroxymethylcelluloses, polyvinylpyrrolidones and the like.

Such carrier solutions also can contain buffers, diluents and other suitable additives. The term "buffer" as used herein refers to a solution or liquid whose chemical makeup neutralizes acids or bases without a significant change in pH. Examples of buffers contemplated herein include, but are not limited to, Dulbecco's phosphate buffered saline (PBS), Ringer's solution, 5% dextrose in water (D5W), normal/physiologic saline (0.9% NaCl).

The pharmaceutically acceptable carriers may be present in amounts sufficient to maintain a pH of the composition of about 7. Alternatively, the composition has a pH in a range from about 6.8 to about 7.4, e.g., 6.8, 6.9, 7.0, 7.1, 7.2, 7.3, and 7.4. In still another embodiment, the composition has a pH of about 7.4.

Compositions contemplated herein may comprise a non-toxic pharmaceutically acceptable medium. The compositions may be a suspension. The term "suspension" as used herein refers to non-adherent conditions in which cells are not attached to a solid support. For example, cells maintained as a suspension may be stirred or agitated and are not adhered to a support, such as a culture dish.

In particular embodiments, compositions contemplated herein are formulated in a suspension, where the modified T cells are dispersed within an acceptable liquid medium or solution, e.g., saline or serum-free medium, in an intravenous (IV) bag or the like. Acceptable diluents include, but are not limited to water, PlasmaLyte, Ringer's solution, isotonic sodium chloride (saline) solution, serum-free cell culture medium, and medium suitable for cryogenic storage, e.g., Cryostor® medium.

In certain embodiments, a pharmaceutically acceptable carrier is substantially free of natural proteins of human or animal origin, and suitable for storing a composition comprising a population of modified T cells. The therapeutic composition is intended to be administered into a human patient, and thus is substantially free of cell culture components such as bovine serum albumin, horse serum, and fetal bovine serum.

In some embodiments, compositions are formulated in a pharmaceutically acceptable cell culture medium. Such compositions are suitable for administration to human subjects. In particular embodiments, the pharmaceutically acceptable cell culture medium is a serum free medium.

Serum-free medium has several advantages over serum containing medium, including a simplified and better defined composition, a reduced degree of contaminants, elimination of a potential source of infectious agents, and lower cost. In various embodiments, the serum-free medium is animal-free, and may optionally be protein-free. Optionally, the medium may contain biopharmaceutically acceptable recombinant proteins. "Animal-free" medium refers to medium wherein the components are derived from non-animal sources. Recombinant proteins replace native animal proteins in animal-free medium and the nutrients are obtained from synthetic, plant or microbial sources. "Protein-free" medium, in contrast, is defined as substantially free of protein.

Illustrative examples of serum-free media used in particular compositions includes, but is not limited to QBSF-60 (Quality Biological, Inc.), StemPro-34 (Life Technologies), and X-VIVO 10.

In a preferred embodiment, the compositions comprising modified T cells are formulated in PlasmaLyte.

In various embodiments, compositions comprising modified T cells are formulated in a cryopreservation medium. For example, cryopreservation media with cryopreservation agents may be used to maintain a high cell viability outcome post-thaw. Illustrative examples of cryopreservation media used in particular compositions includes, but is not limited to, CryoStor CS10, CryoStor CS5, and CryoStor CS2.

In one embodiment, the compositions are formulated in a solution comprising 50:50 PlasmaLyte A to CryoStor CS10.

In particular embodiments, the composition is substantially free of mycoplasma, endotoxin, and microbial contamination. By "substantially free" with respect to endotoxin is meant that there is less endotoxin per dose of cells than is allowed by the FDA for a biologic, which is a total endotoxin of 5 EU/kg body weight per day, which for an average 70 kg person is 350 EU per total dose of cells. In particular embodiments, compositions comprising hematopoietic stem or progenitor cells transduced with a retroviral vector contemplated herein contain about 0.5 EU/mL to about 5.0 EU/mL, or about 0.5 EU/mL, 1.0 EU/mL, 1.5 EU/mL, 2.0 EU/mL, 2.5 EU/mL, 3.0 EU/mL, 3.5 EU/mL, 4.0 EU/mL, 4.5 EU/mL, or 5.0 EU/mL.

In particular embodiments, formulation of pharmaceutically-acceptable carrier solutions is well-known to those of skill in the art, as is the development of suitable dosing and treatment regimens for using the particular compositions described herein in a variety of treatment regimens, including e.g., enteral and parenteral, e.g., intravascular, intravenous, intraarterial, intraosseously, intraventricular, intracerebral, intracranial, intraspinal, intrathecal, and intramedullary administration and formulation. It would be understood by the skilled artisan that particular embodiments contemplated herein may comprise other formulations, such as those that are well known in the pharmaceutical art, and are described, for example, in *Remington: The Science and Practice of Pharmacy*, volume I and volume II. 22$^{nd}$ Edition. Edited by Loyd V. Allen Jr. Philadelphia, Pa.: Pharmaceutical Press; 2012, which is incorporated by reference herein, in its entirety.

In particular embodiments, compositions comprise an amount of immune effector cells, including CAR T cells, that express a CTBR signal convertor contemplated herein. As used herein, the term "amount" refers to "an amount effective" or "an effective amount" of cells comprising a CTBR signal convertor contemplated herein, etc., to achieve a beneficial or desired prophylactic or therapeutic result, including clinical results.

A "prophylactically effective amount" refers to an amount of cells comprising a CTBR signal convertor contemplated herein, etc., effective to achieve the desired prophylactic result. Typically but not necessarily, since a prophylactic dose is used in subjects prior to or at an earlier stage of disease, the prophylactically effective amount is less than the therapeutically effective amount.

A "therapeutically effective amount" refers to an amount of cells comprising a CTBR signal convertor contemplated herein that is effective to "treat" a subject (e.g., a patient). When a therapeutic amount is indicated, the precise amount of the compositions to be administered can be determined by a physician with consideration of individual differences in age, weight, tumor size, extent of infection or metastasis, and condition of the patient (subject). It can generally be stated that a pharmaceutical composition comprising the immune effector cells described herein may be administered at a dosage of $10^2$ to $10^{10}$ cells/kg body weight, preferably $10^5$ to $10^6$ cells/kg body weight, including all integer values within those ranges. The number of cells will depend upon the ultimate use for which the composition is intended as will the type of cells included therein. For uses provided herein, the cells are generally in a volume of a liter or less, can be 500 mLs or less, even 250 mLs or 100 mLs or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. In some embodiments, particularly since all the infused cells will be redirected to a particular target antigen, lower numbers of cells, in the range of $10^6$/kilogram ($10^6$-$10^{11}$ per patient) may be administered. If desired, the treatment may also include administration of mitogens (e.g., PHA) or lymphokines, cytokines, and/or chemokines (e.g., IFN-γ, IL-2, IL-12, TNF-alpha, IL-18, and TNF-beta, GM-CSF, IL-4, IL-13, Flt3-L, RANTES, MIP1α, etc.) as described herein to enhance induction of the immune response.

Generally, compositions comprising the cells activated and expanded as described herein may be utilized in the treatment and prevention of diseases that arise in individuals who are immunocompromised. In particular, compositions contemplated herein are used in the treatment of cancer. In particular embodiments, the immune effector cells may be administered either alone, or as a pharmaceutical compositions in combination with carriers, diluents, excipients, and/or with other components such as IL-2 or other cytokines or cell populations.

In particular embodiments, pharmaceutical compositions comprise an amount of genetically modified T cells, in combination with one or more pharmaceutically or physiologically acceptable carriers, diluents or excipients.

In a particular embodiment, compositions comprise an effective amount of immune effector cells comprising a CTBR signal convertor contemplated herein, alone or in combination with one or more therapeutic agents, such as radiation therapy, chemotherapy, transplantation, immunotherapy, hormone therapy, photodynamic therapy, etc. The compositions may also be administered in combination with antibiotics. Such therapeutic agents may be accepted in the art as a standard treatment for a particular disease state as described herein, such as a particular cancer. Exemplary therapeutic agents contemplated include cytokines, growth factors, steroids, NSAIDs, DMARDs, anti-inflammatories, chemotherapeutics, radiotherapeutics, therapeutic antibodies, or other active and ancillary agents.

In certain embodiments, compositions comprising immune effector cells comprising a CTBR signal convertor contemplated herein may be administered in conjunction with any number of chemotherapeutic agents. Illustrative examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2''-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on cancers such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

A variety of other therapeutic agents may be used in conjunction with the compositions described herein. In one embodiment, the composition comprising immune effector cells comprising a CTBR signal convertor contemplated herein is administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate.

Other exemplary NSAIDs are chosen from the group consisting of ibuprofen, naproxen, naproxen sodium, Cox-2 inhibitors such as VIOXX® (rofecoxib) and CELEBREX® (celecoxib), and sialylates. Exemplary analgesics are chosen from the group consisting of acetaminophen, oxycodone, tramadol of proporxyphene hydrochloride. Exemplary glucocorticoids are chosen from the group consisting of cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular) and minocycline.

Illustrative examples of therapeutic antibodies suitable for combination with the modified T cells comprising a CTBR signal convertor contemplated herein, include but are not limited to, bavituximab, bevacizumab (avastin), bivatuzumab, blinatumomab, conatumumab, daratumumab, duligotumab, dacetuzumab, dalotuzumab, elotuzumab (HuLuc63), gemtuzumab, ibritumomab, indatuximab, inotuzumab, lorvotuzumab, lucatumumab, milatuzumab, moxetumomab, ocaratuzumab, ofatumumab, rituximab, siltuximab, teprotumumab, and ublituximab.

In certain embodiments, the compositions described herein are administered in conjunction with a cytokine. By "cytokine" as used herein is meant a generic term for proteins released by one cell population that act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

I. Therapeutic Methods

The immune effector cells, including CAR T cells, comprising a CTBR contemplated herein provide improved methods of adoptive immunotherapy for use in the prevention, treatment, and amelioration cancers, or for preventing, treating, or ameliorating at least one symptom associated with a cancer.

The immune effector cells that comprise an engineered receptor and a CTBR contemplated herein provide improved drug products for use in the prevention, treatment, or amelioration of at least one symptom of a cancer, GVHD, an infectious disease, an autoimmune disease, an inflammatory disease, or an immunodeficiency. As used herein, the term "drug product" refers to modified cells produced using the compositions and methods contemplated herein. In particular embodiments, the drug product comprises genetically modified immune effector cells, T cells comprising an engineered receptor, or CAR T cells further modified to express a CTBR signal convertor. Moreover, the modified T cells contemplated in particular embodiments provide safer and more efficacious adoptive cell therapies because they are resistant to T cell exhaustion and display increased durability and persistence in the tumor microenvironment that can lead to sustained therapy.

In particular embodiments, an effective amount of modified immune effector cells or T cells comprising an engineered receptor and a CTBR signal convertor are administered to a subject to prevent, treat, or ameliorate at least one symptom of a cancer, GVHD, an infectious disease, an autoimmune disease, an inflammatory disease, or an immunodeficiency.

In particular embodiments, a method of preventing, treating, or ameliorating at least one symptom of a cancer comprises administering the subject an effective amount of modified immune effector cells or T cells comprising a CTBR signal convertor and an engineered TCR, CAR, or Daric, or other therapeutic transgene to redirect the cells to a tumor or cancer. The genetically modified cells are a more durable and persistent drug product because the cells are more resistant to immunosuppressive signals from the tumor microenvironment by virtue of converting an immunosuppressive TGFβ signal to an immunostimulatory signal.

In particular embodiments, the modified immune effector cells contemplated herein are used in the treatment of solid tumors or cancers.

In particular embodiments, the modified immune effector cells contemplated herein are used in the treatment of solid tumors or cancers including, but not limited to: adrenal cancer, adrenocortical carcinoma, anal cancer, appendix cancer, astrocytoma, atypical teratoid/rhabdoid tumor, basal cell carcinoma, bile duct cancer, bladder cancer, bone cancer, brain/CNS cancer, breast cancer, bronchial tumors, cardiac tumors, cervical cancer, cholangiocarcinoma, chondrosarcoma, chordoma, colon cancer, colorectal cancer, craniopharyngioma, ductal carcinoma in situ (DCIS) endometrial cancer, ependymoma, esophageal cancer, esthesioneuroblastoma, Ewing's sarcoma, extracranial germ cell tumor, extragonadal germ cell tumor, eye cancer, fallopian tube cancer, fibrous histiosarcoma, fibrosarcoma, gallbladder cancer, gastric cancer, gastrointestinal carcinoid tumors, gastrointestinal stromal tumor (GIST), germ cell tumors, glioma, glioblastoma, head and neck cancer, hemangioblastoma, hepatocellular cancer, hypopharyngeal cancer, intraocular melanoma, kaposi sarcoma, kidney cancer, laryngeal cancer, leiomyosarcoma, lip cancer, liposarcoma, liver cancer, lung cancer, non-small cell lung cancer, lung carcinoid tumor, malignant mesothelioma, medullary carcinoma, medulloblastoma, menangioma, melanoma, Merkel cell carcinoma, midline tract carcinoma, mouth cancer, myxosarcoma, myelodysplastic syndrome, myeloproliferative neoplasms, nasal cavity and paranasal sinus cancer, nasopharyngeal cancer, neuroblastoma, oligodendroglioma, oral cancer, oral cavity cancer, oropharyngeal cancer, osteosarcoma, ovarian cancer, pancreatic cancer, pancreatic islet cell tumors, papillary carcinoma, paraganglioma, parathyroid cancer, penile cancer, pharyngeal cancer, pheochromocytoma, pinealoma, pituitary tumor, pleuropulmonary blastoma, primary peritoneal cancer, prostate cancer, rectal cancer, retinoblastoma, renal cell carcinoma, renal pelvis and ureter cancer, rhabdomyosarcoma, salivary gland cancer, sebaceous gland carcinoma, skin cancer, soft tissue sarcoma, squamous cell carcinoma, small cell lung cancer, small intestine cancer, stomach cancer, sweat gland carcinoma, synovioma, testicular cancer, throat cancer, thymus cancer, thyroid cancer, urethral cancer, uterine cancer, uterine sarcoma, vaginal cancer, vascular cancer, vulvar cancer, and Wilms Tumor.

In particular embodiments, the modified immune effector cells contemplated herein are used in the treatment of solid tumors or cancers including, without limitation, liver cancer, pancreatic cancer, lung cancer, breast cancer, bladder cancer, brain cancer, bone cancer, thyroid cancer, kidney cancer, or skin cancer.

In particular embodiments, the modified immune effector cells contemplated herein are used in the treatment of various cancers including but not limited to pancreatic, bladder, and lung.

In particular embodiments, the modified immune effector cells contemplated herein are used in the treatment of liquid cancers or hematological cancers.

In particular embodiments, the modified immune effector cells contemplated herein are used in the treatment of B-cell malignancies, including but not limited to: leukemias, lymphomas, and multiple myeloma.

In particular embodiments, the modified immune effector cells contemplated herein are used in the treatment of liquid cancers including, but not limited to leukemias, lymphomas, and multiple myelomas: acute lymphocytic leukemia (ALL), acute myeloid leukemia (AML), myeloblastic, promyelocytic, myelomonocytic, monocytic, erythroleukemia, hairy cell leukemia (HCL), chronic lymphocytic leukemia (CLL), and chronic myeloid leukemia (CIVIL), chronic myelomonocytic leukemia (CMML) and polycythemia vera, Hodgkin lymphoma, nodular lymphocyte-predominant Hodgkin lymphoma, Burkitt lymphoma, small lymphocytic lymphoma (SLL), diffuse large B-cell lymphoma, follicular lymphoma, immunoblastic large cell lymphoma, precursor B-lymphoblastic lymphoma, mantle cell lymphoma, marginal zone lymphoma, mycosis fungoides, anaplastic large cell lymphoma, Sézary syndrome, precursor T-lymphoblastic lymphoma, multiple myeloma, overt multiple myeloma, smoldering multiple myeloma, plasma cell leukemia, non-secretory myeloma, IgD myeloma, osteosclerotic myeloma, solitary plasmacytoma of bone, and extramedullary plasmacytoma.

Preferred cells for use in the methods contemplated herein include autologous/autogeneic ("self") cells, preferably hematopoietic cells, more preferably T cells, and more preferably immune effector cells.

In particular embodiments, methods comprising administering a therapeutically effective amount of modified immune effector cells contemplated herein or a composition comprising the same, to a patient in need thereof, alone or in combination with one or more therapeutic agents, are provided. In certain embodiments, the cells are used in the treatment of patients at risk for developing a cancer, GVHD, an infectious disease, an autoimmune disease, an inflammatory disease, or an immunodeficiency. Thus, particular embodiments comprise the treatment or prevention or amelioration of at least one symptom of a cancer, an infectious disease, an autoimmune disease, an inflammatory disease, or an immunodeficiency comprising administering to a subject in need thereof, a therapeutically effective amount of the genome edited cells contemplated herein.

In one embodiment, a method of treating a cancer, GVHD, an infectious disease, an autoimmune disease, an inflammatory disease, or an immunodeficiency in a subject in need thereof comprises administering an effective amount, e.g., therapeutically effective amount of a composition comprising modified immune effector cells contemplated herein. The quantity and frequency of administration will be determined by such factors as the condition of the patient, and the type and severity of the patient's disease, although appropriate dosages may be determined by clinical trials.

In one illustrative embodiment, the effective amount of modified immune effector cells provided to a subject is at least $2 \times 10^6$ cells/kg, at least $3 \times 10^6$ cells/kg, at least $4 \times 10^6$ cells/kg, at least $5 \times 10^6$ cells/kg, at least $6 \times 10^6$ cells/kg, at least $7 \times 10^6$ cells/kg, at least $8 \times 10^6$ cells/kg, at least $9 \times 10^6$ cells/kg, or at least $10 \times 10^6$ cells/kg, or more cells/kg, including all intervening doses of cells.

In another illustrative embodiment, the effective amount of modified immune effector cells provided to a subject is about $2 \times 10^6$ cells/kg, about $3 \times 10^6$ cells/kg, about $4 \times 10^6$ cells/kg, about $5 \times 10^6$ cells/kg, about $6 \times 10^6$ cells/kg, about $7 \times 10^6$ cells/kg, about $8 \times 10^6$ cells/kg, about $9 \times 10^6$ cells/kg, or about $10 \times 10^6$ cells/kg, or more cells/kg, including all intervening doses of cells.

In another illustrative embodiment, the effective amount of modified immune effector cells provided to a subject is from about $2 \times 10^6$ cells/kg to about $10 \times 10^6$ cells/kg, about $3 \times 10^6$ cells/kg to about $10 \times 10^6$ cells/kg, about $4 \times 10^6$ cells/kg to about $10 \times 10^6$ cells/kg, about $5 \times 10^6$ cells/kg to about $10 \times 10^6$ cells/kg, $2 \times 10^6$ cells/kg to about $6 \times 10^6$ cells/kg, $2 \times 10^6$ cells/kg to about $7 \times 10^6$ cells/kg, $2 \times 10^6$ cells/kg to about $8 \times 10^6$ cells/kg, $3 \times 10^6$ cells/kg to about $6 \times 10^6$ cells/kg, $3 \times 10^6$ cells/kg to about $7 \times 10^6$ cells/kg, $3 \times 10^6$ cells/kg to about $8 \times 10^6$ cells/kg, $4 \times 10^6$ cells/kg to about $6 \times 10^6$ cells/kg, $4 \times 10^6$ cells/kg to about $7 \times 10^6$ cells/kg, $4 \times 10^6$ cells/kg to about $8 \times 10^6$ cells/kg, $5 \times 10^6$ cells/kg to about $6 \times 10^6$ cells/kg, $5 \times 10^6$ cells/kg to about $7 \times 10^6$ cells/kg, $5 \times 10^6$ cells/kg to about $8 \times 10^6$ cells/kg, or $6 \times 10^6$ cells/kg to about $8 \times 10^6$ cells/kg, including all intervening doses of cells.

One of ordinary skill in the art would recognize that multiple administrations of the compositions contemplated in particular embodiments may be required to effect the desired therapy. For example, a composition may be administered 1, 2, 3, 4, 5, 6, 7, 8, 9, or 10 or more times over a span of 1 week, 2 weeks, 3 weeks, 1 month, 2 months, 3 months, 4 months, 5 months, 6 months, 1 year, 2 years, 5, years, 10 years, or more.

In certain embodiments, it may be desirable to administer activated T cells to a subject and then subsequently redraw blood (or have an apheresis performed), activate T cells therefrom, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, 100 cc, 150 cc, 200 cc, 250 cc, 300 cc, 350 cc, or 400 cc or more. Not to be bound by theory, using this multiple blood draw/multiple reinfusion protocol may serve to select out certain populations of T cells.

In one embodiment, a method of treating a subject diagnosed with a cancer, comprises removing immune effector cells from the subject, modifying the immune effector cells by introducing one or more vectors encoding an engineered antigen receptor and a TGFβ signal convertor and producing a population of modified immune effector cells, and administering the population of modified immune effector cells to the same subject. In a preferred embodiment, the immune effector cells comprise T cells.

The methods for administering the cell compositions contemplated in particular embodiments include any method which is effective to result in reintroduction of ex vivo modified immune effector cells or on reintroduction of the modified progenitors of immune effector cells that on introduction into a subject differentiate into mature immune effector cells. One method comprises modifying peripheral blood T cells ex vivo by introducing one or more vectors encoding an engineered antigen receptor and a TGFβ signal convertor and returning the transduced cells into the subject.

All publications, patent applications, and issued patents cited in this specification are herein incorporated by reference as if each individual publication, patent application, or issued patent were specifically and individually indicated to be incorporated by reference.

Although the foregoing embodiments have been described in some detail by way of illustration and example for purposes of clarity of understanding, it will be readily apparent to one of ordinary skill in the art in light of the teachings contemplated herein that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

T Cells Expressing a TGFβ IL-12R Signal Convertor (CTBR12) and a Chimeric Antigen Receptor (CAR)

Illustrative TGFβ IL-12R based signal convertor constructs were designed as shown in FIG. 1.

Optimal IL-12 receptor signaling is initiated by dimerization of the intracellular domains of the IL-12Rβ1 and IL-12Rβ2 subunits following IL-12 ligation. To convert a TGFβ signal to induce IL-12 receptor signaling after exposure to TGFβ, the intracellular domains of TGFβ receptor 1 (TGFβR1) and TGFβ receptor 2 (TGFβR2) were replaced with the IL-12Rβ1 and IL-12Rβ2 signaling domains, respectively. The IL-12Rβ1 and IL-12Rβ2 transmembrane and signaling domains were cloned into a lentiviral vector encoding a CAR and separated by 2A self-cleaving polypeptide sequences (CAR.CTBR12).

Primary human T cells from healthy donor PBMCs were activated with soluble anti-CD3 (1 μg/mL) and anti-CD28 (5 μg/mL) and transduced with vehicle or lentiviral vectors expressing (i) an anti-ROR1 CAR; (ii) an anti-ROR1 CAR and dominant negative TGFβ receptor (anti-ROR1.DNR); (iii) an anti-ROR1 CAR and a TGFβR2 subunit; or (iv) an anti-ROR1 CAR and CTBR12 (anti-ROR1.CTBR12). After 10 days of culture in IL-2 containing growth media, cell surface expression of the anti-ROR1 CAR and TGFβR2 was determined by flow cytometry. A recombinant human ROR1 protein conjugated to R-phycoerythrin (R-PE) was used to specifically stain the anti-ROR1 CAR expressing T cells. A commercially available antibody to TGFBR2 was used to detect CTBR12. Representative expression data is shown in FIG. 2.

Figure 2:
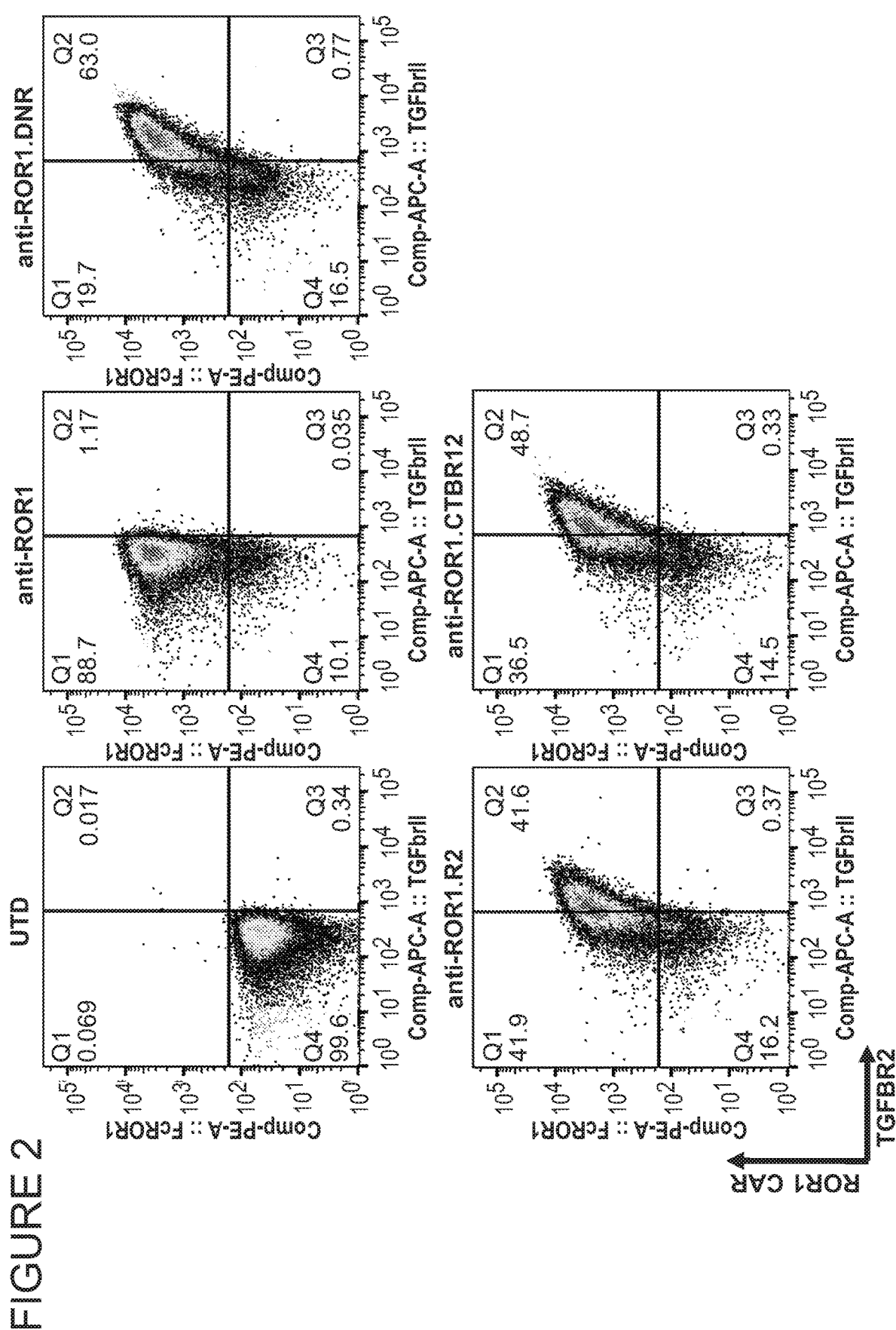
FIG. 2 shows CAR and TGFβR2 subunit expression in primary human T cells transduced with an anti-ROR1 CAR alone and in combination with the TGFβ DNR, TGFβ R2 subunit, and the CTBR12 signal convertor.

Fifty percent of T cells transduced with the lentiviral vector encoding the anti-ROR1 CAR and CTBR12 co-expressed the anti-ROR1 CAR and CTBR12 (rightmost panel of FIG. 2). In contrast, neither the anti-ROR1 CAR nor CTBR12 was detected in untransduced T cells, indicating that the antibody to TGFBR2 did not detect endogenous TGFBR2.

Example 2

Immunosuppressive TGFβ Signaling Inhibited by CTBR12

TGFβ1 ligation to a tetrameric complex containing 2 units of TGFβR1 and 2 units of TGFβR2 induces SMAD2 and SMAD3 phosphorylation to propagate an immunosuppressive signal to the cell nucleus. Overexpression of a truncated TGFβR2 (dominant negative TGFβ receptor—DNR) renders T cells insensitive to TGFβ as shown by loss of SMAD2/3 phosphorylation in response to TGFβ treatment. Thus, phospho-SMAD2/3 expression was used to interrogate TGFβ signaling pathway activation.

Primary human T cells from healthy donor PBMCs were activated with soluble anti-CD3 (1 µg/mL) and anti-CD28 (5 µg/mL) and transduced with vehicle or lentiviral vectors expressing (i) an anti-ROR1 CAR; (ii) an anti-ROR1 CAR and dominant negative TGFβ receptor (anti-ROR1.DNR); (iii) an anti-ROR1 CAR and a TGFβR2 subunit; or (iv) an anti-ROR1 CAR and CTBR12 (anti-ROR1.CTBR12). After 10 days of culture in IL-2 containing growth media, cultures were treated with 10 ng/mL of recombinant human TGFβ1 for 20 minutes. SMAD2/3 phosphorylation was evaluated with antibodies specific to phosphorylated SMAD2/3. T cells expressing either CTBR12 or DNR were completely protected from phosphorylation of SMAD2/3 (FIG. 3). These data demonstrated that expression of CTBR12 rendered anti-ROR1 CAR T cells insensitive to TGFβ immunosuppressive signaling.

Example 3

CTBR12 Transduces IL-12R Signaling Upon Exposure to TGFβ1

The cellular response to IL-12 is initiated by receptor dimerization and phosphorylation of STAT4 and STAT5. Thus, phospho-STAT4 and phospho-STAT5 expression was used to assess IL-12 receptor signaling pathway activation.

Primary human T cells from healthy donor PBMCs were activated with soluble anti-CD3 (1 µg/mL) and anti-CD28 (5 µg/mL) and transduced with vehicle or lentiviral vectors expressing (i) an anti-ROR1 CAR; (ii) an anti-ROR1 CAR and dominant negative TGFβ receptor (anti-ROR1.DNR); (iii) an anti-ROR1 CAR and a TGFβR2 subunit; or (iv) an anti-ROR1 CAR and CTBR12 (anti-ROR1.CTBR12). After 10 days of culture in IL-2 containing growth media, cultures were treated with 50 ng/mL of recombinant human IL-12 or with 10 ng/mL of recombinant human TGFβ1 for 20 minutes.

Figure 4:
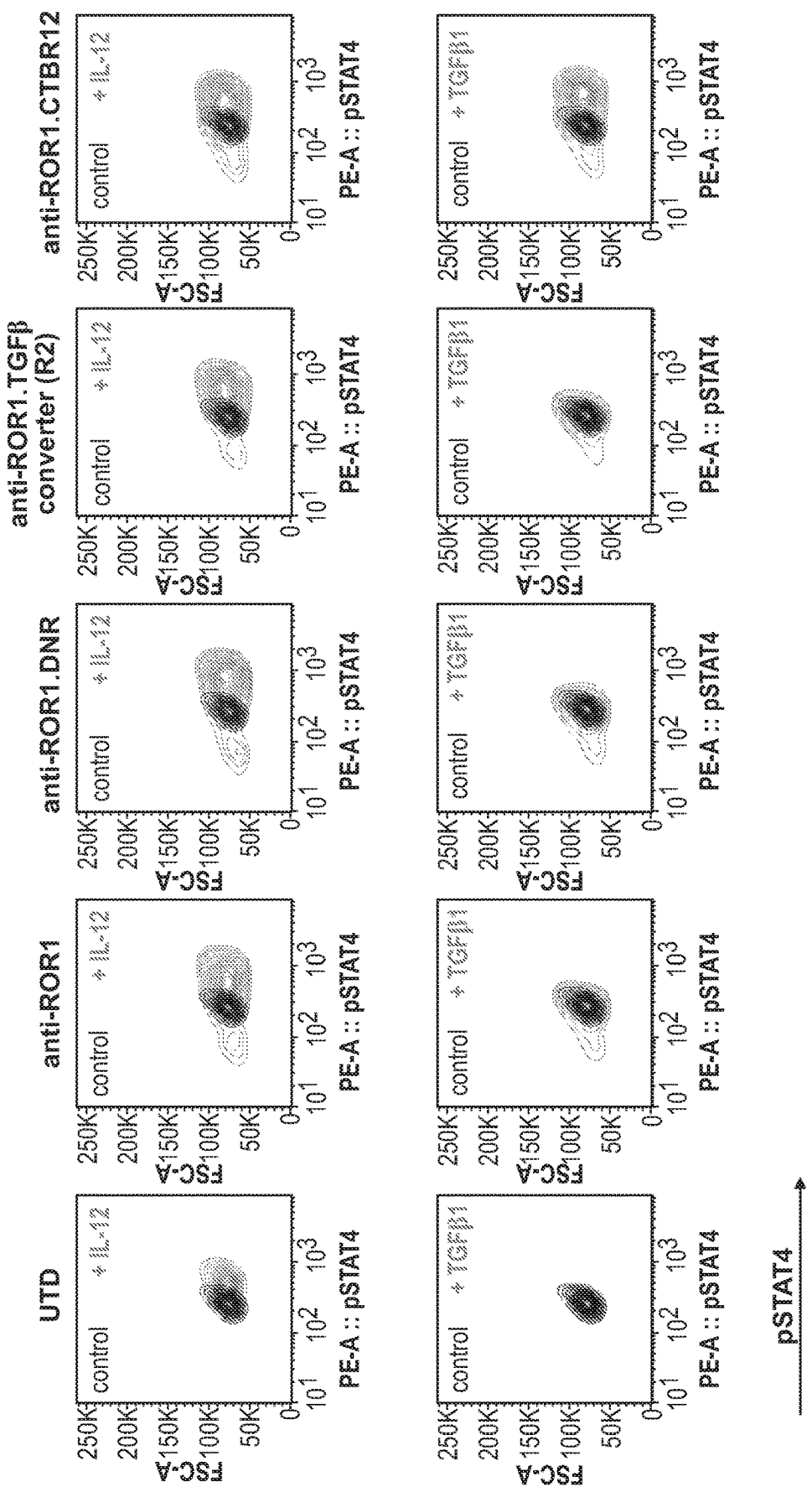
FIG. 4 shows phospho-STAT4 expression in primary human T cells transduced with an anti-ROR1 CAR alone and in combination with the TGFβ DNR, TGFβ R2 subunit, and the CTBR12 signal convertor and treated with either IL-12 (top row) or TGFβ1 (bottom row).

T cells expressing anti-ROR1 CARs cells exhibited increased levels of phosphorylated STAT4 (FIG. 4, top row, compare rightmost 4 panels to untransduced control (UTD)). Only CAR T cells expressing CTBR12 showed detectable levels of phospho-STAT4 expression when treated with recombinant human TGFβ1 (FIG. 4, bottom row, compare rightmost panel to other panels). In contrast, CAR T cells expressing only the TGFβR2 portion of the signal converter did not phosphorylate STAT4 in response to TGFβ treatment (FIG. 4, bottom row, fourth panel from the right).

Figure 5:
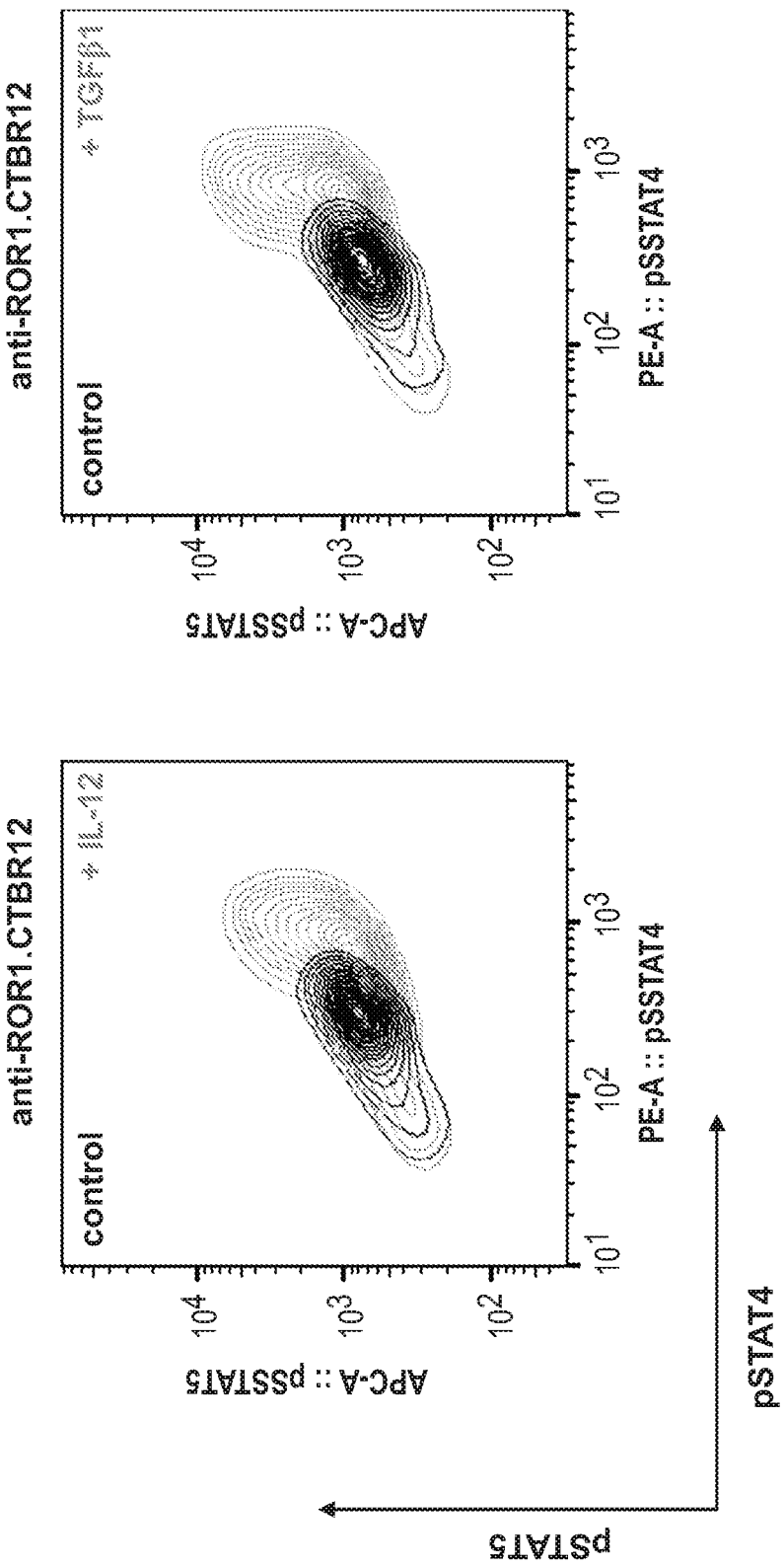
FIG. 5 shows phospho-STAT4 and phospho-STAT5 expression in primary human T cells transduced with an anti-ROR1 CAR and the CTBR12 signal convertor and treated with either IL-12 (left panel) or TGFβ1 (right panel).

CAR T cells expressing CTBR12 also exhibited detectable levels of phospho-STAT5 when treated with either IL-12 or TGFβ1, confirming that the converted TGFβ signal induces endogenous IL-12 receptor signaling (FIG. 5).

Figure 6:
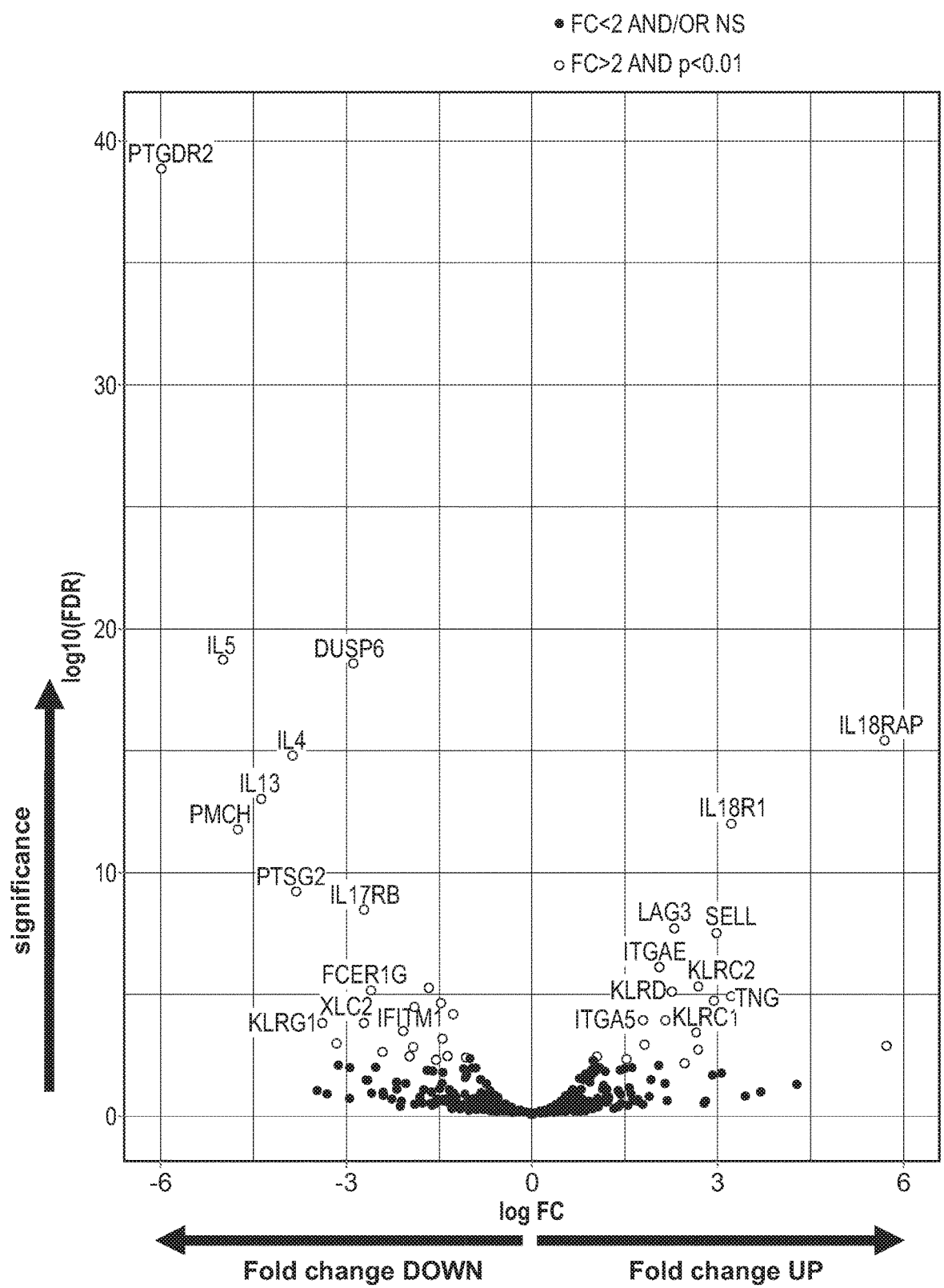
FIG. 6 shows gene expression analysis from primary human T cells transduced with anti-ROR1 CAR in combination with the CTBR12 signal convertor serially re-stimulated with ROR1 expressing target cells for 21 days in the presence or absence of TGFβ1.
Figure 6:
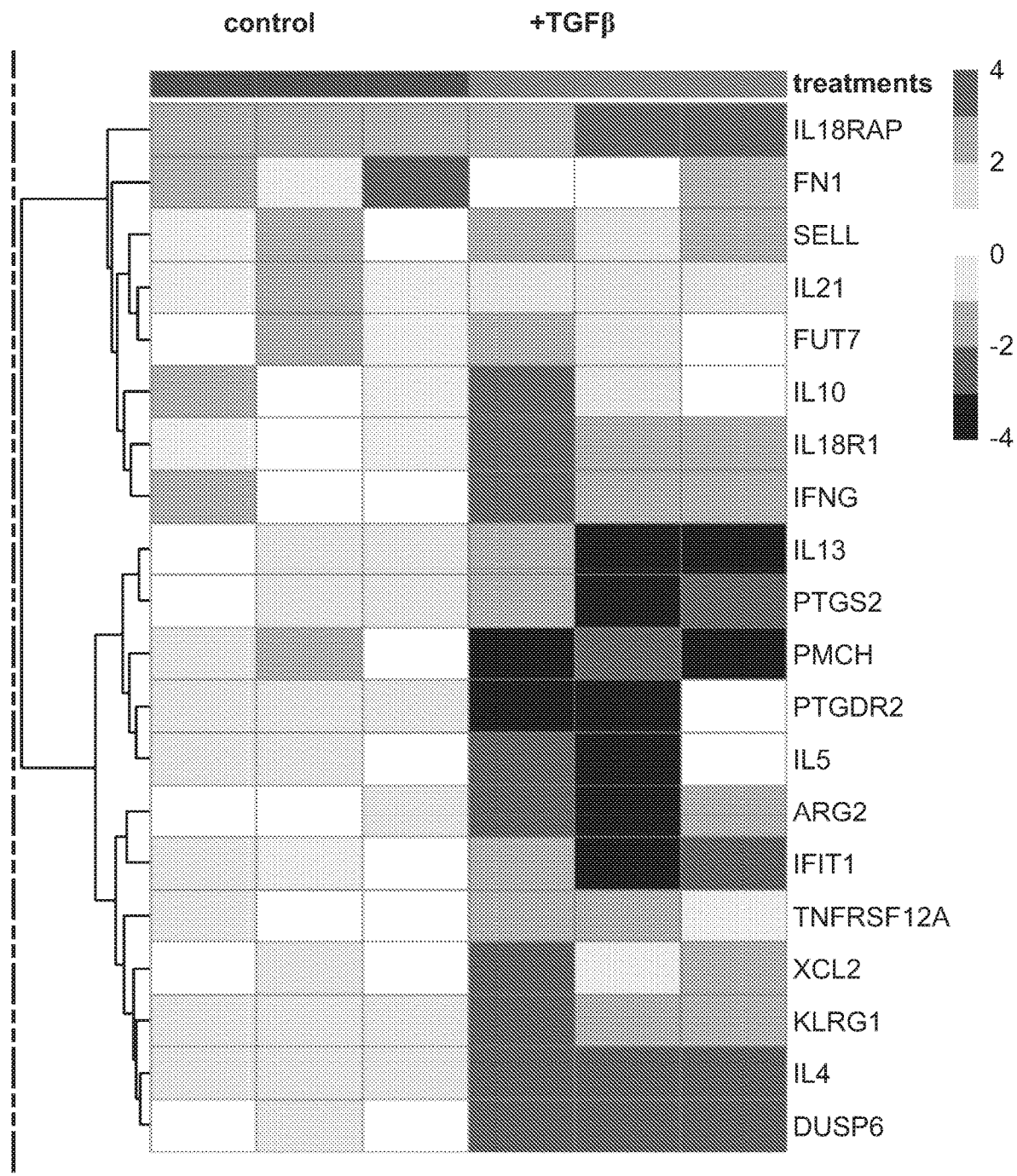

The gene expression of CAR T cells expressing the anti-ROR1.CTBR12 was measured in an antigen-driven serial expansion assay in the presence or absence of TGFβ1. Briefly, GFP-labeled K562 target cells that express human ROR1 antigen were used to serially expand the CAR T cells in the presence or absence of recombinant human TGFβ1. CAR T cells were stimulated with target cells at a 1:1 ratio once every seven days in the presence or absence of 5 ng/mL recombinant human TGFβ1. T cells were harvested and mRNA for gene expression analysis was isolated on day 21 following the initial stimulation. Gene expression analysis was performed using the Nanostring immune profiling panel. Significant gene expression changes driven by TGFβ1 treatment were identified (FIG. 6, left panel) in the anti-ROR1.CTBR12 expressing cells, including upregulation of the known IL-12R-regulated transcripts IFNG, SELL, IL18RAP, IL18R1, and IL21R (FIG. 6, right panel).

Example 4

CAR T Cells Expressing CTBR12 Secrete Increased IFNγ Upon Exposure to Antigen and TGFβ1

IL-12 receptor signaling in human T cells drives TH1 differentiation and increases effector function. IL-12 receptor signaling can cooperate with TCR signals to increase the release of IFNγ in response to antigen stimulation.

The R2/R1 signal converter amplified IFNγ production when T cells were stimulated through either a TCR or CAR in the presence of recombinant human TGFβ1. Primary human T cells from healthy donor PBMCs were activated with soluble anti-CD3 (1 µg/mL) and anti-CD28 (5 µg/mL) and transduced with vehicle or lentiviral vectors expressing (i) an anti-ROR1 CAR; (ii) an anti-ROR1 CAR and dominant negative TGFβ receptor (anti-ROR1.DNR); or (iii) an anti-ROR1 CAR and CTBR12 (anti-ROR1.CTBR12). After 10 days of culture in IL-2 containing growth media, the cells were plated on either plate-bound anti-CD3 antibody (1 µg/mL) or recombinant human ROR1 protein (100 ng/mL) in the presence or absence of 5 ng/mL recombinant human TGFβ1. Forty eight hours post-plating, supernatants were collected and analyzed via Luminex for soluble cytokine content.

Figure 7:
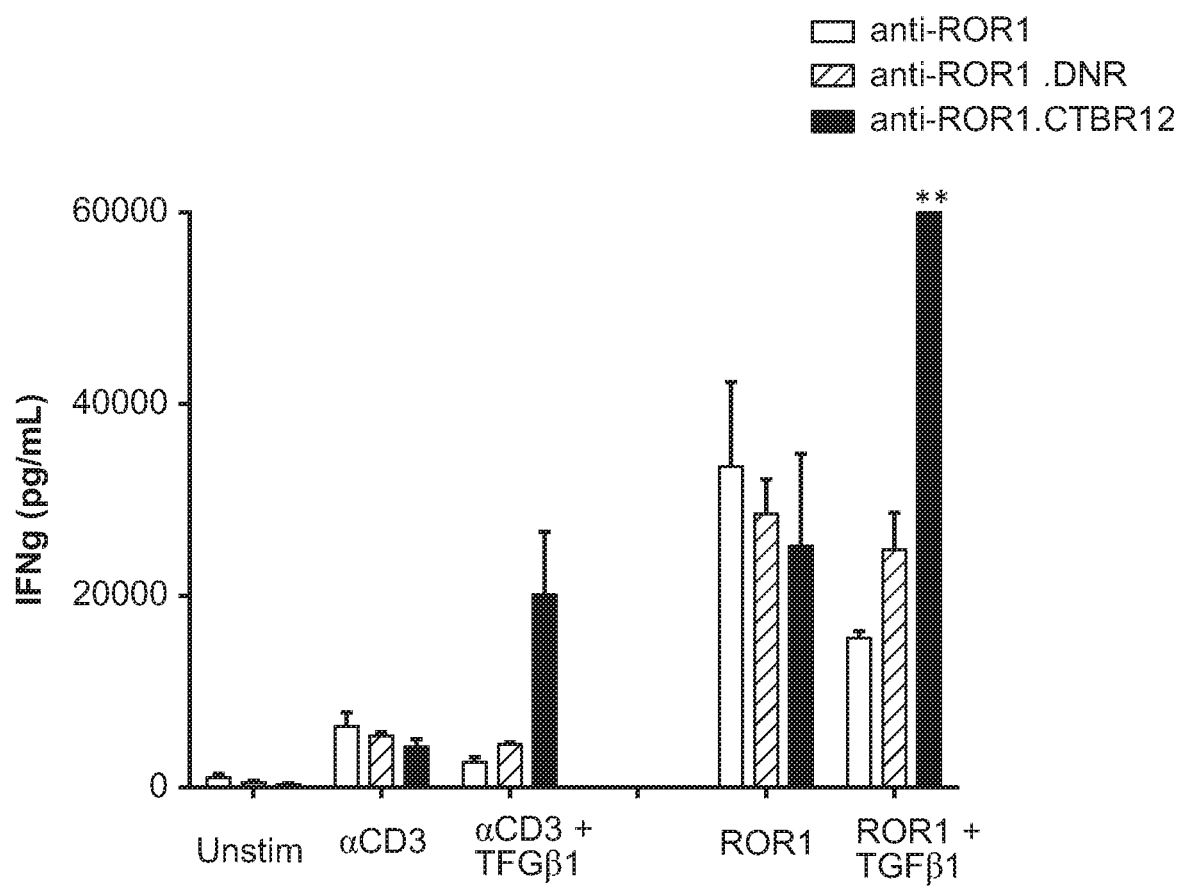
FIG. 7 shows IFNγ secretion from primary human T cells transduced with an anti-ROR1 CAR alone and in combination with the TGFβ DNR or the CTBR12 signal convertor and cultured in the presence or absence of TGFβ1 on plates coated with CD3 or ROR1.

CTBR12 expressing cells produced significantly greater amounts of IFNγ than the other cell types when stimulated through either TCR or CAR in the presence of recombinant human TGFβ1 (FIG. 7).

Example 5

CAR T Cells Expressing CTBR12 are Resistant to TGFβ1 Immunosuppressive Signals

TGFβ signaling decreases T cell expansion in response to antigen stimulation. In contrast, IL-12 signaling increases T cell proliferation and reduces T cell hypofunction resulting from chronic antigen exposure.

Primary human T cells from healthy donor PBMCs were activated with soluble anti-CD3 (1 μg/mL) and anti-CD28 (5 μg/mL) and transduced with vehicle or lentiviral vectors expressing (i) an anti-ROR1 CAR; (ii) an anti-ROR1 CAR and dominant negative TGFβ receptor (anti-ROR1.DNR); or (iii) an anti-ROR1 CAR and CTBR12 (anti-ROR1.CTBR12). After 10 days of culture in IL-2 containing growth media, the cells were subject to an in vitro serial re-stimulation assay.

Figure 8:
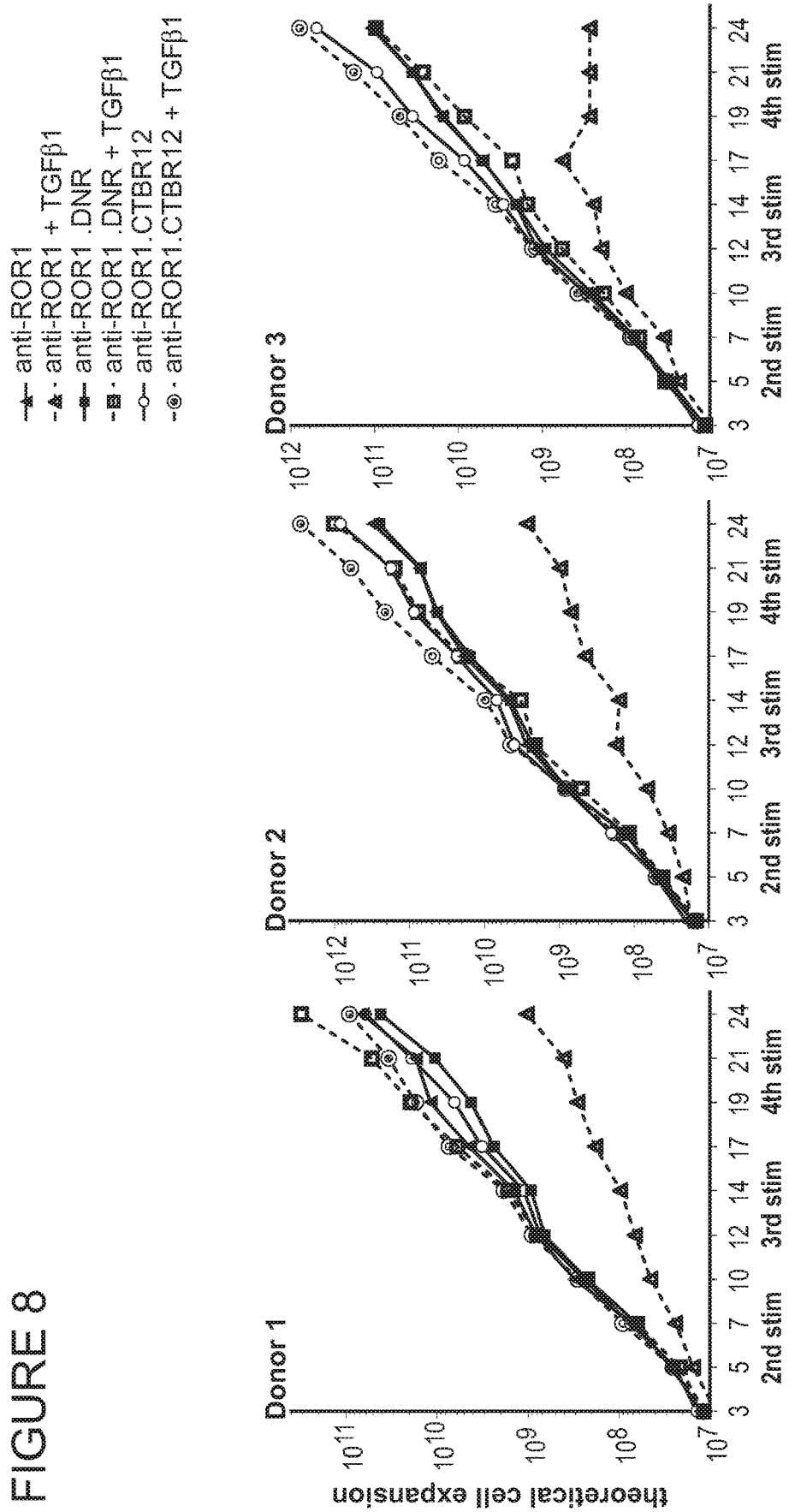
FIG. 8 shows the growth curves for primary human T cells transduced with an anti-ROR1 CAR alone and in combination with the TGFβ DNR or the CTBR12 signal convertor serially re-stimulated with ROR1 expressing target cells in the presence or absence of TGFβ1.

Briefly, GFP-labeled K562 target cells that express human ROR1 antigen were used to serially expand the CAR T cells in the presence or absence of recombinant human TGFβ1. CAR T cells were stimulated with target cells at a 1:1 ratio once every seven days in the presence or absence of 5 ng/mL recombinant human TGFβ1. Control anti-ROR1 CAR-T cells displayed minimal expansion in the presence of 5 ng/mL recombinant human TGFβ1 over the course of the assay. In contrast, anti-ROR1 CAR T cells co-expressing either the TGFβ DNR or CTBR12 were significantly protected from immunosuppressive TGFβ1 mediated signaling. FIG. 8. These results correlated with both the DNR's and CTBR12's ability to block SMAD phosphorylation (FIG. 8).

Example 6

T Cells Expressing a TGFβ-IL-7R Signal Convertor R2/R1 (CTBR7) and a Chimeric Antigen Receptor (CAR)

Illustrative TGFβ IL-7R based signal convertor (CTBR7) constructs were designed as shown in FIG. 1.

Optimal IL-7 receptor signaling is initiated by dimerization of the intracellular domains of the IL-7Rα and the common gamma chain (γc; IL-2Rγ) following IL-7 ligation. To convert a TGFβ signal to induce IL-7 receptor signaling after exposure to TGFβ, the intracellular domains of TGFβ receptor 1 (TGFβR1) and TGFβ receptor 2 (TGFβR2) were replaced with the IL-2Rγ and IL-7Rα signaling domains, respectively to produce an IL-7 signaling chimeric TGFβ receptor (CTBR7). The IL-2Rγ and IL-7Rα transmembrane and signaling domains were cloned into a lentiviral vector encoding a CAR and separated by 2A self-cleaving polypeptide sequences (CAR.CTBR7).

Primary human T cells from healthy donor PBMCs were activated with soluble anti-CD3 (1 μg/mL) and anti-CD28 (5 μg/mL) and transduced with vehicle or lentiviral vectors expressing (i) an anti-ROR1 CAR; (ii) an anti-ROR1 CAR and dominant negative TGFβ receptor (anti-ROR1.DNR); (iii) an anti-ROR1 CAR and CTBR7 (anti-ROR1.CTBR7). After 10 days of culture in IL-2 containing growth media, cell surface expression of the anti-ROR1 CAR and TGFβR2 were determined by flow cytometry. A recombinant human ROR1 protein conjugated to R-phycoerythrin (R-PE) was used to specifically stain the anti-ROR1 CAR expressing T cells. A commercially available antibody to TGFBR2 was used to detect CTBR7. Representative expression data is shown in FIG. 9.

Figure 9:
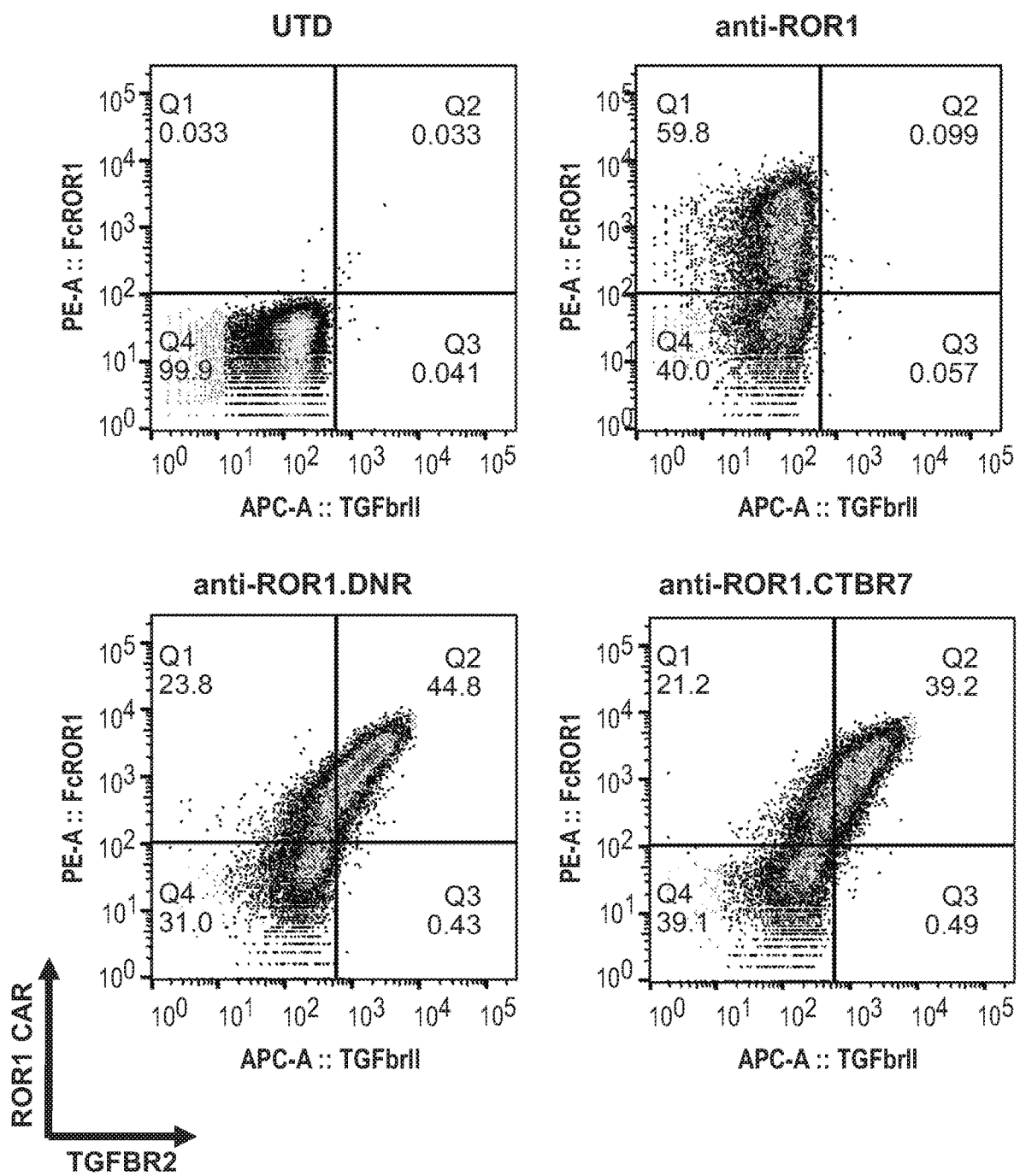
FIG. 9 shows CAR and TGFβR2 subunit expression in primary human T cells transduced with an anti-ROR1 CAR alone and in combination with the TGFβ DNR, and the CTBR7 signal convertor.

Forty percent of T cells transduced with the lentiviral vector encoding the anti-ROR1 CAR and CTBR7 co-expressed the anti-ROR1 CAR and CTBR7 (rightmost panel of FIG. 9). In contrast, neither the anti-ROR1 CAR nor CTBR7 was detected in untransduced T cells, indicating that the antibody to TGFBR2 did not detect endogenous TGFBR2.

Example 7

Immunosuppressive TGFβ Signaling Inhibited by CTBR7

TGFβ1 ligation to a tetrameric complex containing 2 units of TGFβR1 and 2 units of TGFβR2 induces SMAD2 and SMAD3 phosphorylation to propagate an immunosuppressive signal to the cell nucleus. Overexpression of a truncated TGFβR2 (dominant negative TGFβ receptor—DNR) renders T cells insensitive to TGFβ as shown by loss of SMAD2/3 phosphorylation in response to TGFβ treatment. Thus, phospho-SMAD2/3 expression was used to interrogate TGFβ signaling pathway activation.

Figure 10:
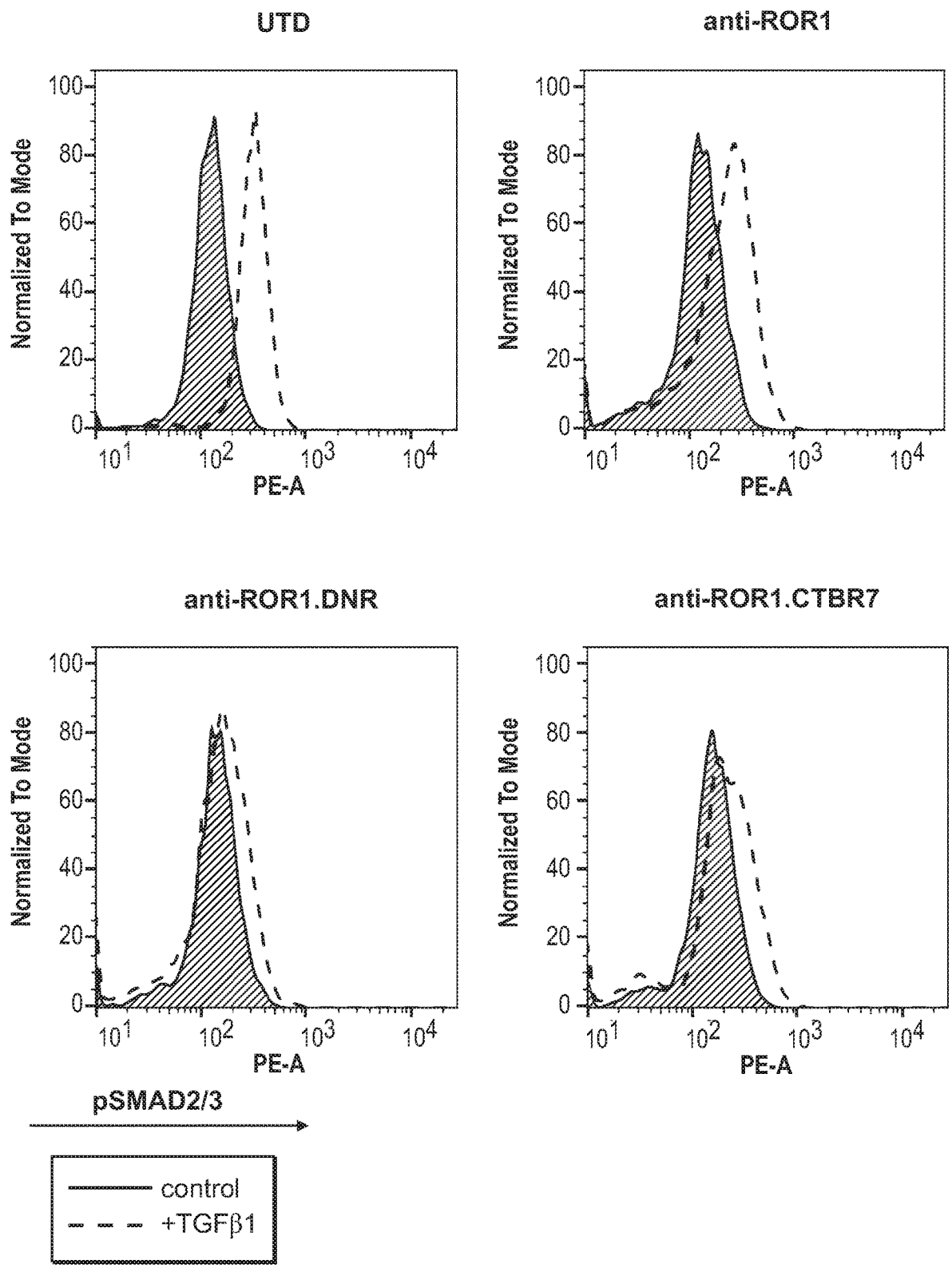
FIG. 10 shows phospho-SMAD2/3 expression in primary human T cells transduced with an anti-ROR1 CAR alone and in combination with the TGFβ DNR, and the CTBR7 signal convertor and treated with TGFβ1.

Primary human T cells from healthy donor PBMCs were activated with soluble anti-CD3 (1 μg/mL) and anti-CD28 (5 μg/mL) and transduced with vehicle or lentiviral vectors expressing (i) an anti-ROR1 CAR; (ii) an anti-ROR1 CAR and dominant negative TGFβ receptor (anti-ROR1.DNR); (iii) an anti-ROR1 CAR and CTBR7 (anti-ROR1.CTBR7). After 10 days of culture in IL-2 containing growth media, cultures were treated with 10 ng/mL of recombinant human TGFβ1 for 20 minutes. SMAD2/3 phosphorylation was evaluated with antibodies specific to phosphorylated SMAD2/3. T cells expressing either CTBR7 or DNR were protected from phosphorylation of SMAD2/3 (FIG. 10). These data demonstrated that expression of CTBR7 rendered anti-ROR1 CAR T cells insensitive to TGFβ immunosuppressive signaling.

Example 8

CTBR7 Transduces IL-7R Signaling Upon Exposure to TGFβ1

The cellular response to IL-7 is initiated by receptor dimerization and phosphorylation of STAT5. Thus, phospho-STAT5 expression was used to assess IL-7 receptor signaling pathway activation for T cells expressing CTBR7.

Figure 11:
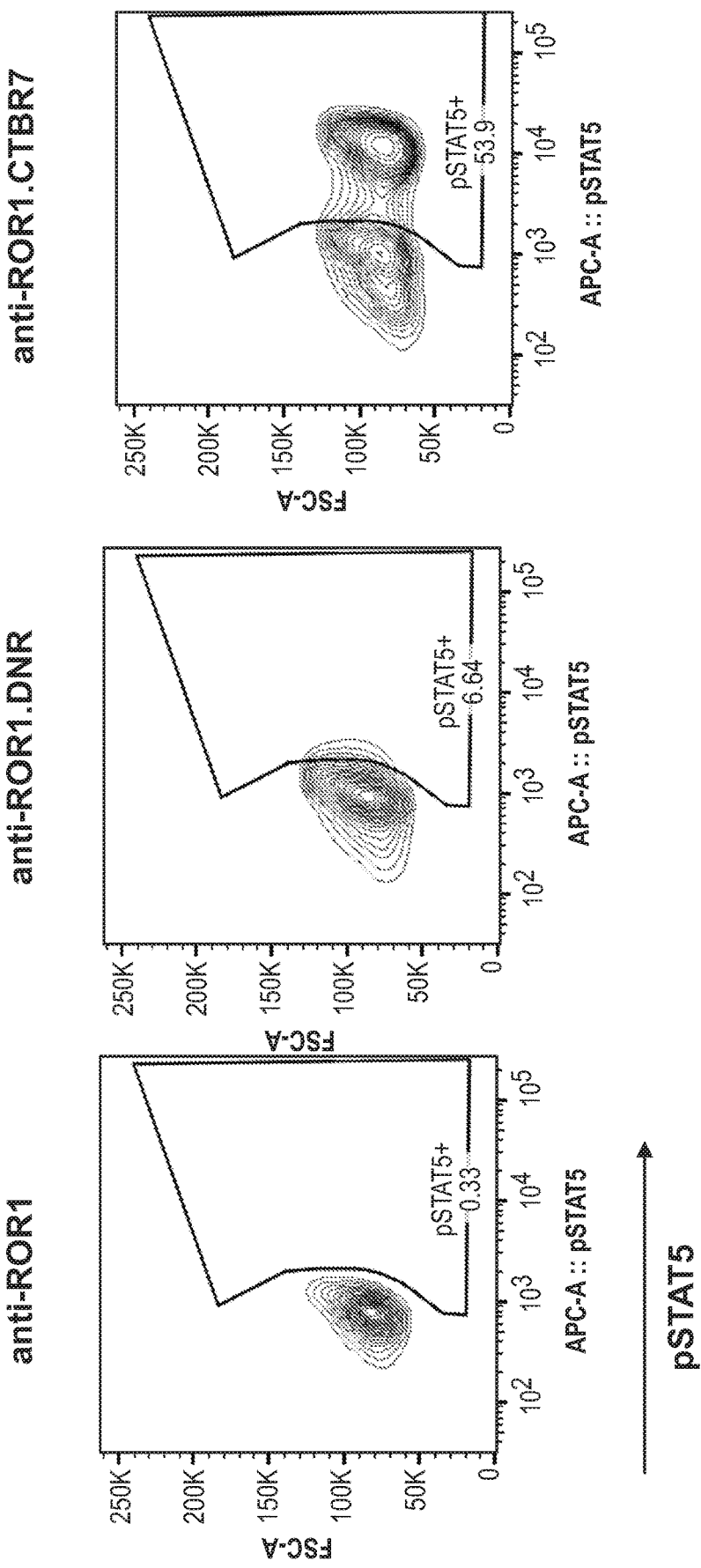
FIG. 11 shows phospho-STAT5 expression in primary human T cells transduced with an anti-ROR1 CAR alone and in combination with the TGFβ DNR, and the CTBR7 signal convertor and treated with TGFβ1.

Primary human T cells from healthy donor PBMCs were activated with soluble anti-CD3 (1 μg/mL) and anti-CD28 (5 μg/mL) and transduced with vehicle or lentiviral vectors expressing (i) an anti-ROR1 CAR; (ii) an anti-ROR1 CAR and dominant negative TGFβ receptor (anti-ROR1.DNR); (iii) an anti-ROR1 CAR and CTBR7 (anti-ROR1.CTBR7). After 10 days of culture in IL-2 containing growth media, cultures were treated with 10 ng/mL of recombinant human TGFβ1 for 20 minutes. Only CAR T cells expressing CTBR7 showed detectable levels of phospho-STAT5 expression when treated with recombinant human TGFβ1 (FIG. 11, compare rightmost panel to other panels).

Figure 12:
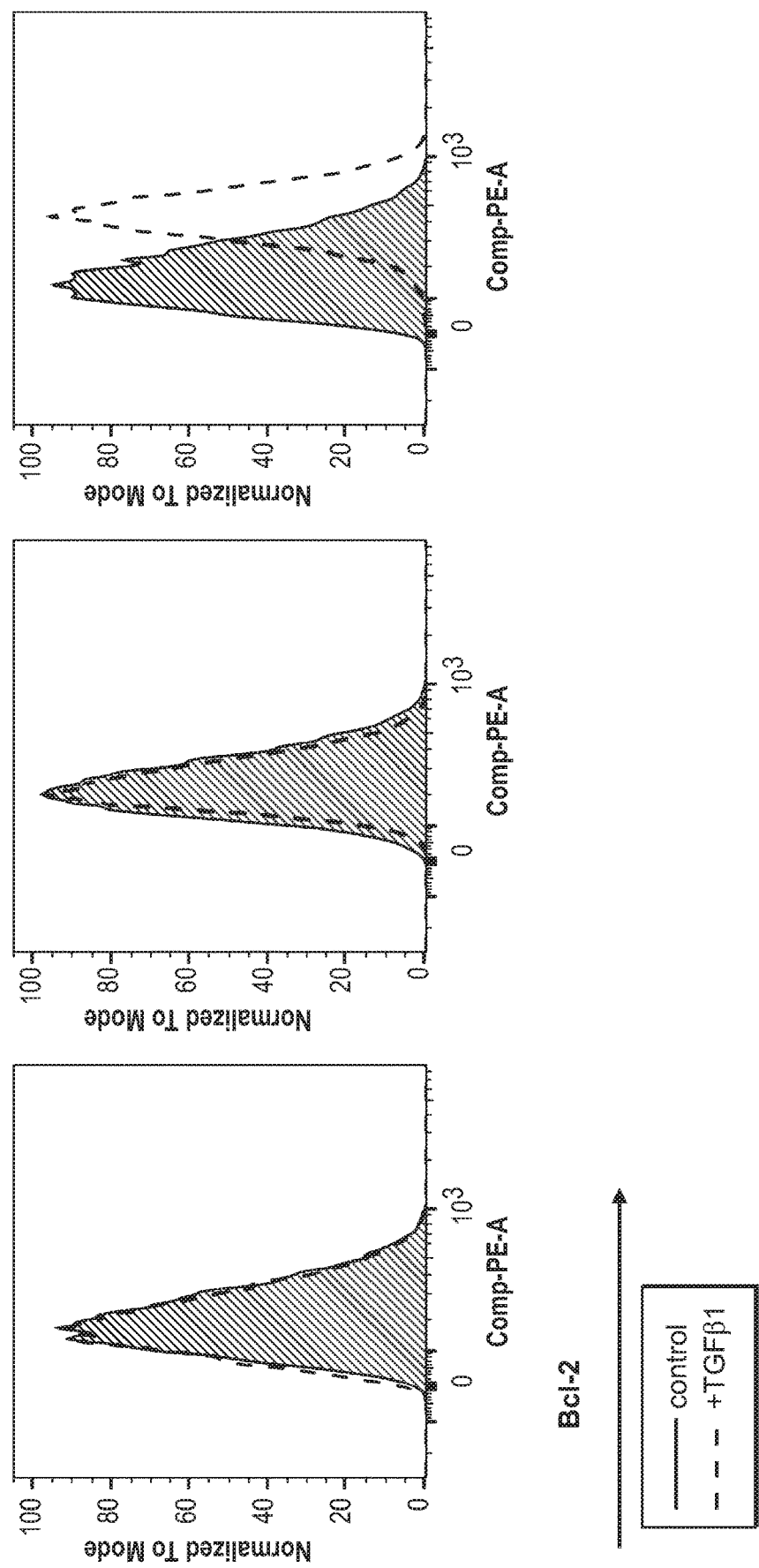
FIG. 12 shows BCL2 expression in primary human T cells transduced with an anti-ROR1 CAR alone and in combination with the TGFβ DNR, and the CTBR7 signal convertor and treated with TGFβ1.

To further interrogate the converted IL-7R signaling, the ability of CTBR7 expressing cells to upregulate Bcl-2 protein expression in response to continuous TGFβ1 exposure was determined. Control CAR T cells or CAR T cells co-expressing either the DNR (anti-ROR1.DNR) or CTBR7 (anti-ROR1.CTBR7) were subjected to an antigen-driven serial expansion assay in absence of exogenous cytokine support and either the presence or absence of TGFβ1. Briefly, GFP-labeled K562 target cells that express human ROR1 antigen were used to serially expand the CAR T cells in the presence or absence of recombinant human TGFβ1. CAR T cells were stimulated with target cells at a 1:1 ratio once every seven days in the presence or absence of 5 ng/mL recombinant human TGFβ1. Six days following the second stimulation, anti-ROR1 CAR, anti-ROR1 CAR.DNR, or anti-ROR1 CAR.CTBR7 T cells were interrogated for Bcl-2 protein expression by flow cytometry. Only CAR T cells expressing CTBR7 demonstrated increased levels of Bcl-2 protein expression when expanded in the presence of TGFβ1 (FIG. 12).

Example 9

CAR T Cells Co-Expressing CTBR7 Demonstrate Sustained Effector Activity in the Absence of Exogenous IL-2 and Presence of TGFβ1

TGFβ signaling decreases T cell expansion in response to antigen stimulation. In contrast, IL-7 signaling can induce T cell proliferation and survival, an activity that is particularly apparent for memory T cell populations. To assess whether CTBR7 signaling could increase CAR T cell effector activity in the presence of TGFβ1, we compared CAR.CTBR7 expansion and anti-tumor activity against control CAR T cells and CAR.DNR T cells in a serial re-stimulation assay where exogenous IL-2 cytokine support was not provided.

Primary human T cells from healthy donor PBMCs were activated with soluble anti-CD3 (1 µg/mL) and anti-CD28 (5 µg/mL) and transduced with vehicle or lentiviral vectors expressing (i) an anti-ROR1 CAR; (ii) an anti-ROR1 CAR and dominant negative TGFβ receptor (anti-ROR1.DNR); or (iii) an anti-ROR1 CAR and CTBR7 (anti-ROR1.CTBR7). After 10 days of culture in IL-2 containing growth media, the cells were subjected to an in vitro serial re-stimulation assay in the absence of exogenous IL-2 cytokine support.

Figure 13:
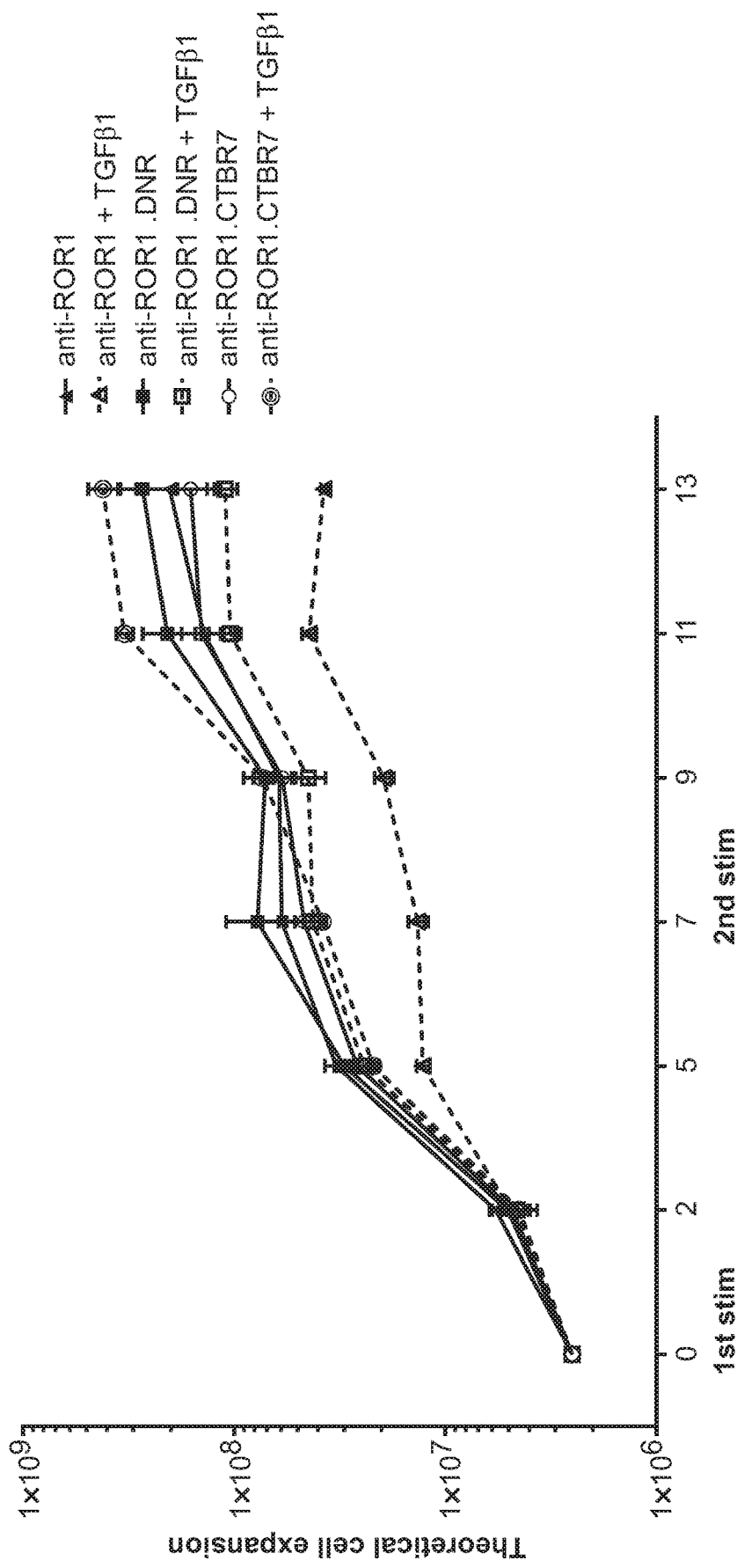
FIG. 13 shows the growth curves for primary human T cells transduced with an anti-ROR1 CAR alone and in combination with the TGFβ DNR or the CTBR7 signal convertor in the presence or absence of TGFβ1.
Figure 14:
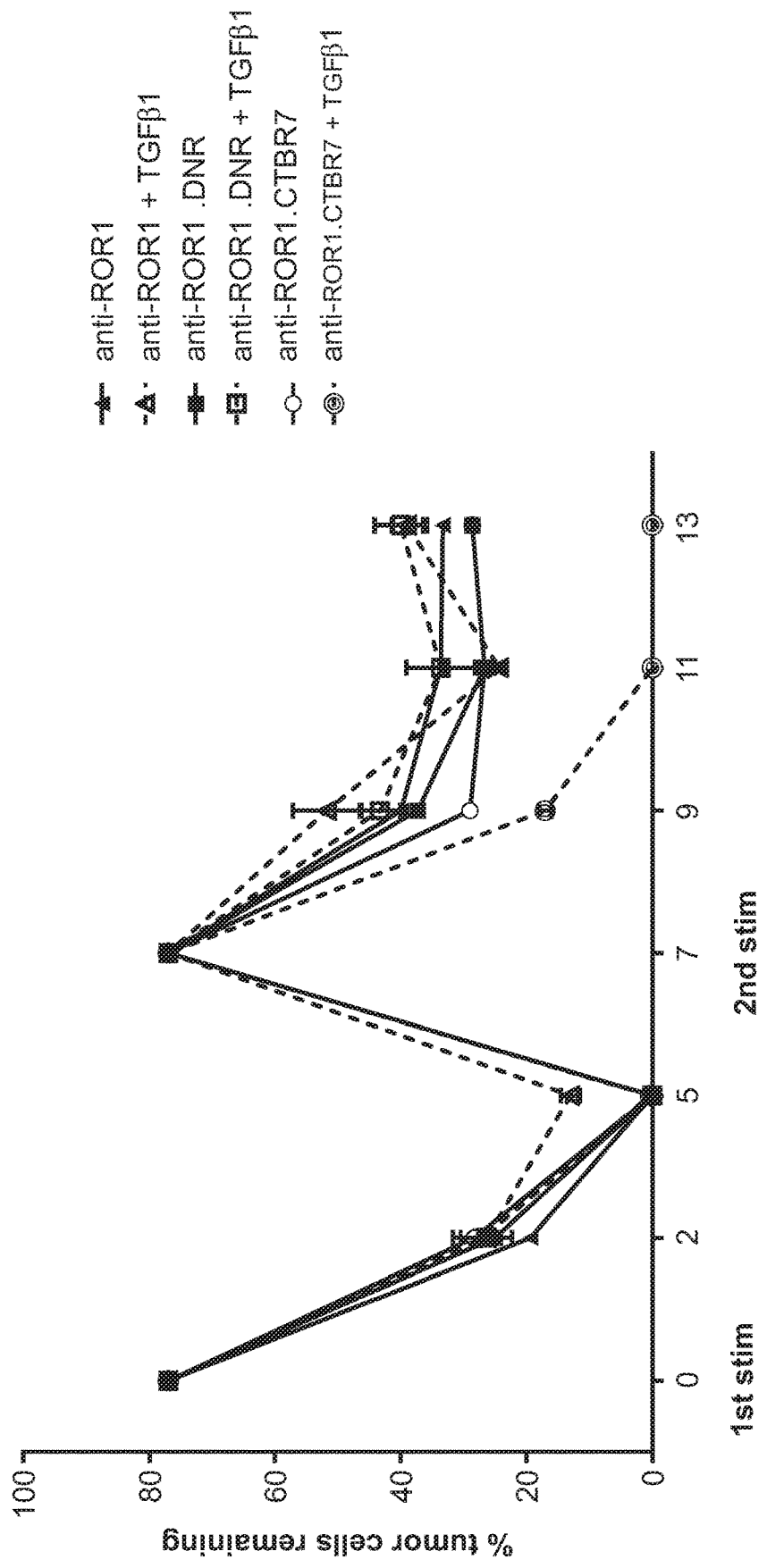
FIG. 14 shows the growth curves for primary human T cells transduced with an anti-ROR1 CAR alone and in combination with the TGFβ DNR or the CTBR7 signal convertor serially re-stimulated with ROR1 expressing target cells in the presence or absence of TGFβ1.

Briefly, GFP-labeled K562 target cells that express human ROR1 antigen were used to serially expand the CAR T cells in the presence or absence of recombinant human TGFβ1. CAR T cells were stimulated with target cells at a 1:1 ratio once every seven days in the presence or absence of 5 ng/mL recombinant human TGFβ1. No exogenous IL-2 was used for support in this assay. Control anti-ROR1 CAR T cells displayed minimal expansion in the presence of 5 ng/mL recombinant human TGFβ1 over the course of the assay. CAR T cells co-expressing the DNR also demonstrated reduced expansion when expanded in the presence of TGFβ1. In contrast, anti-ROR1 CAR T cells co-expressing CTBR7 demonstrated enhanced expansion compared to the same cells expanded in the absence of TGFβ1 (FIG. 13). These data demonstrated that active CTBR7 signaling increased T cell expansion compared to the CAR alone.

CAR T cells co-expressing CTBR7 clear tumor cells from culture in the above-described serial re-stimulation assay with no IL-2 support. After the second round of stimulation, only CAR T cells co-expressing CTBR7 and treated with TGFβ1 completely clear the tumor population (as monitored by the presence of GFP positive tumor cells remaining in culture) (FIG. 13). These data demonstrated that CTBR7 signaling was sufficient to support effector function in conditions where CAR signaling alone was not sufficient.

Example 10

T Cells Expressing a Chimeric Antigen Receptor (CAR) and a CTBR12 or CTBR7

Illustrative TGFβ IL-12R or TGFβ IL-7R signal converter constructs were designed as shown in FIG. 1.

IL-12Rβ1 and IL-12Rβ2 transmembrane and signaling domains were cloned into a lentiviral vector encoding an anti-EGFR CAR and separated by 2A self-cleaving polypeptide sequences (anti-EGFR.CTBR12).

IL-2Rγ and IL-7Rα transmembrane and signaling domains were cloned into a lentiviral vector encoding anti-EGFR CAR and separated by 2A self-cleaving polypeptide sequences (anti-EGFR.CTBR7).

Figure 15:
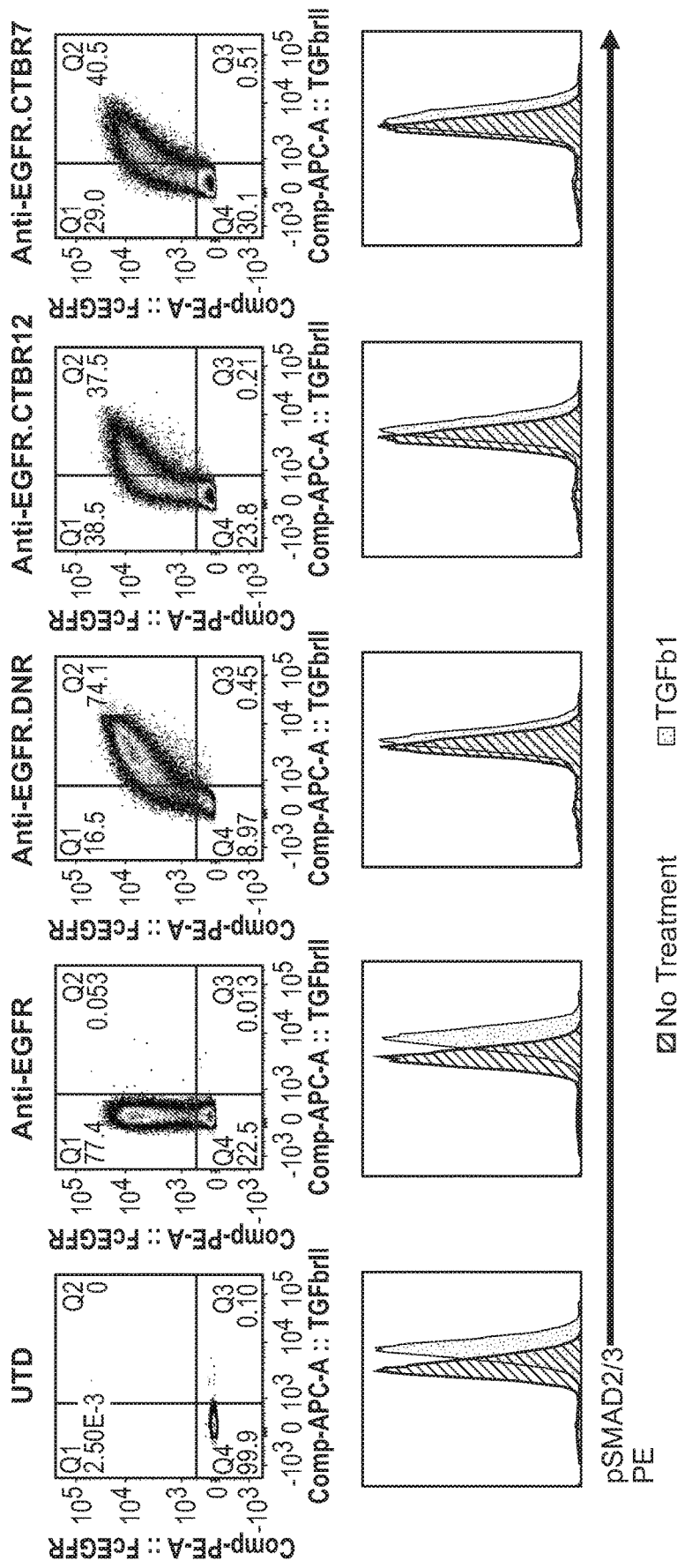
FIG. 15 shows CAR and TGFβR2 subunit expression in primary human T cells transduced with an anti-EGFR CAR alone and in combination with the TGFβ DNR, the CTBR12 signal convertor, and the CTBR7 signal convertor (top panel).

Primary human T cells from healthy donor PBMCs were activated with soluble anti-CD3 (1 µg/mL) and anti-CD28 (5 µg/mL) and transduced with vehicle or lentiviral vectors expressing (i) an anti-EGFR CAR; (ii) an anti-EGFR CAR and dominant negative TGFβ receptor (anti-EGFR.DNR); (iii) an anti-EGFR CAR and CTBR12 (anti-EFGR.CTBR12); and (iv) an anti-EGFR CAR and CTBR7 (anti-EFGR.CTBR7). After 10 days of culture in IL-2 containing growth media, cell surface expression of the anti-EGFR CAR and TGFβR2 was determined by flow cytometry. Representative expression data is shown in FIG. 15 (top panel).

Example 11

Immunosuppressive TGFβ Signaling Inhibited by T Cells Expressing Anti-EGFR CAR and CTBR12 or Anti-EGFR CAR and CTBR7

Primary human T cells from healthy donor PBMCs were activated with soluble anti-CD3 (1 µg/mL) and anti-CD28 (5 µg/mL) and transduced with vehicle or lentiviral vectors expressing (i) an anti-EGFR CAR; (ii) an anti-EGFR CAR and dominant negative TGFβ receptor (anti-EGFR.DNR); (iii) an anti-EGFR CAR and CTBR12 (anti-EFGR.CTBR12); and (iv) an anti-EGFR CAR and CTBR7 (anti-EFGR.CTBR7). After 10 days of culture in IL-2 containing growth media, cultures were treated with 10 ng/mL of recombinant human TGFβ1 for 20 minutes. SMAD2/3 phosphorylation was evaluated with antibodies specific to phosphorylated SMAD2/3. T cells expressing the DNR, CTBR12 or CTBR7 were completely protected from phosphorylation of SMAD2/3 (FIG. 15, bottom panel). These data demonstrated that expression of either CTBR12 or CTBR7 rendered anti-EGFR CAR T cells insensitive to TGFβ immunosuppressive signaling.

Example 12

CTBR Transduce IL-R Signaling Upon Exposure to TGFβ1

The cellular response to IL-12 is initiated by receptor dimerization and phosphorylation of STAT4 and STAT5. Phospho-STAT4 expression was used to assess IL-12 receptor signaling pathway activation for T cells expressing anti-EGFR.CTBR12.

The cellular response to IL-7 is initiated by receptor dimerization and phosphorylation of STAT5. Thus, phospho-STAT5 expression was used to assess IL-7 receptor signaling pathway activation for T cells expressing anti-EGFR.CTBR7.

Primary human T cells from healthy donor PBMCs were activated with soluble anti-CD3 (1 µg/mL) and anti-CD28 (5 µg/mL) and transduced with vehicle or lentiviral vectors expressing (i) an anti-EGFR CAR; (ii) an anti-EGFR CAR and CTBR12 (anti-EFGR.CTBR12); and (iii) an anti-EGFR CAR and CTBR7 (anti-EFGR.CTBR7). After 10 days of culture in IL-2 containing growth media, T cell cultures were treated with recombinant human IL-12 or recombinant human TGFβ1 for 20 minutes (FIG. 16) or with recombinant human IL-7 or recombinant human TGFβ1 for 20 minutes (FIG. 17).

Figure 16:
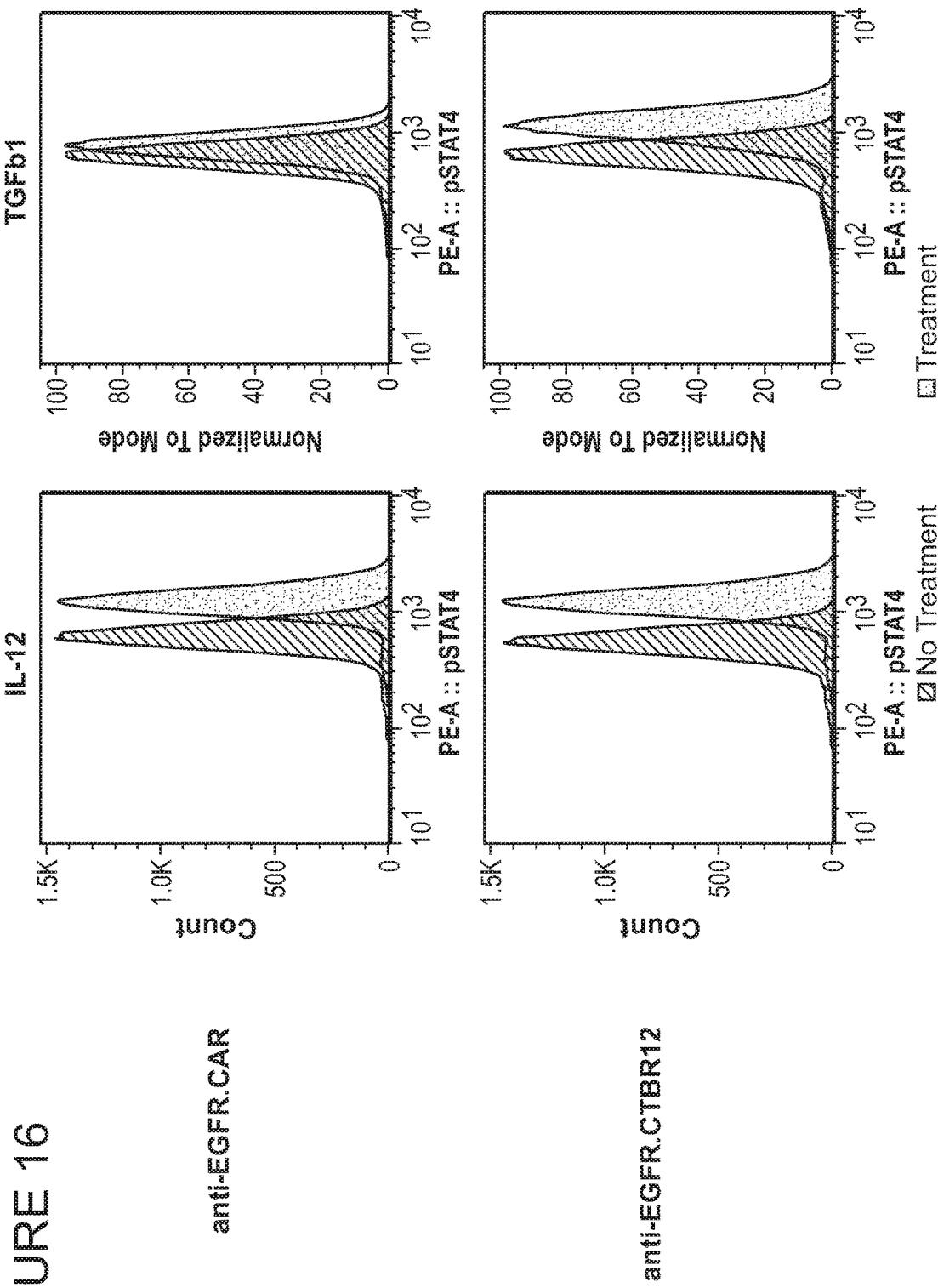
FIG. 16 shows phospho-STAT4 expression in primary human T cells transduced with an anti-EGFR CAR alone and in combination with the TGFβ DNR, and the CTBR12 signal convertor and treated with either IL-12 or TGFβ1.

T cells expressing anti-EGFR CAR or anti-EFGR.CTBR12 shows increased levels of phosphorylated STAT4 in the presence of IL-12 (FIG. 16, left panels), but only T cells expressing anti-EFGR.CTBR12 show increased levels of phosphorylated STAT4 in the presence of TGFβ1 (FIG. 16, lower right panel).

Figure 17:
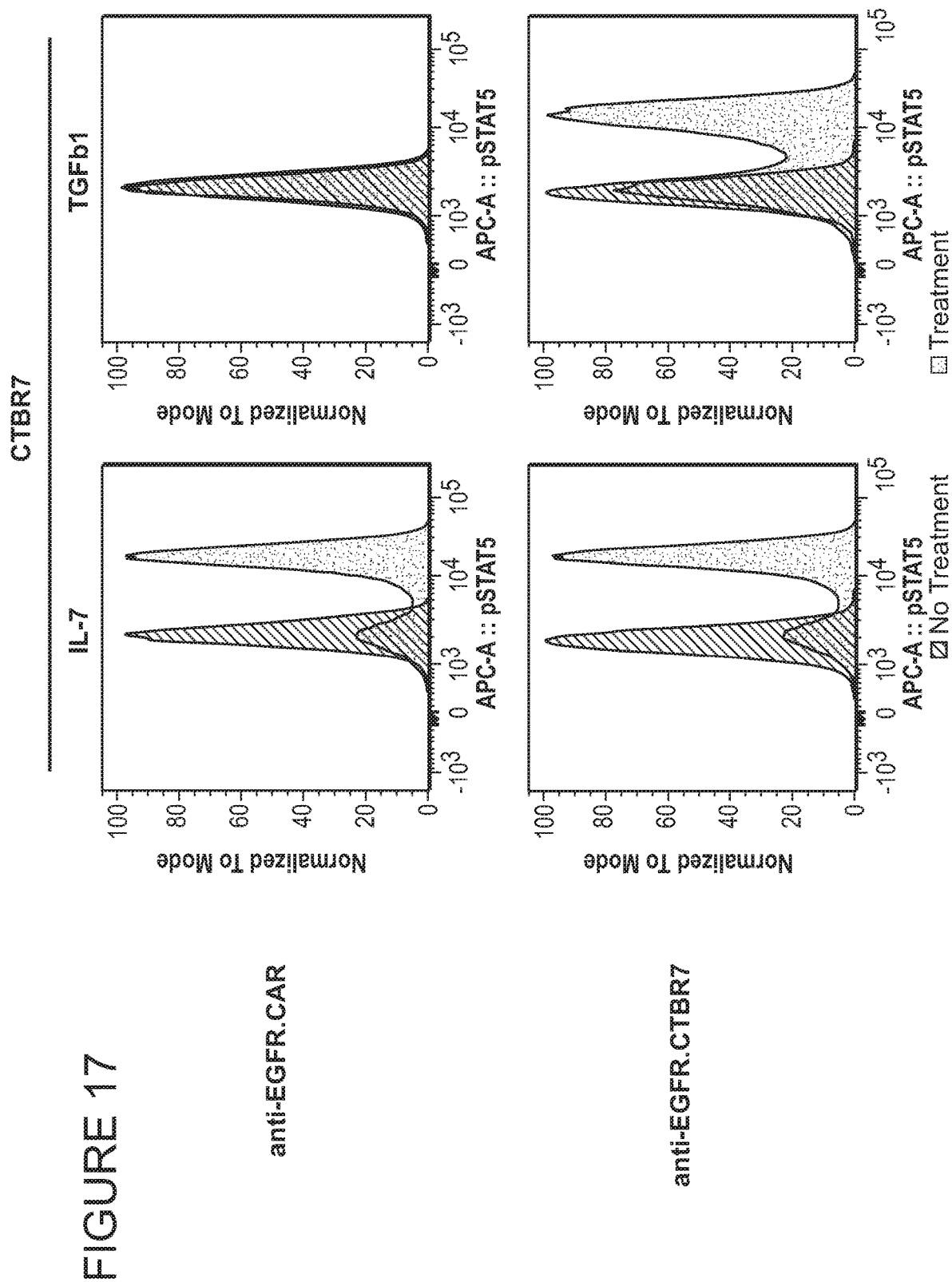
FIG. 17 shows phospho-STAT5 expression in primary human T cells transduced with an anti-EGFR CAR alone and in combination with the TGFβ DNR, and the CTBR7 signal convertor and treated with either IL-7 or TGFβ1.

T cells expressing anti-EGFR CAR or anti-EFGR.CTBR7 shows increased levels of phosphorylated STAT5 in the presence of IL-7 (FIG. 17, left panels), but only T cells expressing anti-EFGR.CTBR7 show increased levels of phosphorylated STAT4 in the presence of TGFβ1 (FIG. 17, lower right panel).

Example 13

CAR T Cells Expressing CTBR12 Secrete Increased IFNγ Upon Exposure to Antigen and TGFβ1

Primary human T cells from healthy donor PBMCs were activated with soluble anti-CD3 (1 µg/mL) and anti-CD28 (5 µg/mL) and transduced with vehicle or lentiviral vectors expressing: (i) an anti-EGFR CAR; (ii) an anti-EGFR CAR and dominant negative TGFβ receptor (anti-EGFR.DNR); or (iii) an anti-EGFR CAR and CTBR12 (anti-EFGR.CTBR12). After 10 days of culture in IL-2 containing growth media, CAR and CTBR expressing T cells were cultured with Jurkat cells (EGFR(−)), A549 cells (EGFR (+)), or HT1080 cells (EGFR(+)) for 48 hours either in the presence or absence of 5 ng/mL recombinant human TGFβ1. Supernatants were collected and analyzed via Luminex for soluble cytokine content.

Figure 18:
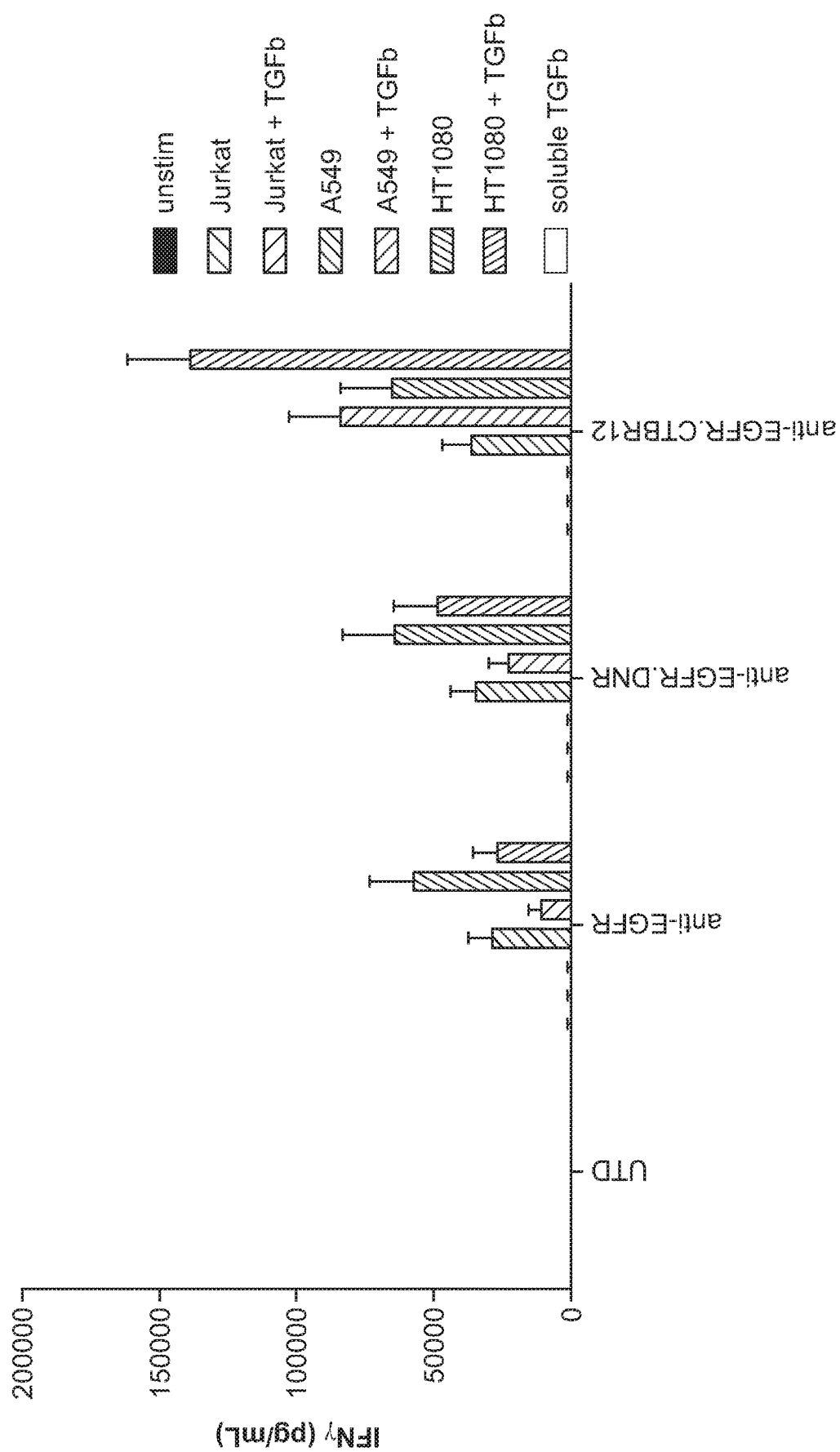
FIG. 18 shows IFNγ secretion from primary human T cells transduced with an anti-EGFR CAR alone and in combination with the TGFβ DNR or the CTBR12 signal convertor and cultured with EGFR (−) or EGFR (+) cell lines in the presence or absence of TGFβ1.

CTBR12 expressing cells produced significantly greater amounts of IFNγ when cultured with EGFR(+) cell lines compared to EGFR(−) cell lines in the presence of recombinant human TGFβ1 (FIG. 18).

Example 14

Anti-EGFR CAR T Cells Co-Expressing CTBR Demonstrate Sustained Effector Activity in the Absence of Exogenous IL-2 and Presence of TGFβ1

Primary human T cells from healthy donor PBMCs were activated with soluble anti-CD3 (1 µg/mL) and anti-CD28 (5 µg/mL) and transduced with vehicle or lentiviral vectors expressing (i) an anti-EGFR CAR; (ii) an anti-EGFR CAR and dominant negative TGFβ receptor (anti-EGFR.DNR); (iii) an anti-EGFR CAR and CTBR12 (anti-EFGR.CTBR12); and (iv) an anti-EGFR CAR and CTBR7 (anti-EFGR.CTBR7). After 10 days of culture in IL-2 containing growth media, the cells were subjected to an in vitro serial re-stimulation assay in the absence of exogenous IL-2 cytokine support.

Figure 19:
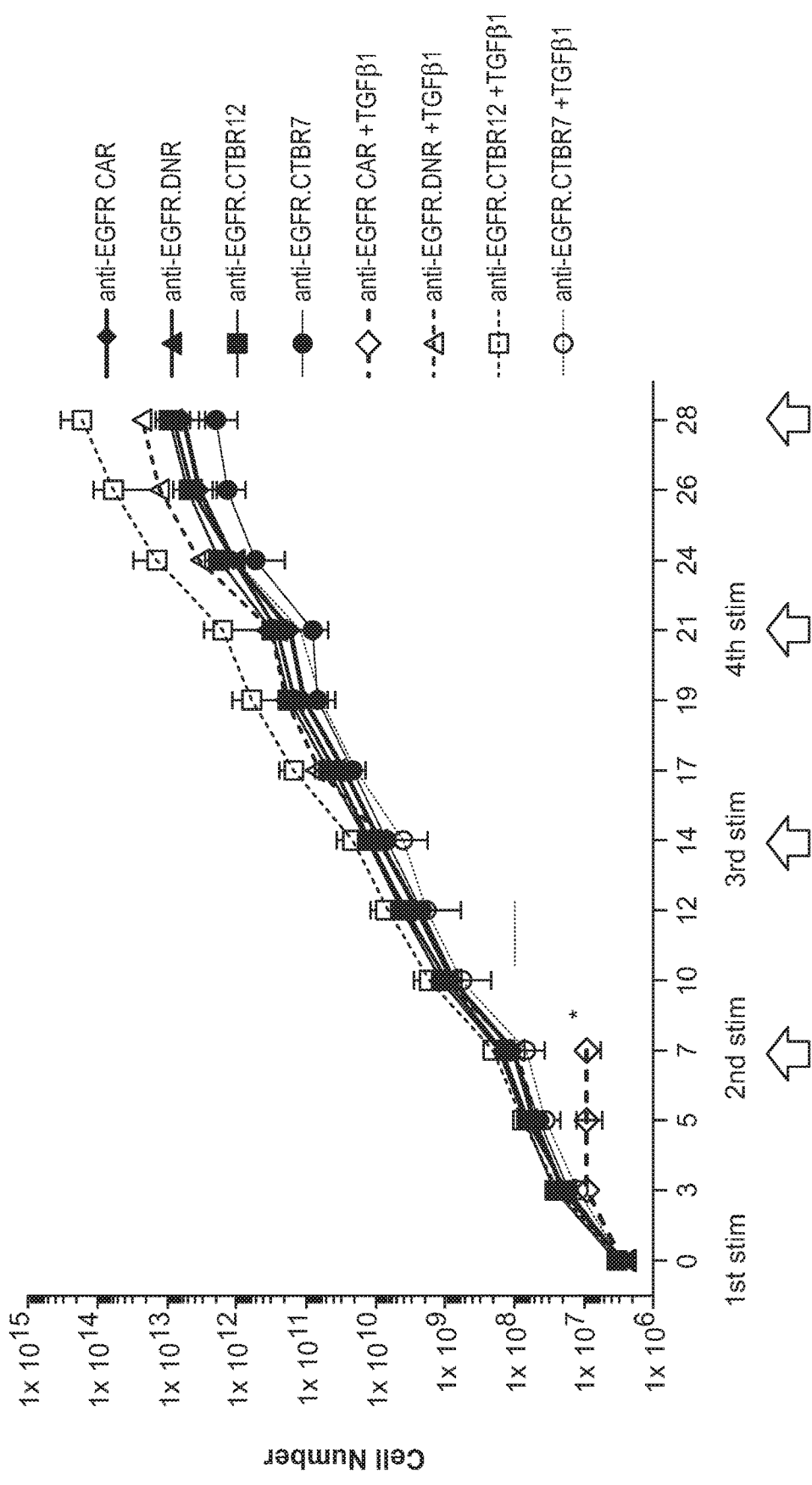
FIG. 19 shows the growth curves for primary human T cells transduced with an anti-EGFR CAR alone and in combination with the TGFβ DNR, the CTBR12 signal convertor, or the CTBR7 signal convertor serially re-stimulated with EGFR expressing target cells in the presence or absence of TGFβ1.

Briefly, GFP-labeled target cells that express human EGFR antigen were used to serially expand the CAR T cells in the presence or absence of recombinant human TGFβ1. CAR T cells were stimulated with target cells at a 1:1 ratio once every seven days in the presence or absence of 5 ng/mL recombinant human TGFβ1. No exogenous IL-2 was used for support in this assay. Control anti-EGFR CAR T cells displayed minimal expansion in the presence of 5 ng/mL recombinant human TGFβ1 through the first stimulation and were not cultured further. CAR T cells co-expressing the DNR also demonstrated reduced expansion when expanded in the presence of TGFβ1. In contrast, anti-EGFR CAR T cells co-expressing CTBR12 or CTBR7 demonstrated enhanced expansion compared to the same cells expanded in the absence of TGFβ1 (FIG. 19). These data demonstrated that active CTBR12 or CTBR7 signaling increased T cell expansion compared to the CAR alone.

Example 15

NY-ESO1 TCR T Cells Co-Expressing CTBR Demonstrate Sustained Effector Activity in the Absence of Exogenous IL-2 and Presence of TGFβ1

Illustrative TCR-based TGFβ IL-12R and TGFβ IL-R signal convertor constructs were designed as shown in FIG. 20.

IL-12Rβ1 and IL-12Rβ2 transmembrane and signaling domains were cloned into a lentiviral vector encoding an anti-NY-ESO1 TCR and separated by 2A self-cleaving polypeptide sequences (NY-ESO1.CTBR12).

IL-2Rγ and IL-7Rα transmembrane and signaling domains were cloned into a lentiviral vector encoding NY-ESO1 TCR and separated by 2A self-cleaving polypeptide sequences (NY-ESO1.CTBR7).

Primary human T cells from healthy donor PBMCs were activated with soluble anti-CD3 (1 µg/mL) and anti-CD28 (5 µg/mL) and transduced with vehicle or lentiviral vectors expressing (i) an NY-ESO1 TCR; (ii) an NY-ESO1 TCR and dominant negative TGFβ receptor (NY-ESO1.DNR); (iii) an NY-ESO1 TCR and CTBR12 (NY-ESO1.CTBR12); and (iv) an NY-ESO1 TCR and CTBR7 (NY-ESO1.CTBR7). After 10 days of culture in IL-2 containing growth media, cell surface expression of the NY-ESO1 TCRR and TGFβR2 was determined by flow cytometry. All constructs were expressed.

Example 16

Immunosuppressive TGFβ Signaling Inhibited by T Cells Expressing NY-ESO TCR and CTBR12 or NY-ESO TCR and CTBR7

Figure 21:
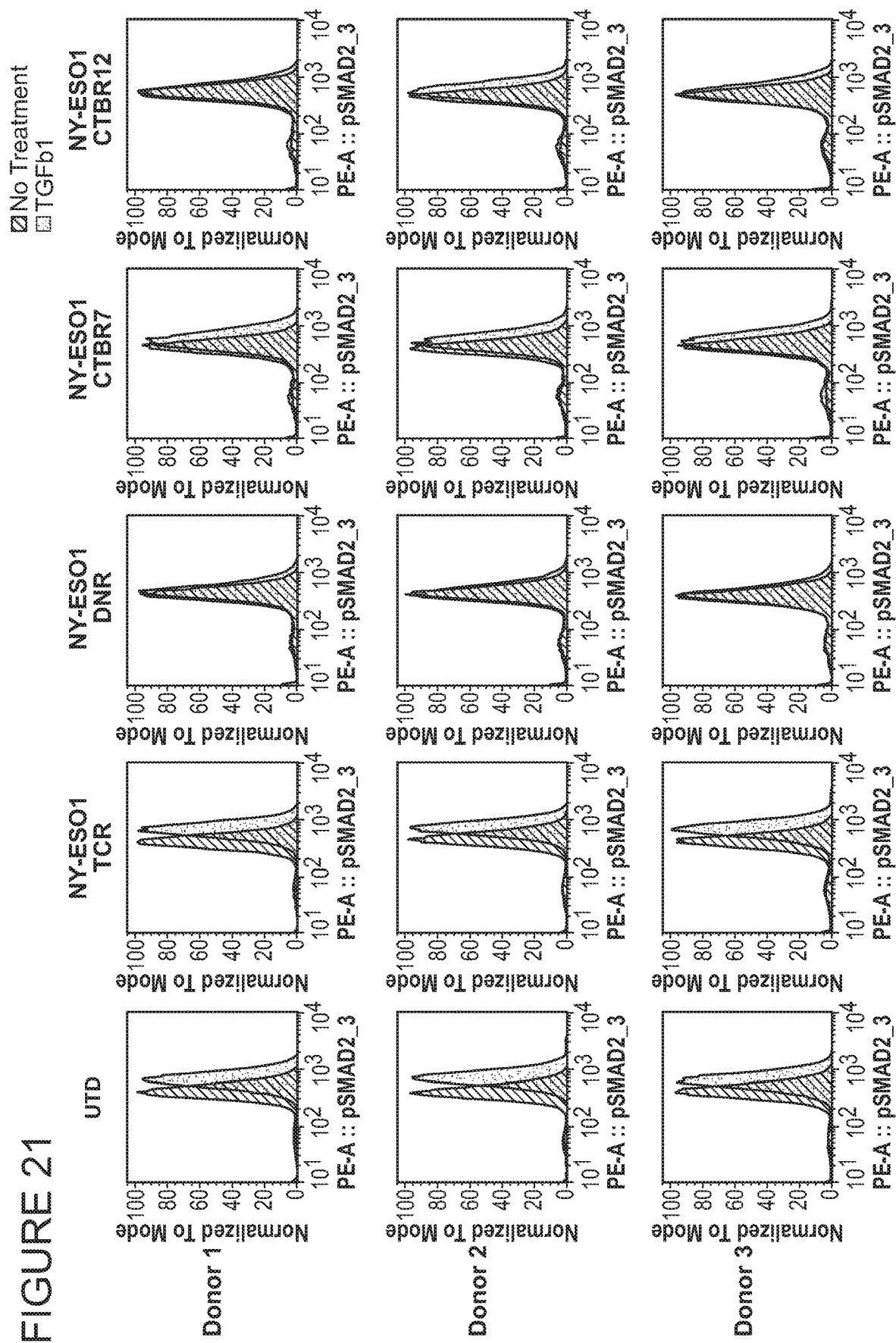
FIG. 21 shows phospho-SMAD2/3 expression in primary human T cells transduced with an NY-ESO1 TCR, NY-ESO1.DNR, NY-ESO1.CTBR7, and NY-ESO1.CTBR12 and treated with TGFβ1 compared to untreated cells.

Primary human T cells from healthy donor PBMCs were activated with soluble anti-CD3 (1 µg/mL) and anti-CD28 (5 µg/mL) and transduced with vehicle or lentiviral vectors expressing (i) an NY-ESO1 TCR; (ii) an NY-ESO1 TCR and dominant negative TGFβ receptor (NY-ESO1.DNR); (iii) an NY-ESO1 TCR and CTBR12 (NY-ESO1.CTBR12); and (iv) an NY-ESO1 TCR and CTBR7 (NY-ESO1.CTBR7). After 10 days of culture in IL-2 containing growth media, cultures were treated with 10 ng/mL of recombinant human TGFβ1 for 20 minutes. SMAD2/3 phosphorylation was evaluated with antibodies specific to phosphorylated SMAD2/3. T cells expressing the DNR, CTBR12 or CTBR7 were completely protected from phosphorylation of SMAD2/3 (FIG. 21). These data demonstrated that expression of either CTBR12 or CTBR7 rendered NY-ESO1 TCR T cells insensitive to TGFβ immunosuppressive signaling.

Example 17

CTBR Transduce IL-R Signaling Upon Exposure to TGFβ1

The cellular response to IL-12 is initiated by receptor dimerization and phosphorylation of STAT4 and STAT5.

Phospho-STAT4 expression was used to assess IL-12 receptor signaling pathway activation for T cells expressing NY-ESO1.CTBR12.

The cellular response to IL-7 is initiated by receptor dimerization and phosphorylation of STAT5. Thus, phospho-STAT5 expression was used to assess IL-7 receptor signaling pathway activation for T cells expressing NY-ESO1.CTBR7.

Figure 22:
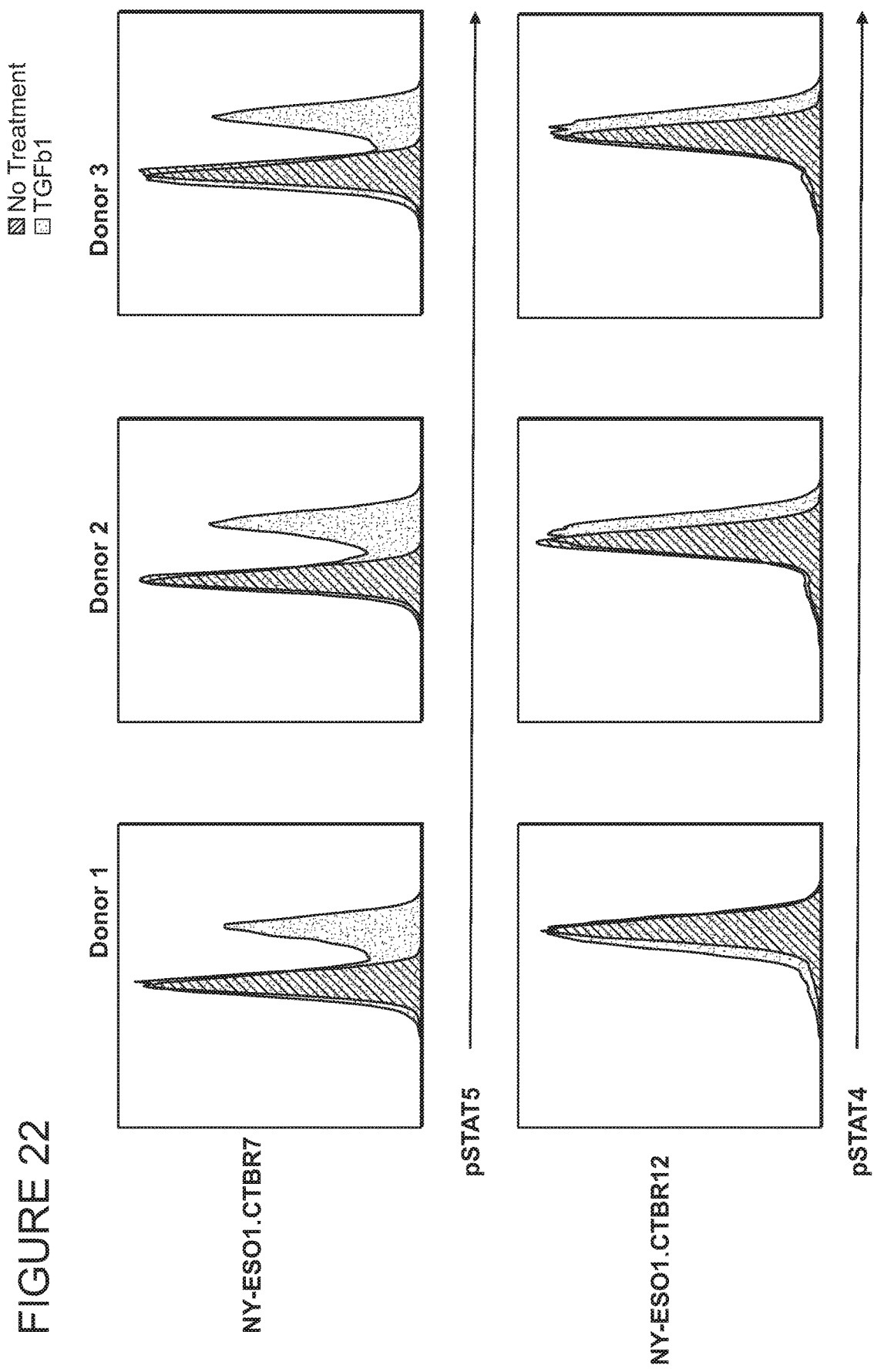
FIG. 22 shows phospho-STAT5 expression in primary human T cells transduced with an NY-ESO1.CTBR7 and treated with either IL-7 or TGFβ1 (top panel).

Primary human T cells from healthy donor PBMCs were activated with soluble anti-CD3 (1 μg/mL) and anti-CD28 (5 μg/mL) and transduced with vehicle or lentiviral vectors expressing (i) an NY-ESO1 TCR and CTBR12 (NY-ESO1.CTBR12); and (ii) an NY-ESO1 TCR and CTBR7 (NY-ESO1.CTBR7). After 10 days of culture in IL-2 containing growth media, T cell cultures were treated with recombinant human IL-7 or recombinant human TGFβ1 for 20 minutes (FIG. 22, top panel) or with recombinant human IL-12 or recombinant human TGFβ1 for 20 minutes (FIG. 22, bottom panel).

Example 18

CAR T Cells Expressing CTBR12 Secrete Increased IFNγ Upon Exposure to Antigen and TGFβ1

Primary human T cells from healthy donor PBMCs were activated with soluble anti-CD3 (1 μg/mL) and anti-CD28 (5 μg/mL) and transduced with vehicle or lentiviral vectors expressing: (i) an NY-ESO1 TCR; (ii) an NY-ESO1 TCR and dominant negative TGFβ receptor (NY-ESO1.DNR); (iii) an NY-ESO1 TCR and CTBR12 (NY-ESO1.CTBR12); and (iv) an NY-ESO1 TCR and CTBR7 (NY-ESO1.CTBR7). After 10 days of culture in IL-2 containing growth media, CAR and CTBR expressing T cells were cultured with SaOs2 cells (A2, NY-ESO1(+)) or A549.A2.NY-ESO1 cells (A2, NY-ESO1(+)) at a 5:1 ratio of T cells to target cells for 48 hours either in the presence or absence of 5 ng/mL recombinant human TGFβ1. Supernatants were collected and analyzed via Luminex for soluble cytokine content.

CTBR12 expressing cells produced significantly greater amounts of IFNγ when cultured with A2 and NY-ESO1 (+) cell lines in the presence of recombinant human TGFβ1 compared to A2 and NY-ESO1 (+) cell lines (FIG. 23). CTBR expressing cells demonstrates resistance to immunosuppressive TGFβ signaling.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A lentiviral vector comprising a polynucleotide encoding a fusion polypeptide comprising:
   (a) a TGFβR2 polypeptide comprising:
      (i) an extracellular TGFβI-binding domain of TGFβR2;
      (ii) an IL-12Rβ2 transmembrane domain; and
      (iii) an IL-12Rβ2 intracellular signaling domain;
   (b) a viral self-cleaving 2A peptide; and
   (c) a TGFβR1 polypeptide comprising:
      (i) an extracellular TGFβ1-binding domain of TGFβR1;
      (ii) an IL-12Rβ1 transmembrane domain; and
      (iii) an IL-12Rβ1 intracellular signaling domain.

2. The lentiviral vector of claim 1, wherein the viral self-cleaving 2A polypeptide is selected from the group consisting of: a foot-and-mouth disease virus (FMDV) (F2A) peptide, an equine rhinitis A virus (ERAV)(E2A) peptide, a Thosea asigna virus (TaV) (T2A) peptide, a porcine teschovirus-1 (PTV-1)(P2A) peptide, a Theilovirus 2A peptide, and an encephalomyocarditis virus 2A peptide.

3. The lentiviral vector of claim 1, wherein the fusion polypeptide further comprises (i) an engineered antigen receptor and (ii) a second polypeptide cleavage signal or viral self-cleaving 2A polypeptide.

4. The lentiviral vector of claim 1, wherein the viral self-cleaving 2A polypeptide is a porcine teschovirus-1 (PTV-1) (P2A) peptide.

5. A cell comprising the lentiviral vector of claim 1.

6. The cell of claim 5, wherein the cell is:
   (a) a hematopoietic cell;
   (b) a T cell;
   (c) a CD3+, CD4+, and/or CD8+ cell;
   (d) an immune effector cell;
   (e) a cytotoxic T lymphocyte (CTL), a tumor infiltrating lymphocyte (TIL), or a helper T cell; or
   (f) a natural killer (NK) cell or natural killer T (NKT) cell.

7. A composition comprising the cell of claim 6.

8. The cell of claim 5, wherein the cell is a hematopoietic cell.

9. The cell of claim 5, wherein the cell is a T cell.

10. The cell of claim 5, wherein the cell is a CD3+, CD4+, and/or CD8+ cell.

11. The cell of claim 5, wherein the cell is an immune effector cell.

12. The cell of claim 5, wherein the cell is a cytotoxic T lymphocyte (CTL).

13. The cell of claim 5, wherein the cell is a tumor infiltrating lymphocyte (TIL).

14. The cell of claim 5, wherein the cell is a helper T cell.

15. A lentiviral vector comprising a polynucleotide encoding a fusion polypeptide comprising:
   (a) a TGFβR2 polypeptide comprising:
      (i) an extracellular TGFβI-binding domain of TGFβR2;
      (ii) an IL-12Rβ2 transmembrane domain; and
      (iii) an IL-12Rβ2 intracellular signaling domain;
   (b) a viral self-cleaving 2A peptide; and
   (c) a TGFβR1 polypeptide comprising:
      (i) an extracellular TGFβ1-binding domain of TGFβR1;
      (ii) an IL-12Rβ1 transmembrane domain; and
      (iii) an IL-12Rβ1 intracellular signaling domain.

16. The lentiviral vector of claim 15, wherein the viral self-cleaving 2A polypeptide is selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide.

17. The lentiviral vector of claim 15, wherein the fusion polypeptide further comprises (i) an engineered antigen receptor and (ii) a second polypeptide cleavage signal or viral self-cleaving 2A polypeptide.

18. A cell comprising the lentiviral vector of claim 15.

19. The cell of claim 18, wherein the cell is:
(a) a hematopoietic cell;
(b) a T cell;
(c) a $CD3^+$, $CD4^+$, and/or $CD8^+$ cell;
(d) an immune effector cell;
(e) a cytotoxic T lymphocyte (CTL), a tumor infiltrating lymphocyte (TIL), or a helper T cell; or
(f) a natural killer (NK) cell or natural killer T (NKT) cell.

20. A composition comprising the cell of claim 18.

* * * * *

UNITED STATES PATENT AND TRADEMARK OFFICE
CERTIFICATE OF CORRECTION

PATENT NO. : 11,654,158 B2
APPLICATION NO. : 16/348450
DATED : May 23, 2023
INVENTOR(S) : Benjamin Boyerinas It is certified that error appears in the above-identified patent and that said Letters Patent is hereby corrected as shown below:

In the Claims

At Column 235, Claim number 1, Line numbers 32-43:
"1. A lentiviral vector comprising a polynucleotide encoding a fusion polypeptide comprising:
(a) a TGFbR2 polypeptide comprising:
    (i) an extracellular TGFb1-binding domain of TGFbR2;
    (ii) an IL-12Rb2 transmembrane domain; and
    (iii) an IL-12Rb2 intracellular signaling domain;
(b) a viral self-cleaving 2A peptide; and
(c) a TGFbR1 polypeptide comprising:
    (i) an extracellular TGFb1-binding domain of TGFbR1;
    (ii) an IL-12Rb1 transmembrane domain; and
    (iii) an IL-12Rb1 intracellular signaling domain."

Should read:
--1. A lentiviral vector comprising a polynucleotide encoding a fusion polypeptide comprising:
(a) a TGFβR2 polypeptide comprising:
    (i) an extracellular TGFβ1-binding domain of TGFβR2;
    (ii) an IL-12Rβ2 transmembrane domain; and
    (iii) an IL-12Rβ2 intracellular signaling domain;
(b) a viral self-cleaving 2A peptide; and
(c) a TGFβR1 polypeptide comprising:
    (i) an extracellular TGFβ1-binding domain of TGFβR1;
    (ii) an IL-12Rβ1 transmembrane domain; and
    (iii) an IL-12Rβ1 intracellular signaling domain.--

At Column 236, Claim number 15, Line numbers 44-55:
"15. A lentiviral vector comprising a polynucleotide encoding a fusion polypeptide comprising:
(a) a TGFbR2 polypeptide comprising:
    (i) an extracellular TGFb1-binding domain of TGFbR2;

Signed and Sealed this
Eleventh Day of July, 2023

*Katherine Kelly Vidal*
Katherine Kelly Vidal
*Director of the United States Patent and Trademark Office*

(ii) an IL-12Rb2 transmembrane domain; and
(iii) an IL-12Rb2 intracellular signaling domain;
(b) a viral self-cleaving 2A peptide; and
(c) a TGFbR1 polypeptide comprising:
(i) an extracellular TGFb1-binding domain of TGFbR1;
(ii) an IL-12Rb1 transmembrane domain; and
(iii) an IL-12Rb1 intracellular signaling domain."

Should read